United States Patent
Yang et al.

(10) Patent No.: US 11,884,734 B2
(45) Date of Patent: Jan. 30, 2024

(54) ANTI-MET ANTIBODIES AND METHODS OF USE THEREOF

(71) Applicant: Celldex Therapeutics, Inc., Hampton, NJ (US)

(72) Inventors: Yan Yang, Hamden, CT (US); Sreekala Mandiyan, Bloomfield, NJ (US); Brett Robinson, Preston, CT (US); Lida Kimmel, Chester, CT (US); Yaron Hadari, Harrison, NY (US); Timothy David Jones, Babraham (GB); Francis Joseph Carr, Balmedie (GB); Robert George Edward Holgate, Royston (GB); Richard Weldon, Wädenswil (CH)

(73) Assignee: Celldex Therapeutics, Inc., Hampton, NJ (US)

( * ) Notice: Subject to any disclaimer, the term of this patent is extended or adjusted under 35 U.S.C. 154(b) by 457 days.

(21) Appl. No.: 17/021,423

(22) Filed: Sep. 15, 2020

(65) Prior Publication Data

US 2021/0130476 A1    May 6, 2021

Related U.S. Application Data

(62) Division of application No. 15/558,306, filed as application No. PCT/US2016/022464 on Mar. 15, 2016, now abandoned.

(60) Provisional application No. 62/149,465, filed on Apr. 17, 2015, provisional application No. 62/133,789, filed on Mar. 16, 2015.

(51) Int. Cl.
| | |
|---|---|
| *C07K 16/28* | (2006.01) |
| *A61K 39/395* | (2006.01) |
| *A61K 45/06* | (2006.01) |
| *C07K 16/30* | (2006.01) |
| *A61K 39/00* | (2006.01) |

(52) U.S. Cl.
CPC .... *C07K 16/2863* (2013.01); *A61K 39/39558* (2013.01); *A61K 45/06* (2013.01); *C07K 16/30* (2013.01); *A61K 2039/505* (2013.01); *C07K 2317/24* (2013.01); *C07K 2317/31* (2013.01); *C07K 2317/33* (2013.01); *C07K 2317/52* (2013.01); *C07K 2317/56* (2013.01); *C07K 2317/565* (2013.01); *C07K 2317/70* (2013.01); *C07K 2317/73* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | |
|---|---|---|
| 2004/0166544 A1 | 8/2004 | Morton et al. |
| 2005/0054019 A1 | 3/2005 | Michaud et al. |
| 2005/0118165 A1 | 6/2005 | Hay et al. |
| 2005/0147612 A1 | 7/2005 | Yayon et al. |
| 2006/0069019 A1 | 3/2006 | Wiesmann et al. |
| 2006/0140940 A1 | 6/2006 | Prat |
| 2006/0263808 A1 | 11/2006 | Yauch |
| 2006/0270594 A1 | 11/2006 | Kong-Beltran et al. |
| 2007/0010443 A1 | 1/2007 | Detmar et al. |
| 2007/0020234 A1 | 1/2007 | Vande Woude et al. |
| 2007/0129301 A1 | 6/2007 | Kirchhofer et al. |
| 2008/0293923 A1 | 11/2008 | Wiesmann et al. |
| 2010/0115639 A1 | 5/2010 | Goetsch |
| 2012/0134996 A1 | 5/2012 | Comoglio et al. |
| 2013/0004484 A1 | 1/2013 | Demeule et al. |
| 2013/0089542 A1 | 4/2013 | Lee et al. |
| 2013/0089557 A1 | 4/2013 | Cheong et al. |
| 2013/0209365 A1 | 8/2013 | Wu et al. |
| 2014/0186308 A1 | 7/2014 | Belmonte et al. |

FOREIGN PATENT DOCUMENTS

| | | |
|---|---|---|
| CN | 101035808 | 9/2007 |
| CN | 103562223 | 2/2014 |
| CN | 103987730 | 8/2014 |
| EP | 2415784 A1 | 2/2012 |
| KR | 20110097839 | 8/2011 |
| TW | 201446805 A | 12/2014 |
| WO | WO 2006/015371 | 2/2006 |
| WO | WO 2009/007427 | 1/2009 |
| WO | WO 2010/059654 | 5/2010 |
| WO | WO 2010/064089 | 6/2010 |

(Continued)

OTHER PUBLICATIONS

Malia et al (Proteins 2016; 84;427-434).*

(Continued)

*Primary Examiner* — Brad Duffy

(74) *Attorney, Agent, or Firm* — Jones Day

(57) ABSTRACT

Provided herein are compositions, methods and uses involving antibodies that specifically bind to MET, a receptor tyrosine kinase, and modulate the expression and/or activity of MET. Also provided are uses and methods for managing, treating, or preventing disorders, such as cancer. In one aspect, provided herein is a monoclonal antibody or antigen-binding fragment thereof that binds to the Sema/PSI domain of human MET. Also provided herein is a kit comprising an antibody or antigen-binding fragment provided herein. Also provided herein is a method of managing, protecting against, or treating cancer in a subject, comprising administering to a subject in need thereof a therapeutically effective amount of an antibody or antigen-binding fragment provided herein.

16 Claims, 26 Drawing Sheets

Figure 2:
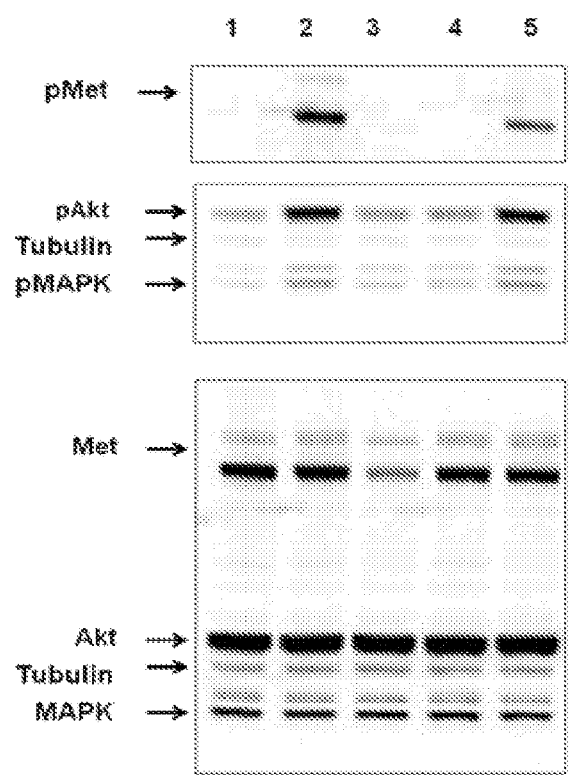

Specification includes a Sequence Listing.

(56) References Cited

FOREIGN PATENT DOCUMENTS

| WO | WO 2010/069765 | 6/2010 |
| WO | WO 2012/059561 | 5/2012 |
| WO | WO 2012/059562 | 5/2012 |
| WO | WO 2013/051878 | 4/2013 |
| WO | WO 2013/064701 | 5/2013 |

OTHER PUBLICATIONS

International Search Report and Written Opinion, dated Aug. 8, 2018, for International Application No. PCT/US2016/022464, filed Mar. 15, 2016, 15 pages.
Giordano et al., 1989, "Tyrosine kinase receptor indistinguishable from the c-met protein," Nature 339(6220):155-156.
Kong-Beltran et al., 2004, "The Sema domain of Met is necessary for receptor dimerization and activation," Cancer Cell 6(1):75-84.
Ponzetto et al., 1994, "A multifunctional docking site mediates signaling and transformation by the hepatocyte growth factor/scatter factor receptor family," Cell. 77(2):261-271.
Trusolino and Comoglio, 2002, "Scatter-factor and semaphorin receptors: cell signalling for invasive growth," Nat Rev Cancer 2(4):289-300.
Trusolino et al., 2010, "MET signalling: principles and functions in development, organ regeneration and cancer," Nat Rev Mol Cell Biol 11(12):834-848.
Extended European Search Report for EP Application No. 16765587.7 dated Sep. 24, 2018.
Boccaccio and Comoglio, 2006, "Invasive growth: a MET-driven genetic programme for cancer and stem cells." Nat Rev Cancer. 6(8):637-645.
Dillon et al., 2008, "Structural and functional characterization of disulfide isoforms of the human IgG2 subclass." J Biol Chem. 283(23):16206-16215.
Engelman et al., 2007, "MET amplification leads to gefitinib resistance in lung cancer by activating ERBB3 signaling." Science. 316(5827):1039-1043.
Gherardi et al., 2003, "Functional map and domain structure of MET, the product of the c-met protooncogene and receptor for hepatocyte growth factor/scatter factor." Proc Natl Acad Sci U S A. 100(21):12039-12044.
Ma et al., 2003, "c-Met: structure, functions and potential for therapeutic inhibition." Cancer Metastasis Rev. 22(4):309-325.
Mandiyan et al., 2015, "Abstract 1696: Blocking activity of a novel anti-MET humanized monoclonal antibody, KTN0216, is enhanced by IgG2 isotype in HGF-dependent and Met-amplified tumors." Abst. # 1696, Proceedings: AACR 106th Annual Meeting 2015; Apr. 18-22, 2015; Philadelphia, PA (1 page).
Mandiyan et al., 2015, "Blocking activity of a novel anti-MET humanized monoclonal antibody, KTN0216, is enhanced by IgG2 isotype in HGF-dependent and Met-amplified tumors." Poster presented at AACR 106th Annual Meeting 2015; Apr. 18-22, 2015; Philadelphia, PA (1 page).
Robinson et al., 2016, "An anti-MET IgG2 monoclonal antibody degrades both wild-type and exon 14 mutant MET receptor tyrosine kinase through a novel exon 14-independent mechanism and inhibits tumor growth." Poster presented at the 107th Annual Meeting of the American Association for Cancer Research (AACR), Apr. 16-20, 2016; New Orleans (1 page).
Stamos et al., 2004, "Crystal structure of the HGF beta-chain in complex with the Sema domain of the Met receptor." EMBO J. 23(12):2325-2335.
Straussman et al., 2012, "Tumour micro-environment elicits innate resistance to RAF inhibitors through HGF secretion." Nature. 487(7408):500-504.
Yang et al., 2016, "Antitumor Properties of an IgG2-Enhanced Next-Generation MET Monoclonal Antibody That Degrades Wild-Type and Mutant MET Receptors." Cancer Res. 76(19):5788-5797.
International Search Report dated Aug. 8, 2016 in PCT Application No. PCT/US2016/022464 (Publication No. WO2016/149265) (7 pages).
Written Opinion dated Aug. 8, 2016 in PCT Application No. PCT/US2016/022464 (Publication No. WO2016/149265) (8 pages).
Cooper et al., 1984, "Molecular cloning of a new transforming gene from a chemically transformed human cell line," Nature, 311(5981):29-33.
Oh et al., 2012, "A new anti-c-Met antibody selected by a mechanism-based dual-screening method: therapeutic potential in cancer," Mol. Cells. 34(6):523-529.
Taher et al. 2002, "c-Cbl is involved in Met signaling in B cells and mediates hepatocyte growth factor-induced receptor ubiquitination," J Immunol. 169(7):3793-3800.
Thiery and Sleeman, 2006, "Complex networks orchestrate epithelial-mesenchymal Transitions," Nat. Rev. Mol. Cell Biol. 2:131-142.
Tsai and Yang, 2013, "Epithelial-mesenchymal plasticity in carcinoma metastasis," Genes & Dev. 27:2192-2206.
Wan, Jia-Yi et al.,2008, "Construction of human naive Fab library, screening and identification of phage antibody against c-Met," Acta Univ Med Nanjing, 28(06): 697-701 (incl. English abstract).
Mariuzza et al., 1987, "The structural basis of antigen-antibody recognition." Annu Rev Biophys Biophys Chem. 16:139-59.
Güssow and Seemann, 1991, "Humanization of monoclonal antibodies." Methods Enzymol. 203:99-121.
Winkler et al. 2000, "Changing the antigen binding specificity by single point mutations of an anti-p24 (HIV-1) antibody." J Immunol. 165(8):4505-4514.

\* cited by examiner

FIG. 1

```
  1  MKAPAVLAPG ILVLLFTLVQ RSNGECKEAL AKSEMNVNMK YQLPNFTAET PIQNVILHEH
 61  HIFLGATNYI YVLNEEDLQK VAEYKTGPVL EHPDCFPCQD CSSKANLSGG VWKDNINMAL
121  VVDTYYDDQL ISCGSVNRGT CQRHVFPHNH TADIQSEVHC IFSPQIEEPS QCPDCVVSAL
181  GAKVLSSVKD RFINFFVGNT INSSYFPDHP LHSISVRRLK ETKDGFMFLT DQSYIDVLPE
241  FRDSYPIKYV HAFESNNFIY FLTVQRETLD AQTFHTRIIR FCSINSGLHS YMEMPLECIL
301  TEKRKKRSTK KEVFNILQAA YVSKPGAQLA RQIGASLNDD ILFGVFAQSK PDSAEPMDRS
361  AMCAFPIKYV NDFFNKIVNK NNVRCLQHFY GPNHEHCFNR TLLRNSSGCE ARRDEYRTEF
421  TTALQRVDLF MGQFSEVLLT SISTFIKGDL TIANLGTSEG RFMQVVVSRS GPSTPHVNFL
481  LDSHPVSPEV IVEHTLNQNG YTLVITGKKI TKIPLNGLGC RHFQSCSQCL SAPPFVQCGW
541  CHDKCVRSEE CLSGTWTQQI CLPAIYKVFP NSAPLEGGTR LTICGWDFGF RRNNKFDLKK
601  TRVLLGNESC TLTLSESTMN TLKCTVGPAM NKHFNMSIII SNGHGTTQYS TFSYVDPVIT
661  SISPKYGPMA GGTLLLTGN YLNSGNSRHI SIGGKTCTLK SVSNSILECY TPAQTISTEF
721  AVKLKIDLAN RETSIFSYRE DPIVYEIHPT KSFISGGSTI TGVGKNLNSV SVPRMVINVH
781  EAGRNFTVAC QHRSNSEIIC CTTPSLQQLN LQLPLKTKAF FMLDGILSKY FDLIYVHNPV
841  FKPFEKPVMI SMGNENVLEI KGNDIDPEAV KGEVLKVGNK SCENIHLHSE AVLCTVPNDL
901  LKLNSELNIE WKQAISSTVL GKVIVQPDQN FTLE
```

FIG. 6B
Control 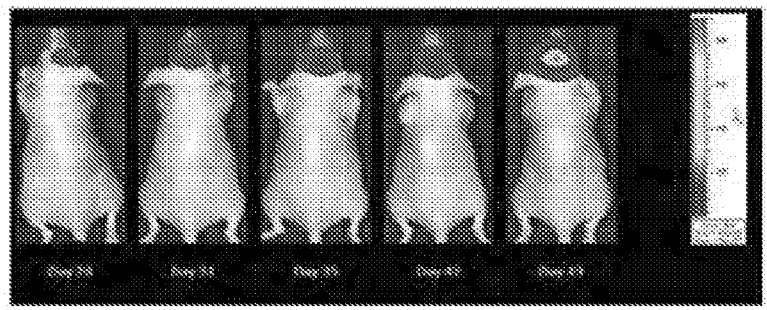
Crizotinib 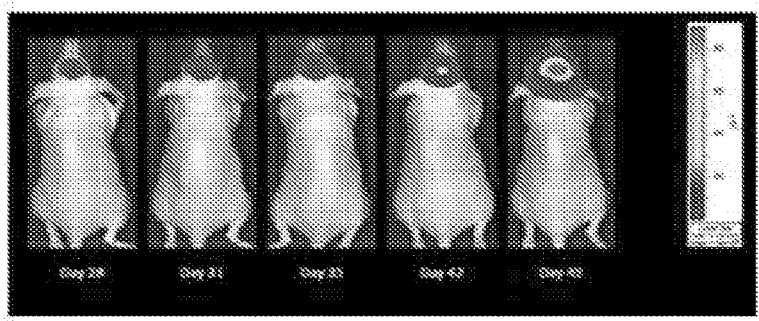
Ab235C 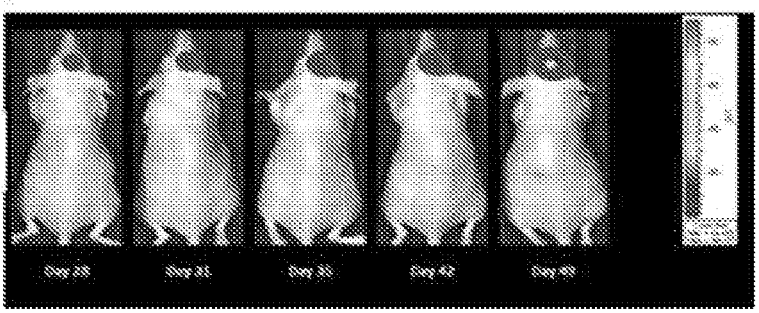
Ab236C 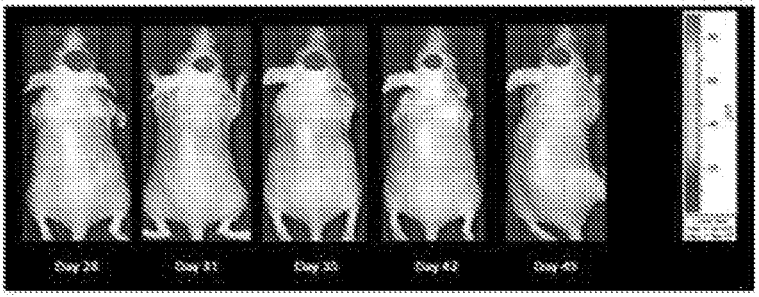

SEQUENCE LISTING

<160> NUMBER OF SEQ ID NOS: 300

<210> SEQ ID NO 1
<211> LENGTH: 10

```
<212> TYPE: PRT
<213> ORGANISM: Artificial Sequence
<220> FEATURE:
<223> OTHER INFORMATION: Ab235 VL CDR1 Kabat

<400> SEQUENCE: 1

Ser Ala Ser Ser Ser Val Asn Tyr Met Phe
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Ab235 VL CDR2 Kabat

<400> SEQUENCE: 2

Asp Thr Phe Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Ab235 VL CDR3 Kabat

<400> SEQUENCE: 3

Gln Gln Trp Ser Ile Tyr Pro Tyr Thr
1               5

<210> SEQ ID NO 4
<211> LENGTH: 6
<212> TYPE: PRT
<213> ORGANISM: Artificial Sequence
<220> FEATURE:
<223> OTHER INFORMATION: Ab235 VH CDR1 Kabat

<400> SEQUENCE: 4

Asn Tyr Trp Ile Glu Trp
1               5

<210> SEQ ID NO 5
<211> LENGTH: 17
<212> TYPE: PRT
<213> ORGANISM: Artificial Sequence
<220> FEATURE:
<223> OTHER INFORMATION: Ab235 VH CDR2 Kabat

<400> SEQUENCE: 5

Glu Ile Leu Pro Gly Ser Asp Tyr Thr Lys Tyr Asn Glu Lys Phe Lys
1               5                   10                  15

Gly

<210> SEQ ID NO 6
<211> LENGTH: 8
<212> TYPE: PRT
<213> ORGANISM: Artificial Sequence
<220> FEATURE:
<223> OTHER INFORMATION: Ab235 VH CDR3 Kabat

<400> SEQUENCE: 6

Pro Ser Thr Ile Pro Pro Asp Cys
1               5

<210> SEQ ID NO 7
```

```
<211> LENGTH: 10
<212> TYPE: PRT
<213> ORGANISM: Artificial Sequence
<220> FEATURE:
<223> OTHER INFORMATION: Ab236 VL CDR1 Kabat

<400> SEQUENCE: 7

Ser Ala Ser Ser Ser Val Ser Tyr Met Phe
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Ab236 VL CDR2 Kabat

<400> SEQUENCE: 8

Asp Thr Ser Asp Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Ab236 VL CDR3 Kabat

<400> SEQUENCE: 9

Gln Gln Trp Ser Asn Tyr Pro Tyr Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Ab236 VH CDR1 Kabat

<400> SEQUENCE: 10

Ser Tyr Trp Ile Glu Trp
1               5

<210> SEQ ID NO 11
<211> LENGTH: 17
<212> TYPE: PRT
<213> ORGANISM: Artificial Sequence
<220> FEATURE:
<223> OTHER INFORMATION: Ab236 VH CDR2 Kabat

<400> SEQUENCE: 11

Glu Ile Leu Pro Gly Ser Asp Phe Ile Lys Tyr Ser Glu Lys Phe Lys
1               5                   10                  15

Gly

<210> SEQ ID NO 12
<211> LENGTH: 8
<212> TYPE: PRT
<213> ORGANISM: Artificial Sequence
<220> FEATURE:
<223> OTHER INFORMATION: Ab236 VH CDR3 Kabat

<400> SEQUENCE: 12

Pro Ser Thr Val Pro Pro Asp Cys
1               5
```

```
<210> SEQ ID NO 13
<211> LENGTH: 11
<212> TYPE: PRT
<213> ORGANISM: Artificial Sequence
<220> FEATURE:
<223> OTHER INFORMATION: Ab237 VL CDR1 Kabat

<400> SEQUENCE: 13

Leu Ala Ser Ala Asp Ile His Ser Asn Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Ab237 VL CDR2 Kabat

<400> SEQUENCE: 14

Tyr Gly Asn Asn Leu Asn Asp
1               5

<210> SEQ ID NO 15
<211> LENGTH: 9
<212> TYPE: PRT
<213> ORGANISM: Artificial Sequence
<220> FEATURE:
<223> OTHER INFORMATION: Ab237 VL CDR3 Kabat

<400> SEQUENCE: 15

Gln Gln Ser Tyr Asp Ser Pro Pro Thr
1               5

<210> SEQ ID NO 16
<211> LENGTH: 5
<212> TYPE: PRT
<213> ORGANISM: Artificial Sequence
<220> FEATURE:
<223> OTHER INFORMATION: Ab237 VH CDR1 Kabat

<400> SEQUENCE: 16

Asp Ser Tyr Met Ala
1               5

<210> SEQ ID NO 17
<211> LENGTH: 17
<212> TYPE: PRT
<213> ORGANISM: Artificial Sequence
<220> FEATURE:
<223> OTHER INFORMATION: Ab237, Ab239 VH CDR2 Kabat

<400> SEQUENCE: 17

Ser Ile Ser Ser Asp Gly Gly Gly Thr Tyr Tyr Arg Asp Ser Val Lys
1               5                   10                  15

Gly

<210> SEQ ID NO 18
<211> LENGTH: 15
<212> TYPE: PRT
<213> ORGANISM: Artificial Sequence
<220> FEATURE:
<223> OTHER INFORMATION: Ab237 VH CDR3 Kabat

<400> SEQUENCE: 18

Glu Gly Ile Tyr Thr Thr Asp Tyr Tyr Pro Tyr Cys Phe Asn Tyr
1               5                   10                  15
```

<210> SEQ ID NO 19
<211> LENGTH: 11
<212> TYPE: PRT
<213> ORGANISM: Artificial Sequence
<220> FEATURE:
<223> OTHER INFORMATION: Ab238 VL CDR1 Kabat

<400> SEQUENCE: 19

Leu Ala Ser Glu Asp Ile Tyr Ser Asp Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Ab238 VL CDR2 Kabat

<400> SEQUENCE: 20

Asn Ala Asn Thr Leu Gln Asn
1               5

<210> SEQ ID NO 21
<211> LENGTH: 9
<212> TYPE: PRT
<213> ORGANISM: Artificial Sequence
<220> FEATURE:
<223> OTHER INFORMATION: Ab238 VL CDR3 Kabat

<400> SEQUENCE: 21

Gln Gln Tyr Asn Asn Tyr Pro Pro Thr
1               5

<210> SEQ ID NO 22
<211> LENGTH: 6
<212> TYPE: PRT
<213> ORGANISM: Artificial Sequence
<220> FEATURE:
<223> OTHER INFORMATION: Ab238 VH CDR1 Kabat

<400> SEQUENCE: 22

Thr Tyr Gly Met Gly Val
1               5

<210> SEQ ID NO 23
<211> LENGTH: 16
<212> TYPE: PRT
<213> ORGANISM: Artificial Sequence
<220> FEATURE:
<223> OTHER INFORMATION: Ab238 VH CDR2 Kabat

<400> SEQUENCE: 23

Asn Ile Trp Trp Asp Asp Val Asn Tyr Ser Asn Pro Ser Leu Lys Asn
1               5                   10                  15

<210> SEQ ID NO 24
<211> LENGTH: 9
<212> TYPE: PRT
<213> ORGANISM: Artificial Sequence
<220> FEATURE:
<223> OTHER INFORMATION: Ab238 VH CDR3 Kabat

<400> SEQUENCE: 24

Ile Gly Thr Ser His Ile Val Asp Ala
1               5

<210> SEQ ID NO 25
<211> LENGTH: 13
<212> TYPE: PRT
<213> ORGANISM: Artificial Sequence
<220> FEATURE:
<223> OTHER INFORMATION: Ab239 VL CDR1 Kabat

<400> SEQUENCE: 25

Val Arg Ser Ser Gly Asp Ile Gly Asp Arg Tyr Val Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Ab239 VL CDR2 Kabat

<400> SEQUENCE: 26

Ala Ala Asp Gln Arg Pro Ser
1               5

<210> SEQ ID NO 27
<211> LENGTH: 10
<212> TYPE: PRT
<213> ORGANISM: Artificial Sequence
<220> FEATURE:
<223> OTHER INFORMATION: Ab239 VL CDR3 Kabat

<400> SEQUENCE: 27

Gln Ser Tyr Asp Ser Asn Ile Asp Ile Val
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Ab239 VH CDR1 Kabat

<400> SEQUENCE: 28

Asp Cys Tyr Met Ala
1               5

<210> SEQ ID NO 29
<211> LENGTH: 16
<212> TYPE: PRT
<213> ORGANISM: Artificial Sequence
<220> FEATURE:
<223> OTHER INFORMATION: Ab239 VH CDR3 Kabat

<400> SEQUENCE: 29

Glu Arg Tyr Tyr Asp Gly Thr Tyr Tyr Gly Tyr Trp Tyr Phe Asp Phe
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Ab240 VL CDR1 Kabat

<400> SEQUENCE: 30

Arg Ala Ser Gln Gly Ile Ser Lys Tyr Leu Asn
1               5                   10

<210> SEQ ID NO 31

-continued

```
<211> LENGTH: 7
<212> TYPE: PRT
<213> ORGANISM: Artificial Sequence
<220> FEATURE:
<223> OTHER INFORMATION: Ab240 VL CDR2 Kabat

<400> SEQUENCE: 31

Tyr Thr Ser Asn Leu Gln Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Ab240 VL CDR3 Kabat

<400> SEQUENCE: 32

Gln Gln Tyr Asp Ser Ser Pro Phe Thr
1               5

<210> SEQ ID NO 33
<211> LENGTH: 5
<212> TYPE: PRT
<213> ORGANISM: Artificial Sequence
<220> FEATURE:
<223> OTHER INFORMATION: Ab240 VH CDR1 Kabat

<400> SEQUENCE: 33

Thr Asn Ser Val His
1               5

<210> SEQ ID NO 34
<211> LENGTH: 16
<212> TYPE: PRT
<213> ORGANISM: Artificial Sequence
<220> FEATURE:
<223> OTHER INFORMATION: Ab240 VH CDR2 Kabat

<400> SEQUENCE: 34

Val Ile Trp Gly Asp Gly Ser Thr Asp Tyr Asn Ser Ala Leu Lys Ser
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Ab240 VH CDR3 Kabat

<400> SEQUENCE: 35

Asp Pro Tyr Gln Asn Tyr Phe Asp Tyr
1               5

<210> SEQ ID NO 36
<211> LENGTH: 6
<212> TYPE: PRT
<213> ORGANISM: Artificial Sequence
<220> FEATURE:
<223> OTHER INFORMATION: Ab235/Ab236 consensus VH CDR1 Kabat
<220> FEATURE:
<221> NAME/KEY: VARIANT
<222> LOCATION: 1
<223> OTHER INFORMATION: Xaa = Asn or Ser

<400> SEQUENCE: 36

Xaa Tyr Trp Ile Glu Trp
1               5
```

```
<210> SEQ ID NO 37
<211> LENGTH: 5
<212> TYPE: PRT
<213> ORGANISM: Artificial Sequence
<220> FEATURE:
<223> OTHER INFORMATION: Ab237/Ab239 consensus VH CDR1 Kabat
<220> FEATURE:
<221> NAME/KEY: VARIANT
<222> LOCATION: 2
<223> OTHER INFORMATION: Xaa = Ser or Cys

<400> SEQUENCE: 37

Asp Xaa Tyr Met Ala
1               5

<210> SEQ ID NO 38
<211> LENGTH: 18
<212> TYPE: PRT
<213> ORGANISM: Artificial Sequence
<220> FEATURE:
<223> OTHER INFORMATION: Ab235/Ab236 consensus VH CDR2 Kabat
<220> FEATURE:
<221> NAME/KEY: VARIANT
<222> LOCATION: 8
<223> OTHER INFORMATION: Xaa = Tyr or Phe
<220> FEATURE:
<221> NAME/KEY: VARIANT
<222> LOCATION: 12
<223> OTHER INFORMATION: Xaa = Asn or Ser

<400> SEQUENCE: 38

Glu Ile Leu Pro Gly Ser Asp Xaa Thr Lys Tyr Xaa Glu Lys Phe Lys
1               5                   10                  15

Gly Lys

<210> SEQ ID NO 39
<211> LENGTH: 18
<212> TYPE: PRT
<213> ORGANISM: Artificial Sequence
<220> FEATURE:
<223> OTHER INFORMATION: Ab237/Ab239 consensus VH CDR2 Kabat
<220> FEATURE:
<221> NAME/KEY: VARIANT
<222> LOCATION: 18
<223> OTHER INFORMATION: Xaa = Arg or Absent

<400> SEQUENCE: 39

Ser Ile Ser Ser Asp Gly Gly Thr Tyr Tyr Arg Asp Ser Val Lys
1               5                   10                  15

Gly Xaa

<210> SEQ ID NO 40
<211> LENGTH: 8
<212> TYPE: PRT
<213> ORGANISM: Artificial Sequence
<220> FEATURE:
<223> OTHER INFORMATION: Ab235/Ab236 consensus VH CDR3 Kabat
<220> FEATURE:
<221> NAME/KEY: VARIANT
<222> LOCATION: 4
<223> OTHER INFORMATION: Xaa = Ile or Val

<400> SEQUENCE: 40

Pro Ser Thr Xaa Pro Pro Asp Cys
1               5

<210> SEQ ID NO 41
```

```
<211> LENGTH: 10
<212> TYPE: PRT
<213> ORGANISM: Artificial Sequence
<220> FEATURE:
<223> OTHER INFORMATION: Ab235/Ab236 consensus VL CDR1 Kabat
<220> FEATURE:
<221> NAME/KEY: VARIANT
<222> LOCATION: 7
<223> OTHER INFORMATION: Xaa = Asn or Ser

<400> SEQUENCE: 41

Ser Ala Ser Ser Ser Val Xaa Tyr Met Phe
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Ab237/Ab239 consensus VL CDR1 Kabat
<220> FEATURE:
<221> NAME/KEY: VARIANT
<222> LOCATION: 4
<223> OTHER INFORMATION: Xaa = Ala or Glu
<220> FEATURE:
<221> NAME/KEY: VARIANT
<222> LOCATION: 7
<223> OTHER INFORMATION: Xaa = Tyr or His
<220> FEATURE:
<221> NAME/KEY: VARIANT
<222> LOCATION: 9
<223> OTHER INFORMATION: Xaa = Asp or Asn
<220> FEATURE:
<221> NAME/KEY: VARIANT
<222> LOCATION: 10
<223> OTHER INFORMATION: Xaa = Leu or Absent
<220> FEATURE:
<221> NAME/KEY: VARIANT
<222> LOCATION: 11
<223> OTHER INFORMATION: Xaa = Aka ir Absebt

<400> SEQUENCE: 42

Leu Ala Ser Xaa Asp Ile Xaa Ser Xaa Xaa Xaa
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Ab235/Ab236 consensus VL CDR2 Kabat
<220> FEATURE:
<221> NAME/KEY: VARIANT
<222> LOCATION: 3
<223> OTHER INFORMATION: Xaa = Phe or Ser
<220> FEATURE:
<221> NAME/KEY: VARIANT
<222> LOCATION: 4
<223> OTHER INFORMATION: Xaa = Asn or Asp

<400> SEQUENCE: 43

Asp Thr Xaa Xaa Leu Ala Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Ab235/Ab236 consensus VL CDR3 Kabat
<220> FEATURE:
<221> NAME/KEY: VARIANT
<222> LOCATION: 5
```

```
<223> OTHER INFORMATION: Xaa = Ile or Asn

<400> SEQUENCE: 44

Gln Gln Trp Ser Xaa Tyr Pro Tyr Thr
1               5

<210> SEQ ID NO 45
<211> LENGTH: 15
<212> TYPE: PRT
<213> ORGANISM: Artificial Sequence
<220> FEATURE:
<223> OTHER INFORMATION: Ab237/Ab239 consensus VH CDR3 Kabat
<220> FEATURE:
<221> NAME/KEY: VARIANT
<222> LOCATION: 2
<223> OTHER INFORMATION: Xaa = Gly or Arg
<220> FEATURE:
<221> NAME/KEY: VARIANT
<222> LOCATION: 3
<223> OTHER INFORMATION: Xaa = Ile or Tyr
<220> FEATURE:
<221> NAME/KEY: VARIANT
<222> LOCATION: 5, 7
<223> OTHER INFORMATION: Xaa = Thr or Asp
<220> FEATURE:
<221> NAME/KEY: VARIANT
<222> LOCATION: 6
<223> OTHER INFORMATION: Xaa = Thr or Gly
<220> FEATURE:
<221> NAME/KEY: VARIANT
<222> LOCATION: 10
<223> OTHER INFORMATION: Xaa = Pro or Gly
<220> FEATURE:
<221> NAME/KEY: VARIANT
<222> LOCATION: 11
<223> OTHER INFORMATION: Xaa = Cys or Trp
<220> FEATURE:
<221> NAME/KEY: VARIANT
<222> LOCATION: 12
<223> OTHER INFORMATION: Xaa = Tyr or Absent
<220> FEATURE:
<221> NAME/KEY: VARIANT
<222> LOCATION: 14
<223> OTHER INFORMATION: Xaa = Asn or Asp
<220> FEATURE:
<221> NAME/KEY: VARIANT
<222> LOCATION: 15
<223> OTHER INFORMATION: Xaa = Tyr or Phe

<400> SEQUENCE: 45

Glu Xaa Xaa Tyr Xaa Xaa Xaa Tyr Tyr Xaa Xaa Xaa Phe Xaa Xaa
1               5                   10                  15

<210> SEQ ID NO 46
<211> LENGTH: 17
<212> TYPE: PRT
<213> ORGANISM: Artificial Sequence
<220> FEATURE:
<223> OTHER INFORMATION: Ab239 VH CDR2 Kabat

<400> SEQUENCE: 46

Ser Ile Ser Ser Asp Gly Gly Gly Thr Tyr Tyr Arg Asp Ser Val Lys
1               5                   10                  15
Gly

<210> SEQ ID NO 47
<211> LENGTH: 105
<212> TYPE: PRT
<213> ORGANISM: Artificial Sequence
<220> FEATURE:
<223> OTHER INFORMATION: Ab237/Ab241-Ab255 consensus VL
<220> FEATURE:
```

```
<221> NAME/KEY: VARIANT
<222> LOCATION: 9
<223> OTHER INFORMATION: Xaa = Ser or Gly
<220> FEATURE:
<221> NAME/KEY: VARIANT
<222> LOCATION: 15
<223> OTHER INFORMATION: Xaa = Val or Leu
<220> FEATURE:
<221> NAME/KEY: VARIANT
<222> LOCATION: 17
<223> OTHER INFORMATION: Xaa = Asp or Glu
<220> FEATURE:
<221> NAME/KEY: VARIANT
<222> LOCATION: 18
<223> OTHER INFORMATION: Xaa = Arp or Thr
<220> FEATURE:
<221> NAME/KEY: VARIANT
<222> LOCATION: 21
<223> OTHER INFORMATION: Xaa = Thr or Glu
<220> FEATURE:
<221> NAME/KEY: VARIANT
<222> LOCATION: 41
<223> OTHER INFORMATION: Xaa = Lys or Asn
<220> FEATURE:
<221> NAME/KEY: VARIANT
<222> LOCATION: 42
<223> OTHER INFORMATION: Xaa = Ala or Ser
<220> FEATURE:
<221> NAME/KEY: VARIANT
<222> LOCATION: 44
<223> OTHER INFORMATION: Xaa = Lys or Gln
<220> FEATURE:
<221> NAME/KEY: VARIANT
<222> LOCATION: 63, 65
<223> OTHER INFORMATION: Xaa = Phe or Ser
<220> FEATURE:
<221> NAME/KEY: VARIANT
<222> LOCATION: 68
<223> OTHER INFORMATION: Xaa = Asp or Gln
<220> FEATURE:
<221> NAME/KEY: VARIANT
<222> LOCATION: 69
<223> OTHER INFORMATION: Xaa = Phe or Tyr
<220> FEATURE:
<221> NAME/KEY: VARIANT
<222> LOCATION: 70
<223> OTHER INFORMATION: Xaa = Thr or Ser
<220> FEATURE:
<221> NAME/KEY: VARIANT
<222> LOCATION: 72
<223> OTHER INFORMATION: Xaa = Thr or Lys
<220> FEATURE:
<221> NAME/KEY: VARIANT
<222> LOCATION: 74
<223> OTHER INFORMATION: Xaa = Ser or Asn
<220> FEATURE:
<221> NAME/KEY: VARIANT
<222> LOCATION: 78
<223> OTHER INFORMATION: Xaa = Pro or Ser
<220> FEATURE:
<221> NAME/KEY: VARIANT
<222> LOCATION: 82
<223> OTHER INFORMATION: Xaa = Ala or Ser

<400> SEQUENCE: 47

Asp Ile Gln Met Thr Gln Ser Pro Xaa Ser Leu Ser Ala Ser Xaa Gly
1               5                   10                  15

Xaa Xaa Thr Ile Xaa Cys Leu Ala Ser Ala Asp Ile His Ser Asn Leu
            20                  25                  30

Ala Trp Tyr Gln Gln Lys Pro Gly Xaa Xaa Pro Xaa Leu Leu Ile Tyr
        35                  40                  45

Gly Asn Asn Leu Asn Asp Gly Val Pro Ser Arg Phe Ser Gly Xaa Gly
    50                  55                  60

Xaa Gly Thr Xaa Xaa Xaa Leu Xaa Ile Xaa Ser Leu Gln Xaa Glu Asp
```

```
                65                  70                  75                  80
Val Xaa Ile Tyr Phe Cys Gln Gln Ser Tyr Asp Ser Pro Pro Thr Phe
                    85                  90                  95

Gly Gln Gly Thr Lys Leu Glu Ile Lys
                100                 105

<210> SEQ ID NO 48
<211> LENGTH: 107
<212> TYPE: PRT
<213> ORGANISM: Artificial Sequence
<220> FEATURE:
<223> OTHER INFORMATION: Ab235/Ab236 consensus VL
<220> FEATURE:
<221> NAME/KEY: VARIANT
<222> LOCATION: 13
<223> OTHER INFORMATION: Xaa = Thr or Ala
<220> FEATURE:
<221> NAME/KEY: VARIANT
<222> LOCATION: 30
<223> OTHER INFORMATION: Xaa = Asn or Ser
<220> FEATURE:
<221> NAME/KEY: VARIANT
<222> LOCATION: 39
<223> OTHER INFORMATION: Xaa = Ala or Pro
<220> FEATURE:
<221> NAME/KEY: VARIANT
<222> LOCATION: 51
<223> OTHER INFORMATION: Xaa = Phe or Ser
<220> FEATURE:
<221> NAME/KEY: VARIANT
<222> LOCATION: 52
<223> OTHER INFORMATION: Xaa = Asn or Asp
<220> FEATURE:
<221> NAME/KEY: VARIANT
<222> LOCATION: 92
<223> OTHER INFORMATION: Xaa = Ile or Asn

<400> SEQUENCE: 48

Gln Ile Val Leu Thr Gln Ser Pro Ala Ile Met Ser Xaa Ser Pro Gly
1               5                   10                  15

Glu Lys Val Thr Met Thr Cys Ser Ala Ser Ser Ser Val Xaa Tyr Met
                20                  25                  30

Phe Trp Tyr Gln Gln Lys Xaa Gly Ser Ser Pro Arg Leu Leu Ile Tyr
            35                  40                  45

Asp Thr Xaa Xaa Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Xaa Ile Tyr Pro Tyr
                85                  90                  95

Thr Phe Gly Gly Gly Thr Lys Leu Glu Ile Lys
                100                 105

<210> SEQ ID NO 49
<211> LENGTH: 124
<212> TYPE: PRT
<213> ORGANISM: Artificial Sequence
<220> FEATURE:
<223> OTHER INFORMATION: Ab237/Ab241-Ab255 consensus VH
<220> FEATURE:
<221> NAME/KEY: VARIANT
<222> LOCATION: 16
<223> OTHER INFORMATION: Xaa = Gly or Arg
<220> FEATURE:
<221> NAME/KEY: VARIANT
<222> LOCATION: 42
<223> OTHER INFORMATION: Xaa = Gly or Thr
<220> FEATURE:
```

```
<221> NAME/KEY: VARIANT
<222> LOCATION: 69
<223> OTHER INFORMATION: Xaa = Thr or Ser
<220> FEATURE:
<221> NAME/KEY: VARIANT
<222> LOCATION: 77
<223> OTHER INFORMATION: Xaa = Ser or Asn
<220> FEATURE:
<221> NAME/KEY: VARIANT
<222> LOCATION: 88
<223> OTHER INFORMATION: Xaa = Thr or Ser
<220> FEATURE:
<221> NAME/KEY: VARIANT
<222> LOCATION: 116
<223> OTHER INFORMATION: Xaa = Gln or His
<220> FEATURE:
<221> NAME/KEY: VARIANT
<222> LOCATION: 118
<223> OTHER INFORMATION: Xaa = Val or Thr
<220> FEATURE:
<221> NAME/KEY: VARIANT
<222> LOCATION: 124
<223> OTHER INFORMATION: Xaa = Ser or Ala

<400> SEQUENCE: 49

Glu Val Gln Leu Val Glu Ser Gly Gly Gly Leu Val Gln Pro Gly Xaa
1               5                   10                  15

Ser Leu Lys Leu Ser Cys Ala Ala Ser Gly Phe Thr Phe Ser Asp Ser
            20                  25                  30

Tyr Met Ala Trp Val Arg Gln Ala Pro Xaa Lys Gly Leu Glu Trp Val
        35                  40                  45

Ala Ser Ile Ser Ser Asp Gly Gly Thr Tyr Tyr Arg Asp Ser Val
    50                  55                  60

Lys Gly Arg Phe Xaa Ile Ser Arg Asp Asn Ala Lys Xaa Ser Leu Tyr
65                  70                  75                  80

Leu Gln Met Asp Ser Leu Arg Xaa Glu Asp Thr Ala Thr Tyr Tyr Cys
                85                  90                  95

Thr Thr Glu Gly Ile Tyr Thr Thr Asp Tyr Tyr Pro Tyr Cys Phe Asn
            100                 105                 110

Tyr Trp Gly Xaa Gly Xaa Met Val Thr Val Ser Xaa
        115                 120

<210> SEQ ID NO 50
<211> LENGTH: 117
<212> TYPE: PRT
<213> ORGANISM: Artificial Sequence
<220> FEATURE:
<223> OTHER INFORMATION: Ab235/Ab236 consensus VH
<220> FEATURE:
<221> NAME/KEY: VARIANT
<222> LOCATION: 2
<223> OTHER INFORMATION: Xaa = Val or Ala
<220> FEATURE:
<221> NAME/KEY: VARIANT
<222> LOCATION: 28
<223> OTHER INFORMATION: Xaa = Ile or Thr
<220> FEATURE:
<221> NAME/KEY: VARIANT
<222> LOCATION: 31
<223> OTHER INFORMATION: Xaa = Asn or Ser
<220> FEATURE:
<221> NAME/KEY: VARIANT
<222> LOCATION: 57
<223> OTHER INFORMATION: Xaa = Tyr or Phe
<220> FEATURE:
<221> NAME/KEY: VARIANT
<222> LOCATION: 58
<223> OTHER INFORMATION: Xaa = Thr or Ile
<220> FEATURE:
<221> NAME/KEY: VARIANT
```

```
<222> LOCATION: 61
<223> OTHER INFORMATION: Xaa = Asn or Ser
<220> FEATURE:
<221> NAME/KEY: VARIANT
<222> LOCATION: 85
<223> OTHER INFORMATION: Xaa = Ser or Asn
<220> FEATURE:
<221> NAME/KEY: VARIANT
<222> LOCATION: 102
<223> OTHER INFORMATION: Xaa = Ile or Val

<400> SEQUENCE: 50

Gln Xaa Gln Leu Gln Gln Ser Gly Ala Glu Leu Met Lys Pro Gly Ala
1               5                   10                  15

Ser Val Lys Ile Ser Cys Lys Ala Thr Gly Tyr Xaa Phe Ser Xaa Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Xaa Xaa Lys Tyr Xaa Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Xaa Leu Thr Ser Glu Asp Ser Ala Val Tyr Tyr Cys
                85                  90                  95

Ala Arg Pro Ser Thr Xaa Pro Pro Asp Cys Trp Gly Gln Gly Thr Thr
            100                 105                 110

Leu Thr Val Ser Ala
        115

<210> SEQ ID NO 51
<211> LENGTH: 11
<212> TYPE: PRT
<213> ORGANISM: Artificial Sequence
<220> FEATURE:
<223> OTHER INFORMATION: Ab237/Ab241-Ab255 consensus VL CDR1
<220> FEATURE:
<221> NAME/KEY: VARIANT
<222> LOCATION: 9
<223> OTHER INFORMATION: Xaa = Asn or Absent
<220> FEATURE:
<221> NAME/KEY: VARIANT
<222> LOCATION: 10
<223> OTHER INFORMATION: Xaa = Leu or Absent
<220> FEATURE:
<221> NAME/KEY: VARIANT
<222> LOCATION: 11
<223> OTHER INFORMATION: Xaa = Ala or Absent

<400> SEQUENCE: 51

Leu Ala Ser Ala Asp Ile His Ser Xaa Xaa Xaa
1               5                   10

<210> SEQ ID NO 52
<211> LENGTH: 108
<212> TYPE: PRT
<213> ORGANISM: Artificial Sequence
<220> FEATURE:
<223> OTHER INFORMATION: VL variant 1

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Leu Ala Ser Ala Asp Ile His Ser Asn
            20                  25                  30

Leu Ala Trp Tyr Gln Gln Lys Pro Gly Lys Ala Pro Gln Leu Leu Ile
```

35                  40                  45
Tyr Tyr Gly Asn Asn Leu Asn Asp Gly Val Pro Ser Arg Phe Ser Gly
        50                  55                  60
Ser Gly Ser Gly Thr Asp Tyr Thr Leu Lys Ile Asn Ser Leu Gln Ser
 65                  70                  75                  80
Glu Asp Val Ala Ile Tyr Phe Cys Gln Gln Ser Tyr Asp Ser Pro Pro
                85                  90                  95
Thr Phe Gly Gln Gly Thr Lys Leu Glu Ile Lys Arg
            100                 105

<210> SEQ ID NO 53
<211> LENGTH: 108
<212> TYPE: PRT
<213> ORGANISM: Artificial Sequence
<220> FEATURE:
<223> OTHER INFORMATION: VL variant 2

<400> SEQUENCE: 53

Asp Ile Gln Met Thr Gln Ser Pro Ser Ser Leu Ser Ala Ser Val Gly
 1               5                  10                  15
Asp Arg Val Thr Ile Thr Cys Leu Ala Ser Ala Asp Ile His Ser Asn
                20                  25                  30
Leu Ala Trp Tyr Gln Gln Lys Pro Gly Lys Ala Pro Lys Leu Leu Ile
            35                  40                  45
Tyr Tyr Gly Asn Asn Leu Asn Asp Gly Val Pro Ser Arg Phe Ser Gly
        50                  55                  60
Phe Gly Phe Gly Thr Asp Tyr Thr Leu Thr Ile Ser Ser Leu Gln Ser
 65                  70                  75                  80
Glu Asp Val Ala Ile Tyr Phe Cys Gln Gln Ser Tyr Asp Ser Pro Pro
                85                  90                  95
Thr Phe Gly Gln Gly Thr Lys Leu Glu Ile Lys Arg
            100                 105

<210> SEQ ID NO 54
<211> LENGTH: 108
<212> TYPE: PRT
<213> ORGANISM: Artificial Sequence
<220> FEATURE:
<223> OTHER INFORMATION: VL variant 3

<400> SEQUENCE: 54

Asp Ile Gln Met Thr Gln Ser Pro Ser Ser Leu Ser Ala Ser Val Gly
 1               5                  10                  15
Asp Arg Val Thr Ile Thr Cys Leu Ala Ser Ala Asp Ile His Ser Asn
                20                  25                  30
Leu Ala Trp Tyr Gln Gln Lys Pro Gly Lys Ala Pro Lys Leu Leu Ile
            35                  40                  45
Tyr Tyr Gly Asn Asn Leu Asn Asp Gly Val Pro Ser Arg Phe Ser Gly
        50                  55                  60
Ser Gly Ser Gly Thr Asp Tyr Thr Leu Thr Ile Ser Ser Leu Gln Pro
 65                  70                  75                  80
Glu Asp Val Ala Ile Tyr Phe Cys Gln Gln Ser Tyr Asp Ser Pro Pro
                85                  90                  95
Thr Phe Gly Gln Gly Thr Lys Leu Glu Ile Lys Arg
            100                 105

<210> SEQ ID NO 55
<211> LENGTH: 108

```
<212> TYPE: PRT
<213> ORGANISM: Artificial Sequence
<220> FEATURE:
<223> OTHER INFORMATION: VL variant 4

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Leu Ala Ser Ala Asp Ile His Ser Asn
            20                  25                  30

Leu Ala Trp Tyr Gln Gln Lys Pro Gly Lys Ala Pro Lys Leu Leu Ile
        35                  40                  45

Tyr Tyr Gly Asn Asn Leu Asn Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Ile Tyr Phe Cys Gln Gln Ser Tyr Asp Ser Pro Pro
                85                  90                  95

Thr Phe Gly Gln Gly Thr Lys Leu Glu Ile Lys Arg
            100                 105

<210> SEQ ID NO 56
<211> LENGTH: 108
<212> TYPE: PRT
<213> ORGANISM: Artificial Sequence
<220> FEATURE:
<223> OTHER INFORMATION: VL variant 5

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Leu Ala Ser Ala Asp Ile His Ser Asn
            20                  25                  30

Leu Ala Trp Tyr Gln Gln Lys Pro Gly Lys Ala Pro Lys Leu Leu Ile
        35                  40                  45

Tyr Tyr Gly Asn Asn Leu Asn Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Ser Tyr Asp Ser Pro Pro
                85                  90                  95

Thr Phe Gly Gln Gly Thr Lys Leu Glu Ile Lys Arg
            100                 105

<210> SEQ ID NO 57
<211> LENGTH: 107
<212> TYPE: PRT
<213> ORGANISM: Artificial Sequence
<220> FEATURE:
<223> OTHER INFORMATION: Ab235 VL

<400> SEQUENCE: 57

Gln Ile Val Leu Thr Gln Ser Pro Ala Ile Met Ser Thr Ser Pro Gly
1               5                   10                  15

Glu Lys Val Thr Met Thr Cys Ser Ala Ser Ser Ser Val Asn Tyr Met
            20                  25                  30

Phe Trp Tyr Gln Gln Lys Ala Gly Ser Ser Pro Arg Leu Leu Ile Tyr
        35                  40                  45

Asp Thr Phe Asn Leu Ala Ser Gly Val Pro Val Arg Phe Ser Gly Ser
```

```
                    50                  55                  60
Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ile Tyr Pro Tyr Thr
                 85                  90                  95

Phe Gly Gly Gly Thr Lys Leu Glu Ile Lys Arg
                100                 105

<210> SEQ ID NO 58
<211> LENGTH: 107
<212> TYPE: PRT
<213> ORGANISM: Artificial Sequence
<220> FEATURE:
<223> OTHER INFORMATION: Ab236 VL

<400> SEQUENCE: 58

Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Val Ser Tyr Met
                 20                  25                  30

Phe Trp Tyr Gln Gln Lys Pro Gly Ser Ser Pro Arg Leu Leu Ile Tyr
             35                  40                  45

Asp Thr Ser Asp Leu Ala Ser Gly Val Pro Val Arg Phe Ser Gly Ser
         50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Asn Tyr Pro Tyr Thr
                 85                  90                  95

Phe Gly Gly Gly Thr Lys Leu Glu Ile Lys Arg
                100                 105

<210> SEQ ID NO 59
<211> LENGTH: 108
<212> TYPE: PRT
<213> ORGANISM: Artificial Sequence
<220> FEATURE:
<223> OTHER INFORMATION: Ab237 VL

<400> SEQUENCE: 59

Asp Ile Gln Met Thr Gln Ser Pro Gly Ser Leu Ser Ala Ser Leu Gly
  1               5                  10                  15

Glu Thr Val Thr Ile Glu Cys Leu Ala Ser Ala Asp Ile His Ser Asn
                 20                  25                  30

Leu Ala Trp Tyr Gln Gln Lys Pro Gly Asn Ser Pro Gln Leu Leu Ile
             35                  40                  45

Tyr Tyr Gly Asn Asn Leu Asn Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Val Ser Ile Tyr Phe Cys Gln Gln Ser Tyr Asp Ser Pro Pro
                 85                  90                  95

Thr Phe Gly Ala Gly Thr Lys Leu Glu Ile Lys Arg
                100                 105

<210> SEQ ID NO 60
<211> LENGTH: 108
<212> TYPE: PRT
<213> ORGANISM: Artificial Sequence
<220> FEATURE:
```

<223> OTHER INFORMATION: Ab238 VL

<400> SEQUENCE: 60

Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Tyr Ser Asp
            20                  25                  30

Leu Ala Trp Tyr Gln Gln Lys Pro Gly Lys Ser Pro Gln Leu Leu Ile
        35                  40                  45

Tyr Asn Ala Asn Thr Leu Gln Asn Gly Val Pro Ser Val Phe Ser Gly
50                  55                  60

Ser Gly Ser Gly Thr Gln Tyr Ser Leu Lys Ile Asn Asn Leu His Ser
65                  70                  75                  80

Glu Asp Val Ala Thr Tyr Phe Cys Gln Gln Tyr Asn Asn Tyr Pro Pro
                85                  90                  95

Thr Phe Gly Gly Gly Thr Lys Leu Glu Ile Lys Arg
            100                 105

<210> SEQ ID NO 61
<211> LENGTH: 113
<212> TYPE: PRT
<213> ORGANISM: Artificial Sequence
<220> FEATURE:
<223> OTHER INFORMATION: Ab239 VL

<400> SEQUENCE: 61

Gly Gln Phe Thr Leu Thr Gln Pro Lys Ser Val Ser Gly Ser Leu Arg
1               5                   10                  15

Ser Thr Ile Thr Ile Pro Cys Val Arg Ser Ser Gly Asp Ile Gly Asp
            20                  25                  30

Arg Tyr Val Ser Trp Tyr Gln Gln Arg Leu Gly Arg Pro Pro Leu Asn
        35                  40                  45

Val Ile Tyr Ala Ala Asp Gln Arg Pro Ser Glu Val Ser Asp Arg Phe
50                  55                  60

Ser Gly Ser Ile Asp Ser Ser Asn Ser Ala Ser Leu Thr Ile Thr
65                  70                  75                  80

Asp Leu Gln Met Asp Asp Glu Ala Asp Tyr Phe Cys Gln Ser Tyr Asp
                85                  90                  95

Ser Asn Ile Asp Ile Val Phe Gly Gly Gly Thr Lys Leu Glu Ile Lys
            100                 105                 110

Arg

<210> SEQ ID NO 62
<211> LENGTH: 117
<212> TYPE: PRT
<213> ORGANISM: Artificial Sequence
<220> FEATURE:
<223> OTHER INFORMATION: Ab240 VL

<400> SEQUENCE: 62

Asp Ile Gln Met Thr Gln Thr Pro Phe Tyr Met Pro Ala Ser Leu Gly
1               5                   10                  15

Glu Arg Val Thr Ile Ser Cys Arg Ala Ser Gln Gly Ile Ser Lys Tyr
            20                  25                  30

Leu Asn Trp Tyr Gln Gln Lys Pro Asp Gly Thr Ile Lys Thr Leu Ile
        35                  40                  45

Tyr Tyr Thr Ser Asn Leu Gln Ser Gly Val Pro Ser Ser Ala Leu Lys
50                  55                  60

```
Ser Arg Leu Thr Ile Ser Arg Asp Thr Ser Arg Ser Gln Val Phe Leu
 65                  70                  75                  80

Lys Met Asn Ser Leu Gln Thr Asp Asp Thr Ala Ile Tyr Phe Cys Ala
                 85                  90                  95

Arg Asp Pro Tyr Gln Asn Tyr Phe Asp Tyr Trp Gly Gln Gly Val Lys
            100                 105                 110

Val Thr Val Ser Ser
            115

<210> SEQ ID NO 63
<211> LENGTH: 124
<212> TYPE: PRT
<213> ORGANISM: Artificial Sequence
<220> FEATURE:
<223> OTHER INFORMATION: VH variant 1

<400> SEQUENCE: 63

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asp Ser
                20                  25                  30

Tyr Met Ala Trp Val Arg Gln Ala Pro Gly Lys Gly Leu Glu Trp Val
            35                  40                  45

Ala Ser Ile Ser Ser Asp Gly Gly Thr Tyr Tyr Arg Asp Ser Val
        50                  55                  60

Lys Gly Arg Phe Thr Ile Ser Arg Asp Asn Ala Lys Ser Ser Leu Tyr
 65                  70                  75                  80

Leu Gln Met Asp Ser Leu Arg Thr Glu Asp Thr Ala Thr Tyr Tyr Cys
                 85                  90                  95

Thr Thr Glu Gly Ile Tyr Thr Thr Asp Tyr Tyr Pro Tyr Cys Phe Asn
            100                 105                 110

Tyr Trp Gly Gln Gly Val Met Val Thr Val Ser Ser
            115                 120

<210> SEQ ID NO 64
<211> LENGTH: 124
<212> TYPE: PRT
<213> ORGANISM: Artificial Sequence
<220> FEATURE:
<223> OTHER INFORMATION: VH variant 2

<400> SEQUENCE: 64

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asp Ser
                20                  25                  30

Tyr Met Ala Trp Val Arg Gln Ala Pro Gly Lys Gly Leu Glu Trp Val
            35                  40                  45

Ala Ser Ile Ser Ser Asp Gly Gly Thr Tyr Tyr Arg Asp Ser Val
        50                  55                  60

Lys Gly Arg Phe Thr Ile Ser Arg Asp Asn Ala Lys Ser Ser Leu Tyr
 65                  70                  75                  80

Leu Gln Met Asn Ser Leu Arg Thr Glu Asp Thr Ala Thr Tyr Tyr Cys
                 85                  90                  95

Thr Thr Glu Gly Ile Tyr Thr Thr Asp Tyr Tyr Pro Tyr Cys Phe Asn
            100                 105                 110

Tyr Trp Gly Gln Gly Val Met Val Thr Val Ser Ser
```

115                 120

<210> SEQ ID NO 65
<211> LENGTH: 124
<212> TYPE: PRT
<213> ORGANISM: Artificial Sequence
<220> FEATURE:
<223> OTHER INFORMATION: VH variant 3

<400> SEQUENCE: 65

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ser
            20                  25                  30

Tyr Met Ala Trp Val Arg Gln Ala Pro Gly Lys Gly Leu Glu Trp Val
        35                  40                  45

Ala Ser Ile Ser Ser Asp Gly Gly Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Thr Tyr Tyr Cys
                85                  90                  95

Thr Thr Glu Gly Ile Tyr Thr Thr Asp Tyr Tyr Pro Tyr Cys Phe Asn
            100                 105                 110

Tyr Trp Gly Gln Gly Thr Met Val Thr Val Ser Ser
        115                 120

<210> SEQ ID NO 66
<211> LENGTH: 117
<212> TYPE: PRT
<213> ORGANISM: Artificial Sequence
<220> FEATURE:
<223> OTHER INFORMATION: Ab235 VH

<400> SEQUENCE: 66

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Tyr Thr Lys Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Pro Ser Thr Ile Pro Pro Asp Cys Trp Gly Gln Gly Thr Thr
            100                 105                 110

Leu Thr Val Ser Ala
        115

<210> SEQ ID NO 67
<211> LENGTH: 117
<212> TYPE: PRT
<213> ORGANISM: Artificial Sequence
<220> FEATURE:
<223> OTHER INFORMATION: Ab236 VH

<400> SEQUENCE: 67

```
Gln Ala Gln Leu Gln Gln Ser Gly Ala Glu Leu Met Lys Pro Gly Ala
1               5                   10                  15

Ser Val Lys Ile Ser Cys Lys Ala Thr Gly Tyr Ile Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Phe Ile Lys Tyr Ser Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Asn Leu Thr Ser Glu Asp Ser Ala Val Tyr Tyr Cys
                85                  90                  95

Ala Arg Pro Ser Thr Val Pro Pro Asp Cys Trp Gly Gln Gly Thr Thr
            100                 105                 110

Leu Thr Val Ser Ala
        115
```

<210> SEQ ID NO 68
<211> LENGTH: 124
<212> TYPE: PRT
<213> ORGANISM: Artificial Sequence
<220> FEATURE:
<223> OTHER INFORMATION: Ab237 VH

<400> SEQUENCE: 68

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Ser
            20                  25                  30

Tyr Met Ala Trp Val Arg Gln Ala Pro Thr Lys Gly Leu Glu Trp Val
        35                  40                  45

Ala Ser Ile Ser Ser Asp Gly Gly Thr Tyr Tyr Arg Asp Ser Val
    50                  55                  60

Lys Gly Arg Phe Ser Ile Ser Arg Asp Asn Ala Lys Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Gly Ile Tyr Thr Thr Asp Tyr Tyr Pro Tyr Cys Phe Asn
            100                 105                 110

Tyr Trp Gly His Gly Val Met Val Thr Val Ser Ala
        115                 120
```

<210> SEQ ID NO 69
<211> LENGTH: 119
<212> TYPE: PRT
<213> ORGANISM: Artificial Sequence
<220> FEATURE:
<223> OTHER INFORMATION: Ab238 VH

<400> SEQUENCE: 69

```
Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Tyr
            20                  25                  30

Gly Met Gly Val Ala Trp Ile Arg Gln Pro Ser Gly Lys Asp Leu Glu
        35                  40                  45

Trp Leu Ala Asn Ile Trp Trp Asp Asp Val Asn Tyr Ser Asn Pro Ser
```

```
                 50                   55                 60
Leu Lys Asn Arg Leu Thr Ile Ser Lys Asp Thr Ser Asn Asn Gln Val
 65                  70                 75                  80

Phe Leu Gln Ile Thr Asn Val Asp Thr Ala Glu Thr Ala Thr Tyr Tyr
                     85                 90                 95

Cys Ala Arg Ile Gly Thr Ser His Ile Val Asp Ala Trp Gly Gln Gly
                    100                105                110

Ala Ser Val Thr Val Ser Ala
            115

<210> SEQ ID NO 70
<211> LENGTH: 125
<212> TYPE: PRT
<213> ORGANISM: Artificial Sequence
<220> FEATURE:
<223> OTHER INFORMATION: Ab239 VH

<400> SEQUENCE: 70

Glu Val Gln Leu Val Glu Ser Gly Gly Gly Leu Val Gln Pro Gly Arg
 1               5                  10                 15

Ser Leu Lys Leu Ser Cys Ala Ala Ser Gly Phe Ser Phe Thr Asp Cys
                20                 25                 30

Tyr Met Ala Trp Val Arg Gln Ala Pro Thr Lys Gly Leu Glu Trp Val
            35                  40                 45

Ala Ser Ile Ser Ser Asp Gly Gly Thr Tyr Tyr Arg Asp Ser Val
        50                  55                 60

Lys Gly Arg Phe Thr Ile Ser Arg Asp Asn Ala Arg Ser Ser Leu Tyr
 65                  70                 75                  80

Leu Glu Met Asp Ser Leu Arg Ser Glu Asp Thr Ala Thr Tyr Tyr Cys
                85                  90                 95

Thr Thr Glu Arg Tyr Tyr Asp Gly Thr Tyr Tyr Gly Tyr Trp Tyr Phe
                   100                105                110

Asp Phe Trp Gly Pro Gly Thr Met Val Thr Val Ser Ala
            115                 120                125

<210> SEQ ID NO 71
<211> LENGTH: 117
<212> TYPE: PRT
<213> ORGANISM: Artificial Sequence
<220> FEATURE:
<223> OTHER INFORMATION: Ab240 VH

<400> SEQUENCE: 71

Gln Val Gln Leu Lys Glu Ser Gly Pro Gly Leu Val Gln Pro Ser Gln
 1               5                  10                 15

Thr Leu Ser Leu Thr Cys Ser Val Ser Gly Leu Ser Leu Thr Thr Asn
                20                 25                 30

Ser Val His Trp Ile Arg Gln Pro Pro Gly Arg Gly Leu Glu Trp Met
            35                  40                 45

Gly Val Ile Trp Gly Asp Gly Ser Thr Asp Tyr Asn Ser Ala Leu Lys
        50                  55                 60

Ser Arg Leu Thr Ile Ser Arg Asp Thr Ser Arg Ser Gln Val Phe Leu
 65                  70                 75                  80

Lys Met Asn Ser Leu Gln Thr Asp Asp Thr Ala Ile Tyr Phe Cys Ala
                85                  90                 95

Arg Asp Pro Tyr Gln Asn Tyr Phe Asp Tyr Trp Gly Gln Gly Val Lys
                   100                105                110
```

```
Val Thr Val Ser Ser
        115

<210> SEQ ID NO 72
<211> LENGTH: 11
<212> TYPE: PRT
<213> ORGANISM: Artificial Sequence
<220> FEATURE:
<223> OTHER INFORMATION: Ab241-255 VL CDR1 Kabat

<400> SEQUENCE: 72

Leu Ala Ser Ala Asp Ile His Ser Asn Leu Ala
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Ab241-255 VH CDR2 Kabat

<400> SEQUENCE: 73

Ser Ile Ser Ser Asp Gly Gly Gly Thr Tyr Tyr Arg Asp Ser Val Lys
1               5                   10                  15

Gly

<210> SEQ ID NO 74
<211> LENGTH: 30
<212> TYPE: PRT
<213> ORGANISM: Artificial Sequence
<220> FEATURE:
<223> OTHER INFORMATION: VH1, VH2, VH3 HFW1 Kabat

<400> SEQUENCE: 74

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Ab235 HFW1 Kabat

<400> SEQUENCE: 75

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: Ab236 HFW1 Kabat

<400> SEQUENCE: 76

Gln Ala Gln Leu Gln Gln Ser Gly Ala Glu Leu Met Lys Pro Gly Ala
1               5                   10                  15

Ser Val Lys Ile Ser Cys Lys Ala Thr Gly Tyr Ile Phe Ser
            20                  25                  30
```

<210> SEQ ID NO 77
<211> LENGTH: 30
<212> TYPE: PRT
<213> ORGANISM: Artificial Sequence
<220> FEATURE:
<223> OTHER INFORMATION: Ab237 HFW1 Kabat

<400> SEQUENCE: 77

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Ab238 HFW1 Kabat

<400> SEQUENCE: 78

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Ab239 HFW1 Kabat Kabat

<400> SEQUENCE: 79

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ser Phe Thr
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Ab240 HFW1 Kabat

<400> SEQUENCE: 80

Gln Val Gln Leu Lys Glu Ser Gly Pro Gly Leu Val Gln Pro Ser Gln
1               5                   10                  15

Thr Leu Ser Leu Thr Cys Ser Val Ser Gly Leu Ser Leu Thr
            20                  25                  30

<210> SEQ ID NO 81
<211> LENGTH: 14
<212> TYPE: PRT
<213> ORGANISM: Artificial Sequence
<220> FEATURE:
<223> OTHER INFORMATION: VH1, VH2, VH3, HFW2 Kabat

<400> SEQUENCE: 81

Trp Val Arg Gln Ala Pro Gly Lys Gly Leu Glu Trp Val Ala
1               5                   10

<210> SEQ ID NO 82

-continued

```
<211> LENGTH: 14
<212> TYPE: PRT
<213> ORGANISM: Artificial Sequence
<220> FEATURE:
<223> OTHER INFORMATION: Ab235, Ab236 HFW2 Kabat

<400> SEQUENCE: 82

Trp Val Lys Gln Arg Pro Gly His Gly Leu Glu Trp Ile Gly
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Ab237, Ab239 HFW2 Kabat

<400> SEQUENCE: 83

Trp Val Arg Gln Ala Pro Thr Lys Gly Leu Glu Trp Val Ala
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Ab238 HFW2 Kabat

<400> SEQUENCE: 84

Ala Trp Ile Arg Gln Pro Ser Gly Lys Asp Leu Glu Trp Leu Ala
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: Ab240 HFW2 Kabat

<400> SEQUENCE: 85

Trp Ile Arg Gln Pro Pro Gly Arg Gly Leu Glu Trp Met Gly
1               5                   10

<210> SEQ ID NO 86
<211> LENGTH: 32
<212> TYPE: PRT
<213> ORGANISM: Artificial Sequence
<220> FEATURE:
<223> OTHER INFORMATION: VH1 HFW3 Kabat

<400> SEQUENCE: 86

Arg Phe Thr Ile Ser Arg Asp Asn Ala Lys Ser Ser Leu Tyr Leu Gln
1               5                   10                  15

Met Asp Ser Leu Arg Thr Glu Asp Thr Ala Thr Tyr Tyr Cys Thr Thr
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: VH2 HFW3 Kabat

<400> SEQUENCE: 87

Arg Phe Thr Ile Ser Arg Asp Asn Ala Lys Ser Ser Leu Tyr Leu Gln
1               5                   10                  15
```

Met Asn Ser Leu Arg Thr Glu Asp Thr Ala Thr Tyr Tyr Cys Thr Thr
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: VH3 HFW3 Kabat

<400> SEQUENCE: 88

Arg Phe Thr Ile Ser Arg Asp Asn Ala Lys Asn Ser Leu Tyr Leu Gln
1               5                   10                  15

Met Asn Ser Leu Arg Thr Glu Asp Thr Ala Thr Tyr Tyr Cys Thr Thr
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Ab235 HFW3 Kabat

<400> SEQUENCE: 89

Ala Thr Phe Thr Ala Asp Thr Ser Ser Asn Thr Ala Tyr Met Gln Leu
1               5                   10                  15

Ser Ser Leu Thr Ser Glu Asp Ser Ala Val Tyr Tyr Cys Ala Arg
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Ab236 HFW3 Kabat

<400> SEQUENCE: 90

Ala Thr Phe Thr Ala Asp Thr Ser Ser Asn Thr Ala Tyr Met Gln Leu
1               5                   10                  15

Ser Asn Leu Thr Ser Glu Asp Ser Ala Val Tyr Tyr Cys Ala Arg
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Ab237 HFW3 Kabat

<400> SEQUENCE: 91

Phe Ser Ile Ser Arg Asp Asn Ala Lys Ser Ser Leu Tyr Leu Gln Met
1               5                   10                  15

Asp Ser Leu Arg Ser Glu Asp Thr Ala Thr Tyr Tyr Cys Thr Thr
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Ab238 HFW3 Kabat

<400> SEQUENCE: 92

Arg Leu Thr Ile Ser Lys Asp Thr Ser Asn Asn Gln Val Phe Leu Gln
1               5                   10                  15

-continued

```
Ile Thr Asn Val Asp Thr Ala Glu Thr Ala Thr Tyr Tyr Cys Ala Arg
            20                  25                  30
```

<210> SEQ ID NO 93
<211> LENGTH: 31
<212> TYPE: PRT
<213> ORGANISM: Artificial Sequence
<220> FEATURE:
<223> OTHER INFORMATION: Ab239 HFW3 Kabat

<400> SEQUENCE: 93

```
Phe Thr Ile Ser Arg Asp Asn Ala Arg Ser Ser Leu Tyr Leu Glu Met
1               5                   10                  15

Asp Ser Leu Arg Ser Glu Asp Thr Ala Thr Tyr Tyr Cys Thr Thr
            20                  25                  30
```

<210> SEQ ID NO 94
<211> LENGTH: 32
<212> TYPE: PRT
<213> ORGANISM: Artificial Sequence
<220> FEATURE:
<223> OTHER INFORMATION: AB240 HFW3 Kabat

<400> SEQUENCE: 94

```
Arg Leu Thr Ile Ser Arg Asp Thr Ser Arg Ser Gln Val Phe Leu Lys
1               5                   10                  15

Met Asn Ser Leu Gln Thr Asp Asp Thr Ala Ile Tyr Phe Cys Ala Arg
            20                  25                  30
```

<210> SEQ ID NO 95
<211> LENGTH: 11
<212> TYPE: PRT
<213> ORGANISM: Artificial Sequence
<220> FEATURE:
<223> OTHER INFORMATION: VH1, VH2 HFW4 Kabat

<400> SEQUENCE: 95

```
Trp Gly Gln Gly Val Met Val Thr Val Ser Ser
1               5                   10
```

<210> SEQ ID NO 96
<211> LENGTH: 11
<212> TYPE: PRT
<213> ORGANISM: Artificial Sequence
<220> FEATURE:
<223> OTHER INFORMATION: VH3, HFW4 Kabat

<400> SEQUENCE: 96

```
Trp Gly Gln Gly Thr Met Val Thr Val Ser Ser
1               5                   10
```

<210> SEQ ID NO 97
<211> LENGTH: 11
<212> TYPE: PRT
<213> ORGANISM: Artificial Sequence
<220> FEATURE:
<223> OTHER INFORMATION: Ab235, Ab236 HFW3 Kabat

<400> SEQUENCE: 97

```
Trp Gly Gln Gly Thr Thr Leu Thr Val Ser Ala
1               5                   10
```

<210> SEQ ID NO 98
<211> LENGTH: 11
<212> TYPE: PRT

```
<213> ORGANISM: Artificial Sequence
<220> FEATURE:
<223> OTHER INFORMATION: Ab237 HFW3 Kabat

<400> SEQUENCE: 98

Trp Gly His Gly Val Met Val Thr Val Ser Ala
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Ab238 HFW3 Kabat

<400> SEQUENCE: 99

Trp Gly Gln Gly Ala Ser Val Thr Val Ser Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Ab239 HFW3 Kabat

<400> SEQUENCE: 100

Trp Gly Pro Gly Thr Met Val Thr Val Ser Ala
1               5                   10

<210> SEQ ID NO 101
<211> LENGTH: 11
<212> TYPE: PRT
<213> ORGANISM: Artificial Sequence
<220> FEATURE:
<223> OTHER INFORMATION: AB240 HFW3 Kabat

<400> SEQUENCE: 101

Trp Gly Gln Gly Val Lys Val Thr Val Ser Ser
1               5                   10

<210> SEQ ID NO 102
<211> LENGTH: 23
<212> TYPE: PRT
<213> ORGANISM: Artificial Sequence
<220> FEATURE:
<223> OTHER INFORMATION: VL1, VL2, VL3, VL4, VL5 LFW1 Kabat

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 103
<211> LENGTH: 23
<212> TYPE: PRT
<213> ORGANISM: Artificial Sequence
<220> FEATURE:
<223> OTHER INFORMATION: Ab235 LFW1 Kabat

<400> SEQUENCE: 103

Gln Ile Val Leu Thr Gln Ser Pro Ala Ile Met Ser Thr Ser Pro Gly
1               5                   10                  15

Glu Lys Val Thr Met Thr Cys
            20
```

<210> SEQ ID NO 104
<211> LENGTH: 23
<212> TYPE: PRT
<213> ORGANISM: Artificial Sequence
<220> FEATURE:
<223> OTHER INFORMATION: Ab236 LFW1 Kabat

<400> SEQUENCE: 104

Gln Ile Val Leu Thr Gln Ser Pro Ala Ile Met Ser Ala Ser Pro Gly
1               5                   10                  15

Glu Lys Val Thr Met Thr Cys
            20

<210> SEQ ID NO 105
<211> LENGTH: 23
<212> TYPE: PRT
<213> ORGANISM: Artificial Sequence
<220> FEATURE:
<223> OTHER INFORMATION: Ab237 LFW1 Kabat

<400> SEQUENCE: 105

Asp Ile Gln Met Thr Gln Ser Pro Gly Ser Leu Ser Ala Ser Leu Gly
1               5                   10                  15

Glu Thr Val Thr Ile Glu Cys
            20

<210> SEQ ID NO 106
<211> LENGTH: 23
<212> TYPE: PRT
<213> ORGANISM: Artificial Sequence
<220> FEATURE:
<223> OTHER INFORMATION: Ab238 LFW1 Kabat

<400> SEQUENCE: 106

Asp Ile Arg Met Thr Gln Ser Pro Ala Ser Leu Ser Ala Ser Leu Gly
1               5                   10                  15

Glu Thr Val Asn Ile Glu Cys
            20

<210> SEQ ID NO 107
<211> LENGTH: 23
<212> TYPE: PRT
<213> ORGANISM: Artificial Sequence
<220> FEATURE:
<223> OTHER INFORMATION: Ab239 LFW1 Kabat

<400> SEQUENCE: 107

Gly Gln Phe Thr Leu Thr Gln Pro Lys Ser Val Ser Gly Ser Leu Arg
1               5                   10                  15

Ser Thr Ile Thr Ile Pro Cys
            20

<210> SEQ ID NO 108
<211> LENGTH: 23
<212> TYPE: PRT
<213> ORGANISM: Artificial Sequence
<220> FEATURE:
<223> OTHER INFORMATION: AB240 LFW1 Kabat

<400> SEQUENCE: 108

Asp Ile Gln Met Thr Gln Thr Pro Phe Tyr Met Pro Ala Ser Leu Gly
1               5                   10                  15

Glu Arg Val Thr Ile Ser Cys

-continued

```
<210> SEQ ID NO 109
<211> LENGTH: 15
<212> TYPE: PRT
<213> ORGANISM: Artificial Sequence
<220> FEATURE:
<223> OTHER INFORMATION: VL1 LFW2 Kabat

<400> SEQUENCE: 109

Trp Tyr Gln Gln Lys Pro Gly Lys Ala Pro Gln Leu Leu Ile Tyr
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: VL2, VL3, VL4, VL5 LFW2 Kabat

<400> SEQUENCE: 110

Trp Tyr Gln Gln Lys Pro Gly Lys Ala Pro Lys Leu Leu Ile Tyr
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Ab235 LFW2 Kabat

<400> SEQUENCE: 111

Trp Tyr Gln Gln Lys Ala Gly Ser Ser Pro Arg Leu Leu Ile Tyr
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Ab236 LFW2 Kabat

<400> SEQUENCE: 112

Trp Tyr Gln Gln Lys Pro Gly Ser Ser Pro Arg Leu Leu Ile Tyr
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Ab237 LFW2 Kabat

<400> SEQUENCE: 113

Trp Tyr Gln Gln Lys Pro Gly Asn Ser Pro Gln Leu Leu Ile Tyr
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Ab238 LFW2 Kabat

<400> SEQUENCE: 114

Trp Tyr Gln Gln Lys Pro Gly Lys Ser Pro Gln Leu Leu Ile Tyr
1               5                   10                  15
```

<210> SEQ ID NO 115
<211> LENGTH: 15
<212> TYPE: PRT
<213> ORGANISM: Artificial Sequence
<220> FEATURE:
<223> OTHER INFORMATION: Ab239 LFW2 Kabat

<400> SEQUENCE: 115

Trp Tyr Gln Gln Arg Leu Gly Arg Pro Pro Leu Asn Val Ile Tyr
1               5                  10                  15

<210> SEQ ID NO 116
<211> LENGTH: 15
<212> TYPE: PRT
<213> ORGANISM: Artificial Sequence
<220> FEATURE:
<223> OTHER INFORMATION: AB240 LFW2 Kabat

<400> SEQUENCE: 116

Trp Tyr Gln Gln Lys Pro Asp Gly Thr Ile Lys Thr Leu Ile Tyr
1               5                  10                  15

<210> SEQ ID NO 117
<211> LENGTH: 32
<212> TYPE: PRT
<213> ORGANISM: Artificial Sequence
<220> FEATURE:
<223> OTHER INFORMATION: VL1 LFW1 Kabat

<400> SEQUENCE: 117

Gly Val Pro Ser Arg Phe Ser Gly Ser Gly Ser Gly Thr Asp Tyr Thr
1               5                  10                  15

Leu Lys Ile Asn Ser Leu Gln Ser Glu Asp Val Ala Ile Tyr Phe Cys
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: VL2 LFW2 Kabat

<400> SEQUENCE: 118

Gly Val Pro Ser Arg Phe Ser Gly Phe Gly Phe Gly Thr Asp Tyr Thr
1               5                  10                  15

Leu Thr Ile Ser Ser Leu Gln Ser Glu Asp Val Ala Ile Tyr Phe Cys
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: VL3 LFW3 Kabat

<400> SEQUENCE: 119

Gly Val Pro Ser Arg Phe Ser Gly Ser Gly Ser Gly Thr Asp Tyr Thr
1               5                  10                  15

Leu Thr Ile Ser Ser Leu Gln Pro Glu Asp Val Ala Ile Tyr Phe Cys
            20                  25                  30

<210> SEQ ID NO 120
<211> LENGTH: 32
<212> TYPE: PRT

<213> ORGANISM: Artificial Sequence
<220> FEATURE:
<223> OTHER INFORMATION: VL4 LFW4 Kabat

<400> SEQUENCE: 120

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Ile Tyr Phe Cys
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: VL5 LFW5 Kabat

<400> SEQUENCE: 121

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Phe Cys
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Ab235, Ab236 LFW3 Kabat Kabat

<400> SEQUENCE: 122

Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Ab237 LFW3 Kabat

<400> SEQUENCE: 123

Gly Val Pro Ser Arg Phe Ser Gly Ser Gly Ser Gly Thr Gln Tyr Ser
1               5                   10                  15

Leu Lys Ile Asn Ser Leu Gln Ser Glu Asp Val Ser Ile Tyr Phe Cys
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Ab238 LFW3 Kabat

<400> SEQUENCE: 124

Gly Val Pro Ser Val Phe Ser Gly Ser Gly Ser Gly Thr Gln Tyr Ser
1               5                   10                  15

Leu Lys Ile Asn Asn Leu His Ser Glu Asp Val Ala Thr Tyr Phe Cys
            20                  25                  30

<210> SEQ ID NO 125
<211> LENGTH: 34

```
<212> TYPE: PRT
<213> ORGANISM: Artificial Sequence
<220> FEATURE:
<223> OTHER INFORMATION: Ab239 LFW3 Kabat

<400> SEQUENCE: 125

Glu Val Ser Asp Arg Phe Ser Gly Ser Ile Asp Ser Ser Asn Ser
1               5                   10                  15

Ala Ser Leu Thr Ile Thr Asp Leu Gln Met Asp Asp Glu Ala Asp Tyr
            20                  25                  30

Phe Cys

<210> SEQ ID NO 126
<211> LENGTH: 32
<212> TYPE: PRT
<213> ORGANISM: Artificial Sequence
<220> FEATURE:
<223> OTHER INFORMATION: AB240 LFW3 Kabat

<400> SEQUENCE: 126

Gly Val Pro Ser Arg Phe Ser Gly Ser Gly Ser Gly Thr Asp Tyr Ser
1               5                   10                  15

Leu Thr Ile Ser Gly Leu Glu Pro Glu Asp Phe Ala Val Tyr Tyr Cys
            20                  25                  30

<210> SEQ ID NO 127
<211> LENGTH: 11
<212> TYPE: PRT
<213> ORGANISM: Artificial Sequence
<220> FEATURE:
<223> OTHER INFORMATION: VL1, VL2, VL3, VL4, VL5, Ab237 LFW4 Kabat

<400> SEQUENCE: 127

Phe Gly Gln Gly Thr Lys Leu Glu Ile Lys Arg
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Ab235, Ab236, Ab238, Ab239 LFW4 Kabat

<400> SEQUENCE: 128

Phe Gly Gly Gly Thr Lys Leu Glu Ile Lys Arg
1               5                   10

<210> SEQ ID NO 129
<211> LENGTH: 12
<212> TYPE: PRT
<213> ORGANISM: Artificial Sequence
<220> FEATURE:
<223> OTHER INFORMATION: AB240 LFW4 Kabat

<400> SEQUENCE: 129

Phe Gly Ser Gly Thr Lys Leu Glu Ile Lys Arg Arg
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Ab235 HCDR1 Chothia

<400> SEQUENCE: 130
```

```
Gly Tyr Thr Phe Ser Asn Tyr
1               5

<210> SEQ ID NO 131
<211> LENGTH: 6
<212> TYPE: PRT
<213> ORGANISM: Artificial Sequence
<220> FEATURE:
<223> OTHER INFORMATION: Ab235 HCDR2 Chothia

<400> SEQUENCE: 131

Leu Pro Gly Ser Asp Tyr
1               5

<210> SEQ ID NO 132
<211> LENGTH: 8
<212> TYPE: PRT
<213> ORGANISM: Artificial Sequence
<220> FEATURE:
<223> OTHER INFORMATION: Ab235 HCDR3 Chothia

<400> SEQUENCE: 132

Pro Ser Thr Ile Pro Pro Asp Cys
1               5

<210> SEQ ID NO 133
<211> LENGTH: 10
<212> TYPE: PRT
<213> ORGANISM: Artificial Sequence
<220> FEATURE:
<223> OTHER INFORMATION: Ab235 LCDR1 Chothia

<400> SEQUENCE: 133

Ser Ala Ser Ser Ser Val Asn Tyr Met Phe
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Ab235 LCDR2 Chothia

<400> SEQUENCE: 134

Asp Thr Phe Asn Leu Ala Ser
1               5

<210> SEQ ID NO 135
<211> LENGTH: 8
<212> TYPE: PRT
<213> ORGANISM: Artificial Sequence
<220> FEATURE:
<223> OTHER INFORMATION: Ab235 LCDR3 Chothia

<400> SEQUENCE: 135

Gln Gln Trp Ser Tyr Pro Tyr Thr
1               5

<210> SEQ ID NO 136
<211> LENGTH: 7
<212> TYPE: PRT
<213> ORGANISM: Artificial Sequence
<220> FEATURE:
<223> OTHER INFORMATION: Ab236 HCDR1 Chothia

<400> SEQUENCE: 136
```

```
Gly Tyr Ile Phe Ser Ser Tyr
1               5
```

<210> SEQ ID NO 137
<211> LENGTH: 6
<212> TYPE: PRT
<213> ORGANISM: Artificial Sequence
<220> FEATURE:
<223> OTHER INFORMATION: Ab236 HCDR2 Chothia

<400> SEQUENCE: 137

```
Leu Pro Gly Ser Asp Phe
1               5
```

<210> SEQ ID NO 138
<211> LENGTH: 8
<212> TYPE: PRT
<213> ORGANISM: Artificial Sequence
<220> FEATURE:
<223> OTHER INFORMATION: Ab236 HCDR3 Chothia

<400> SEQUENCE: 138

```
Pro Ser Thr Val Pro Pro Asp Cys
1               5
```

<210> SEQ ID NO 139
<211> LENGTH: 10
<212> TYPE: PRT
<213> ORGANISM: Artificial Sequence
<220> FEATURE:
<223> OTHER INFORMATION: Ab236 LCDR1 Chothia

<400> SEQUENCE: 139

```
Ser Ala Ser Ser Ser Val Ser Tyr Met Phe
1               5                   10
```

<210> SEQ ID NO 140
<211> LENGTH: 7
<212> TYPE: PRT
<213> ORGANISM: Artificial Sequence
<220> FEATURE:
<223> OTHER INFORMATION: Ab236 LCDR2 Chothia

<400> SEQUENCE: 140

```
Asp Thr Ser Asp Leu Ala Ser
1               5
```

<210> SEQ ID NO 141
<211> LENGTH: 9
<212> TYPE: PRT
<213> ORGANISM: Artificial Sequence
<220> FEATURE:
<223> OTHER INFORMATION: Ab236 LCDR3 Chothia

<400> SEQUENCE: 141

```
Gln Gln Trp Ser Asn Tyr Pro Tyr Thr
1               5
```

<210> SEQ ID NO 142
<211> LENGTH: 7
<212> TYPE: PRT
<213> ORGANISM: Artificial Sequence
<220> FEATURE:
<223> OTHER INFORMATION: Ab237 HCDR1 Chothia

<400> SEQUENCE: 142

Gly Phe Thr Phe Ser Asp Ser

```
1               5

<210> SEQ ID NO 143
<211> LENGTH: 6
<212> TYPE: PRT
<213> ORGANISM: Artificial Sequence
<220> FEATURE:
<223> OTHER INFORMATION: Ab237 HCDR2 Chothia

<400> SEQUENCE: 143

Ser Ser Asp Gly Gly Gly
1               5

<210> SEQ ID NO 144
<211> LENGTH: 15
<212> TYPE: PRT
<213> ORGANISM: Artificial Sequence
<220> FEATURE:
<223> OTHER INFORMATION: Ab237 HCDR3 Chothia

<400> SEQUENCE: 144

Glu Gly Ile Tyr Thr Thr Asp Tyr Tyr Pro Tyr Cys Phe Asn Tyr
1               5                   10                  15

<210> SEQ ID NO 145
<211> LENGTH: 11
<212> TYPE: PRT
<213> ORGANISM: Artificial Sequence
<220> FEATURE:
<223> OTHER INFORMATION: Ab237 LCDR1 Chothia

<400> SEQUENCE: 145

Leu Ala Ser Ala Asp Ile His Ser Asn Leu Ala
1               5                   10

<210> SEQ ID NO 146
<211> LENGTH: 5
<212> TYPE: PRT
<213> ORGANISM: Artificial Sequence
<220> FEATURE:
<223> OTHER INFORMATION: Ab237 LCDR2 Chothia

<400> SEQUENCE: 146

Asn Asn Leu Asn Asp
1               5

<210> SEQ ID NO 147
<211> LENGTH: 8
<212> TYPE: PRT
<213> ORGANISM: Artificial Sequence
<220> FEATURE:
<223> OTHER INFORMATION: Ab237 LCDR3 Chothia

<400> SEQUENCE: 147

Pro Pro Thr Phe Gly Ala Gly Thr
1               5

<210> SEQ ID NO 148
<211> LENGTH: 9
<212> TYPE: PRT
<213> ORGANISM: Artificial Sequence
<220> FEATURE:
<223> OTHER INFORMATION: Ab238 HCDR1 Chothia

<400> SEQUENCE: 148

Gly Phe Ser Leu Ser Thr Tyr Gly Met
1               5
```

<210> SEQ ID NO 149
<211> LENGTH: 5
<212> TYPE: PRT
<213> ORGANISM: Artificial Sequence
<220> FEATURE:
<223> OTHER INFORMATION: Ab238 HCDR2 Chothia

<400> SEQUENCE: 149

Trp Trp Asp Asp Val
1               5

<210> SEQ ID NO 150
<211> LENGTH: 9
<212> TYPE: PRT
<213> ORGANISM: Artificial Sequence
<220> FEATURE:
<223> OTHER INFORMATION: Ab238 HCDR3 Chothia

<400> SEQUENCE: 150

Ile Gly Thr Ser His Ile Val Asp Ala
1               5

<210> SEQ ID NO 151
<211> LENGTH: 11
<212> TYPE: PRT
<213> ORGANISM: Artificial Sequence
<220> FEATURE:
<223> OTHER INFORMATION: Ab238 LCDR1 Chothia

<400> SEQUENCE: 151

Leu Ala Ser Glu Asp Ile Tyr Ser Asp Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Ab238 LCDR2 Chothia

<400> SEQUENCE: 152

Asn Ala Asn Thr Leu Gln Asn
1               5

<210> SEQ ID NO 153
<211> LENGTH: 9
<212> TYPE: PRT
<213> ORGANISM: Artificial Sequence
<220> FEATURE:
<223> OTHER INFORMATION: Ab238 LCDR3 Chothia

<400> SEQUENCE: 153

Gln Gln Tyr Asn Asn Tyr Pro Pro Thr
1               5

<210> SEQ ID NO 154
<211> LENGTH: 7
<212> TYPE: PRT
<213> ORGANISM: Artificial Sequence
<220> FEATURE:
<223> OTHER INFORMATION: Ab239 HCDR1 Chothia

<400> SEQUENCE: 154

Gly Phe Ser Phe Thr Asp Cys
1               5

```
<210> SEQ ID NO 155
<211> LENGTH: 6
<212> TYPE: PRT
<213> ORGANISM: Artificial Sequence
<220> FEATURE:
<223> OTHER INFORMATION: Ab239 HCDR2 Chothia

<400> SEQUENCE: 155

Ser Ser Asp Gly Gly Gly
1               5

<210> SEQ ID NO 156
<211> LENGTH: 16
<212> TYPE: PRT
<213> ORGANISM: Artificial Sequence
<220> FEATURE:
<223> OTHER INFORMATION: Ab239 HCDR3 Chothia

<400> SEQUENCE: 156

Glu Arg Tyr Tyr Asp Gly Thr Tyr Tyr Gly Tyr Trp Tyr Phe Asp Phe
1               5                   10                  15

<210> SEQ ID NO 157
<211> LENGTH: 13
<212> TYPE: PRT
<213> ORGANISM: Artificial Sequence
<220> FEATURE:
<223> OTHER INFORMATION: Ab239 LCDR1 Chothia

<400> SEQUENCE: 157

Val Arg Ser Ser Gly Asp Ile Gly Asp Arg Tyr Val Ser
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Ab239 LCDR2 Chothia

<400> SEQUENCE: 158

Ala Ala Asp Gln Arg Pro Ser
1               5

<210> SEQ ID NO 159
<211> LENGTH: 10
<212> TYPE: PRT
<213> ORGANISM: Artificial Sequence
<220> FEATURE:
<223> OTHER INFORMATION: Ab239 LCDR3 Chothia

<400> SEQUENCE: 159

Gln Ser Tyr Asp Ser Asn Ile Asp Ile Val
1               5                   10

<210> SEQ ID NO 160
<211> LENGTH: 8
<212> TYPE: PRT
<213> ORGANISM: Artificial Sequence
<220> FEATURE:
<223> OTHER INFORMATION: Ab235 HCDR1 IMGT

<400> SEQUENCE: 160

Gly Tyr Thr Phe Ser Asn Tyr Trp
1               5
```

```
<210> SEQ ID NO 161
<211> LENGTH: 8
<212> TYPE: PRT
<213> ORGANISM: Artificial Sequence
<220> FEATURE:
<223> OTHER INFORMATION: Ab235 HCDR2 IMGT

<400> SEQUENCE: 161

Ile Leu Pro Gly Ser Asp Tyr Thr
1               5

<210> SEQ ID NO 162
<211> LENGTH: 10
<212> TYPE: PRT
<213> ORGANISM: Artificial Sequence
<220> FEATURE:
<223> OTHER INFORMATION: Ab235 HCDR3 IMGT

<400> SEQUENCE: 162

Ala Arg Pro Ser Thr Ile Pro Pro Asp Cys
1               5                   10

<210> SEQ ID NO 163
<211> LENGTH: 5
<212> TYPE: PRT
<213> ORGANISM: Artificial Sequence
<220> FEATURE:
<223> OTHER INFORMATION: Ab235 LCDR1 IMGT

<400> SEQUENCE: 163

Ser Ser Val Asn Tyr
1               5

<210> SEQ ID NO 164
<211> LENGTH: 3
<212> TYPE: PRT
<213> ORGANISM: Artificial Sequence
<220> FEATURE:
<223> OTHER INFORMATION: Ab235 LCDR2 IMGT

<400> SEQUENCE: 164

Asp Thr Phe
1

<210> SEQ ID NO 165
<211> LENGTH: 9
<212> TYPE: PRT
<213> ORGANISM: Artificial Sequence
<220> FEATURE:
<223> OTHER INFORMATION: Ab235 LCDR3 IMGT

<400> SEQUENCE: 165

Gln Gln Trp Ser Ile Tyr Pro Tyr Thr
1               5

<210> SEQ ID NO 166
<211> LENGTH: 8
<212> TYPE: PRT
<213> ORGANISM: Artificial Sequence
<220> FEATURE:
<223> OTHER INFORMATION: Ab236 HCDR1 IMGT

<400> SEQUENCE: 166

Gly Tyr Ile Phe Ser Ser Tyr Trp
1               5

<210> SEQ ID NO 167
```

```
<211> LENGTH: 8
<212> TYPE: PRT
<213> ORGANISM: Artificial Sequence
<220> FEATURE:
<223> OTHER INFORMATION: Ab236 HCDR2 IMGT

<400> SEQUENCE: 167

Ile Leu Pro Gly Ser Asp Phe Ile
1               5

<210> SEQ ID NO 168
<211> LENGTH: 10
<212> TYPE: PRT
<213> ORGANISM: Artificial Sequence
<220> FEATURE:
<223> OTHER INFORMATION: Ab236 HCDR3 IMGT

<400> SEQUENCE: 168

Ala Arg Pro Ser Thr Val Pro Pro Asp Cys
1               5                   10

<210> SEQ ID NO 169
<211> LENGTH: 5
<212> TYPE: PRT
<213> ORGANISM: Artificial Sequence
<220> FEATURE:
<223> OTHER INFORMATION: Ab236 LCDR1 IMGT

<400> SEQUENCE: 169

Ser Ser Val Ser Tyr
1               5

<210> SEQ ID NO 170
<211> LENGTH: 3
<212> TYPE: PRT
<213> ORGANISM: Artificial Sequence
<220> FEATURE:
<223> OTHER INFORMATION: Ab236 LCDR2 IMGT

<400> SEQUENCE: 170

Asp Thr Ser
1

<210> SEQ ID NO 171
<211> LENGTH: 9
<212> TYPE: PRT
<213> ORGANISM: Artificial Sequence
<220> FEATURE:
<223> OTHER INFORMATION: Ab236 LCDR3 IMGT

<400> SEQUENCE: 171

Gln Gln Trp Ser Asn Tyr Pro Tyr Thr
1               5

<210> SEQ ID NO 172
<211> LENGTH: 8
<212> TYPE: PRT
<213> ORGANISM: Artificial Sequence
<220> FEATURE:
<223> OTHER INFORMATION: Ab237 HCDR1 IMGT

<400> SEQUENCE: 172

Gly Phe Thr Phe Ser Asp Ser Tyr
1               5

<210> SEQ ID NO 173
<211> LENGTH: 8
```

```
<212> TYPE: PRT
<213> ORGANISM: Artificial Sequence
<220> FEATURE:
<223> OTHER INFORMATION: Ab237 HCDR2 IMGT

<400> SEQUENCE: 173

Ile Ser Ser Asp Gly Gly Gly Thr
1               5

<210> SEQ ID NO 174
<211> LENGTH: 17
<212> TYPE: PRT
<213> ORGANISM: Artificial Sequence
<220> FEATURE:
<223> OTHER INFORMATION: Ab237 HCDR3 IMGT

<400> SEQUENCE: 174

Thr Thr Glu Gly Ile Tyr Thr Thr Asp Tyr Tyr Pro Tyr Cys Phe Asn
1               5                   10                  15

Tyr

<210> SEQ ID NO 175
<211> LENGTH: 6
<212> TYPE: PRT
<213> ORGANISM: Artificial Sequence
<220> FEATURE:
<223> OTHER INFORMATION: Ab237 LCDR1 IMGT

<400> SEQUENCE: 175

Ala Asp Ile His Ser Asn
1               5

<210> SEQ ID NO 176
<211> LENGTH: 3
<212> TYPE: PRT
<213> ORGANISM: Artificial Sequence
<220> FEATURE:
<223> OTHER INFORMATION: Ab237 LCDR2 IMGT

<400> SEQUENCE: 176

Tyr Gly Asn
1

<210> SEQ ID NO 177
<211> LENGTH: 9
<212> TYPE: PRT
<213> ORGANISM: Artificial Sequence
<220> FEATURE:
<223> OTHER INFORMATION: Ab237 LCDR3 IMGT

<400> SEQUENCE: 177

Gln Gln Ser Tyr Asp Ser Pro Pro Thr
1               5

<210> SEQ ID NO 178
<211> LENGTH: 12
<212> TYPE: PRT
<213> ORGANISM: Artificial Sequence
<220> FEATURE:
<223> OTHER INFORMATION: Ab238 HCDR1 IMGT

<400> SEQUENCE: 178

Phe Ser Gly Phe Ser Leu Ser Thr Tyr Gly Met Gly
1               5                   10

<210> SEQ ID NO 179
```

```
<211> LENGTH: 7
<212> TYPE: PRT
<213> ORGANISM: Artificial Sequence
<220> FEATURE:
<223> OTHER INFORMATION: Ab238 HCDR2 IMGT

<400> SEQUENCE: 179

Ile Trp Trp Asp Asp Val Asn
1               5

<210> SEQ ID NO 180
<211> LENGTH: 11
<212> TYPE: PRT
<213> ORGANISM: Artificial Sequence
<220> FEATURE:
<223> OTHER INFORMATION: Ab238 HCDR3 IMGT

<400> SEQUENCE: 180

Ala Arg Ile Gly Thr Ser His Ile Val Asp Ala
1               5                   10

<210> SEQ ID NO 181
<211> LENGTH: 6
<212> TYPE: PRT
<213> ORGANISM: Artificial Sequence
<220> FEATURE:
<223> OTHER INFORMATION: Ab238 LCDR1 IMGT

<400> SEQUENCE: 181

Glu Asp Ile Tyr Ser Asp
1               5

<210> SEQ ID NO 182
<211> LENGTH: 3
<212> TYPE: PRT
<213> ORGANISM: Artificial Sequence
<220> FEATURE:
<223> OTHER INFORMATION: Ab238 LCDR2 IMGT

<400> SEQUENCE: 182

Asn Ala Asn
1

<210> SEQ ID NO 183
<211> LENGTH: 9
<212> TYPE: PRT
<213> ORGANISM: Artificial Sequence
<220> FEATURE:
<223> OTHER INFORMATION: Ab238 LCDR3 IMGT

<400> SEQUENCE: 183

Gln Gln Tyr Asn Asn Tyr Pro Pro Thr
1               5

<210> SEQ ID NO 184
<211> LENGTH: 9
<212> TYPE: PRT
<213> ORGANISM: Artificial Sequence
<220> FEATURE:
<223> OTHER INFORMATION: Ab239 HCDR1 IMGT

<400> SEQUENCE: 184

Gly Phe Ser Phe Thr Asp Cys Tyr Ile
1               5

<210> SEQ ID NO 185
<211> LENGTH: 8
```

```
<212> TYPE: PRT
<213> ORGANISM: Artificial Sequence
<220> FEATURE:
<223> OTHER INFORMATION: Ab239 HCDR2 IMGT

<400> SEQUENCE: 185

Ile Ser Ser Asp Gly Gly Gly Thr
1               5

<210> SEQ ID NO 186
<211> LENGTH: 13
<212> TYPE: PRT
<213> ORGANISM: Artificial Sequence
<220> FEATURE:
<223> OTHER INFORMATION: Ab239 HCDR3 IMGT

<400> SEQUENCE: 186

Thr Thr Glu Arg Tyr Tyr Asp Gly Thr Tyr Tyr Gly Tyr
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Ab239 LCDR1 IMGT

<400> SEQUENCE: 187

Ser Gly Asp Ile Gly Asp Arg Tyr
1               5

<210> SEQ ID NO 188
<211> LENGTH: 3
<212> TYPE: PRT
<213> ORGANISM: Artificial Sequence
<220> FEATURE:
<223> OTHER INFORMATION: Ab239 LCDR2 IMGT

<400> SEQUENCE: 188

Ala Ala Asp
1

<210> SEQ ID NO 189
<211> LENGTH: 10
<212> TYPE: PRT
<213> ORGANISM: Artificial Sequence
<220> FEATURE:
<223> OTHER INFORMATION: Ab239 LCDR3 IMGT

<400> SEQUENCE: 189

Gln Ser Tyr Asp Ser Asn Ile Asp Ile Val
1               5                   10

<210> SEQ ID NO 190
<211> LENGTH: 1384
<212> TYPE: PRT
<213> ORGANISM: Homo sapiens
<220> FEATURE:
<223> OTHER INFORMATION: Human Met protein

<400> SEQUENCE: 190

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
```

```
               35                  40                  45
Leu Asn Glu Glu Asp Leu Gln Lys Val Ala Glu Tyr Lys Thr Gly Pro
 50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                 85                  90                  95

Val Val Asp Thr Tyr Tyr Asp Asp Gln Leu Ile Ser Cys Gly Ser Val
                100                 105                 110

Asn Arg Gly Thr Cys Gln Arg His Val Phe Pro His Asn His Thr Ala
            115                 120                 125

Asp Ile Gln Ser Glu Val His Cys Ile Phe Ser Pro Gln Ile Glu Glu
        130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
                180                 185                 190

Arg Arg Leu Lys Glu Thr Lys Asp Gly Phe Met Phe Leu Thr Asp Gln
            195                 200                 205

Ser Tyr Ile Asp Val Leu Pro Glu Phe Arg Asp Ser Tyr Pro Ile Lys
210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
                260                 265                 270

Glu Cys Ile Leu Thr Glu Lys Arg Lys Lys Arg Ser Thr Lys Lys Glu
            275                 280                 285

Val Phe Asn Ile Leu Gln Ala Ala Tyr Val Ser Lys Pro Gly Ala Gln
290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
                340                 345                 350

Ile Val Asn Lys Asn Asn Val Arg Cys Leu Gln His Phe Tyr Gly Pro
            355                 360                 365

Asn His Glu His Cys Phe Asn Arg Thr Leu Leu Arg Asn Ser Ser Gly
        370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
                420                 425                 430

Thr Ser Glu Gly Arg Phe Met Gln Val Val Val Ser Arg Ser Gly Pro
            435                 440                 445

Ser Thr Pro His Val Asn Phe Leu Leu Asp Ser His Pro Val Ser Pro
450                 455                 460
```

```
Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
                500                 505                 510

Gln Cys Gly Trp Cys His Asp Lys Cys Val Arg Ser Glu Glu Cys Leu
            515                 520                 525

Ser Gly Thr Trp Thr Gln Gln Ile Cys Leu Pro Ala Ile Tyr Lys Val
            530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
                580                 585                 590

Ser Thr Met Asn Thr Leu Lys Cys Thr Val Gly Pro Ala Met Asn Lys
            595                 600                 605

His Phe Asn Met Ser Ile Ile Ser Asn Gly His Gly Thr Thr Gln
610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
                660                 665                 670

Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Thr Trp Trp Lys Glu
                725                 730                 735

Pro Leu Asn Ile Val Ser Phe Leu Phe Cys Phe Ala Ser Gly Gly Ser
                740                 745                 750

Thr Ile Thr Gly Val Gly Lys Asn Leu Asn Ser Val Ser Val Pro Arg
            755                 760                 765

Met Val Ile Asn Val His Glu Ala Gly Arg Asn Phe Thr Val Ala Cys
            770                 775                 780

Gln His Arg Ser Asn Ser Glu Ile Ile Cys Cys Thr Thr Pro Ser Leu
785                 790                 795                 800

Gln Gln Leu Asn Leu Gln Leu Pro Leu Lys Thr Lys Ala Phe Phe Met
                805                 810                 815

Leu Asp Gly Ile Leu Ser Lys Tyr Phe Asp Leu Ile Tyr Val His Asn
                820                 825                 830

Pro Val Phe Lys Pro Phe Glu Lys Pro Val Met Ile Ser Met Gly Asn
                835                 840                 845

Glu Asn Val Leu Glu Ile Lys Gly Asn Asp Ile Asp Pro Glu Ala Val
            850                 855                 860

Lys Gly Glu Val Leu Lys Val Gly Asn Lys Ser Cys Glu Asn Ile His
865                 870                 875                 880
```

Leu His Ser Glu Ala Val Leu Cys Thr Val Pro Asn Asp Leu Leu Lys
            885                 890                 895

Leu Asn Ser Glu Leu Asn Ile Glu Trp Lys Gln Ala Ile Ser Ser Thr
            900                 905                 910

Val Leu Gly Lys Val Ile Val Gln Pro Asp Gln Asn Phe Thr Gly Leu
            915                 920                 925

Ile Ala Gly Val Val Ser Ile Ser Thr Ala Leu Leu Leu Leu Leu Gly
            930                 935                 940

Phe Phe Leu Trp Leu Lys Lys Arg Lys Gln Ile Lys Asp Leu Gly Ser
945                 950                 955                 960

Glu Leu Val Arg Tyr Asp Ala Arg Val His Thr Pro His Leu Asp Arg
            965                 970                 975

Leu Val Ser Ala Arg Ser Val Ser Pro Thr Thr Glu Met Val Ser Asn
            980                 985                 990

Glu Ser Val Asp Tyr Arg Ala Thr Phe Pro Glu Asp Gln Phe Pro Asn
            995                 1000                1005

Ser Ser Gln Asn Gly Ser Cys Arg Gln Val Gln Tyr Pro Leu Thr Asp
            1010                1015                1020

Met Ser Pro Ile Leu Thr Ser Gly Asp Ser Asp Ile Ser Ser Pro Leu
1025                1030                1035                1040

Leu Gln Asn Thr Val His Ile Asp Leu Ser Ala Leu Asn Pro Glu Leu
            1045                1050                1055

Val Gln Ala Val Gln His Val Val Ile Gly Pro Ser Ser Leu Ile Val
            1060                1065                1070

His Phe Asn Glu Val Ile Gly Arg Gly His Phe Gly Cys Val Tyr His
            1075                1080                1085

Gly Thr Leu Leu Asp Asn Asp Gly Lys Lys Ile His Cys Ala Val Lys
            1090                1095                1100

Ser Leu Asn Arg Ile Thr Asp Ile Gly Glu Val Ser Gln Phe Leu Thr
1105                1110                1115                1120

Glu Gly Ile Ile Met Lys Asp Phe Ser His Pro Asn Val Leu Ser Leu
            1125                1130                1135

Leu Gly Ile Cys Leu Arg Ser Glu Gly Ser Pro Leu Val Val Leu Pro
            1140                1145                1150

Tyr Met Lys His Gly Asp Leu Arg Asn Phe Ile Arg Asn Glu Thr His
            1155                1160                1165

Asn Pro Thr Val Lys Asp Leu Ile Gly Phe Gly Leu Gln Val Ala Lys
            1170                1175                1180

Gly Met Lys Tyr Leu Ala Ser Lys Lys Phe Val His Arg Asp Leu Ala
1185                1190                1195                1200

Ala Arg Asn Cys Met Leu Asp Glu Lys Phe Thr Val Lys Val Ala Asp
            1205                1210                1215

Phe Gly Leu Ala Arg Asp Met Tyr Asp Lys Glu Tyr Tyr Ser Val His
            1220                1225                1230

Asn Lys Thr Gly Ala Lys Leu Pro Val Lys Trp Met Ala Leu Glu Ser
            1235                1240                1245

Leu Gln Thr Gln Lys Phe Thr Thr Lys Ser Asp Val Trp Ser Phe Gly
            1250                1255                1260

Val Leu Leu Trp Glu Leu Met Thr Arg Gly Ala Pro Pro Tyr Pro Asp
1265                1270                1275                1280

Val Asn Thr Phe Asp Ile Thr Val Tyr Leu Leu Gln Gly Arg Arg Leu
            1285                1290                1295

Leu Gln Pro Glu Tyr Cys Pro Asp Pro Leu Tyr Glu Val Met Leu Lys

```
                1300            1305            1310
Cys Trp His Pro Lys Ala Glu Met Arg Pro Ser Phe Ser Glu Leu Val
            1315            1320            1325

Ser Arg Ile Ser Ala Ile Phe Ser Thr Phe Ile Gly Glu His Tyr Val
            1330            1335            1340

His Val Asn Ala Thr Tyr Val Asn Val Lys Cys Val Ala Pro Tyr Pro
1345            1350            1355            1360

Ser Leu Leu Ser Ser Glu Asp Asn Ala Asp Asp Glu Val Asp Thr Arg
            1365            1370            1375

Pro Ala Ser Phe Trp Glu Thr Ser
            1380

<210> SEQ ID NO 191
<211> LENGTH: 326
<212> TYPE: PRT
<213> ORGANISM: Homo sapiens
<220> FEATURE:
<223> OTHER INFORMATION: Human IgG2 constant region

<400> SEQUENCE: 191

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

```
                275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 192
<211> LENGTH: 106
<212> TYPE: PRT
<213> ORGANISM: Homo sapiens
<220> FEATURE:
<223> OTHER INFORMATION: Human kappa light chain region

<400> SEQUENCE: 192

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 193
<211> LENGTH: 214
<212> TYPE: PRT
<213> ORGANISM: Homo sapiens
<220> FEATURE:
<223> OTHER INFORMATION: Light chain

<400> SEQUENCE: 193

Asp Ile Gln Met Thr Gln Ser Pro Gly Ser Leu Ser Ala Ser Leu Gly
1               5                   10                  15
Glu Thr Val Thr Ile Glu Cys Leu Ala Ser Ala Asp Ile His Ser Asn
            20                  25                  30
Leu Ala Trp Tyr Gln Gln Lys Pro Gly Asn Ser Pro Gln Leu Leu Ile
        35                  40                  45
Tyr Tyr Gly Asn Asn Leu Asn Asp Gly Val Pro Ser Arg Phe Ser Gly
    50                  55                  60
Ser Gly Ser Gly Thr Gln Tyr Ser Leu Lys Ile Asn Ser Leu Gln Ser
65                  70                  75                  80
Glu Asp Val Ser Ile Tyr Phe Cys Gln Gln Ser Tyr Asp Ser Pro Pro
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
```

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 194
<211> LENGTH: 450
<212> TYPE: PRT
<213> ORGANISM: Homo sapiens
<220> FEATURE:
<223> OTHER INFORMATION: Heavy chain

<400> SEQUENCE: 194

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Ser
                20                  25                  30

Tyr Met Ala Trp Val Arg Gln Ala Pro Thr Lys Gly Leu Glu Trp Val
                35                  40                  45

Ala Ser Ile Ser Ser Asp Gly Gly Thr Tyr Tyr Arg Asp Ser Val
                50                  55                  60

Lys Gly Arg Phe Ser Ile Ser Arg Asp Asn Ala Lys Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Gly Ile Tyr Thr Thr Asp Tyr Tyr Pro Tyr Cys Phe Asn
                100                 105                 110

Tyr Trp Gly His Gly Val Met Val Thr Val Ser Ser Ala Ser Thr Lys
                115                 120                 125

Gly Pro Ser Val Phe Pro Leu Ala Pro Cys Ser Arg Ser Thr Ser Glu
                130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Asn Phe Gly Thr Gln Thr Tyr Thr Cys Asn
                195                 200                 205

Val Asp His Lys Pro Ser Asn Thr Lys Val Asp Lys Thr Val Glu Arg
                210                 215                 220

Lys Cys Cys Val Glu Cys Pro Pro Cys Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 195
<211> LENGTH: 942
<212> TYPE: PRT
<213> ORGANISM: Homo sapiens
<220> FEATURE:
<223> OTHER INFORMATION: hu-MET-ECD

<400> SEQUENCE: 195

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

```
Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
        210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
        290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
```

|   |   |   |   |   | 610 |   |   |   |   | 615 |   |   |   |   | 620 |   |

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Leu Glu His His His His His His
930                 935                 940

<210> SEQ ID NO 196
<211> LENGTH: 321
<212> TYPE: DNA
<213> ORGANISM: Artificial Sequence
<220> FEATURE:
<223> OTHER INFORMATION: Ab235 VL nucleic acid sequence sequence

<400> SEQUENCE: 196
caaattgttc tcacccagtc tccagcaatc atgtctacgt ctccagggga gaaggtcacc    60
atgacctgca gtgccagctc aagtgtaaat tatatgttct ggtaccagca gaaggcagga   120
tcctccccca gactcctgat ttatgacaca ttcaatctgg cttctggagt ccctgttcgc   180
ttcagtggca gtgggtctgg gacctcttac tctctcacaa tcagccgaat ggaggctgaa   240

```
gatgctgcca cttattactg ccagcagtgg agtatttacc cgtacacgtt cggagggggg      300
accaagctgg aaataaagcg g                                                 321
```

<210> SEQ ID NO 197
<211> LENGTH: 321
<212> TYPE: DNA
<213> ORGANISM: Artificial Sequence
<220> FEATURE:
<223> OTHER INFORMATION: Ab236 VL nucleic acid sequence sequence

<400> SEQUENCE: 197

```
caaattgttc tcacccagtc tccagcaatc atgtctgcat ctccagggga gaaggtcacc       60
atgacctgca gtgccagctc aagtgtaagt tacatgttct ggtaccagca gaagccagga      120
tcctccccca gactcctgat ttatgacaca tccgacctgg cttctggagt ccctgttcgc      180
ttcagtggca gtgggtctgg gacctcttac tctctcacaa tcagccgaat ggaggctgaa      240
gatgctgcca cttattactg ccagcagtgg agtaattacc cgtacacgtt cggagggggg      300
accaagctgg aaataaaacg g                                                 321
```

<210> SEQ ID NO 198
<211> LENGTH: 324
<212> TYPE: DNA
<213> ORGANISM: Artificial Sequence
<220> FEATURE:
<223> OTHER INFORMATION: Ab237 VL nucleic acid sequence sequence

<400> SEQUENCE: 198

```
gacattcaga tgacacagtc tccaggttcc ctgtctgcat ctctgggaga aactgtcacc       60
atcgaatgtc tagcaagtgc ggatattcac agtaatttag cttggtatca gcagaagcca      120
gggaattctc ctcagctcct gatctattat ggaaataact tgaatgatgg cgtcccatca      180
cggttcagtg gcagtggatc tggcacacag tattctctga agatcaacag cctgcaatct      240
gaagatgtct cgatttattt ctgtcaacag agttatgata gtcctccaac gtttggagct      300
gggaccaagc tggaactgaa acgg                                              324
```

<210> SEQ ID NO 199
<211> LENGTH: 324
<212> TYPE: DNA
<213> ORGANISM: Artificial Sequence
<220> FEATURE:
<223> OTHER INFORMATION: Ab238 VL nucleic acid sequence

<400> SEQUENCE: 199

```
gatatccgga tgacacagtc tccagcttcc ctgtctgcat ctctgggaga aactgtcaac       60
atcgaatgtc tagcaagtga ggacatttac agtgatttag catggtatca gcagaagcca      120
gggaaatctc ctcaactcct gatctataat gcaaatacct tgcaaaatgg ggtcccttca      180
gtgtttagtg gcagtggatc tggcacacag tattctctaa aaataaacaa cctgcactct      240
gaagatgtcg cgacttactt ctgtcaacaa tataacaatt atcctccgac gttcggtgga      300
ggcaccaagg tggaattgaa acgg                                              324
```

<210> SEQ ID NO 200
<211> LENGTH: 336
<212> TYPE: DNA
<213> ORGANISM: Artificial Sequence
<220> FEATURE:
<223> OTHER INFORMATION: Ab239 VL nucleic acid sequence

<400> SEQUENCE: 200

```
cagttcacgc tgactcaacc aaagtccgtg tcaggatctt taagaagcac tatcaccatt    60
ccctgtgtgc gcagcagtgg tgacattggc gataggtatg tgagctggta ccagcaacgc   120
ttgggaagac ccccctcaa tgtgatctat gctgctgatc aaagaccttc tgaagtgtct   180
gatcggttct cgggctccat cgacagctcc tctaactcag cctcactgac catcactgat   240
ctgcagatgg atgatgaggc cgactacttc tgtcagtctt acgatagtaa tattgatatt   300
gttttcggtg gtggaaccaa gctcactgtc ctcggt                             336
```

<210> SEQ ID NO 201
<211> LENGTH: 324
<212> TYPE: DNA
<213> ORGANISM: Artificial Sequence
<220> FEATURE:
<223> OTHER INFORMATION: Ab240 VL nucleic acid sequence

<400> SEQUENCE: 201

```
gacatccaga tgacccagac tccattctac atgcctgcat ctctgggaga gcgagtcacc    60
atcagttgca gagcaagtca gggtattagt aaatatctaa attggtatca gcagaaacca   120
gatggaacga ttaaaaccct gatctactac acatccaatt tacagtctgg tgtcccatca   180
aggttcagtg gcagtgggtc tgggacagat tattctctca ccatcagcgg cctggagcct   240
gaagattttg cagtgtatta ctgccaacag tacgatagtt ctccattcac gttcggctca   300
gggacgaagt tggaaataaa acgg                                          324
```

<210> SEQ ID NO 202
<211> LENGTH: 321
<212> TYPE: DNA
<213> ORGANISM: Artificial Sequence
<220> FEATURE:
<223> OTHER INFORMATION: Ab241 VL nucleic acid sequence

<400> SEQUENCE: 202

```
gacattcaga tgacacagtc tccaagctcc ctgtctgcat ctgtgggaga cagagtcacc    60
atcacctgtc tagcaagtgc ggatattcac agtaatttag cttggtatca gcagaagcca   120
gggaaggccc ctcagctcct gatctattat ggaaataact tgaatgatgg cgtcccatca   180
cggttcagtg gcagtggatc tggcacagac tataccctga agatcaacag cctgcaatct   240
gaagatgtcg ccatttattt ctgtcaacag agttatgata gtcctccaac gtttggacag   300
gggaccaagc tggaaatcaa a                                             321
```

<210> SEQ ID NO 203
<211> LENGTH: 321
<212> TYPE: DNA
<213> ORGANISM: Artificial Sequence
<220> FEATURE:
<223> OTHER INFORMATION: Ab242 VL nucleic acid sequence

<400> SEQUENCE: 203

```
gacattcaga tgacacagtc tccaagctcc ctgtctgcat ctgtgggaga cagagtcacc    60
atcacctgtc tagcaagtgc ggatattcac agtaatttag cttggtatca gcagaagcca   120
gggaaggccc ctaagctcct gatctattat ggaaataact tgaatgatgg cgtcccatca   180
cggttcagtg gcagtggatc tggcacagac tataccctga ccatcagcag cctgcaatct   240
gaagatgtcg ccatttattt ctgtcaacag agttatgata gtcctccaac gtttggacag   300
gggaccaagc tggaaatcaa a                                             321
```

<210> SEQ ID NO 204
<211> LENGTH: 321
<212> TYPE: DNA
<213> ORGANISM: Artificial Sequence
<220> FEATURE:
<223> OTHER INFORMATION: Ab243 VL nucleic acid sequence

<400> SEQUENCE: 204

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctaagctcct gatctattat ggaaataact tgaatgatgg cgtcccatca     180
cggttcagtg gcagtggatc tggcacagac tataccctga ccatcagcag cctgcaaccc     240
gaagatgtcg ccatttattt ctgtcaacag agttatgata gtcctccaac gtttggacag     300
gggaccaagc tggaaatcaa a                                               321
```

<210> SEQ ID NO 205
<211> LENGTH: 321
<212> TYPE: DNA
<213> ORGANISM: Artificial Sequence
<220> FEATURE:
<223> OTHER INFORMATION: Ab244 VL nucleic acid sequence

<400> SEQUENCE: 205

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctaagctcct gatctattat ggaaataact tgaatgatgg cgtcccatca     180
cggttcagtg gcagtggatc tggcacagac ttcaccctga ccatcagcag cctgcaaccc     240
gaagatgtcg ccatttattt ctgtcaacag agttatgata gtcctccaac gtttggacag     300
gggaccaagc tggaaatcaa a                                               321
```

<210> SEQ ID NO 206
<211> LENGTH: 321
<212> TYPE: DNA
<213> ORGANISM: Artificial Sequence
<220> FEATURE:
<223> OTHER INFORMATION: Ab245 VL nucleic acid sequence

<400> SEQUENCE: 206

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctaagctcct gatctattat ggaaataact tgaatgatgg cgtcccatca     180
cggttcagtg gcagtggatc tggcacagac ttcaccctga ccatcagcag cctgcaaccc     240
gaagatgtcg ccacctattt ctgtcaacag agttatgata gtcctccaac gtttggacag     300
gggaccaagc tggaaatcaa a                                               321
```

<210> SEQ ID NO 207
<211> LENGTH: 321
<212> TYPE: DNA
<213> ORGANISM: Artificial Sequence
<220> FEATURE:
<223> OTHER INFORMATION: Ab246 VL nucleic acid sequence

<400> SEQUENCE: 207

```
gacattcaga tgacacagtc tccaagctcc ctgtctgcat ctgtgggaga cagagtcacc      60
```

```
atcacctgtc tagcaagtgc ggatattcac agtaatttag cttggtatca gcagaagcca    120
gggaaggccc ctcagctcct gatctattat ggaaataact tgaatgatgg cgtcccatca    180
cggttcagtg gcagtggatc tggcacagac tataccctga agatcaacag cctgcaatct    240
gaagatgtcg ccatttattt ctgtcaacag agttatgata gtcctccaac gtttggacag    300
gggaccaagc tggaaatcaa a                                              321

<210> SEQ ID NO 208
<211> LENGTH: 321
<212> TYPE: DNA
<213> ORGANISM: Artificial Sequence
<220> FEATURE:
<223> OTHER INFORMATION: Ab247 VL nucleic acid sequence

<400> SEQUENCE: 208
gacattcaga tgacacagtc tccaagctcc ctgtctgcat ctgtgggaga cagagtcacc     60
atcacctgtc tagcaagtgc ggatattcac agtaatttag cttggtatca gcagaagcca    120
gggaaggccc ctaagctcct gatctattat ggaaataact tgaatgatgg cgtcccatca    180
cggttcagtg gcagtggatc tggcacagac tataccctga ccatcagcag cctgcaatct    240
gaagatgtcg ccatttattt ctgtcaacag agttatgata gtcctccaac gtttggacag    300
gggaccaagc tggaaatcaa a                                              321

<210> SEQ ID NO 209
<211> LENGTH: 321
<212> TYPE: DNA
<213> ORGANISM: Artificial Sequence
<220> FEATURE:
<223> OTHER INFORMATION: Ab248 VL nucleic acid sequence

<400> SEQUENCE: 209
gacattcaga tgacacagtc tccaagctcc ctgtctgcat ctgtgggaga cagagtcacc     60
atcacctgtc tagcaagtgc ggatattcac agtaatttag cttggtatca gcagaagcca    120
gggaaggccc ctaagctcct gatctattat ggaaataact tgaatgatgg cgtcccatca    180
cggttcagtg gcagtggatc tggcacagac tataccctga ccatcagcag cctgcaaccc    240
gaagatgtcg ccatttattt ctgtcaacag agttatgata gtcctccaac gtttggacag    300
gggaccaagc tggaaatcaa a                                              321

<210> SEQ ID NO 210
<211> LENGTH: 321
<212> TYPE: DNA
<213> ORGANISM: Artificial Sequence
<220> FEATURE:
<223> OTHER INFORMATION: Ab249 VL nucleic acid sequence

<400> SEQUENCE: 210
gacattcaga tgacacagtc tccaagctcc ctgtctgcat ctgtgggaga cagagtcacc     60
atcacctgtc tagcaagtgc ggatattcac agtaatttag cttggtatca gcagaagcca    120
gggaaggccc ctaagctcct gatctattat ggaaataact tgaatgatgg cgtcccatca    180
cggttcagtg gcagtggatc tggcacagac ttcaccctga ccatcagcag cctgcaaccc    240
gaagatgtcg ccatttattt ctgtcaacag agttatgata gtcctccaac gtttggacag    300
gggaccaagc tggaaatcaa a                                              321

<210> SEQ ID NO 211
<211> LENGTH: 321
```

<212> TYPE: DNA
<213> ORGANISM: Artificial Sequence
<220> FEATURE:
<223> OTHER INFORMATION: Ab250 VL nucleic acid sequence

<400> SEQUENCE: 211

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctaagctcct gatctattat ggaaataact tgaatgatgg cgtcccatca     180
cggttcagtg gcagtggatc tggcacagac ttcaccctga ccatcagcag cctgcaaccc     240
gaagatgtcg ccacctattt ctgtcaacag agttatgata gtcctccaac gtttggacag     300
gggaccaagc tggaaatcaa a                                               321
```

<210> SEQ ID NO 212
<211> LENGTH: 321
<212> TYPE: DNA
<213> ORGANISM: Artificial Sequence
<220> FEATURE:
<223> OTHER INFORMATION: Ab251 VL nucleic acid sequence

<400> SEQUENCE: 212

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctcagctcct gatctattat ggaaataact tgaatgatgg cgtcccatca     180
cggttcagtg gcagtggatc tggcacagac tatacccctga agatcaacag cctgcaatct    240
gaagatgtcg ccatttattt ctgtcaacag agttatgata gtcctccaac gtttggacag     300
gggaccaagc tggaaatcaa a                                               321
```

<210> SEQ ID NO 213
<211> LENGTH: 321
<212> TYPE: DNA
<213> ORGANISM: Artificial Sequence
<220> FEATURE:
<223> OTHER INFORMATION: Ab252 VL nucleic acid sequence

<400> SEQUENCE: 213

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctaagctcct gatctattat ggaaataact tgaatgatgg cgtcccatca     180
cggttcagtg gcagtggatc tggcacagac tatacccctga ccatcagcag cctgcaatct    240
gaagatgtcg ccatttattt ctgtcaacag agttatgata gtcctccaac gtttggacag     300
gggaccaagc tggaaatcaa a                                               321
```

<210> SEQ ID NO 214
<211> LENGTH: 321
<212> TYPE: DNA
<213> ORGANISM: Artificial Sequence
<220> FEATURE:
<223> OTHER INFORMATION: Ab253 VL nucleic acid sequence

<400> SEQUENCE: 214

```
gacattcaga tgacacagtc tccaagctcc ctgtctgcat ctgtgggaga cagagtcacc      60
atcacctgtc tagcaagtgc ggatattcac agtaatttag cttggtatca gcagaagcca     120
gggaaggccc ctaagctcct gatctattat ggaaataact tgaatgatgg cgtcccatca     180
```

```
cggttcagtg gcagtggatc tggcacagac tatacctga ccatcagcag cctgcaaccc    240
gaagatgtcg ccatttattt ctgtcaacag agttatgata gtcctccaac gtttggacag    300
gggaccaagc tggaaatcaa a                                              321
```

<210> SEQ ID NO 215
<211> LENGTH: 321
<212> TYPE: DNA
<213> ORGANISM: Artificial Sequence
<220> FEATURE:
<223> OTHER INFORMATION: Ab254 VL nucleic acid sequence

<400> SEQUENCE: 215

```
gacattcaga tgacacagtc tccaagctcc ctgtctgcat ctgtgggaga cagagtcacc    60
atcacctgtc tagcaagtgc ggatattcac agtaatttag cttggtatca gcagaagcca    120
gggaaggccc ctaagctcct gatctattat ggaaataact tgaatgatgg cgtcccatca    180
cggttcagtg gcagtggatc tggcacagac ttcaccctga ccatcagcag cctgcaaccc    240
gaagatgtcg ccatttattt ctgtcaacag agttatgata gtcctccaac gtttggacag    300
gggaccaagc tggaaatcaa a                                              321
```

<210> SEQ ID NO 216
<211> LENGTH: 321
<212> TYPE: DNA
<213> ORGANISM: Artificial Sequence
<220> FEATURE:
<223> OTHER INFORMATION: Ab255 VL nucleic acid sequence

<400> SEQUENCE: 216

```
gacattcaga tgacacagtc tccaagctcc ctgtctgcat ctgtgggaga cagagtcacc    60
atcacctgtc tagcaagtgc ggatattcac agtaatttag cttggtatca gcagaagcca    120
gggaaggccc ctaagctcct gatctattat ggaaataact tgaatgatgg cgtcccatca    180
cggttcagtg gcagtggatc tggcacagac ttcaccctga ccatcagcag cctgcaaccc    240
gaagatgtcg ccacctattt ctgtcaacag agttatgata gtcctccaac gtttggacag    300
gggaccaagc tggaaatcaa a                                              321
```

<210> SEQ ID NO 217
<211> LENGTH: 351
<212> TYPE: DNA
<213> ORGANISM: Artificial Sequence
<220> FEATURE:
<223> OTHER INFORMATION: Ab235 VH nucleic acid sequence

<400> SEQUENCE: 217

```
caggttcagc tgcagcagtc tggagctgag ttgatgaagc ctggggcctc agtgaagata    60
tcctgcaagg ctactggcta cacattcagt aactactgga tagagtgggt aaagcagagg    120
cctggacatg gccttgaatg gattggagag atttttacctg gaagtgatta tactaagtat    180
aatgagaaat tcaagggcaa ggccacattc actgcagata catcctccaa cacagcctac    240
atgcagctca gcagcctgac atctgaggac tctgccgtct attactgtgc aagaccctct    300
acaattcccc ctgactgctg gggccaaggc accactctca cagtctcctc a             351
```

<210> SEQ ID NO 218
<211> LENGTH: 351
<212> TYPE: DNA
<213> ORGANISM: Artificial Sequence
<220> FEATURE:
<223> OTHER INFORMATION: Ab236 VH nucleic acid sequence

<400> SEQUENCE: 218

```
caggctcagc tgcaacagtc tggagctgag ctgatgaagc tggggcctc agtgaagata      60
tcctgcaagg ctactggcta catattcagt agttattgga tagagtgggt aaagcagagg    120
cctggacatg gccttgagtg gattggagag atttttacctg gaagtgattt tattaagtac   180
agtgagaagt tcaagggcaa ggccacattc actgcagata cgtcctccaa tacagcctac   240
atgcaactca gcaacctgac atctgaggac tctgccgtct attactgtgc aagaccctct   300
acggttcccc ctgactgctg gggccaaggc accactctca cagtctcctc a             351
```

<210> SEQ ID NO 219
<211> LENGTH: 372
<212> TYPE: DNA
<213> ORGANISM: Artificial Sequence
<220> FEATURE:
<223> OTHER INFORMATION: Ab237 VH nucleic acid sequence

<400> SEQUENCE: 219

```
gaggtgcagc tggtggagtc tggaggaggc ttggtgcagc ctggaaggtc cctgaaactc     60
tcctgtgcag cctcaggatt cactttcagt gactcgtaca tggcctgggt ccgccaggct    120
ccgacgaagg gtctggaatg ggtcgcatcc attagttctg atggtggtgg cacttactat   180
cgagactccg tgaagggccg attctctatc tccagagata tgcgaaaag cagcctctac    240
ctgcaaatgg acagtctgcg gtctgaggac acggccactt attactgtac aacagagggg   300
atttatacta cggattatta cccttattgc tttaattatt ggggccacgg agtcatggtc   360
acagtctcct ca                                                        372
```

<210> SEQ ID NO 220
<211> LENGTH: 357
<212> TYPE: DNA
<213> ORGANISM: Artificial Sequence
<220> FEATURE:
<223> OTHER INFORMATION: Ab238 VH nucleic acid sequence

<400> SEQUENCE: 220

```
caggttactc tgaaagagtc tggccctggg atattgcagc cctcccagac cctcagtctg     60
acttgcactt tctctgggtt ttcactgagc acttatggta tgggtgtggc ctggattcgt    120
cagccgtcag gaaggatct ggagtggctg gcaaacattt ggtgggatga tgttaactac    180
tccaatccat ctctgaagaa ccgactcaca atctccaagg acacctccaa caaccaagtt   240
ttcctcaga tcaccaatgt ggacactgca gaaactgcca catattactg tgctcggatc    300
ggtacatccc atattgtgga tgcctgggt caaggagctt cagtcactgt ctcctca        357
```

<210> SEQ ID NO 221
<211> LENGTH: 375
<212> TYPE: DNA
<213> ORGANISM: Artificial Sequence
<220> FEATURE:
<223> OTHER INFORMATION: Ab239 VH nucleic acid sequence

<400> SEQUENCE: 221

```
gaggtgcagc tggtggaatc tgggggaggc ttagtgcagc ctggaaggtc cctgaaactc     60
tcctgtgcag cctcaggatt cagtttcact gactgttaca tggcctgggt ccgccaggct    120
ccaacgaagg gtctggagtg ggtcgcatcc attagttctg atggtggtgg cacttactat   180
cgagactccg tgaagggccg atttactatc tccagagata tgcaagaag cagcctatac    240
```

```
ctagaaatgg acagtctgag gtctgaggac acggccactt attattgtac cacagaaaga    300
tactatgatg gtacttacta cggctactgg tactttgact tctgggccc aggaaccatg    360 gtcaccgtgt cctca                                                    375

<210> SEQ ID NO 222
<211> LENGTH: 351
<212> TYPE: DNA
<213> ORGANISM: Artificial Sequence
<220> FEATURE:
<223> OTHER INFORMATION: Ab240 VH nucleic acid sequence

<400> SEQUENCE: 222
caggtgcagc tgaaggagtc aggacctggt ctggtgcagc cctcacagac cctgtccctc     60
acctgctctg tctctggact ctcactaacc accaatagtg tacactggat tcgccagcct    120
ccgggaaggg gtctggagtg gatgggagta atatggggtg atggaagcac agactataat    180
tcagctctca aatcccgact gaccatcagc cgggacacct ccaggagcca agtcttctta    240
aaaatgaaca gtctgcaaac tgatgacaca gccatttact tctgtgccag agacccgtat    300
cagaactact ttgattactg gggccaagga gtcaaggtca cagtctcctc a             351

<210> SEQ ID NO 223
<211> LENGTH: 372
<212> TYPE: DNA
<213> ORGANISM: Artificial Sequence
<220> FEATURE:
<223> OTHER INFORMATION: Ab241 VH nucleic acid sequence

<400> SEQUENCE: 223
gaggtgcagc tggtggagtc tggaggaggc ttggtgcagc ctggaggctc cctgaaactc     60
tcctgtgcag cctcaggatt cacttccagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaag cagcctctac    240 ctgcaaatgg acagtctgcg gaccgaggac acggccactt attactgtac aacagagggg    300
atttatacta cggattatta cccttattgc tttaattatt ggggccaggg agtcatggtc    360
acagtctcct ca                                                       372

<210> SEQ ID NO 224
<211> LENGTH: 372
<212> TYPE: DNA
<213> ORGANISM: Artificial Sequence
<220> FEATURE:
<223> OTHER INFORMATION: Ab242 VH nucleic acid sequence

<400> SEQUENCE: 224
gaggtgcagc tggtggagtc tggaggaggc ttggtgcagc ctggaggctc cctgaaactc     60
tcctgtgcag cctcaggatt cacttccagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaag cagcctctac    240 ctgcaaatgg acagtctgcg gaccgaggac acggccactt attactgtac aacagagggg    300
atttatacta cggattatta cccttattgc tttaattatt ggggccaggg agtcatggtc    360
acagtctcct ca                                                       372

<210> SEQ ID NO 225
<211> LENGTH: 372
```

```
<212> TYPE: DNA
<213> ORGANISM: Artificial Sequence
<220> FEATURE:
<223> OTHER INFORMATION: Ab243 VH nucleic acid sequence

<400> SEQUENCE: 225
gaggtgcagc tggtggagtc tggaggaggc ttggtgcagc ctggaggctc cctgaaactc      60
tcctgtgcag cctcaggatt cactttcagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaag cagcctctac     240 ctgcaaatgg acagtctgcg gaccgaggac acggccactt attactgtac aacagagggg    300
atttatacta cggattatta cccttattgc tttaattatt ggggccaggg agtcatggtc    360
acagtctcct ca                                                         372

<210> SEQ ID NO 226
<211> LENGTH: 372
<212> TYPE: DNA
<213> ORGANISM: Artificial Sequence
<220> FEATURE:
<223> OTHER INFORMATION: Ab244 VH nucleic acid sequence

<400> SEQUENCE: 226
gaggtgcagc tggtggagtc tggaggaggc ttggtgcagc ctggaggctc cctgaaactc      60
tcctgtgcag cctcaggatt cactttcagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaag cagcctctac     240 ctgcaaatgg acagtctgcg gaccgaggac acggccactt attactgtac aacagagggg    300
atttatacta cggattatta cccttattgc tttaattatt ggggccaggg agtcatggtc    360
acagtctcct ca                                                         372

<210> SEQ ID NO 227
<211> LENGTH: 372
<212> TYPE: DNA
<213> ORGANISM: Artificial Sequence
<220> FEATURE:
<223> OTHER INFORMATION: Ab245 VH nucleic acid sequence

<400> SEQUENCE: 227
gaggtgcagc tggtggagtc tggaggaggc ttggtgcagc ctggaggctc cctgaaactc      60
tcctgtgcag cctcaggatt cactttcagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaag cagcctctac     240 ctgcaaatgg acagtctgcg gaccgaggac acggccactt attactgtac aacagagggg    300
atttatacta cggattatta cccttattgc tttaattatt ggggccaggg agtcatggtc    360
acagtctcct ca                                                         372

<210> SEQ ID NO 228
<211> LENGTH: 372
<212> TYPE: DNA
<213> ORGANISM: Artificial Sequence
<220> FEATURE:
<223> OTHER INFORMATION: Ab246 VH nucleic acid sequence

<400> SEQUENCE: 228
```

| | |
|---|---:|
| gaggtgcagc tggtggagtc tggaggaggc ttggtgcagc tggaggctc cctgaaactc | 60 |
| tcctgtgcag cctcaggatt cactttcagt gactcgtaca tggcctgggt ccgccaggct | 120 |
| ccgggcaagg gtctggaatg ggtcgcatcc attagttctg atggtggtgg cacttactat | 180 |
| cgagactccg tgaagggccg attcaccatc tccagagata tgcgaaaag cagcctctac | 240 |
| ctgcaaatga acagtctgcg gaccgaggac acggccactt attactgtac aacagagggg | 300 |
| atttatacta cggattatta cccttattgc tttaattatt ggggccaggg agtcatggtc | 360 |
| acagtctcct ca | 372 |

<210> SEQ ID NO 229
<211> LENGTH: 372
<212> TYPE: DNA
<213> ORGANISM: Artificial Sequence
<220> FEATURE:
<223> OTHER INFORMATION: Ab247 VH nucleic acid sequence

<400> SEQUENCE: 229

| | |
|---|---:|
| gaggtgcagc tggtggagtc tggaggaggc ttggtgcagc tggaggctc cctgaaactc | 60 |
| tcctgtgcag cctcaggatt cactttcagt gactcgtaca tggcctgggt ccgccaggct | 120 |
| ccgggcaagg gtctggaatg ggtcgcatcc attagttctg atggtggtgg cacttactat | 180 |
| cgagactccg tgaagggccg attcaccatc tccagagata tgcgaaaag cagcctctac | 240 |
| ctgcaaatga acagtctgcg gaccgaggac acggccactt attactgtac aacagagggg | 300 |
| atttatacta cggattatta cccttattgc tttaattatt ggggccaggg agtcatggtc | 360 |
| acagtctcct ca | 372 |

<210> SEQ ID NO 230
<211> LENGTH: 372
<212> TYPE: DNA
<213> ORGANISM: Artificial Sequence
<220> FEATURE:
<223> OTHER INFORMATION: Ab248 VH nucleic acid sequence

<400> SEQUENCE: 230

| | |
|---|---:|
| gaggtgcagc tggtggagtc tggaggaggc ttggtgcagc tggaggctc cctgaaactc | 60 |
| tcctgtgcag cctcaggatt cactttcagt gactcgtaca tggcctgggt ccgccaggct | 120 |
| ccgggcaagg gtctggaatg ggtcgcatcc attagttctg atggtggtgg cacttactat | 180 |
| cgagactccg tgaagggccg attcaccatc tccagagata tgcgaaaag cagcctctac | 240 |
| ctgcaaatga acagtctgcg gaccgaggac acggccactt attactgtac aacagagggg | 300 |
| atttatacta cggattatta cccttattgc tttaattatt ggggccaggg agtcatggtc | 360 |
| acagtctcct ca | 372 |

<210> SEQ ID NO 231
<211> LENGTH: 372
<212> TYPE: DNA
<213> ORGANISM: Artificial Sequence
<220> FEATURE:
<223> OTHER INFORMATION: Ab249 VH nucleic acid sequence

<400> SEQUENCE: 231

| | |
|---|---:|
| gaggtgcagc tggtggagtc tggaggaggc ttggtgcagc tggaggctc cctgaaactc | 60 |
| tcctgtgcag cctcaggatt cactttcagt gactcgtaca tggcctgggt ccgccaggct | 120 |
| ccgggcaagg gtctggaatg ggtcgcatcc attagttctg atggtggtgg cacttactat | 180 |
| cgagactccg tgaagggccg attcaccatc tccagagata tgcgaaaag cagcctctac | 240 |

```
ctgcaaatga acagtctgcg gaccgaggac acggccactt attactgtac aacagagggg    300
atttatacta cggattatta cccttattgc tttaattatt ggggccaggg agtcatggtc    360
acagtctcct ca                                                        372
```

<210> SEQ ID NO 232
<211> LENGTH: 372
<212> TYPE: DNA
<213> ORGANISM: Artificial Sequence
<220> FEATURE:
<223> OTHER INFORMATION: Ab250 VH nucleic acid sequence

<400> SEQUENCE: 232

```
gaggtgcagc tggtggagtc tggaggaggc ttggtgcagc ctggaggctc cctgaaactc    60
tcctgtgcag cctcaggatt cactttcagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaag cagcctctac    240 ctgcaaatga acagtctgcg gaccgaggac acggccactt attactgtac aacagagggg    300
atttatacta cggattatta cccttattgc tttaattatt ggggccaggg agtcatggtc    360
acagtctcct ca                                                        372
```

<210> SEQ ID NO 233
<211> LENGTH: 372
<212> TYPE: DNA
<213> ORGANISM: Artificial Sequence
<220> FEATURE:
<223> OTHER INFORMATION: Ab251 VH nucleic acid sequence

<400> SEQUENCE: 233

```
gaggtgcagc tggtggagtc tggaggaggc ttggtgcagc ctggaggctc cctgaaactc    60
tcctgtgcag cctcaggatt cactttcagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaaa cagcctctac    240 ctgcaaatga acagtctgcg gaccgaggac acggccactt attactgtac aacagagggg    300
atttatacta cggattatta cccttattgc tttaattatt ggggccaggg aaccatggtc    360
acagtctcct ca                                                        372
```

<210> SEQ ID NO 234
<211> LENGTH: 372
<212> TYPE: DNA
<213> ORGANISM: Artificial Sequence
<220> FEATURE:
<223> OTHER INFORMATION: Ab252 VH nucleic acid sequence

<400> SEQUENCE: 234

```
gaggtgcagc tggtggagtc tggaggaggc ttggtgcagc ctggaggctc cctgaaactc    60
tcctgtgcag cctcaggatt cactttcagt gactcgtaca tggcctgggt ccgccaggct    120
ccgggcaagg gtctggaatg ggtcgcatcc attagttctg atggtggtgg cacttactat    180
cgagactccg tgaagggccg attcaccatc tccagagata tgcgaaaaa cagcctctac    240 ctgcaaatga acagtctgcg gaccgaggac acggccactt attactgtac aacagagggg    300
atttatacta cggattatta cccttattgc tttaattatt ggggccaggg aaccatggtc    360
acagtctcct ca                                                        372
```

<210> SEQ ID NO 235
<211> LENGTH: 372
<212> TYPE: DNA
<213> ORGANISM: Artificial Sequence
<220> FEATURE:
<223> OTHER INFORMATION: Ab253 VH nucleic acid sequence

<400> SEQUENCE: 235

```
gaggtgcagc tggtggagtc tggaggaggc ttggtgcagc ctggaggctc cctgaaactc      60
tcctgtgcag cctcaggatt cactttcagt gactcgtaca tggcctgggt ccgccaggct     120
ccgggcaagg gtctggaatg ggtcgcatcc attagttctg atggtggtgg cacttactat     180
cgagactccg tgaagggccg attcaccatc tccagagata tgcgaaaaa cagcctctac      240
ctgcaaatga acagtctgcg gaccgaggac acggccactt attactgtac aacagagggg     300
atttatacta cggattatta cccttattgc tttaattatt ggggccaggg aaccatggtc     360
acagtctcct ca                                                          372
```

<210> SEQ ID NO 236
<211> LENGTH: 372
<212> TYPE: DNA
<213> ORGANISM: Artificial Sequence
<220> FEATURE:
<223> OTHER INFORMATION: Ab254 VH nucleic acid sequence

<400> SEQUENCE: 236

```
gaggtgcagc tggtggagtc tggaggaggc ttggtgcagc ctggaggctc cctgaaactc      60
tcctgtgcag cctcaggatt cactttcagt gactcgtaca tggcctgggt ccgccaggct     120
ccgggcaagg gtctggaatg ggtcgcatcc attagttctg atggtggtgg cacttactat     180
cgagactccg tgaagggccg attcaccatc tccagagata tgcgaaaaa cagcctctac      240
ctgcaaatga acagtctgcg gaccgaggac acggccactt attactgtac aacagagggg     300
atttatacta cggattatta cccttattgc tttaattatt ggggccaggg aaccatggtc     360
acagtctcct ca                                                          372
```

<210> SEQ ID NO 237
<211> LENGTH: 372
<212> TYPE: DNA
<213> ORGANISM: Artificial Sequence
<220> FEATURE:
<223> OTHER INFORMATION: Ab255 VH nucleic acid sequence

<400> SEQUENCE: 237

```
gaggtgcagc tggtggagtc tggaggaggc ttggtgcagc ctggaggctc cctgaaactc      60
tcctgtgcag cctcaggatt cactttcagt gactcgtaca tggcctgggt ccgccaggct     120
ccgggcaagg gtctggaatg ggtcgcatcc attagttctg atggtggtgg cacttactat     180
cgagactccg tgaagggccg attcaccatc tccagagata tgcgaaaaa cagcctctac      240
ctgcaaatga acagtctgcg gaccgaggac acggccactt attactgtac aacagagggg     300
atttatacta cggattatta cccttattgc tttaattatt ggggccaggg aaccatggtc     360
acagtctcct ca                                                          372
```

<210> SEQ ID NO 238
<211> LENGTH: 107
<212> TYPE: PRT
<213> ORGANISM: Artificial Sequence
<220> FEATURE:
<223> OTHER INFORMATION: Ab241-Ab255 VL consensus

```
<220> FEATURE:
<221> NAME/KEY: VARIANT
<222> LOCATION: 45
<223> OTHER INFORMATION: Xaa = Lys or Gln
<220> FEATURE:
<221> NAME/KEY: VARIANT
<222> LOCATION: 65, 67
<223> OTHER INFORMATION: Xaa = Ser or Phe
<220> FEATURE:
<221> NAME/KEY: VARIANT
<222> LOCATION: 71
<223> OTHER INFORMATION: Xaa = Tyr or Phe
<220> FEATURE:
<221> NAME/KEY: VARIANT
<222> LOCATION: 74
<223> OTHER INFORMATION: Xaa = Thr or Lys
<220> FEATURE:
<221> NAME/KEY: VARIANT
<222> LOCATION: 76
<223> OTHER INFORMATION: Xaa = Ser or Asn
<220> FEATURE:
<221> NAME/KEY: VARIANT
<222> LOCATION: 80
<223> OTHER INFORMATION: Xaa = Pro or Ser
<220> FEATURE:
<221> NAME/KEY: VARIANT
<222> LOCATION: 85
<223> OTHER INFORMATION: Xaa = Ile or Thr

<400> SEQUENCE: 238

Asp Ile Gln Met Thr Gln Ser Pro Ser Leu Ser Ala Ser Val Gly
1               5                   10                  15

Asp Arg Val Thr Ile Thr Cys Leu Ala Ser Ala Asp Ile His Ser Asn
                20                  25                  30

Leu Ala Trp Tyr Gln Gln Lys Pro Gly Lys Ala Pro Xaa Leu Leu Ile
            35                  40                  45

Tyr Tyr Gly Asn Asn Leu Asn Asp Gly Val Pro Ser Arg Phe Ser Gly
        50                  55                  60

Xaa Gly Xaa Gly Thr Asp Xaa Thr Leu Xaa Ile Xaa Ser Leu Gln Xaa
65              70                  75                  80

Glu Asp Val Ala Xaa Tyr Phe Cys Gln Gln Ser Tyr Asp Ser Pro Pro
                85                  90                  95

Thr Phe Gly Gln Gly Thr Lys Leu Glu Ile Lys
            100                 105

<210> SEQ ID NO 239
<211> LENGTH: 120
<212> TYPE: PRT
<213> ORGANISM: Artificial Sequence
<220> FEATURE:
<223> OTHER INFORMATION: Ab241-Ab255 VH consensus
<220> FEATURE:
<221> NAME/KEY: VARIANT
<222> LOCATION: 77
<223> OTHER INFORMATION: Xaa = Ser or Asn
<220> FEATURE:
<221> NAME/KEY: VARIANT
<222> LOCATION: 84
<223> OTHER INFORMATION: Xaa = Asp or Asn
<220> FEATURE:
<221> NAME/KEY: VARIANT
<222> LOCATION: 118
<223> OTHER INFORMATION: Xaa = Thr or Val

<400> SEQUENCE: 239

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ser
                20                  25                  30
```

```
Tyr Met Ala Trp Val Arg Gln Ala Pro Gly Lys Gly Leu Glu Trp Val
        35                  40                  45

Ala Ser Ile Ser Ser Asp Gly Gly Thr Tyr Tyr Arg Asp Ser Val
    50                  55                  60

Lys Gly Arg Phe Thr Ile Ser Arg Asp Asn Ala Lys Xaa Ser Leu Tyr
65                  70                  75                  80

Leu Gln Met Xaa Ser Leu Arg Thr Glu Asp Thr Ala Thr Tyr Tyr Cys
            85                  90                  95

Thr Thr Glu Gly Ile Tyr Thr Thr Asp Tyr Tyr Pro Tyr Cys Phe Asn
                100                 105                 110

Tyr Trp Gly Gln Gly Xaa Met Val
        115                 120

<210> SEQ ID NO 240
<211> LENGTH: 23
<212> TYPE: PRT
<213> ORGANISM: Artificial Sequence
<220> FEATURE:
<223> OTHER INFORMATION: Ab241-Ab255 LFW1 consensus Kabat

<400> SEQUENCE: 240

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 241
<211> LENGTH: 15
<212> TYPE: PRT
<213> ORGANISM: Artificial Sequence
<220> FEATURE:
<223> OTHER INFORMATION: Ab241-Ab255 LFW2 consensus Kabat
<220> FEATURE:
<221> NAME/KEY: VARIANT
<222> LOCATION: 11
<223> OTHER INFORMATION: Xaa = Lys or Gln

<400> SEQUENCE: 241

Trp Tyr Gln Gln Lys Pro Gly Lys Ala Pro Xaa Leu Leu Ile Tyr
1               5                   10                  15

<210> SEQ ID NO 242
<211> LENGTH: 32
<212> TYPE: PRT
<213> ORGANISM: Artificial Sequence
<220> FEATURE:
<223> OTHER INFORMATION: Ab241-Ab255 LFW3 consensus Kabat
<220> FEATURE:
<221> NAME/KEY: VARIANT
<222> LOCATION: 9, 11
<223> OTHER INFORMATION: Xaa = Ser or Phe
<220> FEATURE:
<221> NAME/KEY: VARIANT
<222> LOCATION: 15
<223> OTHER INFORMATION: Xaa = Tyr or Phe
<220> FEATURE:
<221> NAME/KEY: VARIANT
<222> LOCATION: 18
<223> OTHER INFORMATION: Xaa = Thr or Lys
<220> FEATURE:
<221> NAME/KEY: VARIANT
<222> LOCATION: 20
<223> OTHER INFORMATION: Xaa = Ser or Asn
<220> FEATURE:
<221> NAME/KEY: VARIANT
<222> LOCATION: 24
<223> OTHER INFORMATION: Xaa = Pro or Ser
```

```
<220> FEATURE:
<221> NAME/KEY: VARIANT
<222> LOCATION: 29
<223> OTHER INFORMATION: Xaa = Ile or Thr

<400> SEQUENCE: 242

Gly Val Pro Ser Arg Phe Ser Gly Xaa Gly Xaa Gly Thr Asp Xaa Thr
1               5                   10                  15

Leu Xaa Ile Xaa Ser Leu Gln Xaa Glu Asp Val Ala Xaa Tyr Phe Cys
            20                  25                  30

<210> SEQ ID NO 243
<211> LENGTH: 10
<212> TYPE: PRT
<213> ORGANISM: Artificial Sequence
<220> FEATURE:
<223> OTHER INFORMATION: Ab241-Ab255 LFW4 consensus Kabat

<400> SEQUENCE: 243

Phe Gly Gln Gly Thr Lys Leu Glu Ile Lys
1               5                   10

<210> SEQ ID NO 244
<211> LENGTH: 30
<212> TYPE: PRT
<213> ORGANISM: Artificial Sequence
<220> FEATURE:
<223> OTHER INFORMATION: Ab241-Ab255 HFW1 consensus Kabat

<400> SEQUENCE: 244

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 245
<211> LENGTH: 14
<212> TYPE: PRT
<213> ORGANISM: Artificial Sequence
<220> FEATURE:
<223> OTHER INFORMATION: Ab241-Ab255 HFW2 consensus Kabat

<400> SEQUENCE: 245

Trp Val Arg Gln Ala Pro Gly Lys Gly Leu Glu Trp Val Ala
1               5                   10

<210> SEQ ID NO 246
<211> LENGTH: 32
<212> TYPE: PRT
<213> ORGANISM: Artificial Sequence
<220> FEATURE:
<223> OTHER INFORMATION: Ab241-Ab255 HFW3 consensus Kabat
<220> FEATURE:
<221> NAME/KEY: VARIANT
<222> LOCATION: 11
<223> OTHER INFORMATION: Xaa = Ser or Asn
<220> FEATURE:
<221> NAME/KEY: VARIANT
<222> LOCATION: 18
<223> OTHER INFORMATION: Xaa = Asp or Asn

<400> SEQUENCE: 246

Arg Phe Thr Ile Ser Arg Asp Asn Ala Lys Xaa Ser Leu Tyr Leu Gln
1               5                   10                  15

Met Xaa Ser Leu Arg Thr Glu Asp Thr Ala Thr Tyr Tyr Cys Thr Thr
            20                  25                  30
```

```
<210> SEQ ID NO 247
<211> LENGTH: 7
<212> TYPE: PRT
<213> ORGANISM: Artificial Sequence
<220> FEATURE:
<223> OTHER INFORMATION: Ab241-Ab255 HFW4 consensus Kabat
<220> FEATURE:
<221> NAME/KEY: VARIANT
<222> LOCATION: 5
<223> OTHER INFORMATION: Xaa = Thr or Val

<400> SEQUENCE: 247

Trp Gly Gln Gly Xaa Met Val
1               5

<210> SEQ ID NO 248
<211> LENGTH: 10
<212> TYPE: PRT
<213> ORGANISM: Artificial Sequence
<220> FEATURE:
<223> OTHER INFORMATION: Ab235/Ab236 LCDR1 consensus Chothia
<220> FEATURE:
<221> NAME/KEY: VARIANT
<222> LOCATION: 7
<223> OTHER INFORMATION: Xaa = Ser or Asn

<400> SEQUENCE: 248

Ser Ala Ser Ser Ser Val Xaa Tyr Met Phe
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Ab235/Ab236 LCDR2 consensus Chothia
<220> FEATURE:
<221> NAME/KEY: VARIANT
<222> LOCATION: 2
<223> OTHER INFORMATION: Xaa = Tyr or Asp
<220> FEATURE:
<221> NAME/KEY: VARIANT
<222> LOCATION: 3
<223> OTHER INFORMATION: Xaa = Phe or Ser
<220> FEATURE:
<221> NAME/KEY: VARIANT
<222> LOCATION: 4
<223> OTHER INFORMATION: Xaa = Asn or Asp

<400> SEQUENCE: 249

Asp Xaa Xaa Xaa Leu Ala Ser
1               5

<210> SEQ ID NO 250
<211> LENGTH: 9
<212> TYPE: PRT
<213> ORGANISM: Artificial Sequence
<220> FEATURE:
<223> OTHER INFORMATION: Ab235/Ab236 LCDR3 consensus Chothia
<220> FEATURE:
<221> NAME/KEY: VARIANT
<222> LOCATION: 5
<223> OTHER INFORMATION: Xaa = Tyr or Asn
<220> FEATURE:
<221> NAME/KEY: VARIANT
<222> LOCATION: 6
<223> OTHER INFORMATION: Xaa = Tyr or Absent

<400> SEQUENCE: 250

Gln Gln Trp Ser Xaa Xaa Pro Tyr Thr
1               5
```

```
<210> SEQ ID NO 251
<211> LENGTH: 7
<212> TYPE: PRT
<213> ORGANISM: Artificial Sequence
<220> FEATURE:
<223> OTHER INFORMATION: Ab235/Ab236 HCDR1 consensus Chothia
<220> FEATURE:
<221> NAME/KEY: VARIANT
<222> LOCATION: 3
<223> OTHER INFORMATION: Xaa = Ile or Thr
<220> FEATURE:
<221> NAME/KEY: VARIANT
<222> LOCATION: 6
<223> OTHER INFORMATION: Xaa = Ser or Asn

<400> SEQUENCE: 251

Gly Tyr Xaa Phe Ser Xaa Tyr
1               5

<210> SEQ ID NO 252
<211> LENGTH: 6
<212> TYPE: PRT
<213> ORGANISM: Artificial Sequence
<220> FEATURE:
<223> OTHER INFORMATION: Ab235/Ab236 HCDR2 consensus Chothia
<220> FEATURE:
<221> NAME/KEY: VARIANT
<222> LOCATION: 6
<223> OTHER INFORMATION: Xaa = Tyr or Phe

<400> SEQUENCE: 252

Leu Pro Gly Ser Asp Xaa
1               5

<210> SEQ ID NO 253
<211> LENGTH: 8
<212> TYPE: PRT
<213> ORGANISM: Artificial Sequence
<220> FEATURE:
<223> OTHER INFORMATION: Ab235/Ab236 HCDR3 consensus Chothia
<220> FEATURE:
<221> NAME/KEY: VARIANT
<222> LOCATION: 4
<223> OTHER INFORMATION: Xaa = Ile or Val

<400> SEQUENCE: 253

Pro Ser Thr Xaa Pro Pro Asp Cys
1               5

<210> SEQ ID NO 254
<211> LENGTH: 7
<212> TYPE: PRT
<213> ORGANISM: Artificial Sequence
<220> FEATURE:
<223> OTHER INFORMATION: Ab235/Ab236 HCDR1 consensus Chothia
<220> FEATURE:
<221> NAME/KEY: VARIANT
<222> LOCATION: 3, 5
<223> OTHER INFORMATION: Xaa = Thr or Ser
<220> FEATURE:
<221> NAME/KEY: VARIANT
<222> LOCATION: 7
<223> OTHER INFORMATION: Xaa = Ser or Cys

<400> SEQUENCE: 254

Gly Phe Xaa Phe Xaa Asp Xaa
1               5

<210> SEQ ID NO 255
```

```
<211> LENGTH: 16
<212> TYPE: PRT
<213> ORGANISM: Artificial Sequence
<220> FEATURE:
<223> OTHER INFORMATION: Ab235/Ab236 HCDR3 consensus Chothia
<220> FEATURE:
<221> NAME/KEY: VARIANT
<222> LOCATION: 2
<223> OTHER INFORMATION: Xaa = Gly or Arg
<220> FEATURE:
<221> NAME/KEY: VARIANT
<222> LOCATION: 3
<223> OTHER INFORMATION: Xaa = Ile or Tyr
<220> FEATURE:
<221> NAME/KEY: VARIANT
<222> LOCATION: 5
<223> OTHER INFORMATION: Xaa = Thr or Asp
<220> FEATURE:
<221> NAME/KEY: VARIANT
<222> LOCATION: 6
<223> OTHER INFORMATION: Xaa = Thr or Gly
<220> FEATURE:
<221> NAME/KEY: VARIANT
<222> LOCATION: 7
<223> OTHER INFORMATION: Xaa = Asp or Thr
<220> FEATURE:
<221> NAME/KEY: VARIANT
<222> LOCATION: 10
<223> OTHER INFORMATION: Xaa = Pro or Gly
<220> FEATURE:
<221> NAME/KEY: VARIANT
<222> LOCATION: 12
<223> OTHER INFORMATION: Xaa = Cys or Trp
<220> FEATURE:
<221> NAME/KEY: VARIANT
<222> LOCATION: 13
<223> OTHER INFORMATION: Xaa = Tyr or Absent
<220> FEATURE:
<221> NAME/KEY: VARIANT
<222> LOCATION: 15
<223> OTHER INFORMATION: Xaa = Asn or Asp
<220> FEATURE:
<221> NAME/KEY: VARIANT
<222> LOCATION: 16
<223> OTHER INFORMATION: Xaa = Tyr or Phe

<400> SEQUENCE: 255

Glu Xaa Xaa Tyr Xaa Xaa Xaa Tyr Tyr Xaa Tyr Xaa Xaa Phe Xaa Xaa
1               5                   10                  15

<210> SEQ ID NO 256
<211> LENGTH: 5
<212> TYPE: PRT
<213> ORGANISM: Artificial Sequence
<220> FEATURE:
<223> OTHER INFORMATION: Ab235/Ab236 LCDR1 consensus IMGT
<220> FEATURE:
<221> NAME/KEY: VARIANT
<222> LOCATION: 4
<223> OTHER INFORMATION: Xaa = Asn or Ser

<400> SEQUENCE: 256

Ser Ser Val Xaa Tyr
1               5

<210> SEQ ID NO 257
<211> LENGTH: 3
<212> TYPE: PRT
<213> ORGANISM: Artificial Sequence
<220> FEATURE:
<223> OTHER INFORMATION: Ab235/Ab236 LCDR2 consensus IMGT
<220> FEATURE:
<221> NAME/KEY: VARIANT
<222> LOCATION: 3
<223> OTHER INFORMATION: Xaa = Phe or Ser
```

<400> SEQUENCE: 257

Asp Thr Xaa
1

<210> SEQ ID NO 258
<211> LENGTH: 9
<212> TYPE: PRT
<213> ORGANISM: Artificial Sequence
<220> FEATURE:
<223> OTHER INFORMATION: Ab235/Ab236 LCDR3 consensus IMGT
<220> FEATURE:
<221> NAME/KEY: VARIANT
<222> LOCATION: 5
<223> OTHER INFORMATION: Xaa = Ile or Asn

<400> SEQUENCE: 258

Gln Gln Trp Ser Xaa Tyr Pro Tyr Thr
1               5

<210> SEQ ID NO 259
<211> LENGTH: 8
<212> TYPE: PRT
<213> ORGANISM: Artificial Sequence
<220> FEATURE:
<223> OTHER INFORMATION: Ab235/Ab236 HCDR1 consensus IMGT
<220> FEATURE:
<221> NAME/KEY: VARIANT
<222> LOCATION: 3
<223> OTHER INFORMATION: Xaa = Thr or Ile
<220> FEATURE:
<221> NAME/KEY: VARIANT
<222> LOCATION: 6
<223> OTHER INFORMATION: Xaa = Asn or Ser

<400> SEQUENCE: 259

Gly Tyr Xaa Phe Ser Xaa Tyr Trp
1               5

<210> SEQ ID NO 260
<211> LENGTH: 8
<212> TYPE: PRT
<213> ORGANISM: Artificial Sequence
<220> FEATURE:
<223> OTHER INFORMATION: Ab235/Ab236 HCDR2 consensus IMGT
<220> FEATURE:
<221> NAME/KEY: VARIANT
<222> LOCATION: 7
<223> OTHER INFORMATION: Xaa = Tyr or Phe
<220> FEATURE:
<221> NAME/KEY: VARIANT
<222> LOCATION: 8
<223> OTHER INFORMATION: Xaa = Ile or Thr

<400> SEQUENCE: 260

Ile Leu Pro Gly Ser Asp Xaa Xaa
1               5

<210> SEQ ID NO 261
<211> LENGTH: 10
<212> TYPE: PRT
<213> ORGANISM: Artificial Sequence
<220> FEATURE:
<223> OTHER INFORMATION: Ab235/Ab236 HCDR3 consensus IMGT
<220> FEATURE:
<221> NAME/KEY: VARIANT
<222> LOCATION: 6
<223> OTHER INFORMATION: Xaa = Ile or Val

<400> SEQUENCE: 261

```
Ala Arg Pro Ser Thr Xaa Pro Pro Asp Cys
1               5                   10

<210> SEQ ID NO 262
<211> LENGTH: 9
<212> TYPE: PRT
<213> ORGANISM: Artificial Sequence
<220> FEATURE:
<223> OTHER INFORMATION: Ab237/Ab239/Ab241-Ab255 HCDR1 consensus IMGT
<220> FEATURE:
<221> NAME/KEY: VARIANT
<222> LOCATION: 3, 5
<223> OTHER INFORMATION: Xaa = Ser or Thr
<220> FEATURE:
<221> NAME/KEY: VARIANT
<222> LOCATION: 7
<223> OTHER INFORMATION: Xaa = Cys or Ser
<220> FEATURE:
<221> NAME/KEY: VARIANT
<222> LOCATION: 9
<223> OTHER INFORMATION: Xaa = Ile or Absent

<400> SEQUENCE: 262

Gly Phe Xaa Phe Xaa Asp Xaa Tyr Xaa
1               5

<210> SEQ ID NO 263
<211> LENGTH: 18
<212> TYPE: PRT
<213> ORGANISM: Artificial Sequence
<220> FEATURE:
<223> OTHER INFORMATION: Ab237/Ab239/Ab241-Ab255 HCDR3 consensus IMGT
<220> FEATURE:
<221> NAME/KEY: VARIANT
<222> LOCATION: 4
<223> OTHER INFORMATION: Xaa = Arg or Gly
<220> FEATURE:
<221> NAME/KEY: VARIANT
<222> LOCATION: 5
<223> OTHER INFORMATION: Xaa = Ile or Tyr
<220> FEATURE:
<221> NAME/KEY: VARIANT
<222> LOCATION: 7
<223> OTHER INFORMATION: Xaa = Thr or Asp
<220> FEATURE:
<221> NAME/KEY: VARIANT
<222> LOCATION: 8
<223> OTHER INFORMATION: Xaa = Gly or Thr
<220> FEATURE:
<221> NAME/KEY: VARIANT
<222> LOCATION: 9, 12
<223> OTHER INFORMATION: Xaa = Thr or Asp
<220> FEATURE:
<221> NAME/KEY: VARIANT
<222> LOCATION: 14
<223> OTHER INFORMATION: Xaa = Gly or Pro
<220> FEATURE:
<221> NAME/KEY: VARIANT
<222> LOCATION: 15
<223> OTHER INFORMATION: Xaa = Cys or Absent
<220> FEATURE:
<221> NAME/KEY: VARIANT
<222> LOCATION: 16
<223> OTHER INFORMATION: Xaa = Phe or Absent
<220> FEATURE:
<221> NAME/KEY: VARIANT
<222> LOCATION: 17
<223> OTHER INFORMATION: Xaa = Asn or Absent
<220> FEATURE:
<221> NAME/KEY: VARIANT
<222> LOCATION: 18
<223> OTHER INFORMATION: Xaa = Tyr or Absent

<400> SEQUENCE: 263

Thr Thr Glu Xaa Xaa Tyr Xaa Xaa Xaa Tyr Tyr Xaa Tyr Xaa Xaa Xaa
```

```
1               5                  10                  15

Xaa Xaa

<210> SEQ ID NO 264
<211> LENGTH: 8
<212> TYPE: PRT
<213> ORGANISM: Artificial Sequence
<220> FEATURE:
<223> OTHER INFORMATION: Ab241-Ab255 LCDR3 Chothia

<400> SEQUENCE: 264

Pro Pro Thr Phe Gly Gln Gly Thr
1               5

<210> SEQ ID NO 265
<211> LENGTH: 5
<212> TYPE: PRT
<213> ORGANISM: Artificial Sequence
<220> FEATURE:
<223> OTHER INFORMATION: Ab235 HCDR1

<400> SEQUENCE: 265

Asn Tyr Trp Ile Glu
1               5

<210> SEQ ID NO 266
<211> LENGTH: 5
<212> TYPE: PRT
<213> ORGANISM: Artificial Sequence
<220> FEATURE:
<223> OTHER INFORMATION: Ab236 HCDR1

<400> SEQUENCE: 266

Ser Tyr Trp Ile Glu
1               5

<210> SEQ ID NO 267
<211> LENGTH: 7
<212> TYPE: PRT
<213> ORGANISM: Artificial Sequence
<220> FEATURE:
<223> OTHER INFORMATION: Ab238, HCDR1

<400> SEQUENCE: 267

Thr Tyr Gly Met Gly Val Ala
1               5

<210> SEQ ID NO 268
<211> LENGTH: 32
<212> TYPE: PRT
<213> ORGANISM: Artificial Sequence
<220> FEATURE:
<223> OTHER INFORMATION: Ab235 VH FR3

<400> SEQUENCE: 268

Lys Ala Thr Phe Thr Ala Asp Thr Ser Ser Asn Thr Ala Tyr Met Gln
1               5                  10                  15

Leu Ser Ser Leu Thr Ser Glu Asp Ser Ala Val Tyr Tyr Cys Ala Arg
                20                  25                  30

<210> SEQ ID NO 269
<211> LENGTH: 32
<212> TYPE: PRT
<213> ORGANISM: Artificial Sequence
<220> FEATURE:
<223> OTHER INFORMATION: Ab236 VH FR3
```

```
<400> SEQUENCE: 269

Lys Ala Thr Phe Thr Ala Asp Thr Ser Ser Asn Thr Ala Tyr Met Gln
1               5                   10                  15

Leu Ser Asn Leu Thr Ser Glu Asp Ser Ala Val Tyr Tyr Cys Ala Arg
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Ab237 VH FR3

<400> SEQUENCE: 270

Arg Phe Ser Ile Ser Arg Asp Asn Ala Lys Ser Ser Leu Tyr Leu Gln
1               5                   10                  15

Met Asp Ser Leu Arg Ser Glu Asp Thr Ala Thr Tyr Tyr Cys Thr Thr
            20                  25                  30

<210> SEQ ID NO 271
<211> LENGTH: 14
<212> TYPE: PRT
<213> ORGANISM: Artificial Sequence
<220> FEATURE:
<223> OTHER INFORMATION: Ab238 VH FR2

<400> SEQUENCE: 271

Trp Ile Arg Gln Pro Ser Gly Lys Asp Leu Glu Trp Leu Ala
1               5                   10

<210> SEQ ID NO 272
<211> LENGTH: 8
<212> TYPE: PRT
<213> ORGANISM: Artificial Sequence
<220> FEATURE:
<223> OTHER INFORMATION: Ab237, Ab241-Ab255 LCDR3 Chothia consensus
<220> FEATURE:
<221> NAME/KEY: VARIANT
<222> LOCATION: 6
<223> OTHER INFORMATION: Xaa = Ala or Gln

<400> SEQUENCE: 272

Pro Pro Thr Phe Gly Xaa Gly Thr
1               5

<210> SEQ ID NO 273
<211> LENGTH: 126
<212> TYPE: PRT
<213> ORGANISM: Artificial Sequence
<220> FEATURE:
<223> OTHER INFORMATION: Ab235/Ab236 Consensus VL (With Signal Sequence)
<220> FEATURE:
<221> NAME/KEY: misc_feature
<222> LOCATION: (32)..(32)
<223> OTHER INFORMATION: Xaa = Thr or Ala
<220> FEATURE:
<221> NAME/KEY: misc_feature
<222> LOCATION: (49)..(49)
<223> OTHER INFORMATION: Xaa = Asn or Ser
<220> FEATURE:
<221> NAME/KEY: misc_feature
<222> LOCATION: (58)..(58)
<223> OTHER INFORMATION: Xaa = Ala or Pro
<220> FEATURE:
<221> NAME/KEY: misc_feature
<222> LOCATION: (70)..(70)
<223> OTHER INFORMATION: Xaa = Phe or Ser
<220> FEATURE:
```

```
<221> NAME/KEY: misc_feature
<222> LOCATION: (71)..(71)
<223> OTHER INFORMATION: Xaa = Asn or Asp
<220> FEATURE:
<221> NAME/KEY: misc_feature
<222> LOCATION: (111)..(111)
<223> OTHER INFORMATION: Xaa = Ile or Asn

<400> SEQUENCE: 273

Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Ile Met Ser Xaa
                20                  25                  30

Ser Pro Gly Glu Lys Val Thr Met Thr Cys Ser Ala Ser Ser Ser Val
            35                  40                  45

Xaa Tyr Met Phe Trp Tyr Gln Gln Lys Xaa Gly Ser Ser Pro Arg Leu
        50                  55                  60

Leu Ile Tyr Asp Thr Xaa Xaa Leu Ala Ser Gly Val Pro Val Arg Phe
65                  70                  75                  80

Ser Gly Ser Gly Ser Gly Thr Ser Tyr Ser Leu Thr Ile Ser Arg Met
                85                  90                  95

Glu Ala Glu Asp Ala Ala Thr Tyr Tyr Cys Gln Gln Trp Ser Xaa Ile
            100                 105                 110

Tyr Pro Tyr Thr Phe Gly Gly Gly Thr Lys Leu Glu Ile Lys
        115                 120                 125

<210> SEQ ID NO 274
<211> LENGTH: 17
<212> TYPE: PRT
<213> ORGANISM: Artificial Sequence
<220> FEATURE:
<223> OTHER INFORMATION: Ab256 LCDR1

<400> SEQUENCE: 274

Lys Ser Ser Gln Ser Leu Leu Tyr Thr Ser Ser Gln Lys Asn Tyr Leu
1               5                   10                  15

Ala

<210> SEQ ID NO 275
<211> LENGTH: 7
<212> TYPE: PRT
<213> ORGANISM: Artificial Sequence
<220> FEATURE:
<223> OTHER INFORMATION: Ab256 LCDR2

<400> SEQUENCE: 275

Trp Ala Ser Thr Arg Glu Ser
1               5

<210> SEQ ID NO 276
<211> LENGTH: 9
<212> TYPE: PRT
<213> ORGANISM: Artificial Sequence
<220> FEATURE:
<223> OTHER INFORMATION: Ab256 LCDR3

<400> SEQUENCE: 276

Gln Gln Tyr Tyr Ala Tyr Pro Trp Thr
1               5

<210> SEQ ID NO 277
<211> LENGTH: 5
<212> TYPE: PRT
```

<213> ORGANISM: Artificial Sequence
<220> FEATURE:
<223> OTHER INFORMATION: Ab256 HCDR1

<400> SEQUENCE: 277

Ser Tyr Trp Leu His
1               5

<210> SEQ ID NO 278
<211> LENGTH: 17
<212> TYPE: PRT
<213> ORGANISM: Artificial Sequence
<220> FEATURE:
<223> OTHER INFORMATION: Ab256 HCDR2

<400> SEQUENCE: 278

Met Ile Asp Pro Ser Asn Ser Asp Thr Arg Phe Asn Pro Asn Phe Lys
1               5                   10                  15
Asp

<210> SEQ ID NO 279
<211> LENGTH: 10
<212> TYPE: PRT
<213> ORGANISM: Artificial Sequence
<220> FEATURE:
<223> OTHER INFORMATION: Ab256 HCDR3

<400> SEQUENCE: 279

Tyr Arg Ser Tyr Val Thr Pro Leu Asp Tyr
1               5                   10

<210> SEQ ID NO 280
<211> LENGTH: 12
<212> TYPE: PRT
<213> ORGANISM: Artificial Sequence
<220> FEATURE:
<223> OTHER INFORMATION: Ab257 LCDR1

<400> SEQUENCE: 280

Ser Val Ser Ser Ser Val Ser Ser Ile Tyr Leu His
1               5                   10

<210> SEQ ID NO 281
<211> LENGTH: 7
<212> TYPE: PRT
<213> ORGANISM: Artificial Sequence
<220> FEATURE:
<223> OTHER INFORMATION: Ab257 LCDR2

<400> SEQUENCE: 281

Ser Thr Ser Asn Leu Ala Ser
1               5

<210> SEQ ID NO 282
<211> LENGTH: 9
<212> TYPE: PRT
<213> ORGANISM: Artificial Sequence
<220> FEATURE:
<223> OTHER INFORMATION: Ab257 LCDR3

<400> SEQUENCE: 282

Gln Val Tyr Ser Gly Tyr Pro Leu Thr
1               5

<210> SEQ ID NO 283
<211> LENGTH: 5

```
<212> TYPE: PRT
<213> ORGANISM: Artificial Sequence
<220> FEATURE:
<223> OTHER INFORMATION: Ab257 HCDR1

<400> SEQUENCE: 283

Asp Tyr Tyr Met His
1               5

<210> SEQ ID NO 284
<211> LENGTH: 17
<212> TYPE: PRT
<213> ORGANISM: Artificial Sequence
<220> FEATURE:
<223> OTHER INFORMATION: Ab257 HCDR2

<400> SEQUENCE: 284

Arg Val Asn Pro Asn Arg Arg Gly Thr Thr Tyr Asn Gln Lys Phe Glu
1               5                   10                  15

Gly

<210> SEQ ID NO 285
<211> LENGTH: 6
<212> TYPE: PRT
<213> ORGANISM: Artificial Sequence
<220> FEATURE:
<223> OTHER INFORMATION: Ab257 HCDR3

<400> SEQUENCE: 285

Ala Asn Trp Leu Asp Tyr
1               5

<210> SEQ ID NO 286
<211> LENGTH: 15
<212> TYPE: PRT
<213> ORGANISM: Artificial Sequence
<220> FEATURE:
<223> OTHER INFORMATION: Ab258 LCDR1

<400> SEQUENCE: 286

Lys Ser Ser Glu Ser Val Asp Ser Tyr Ala Asn Ser Phe Met His
1               5                   10                  15

<210> SEQ ID NO 287
<211> LENGTH: 7
<212> TYPE: PRT
<213> ORGANISM: Artificial Sequence
<220> FEATURE:
<223> OTHER INFORMATION: Ab258 LCDR2

<400> SEQUENCE: 287

Arg Ala Ser Thr Arg Glu Ser
1               5

<210> SEQ ID NO 288
<211> LENGTH: 9
<212> TYPE: PRT
<213> ORGANISM: Artificial Sequence
<220> FEATURE:
<223> OTHER INFORMATION: Ab258 LCDR3

<400> SEQUENCE: 288

Gln Gln Ser Lys Glu Asp Pro Leu Thr
1               5

<210> SEQ ID NO 289
```

```
<211> LENGTH: 5
<212> TYPE: PRT
<213> ORGANISM: Artificial Sequence
<220> FEATURE:
<223> OTHER INFORMATION: Ab258 HCDR1

<400> SEQUENCE: 289

Ala Tyr Thr Met His
1               5

<210> SEQ ID NO 290
<211> LENGTH: 17
<212> TYPE: PRT
<213> ORGANISM: Artificial Sequence
<220> FEATURE:
<223> OTHER INFORMATION: Ab258 HCDR2

<400> SEQUENCE: 290

Trp Ile Lys Pro Asn Asn Gly Leu Ala Asn Tyr Ala Gln Lys Phe Gln
1               5                   10                  15

Gly

<210> SEQ ID NO 291
<211> LENGTH: 9
<212> TYPE: PRT
<213> ORGANISM: Artificial Sequence
<220> FEATURE:
<223> OTHER INFORMATION: Ab258 HCDR3

<400> SEQUENCE: 291

Ser Glu Ile Thr Thr Glu Phe Asp Tyr
1               5

<210> SEQ ID NO 292
<211> LENGTH: 119
<212> TYPE: PRT
<213> ORGANISM: Artificial Sequence
<220> FEATURE:
<223> OTHER INFORMATION: Ab256 VH

<400> SEQUENCE: 292

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
        115

<210> SEQ ID NO 293
<211> LENGTH: 114
<212> TYPE: PRT
<213> ORGANISM: Artificial Sequence
<220> FEATURE:
```

<223> OTHER INFORMATION: Ab256 VL

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg

<210> SEQ ID NO 294
<211> LENGTH: 115
<212> TYPE: PRT
<213> ORGANISM: Artificial Sequence
<220> FEATURE:
<223> OTHER INFORMATION: Ab257 VH

<400> SEQUENCE: 294

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser
        115

<210> SEQ ID NO 295
<211> LENGTH: 109
<212> TYPE: PRT
<213> ORGANISM: Artificial Sequence
<220> FEATURE:
<223> OTHER INFORMATION: Ab257 VL

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
        35                  40                  45

```
Ile Tyr Ser Thr Ser Asn Leu Ala Ser Gly Val Pro Ser Arg Phe Ser
         50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Val Tyr Ser Gly Tyr Pro
                 85                  90                  95

Leu Thr Phe Gly Gly Gly Thr Lys Val Glu Ile Lys Arg
            100                 105
```

<210> SEQ ID NO 296
<211> LENGTH: 118
<212> TYPE: PRT
<213> ORGANISM: Artificial Sequence
<220> FEATURE:
<223> OTHER INFORMATION: Ab258 VH

<400> SEQUENCE: 296

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Thr Ala Tyr
             20                  25                  30

Thr Met His Trp Val Arg Gln Ala Pro Gly Gln Gly Leu Glu Trp Met
         35                  40                  45

Gly Trp Ile Lys Pro Asn Asn Gly Leu Ala Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Glu Ile Thr Thr Glu Phe Asp Tyr Trp Gly Gln Gly Thr
            100                 105                 110

Leu Val Thr Val Ser Ser
        115
```

<210> SEQ ID NO 297
<211> LENGTH: 112
<212> TYPE: PRT
<213> ORGANISM: Artificial Sequence
<220> FEATURE:
<223> OTHER INFORMATION: Ab258 VL

<400> SEQUENCE: 297

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Glu Ser Val Asp Ser Tyr
             20                  25                  30

Ala Asn Ser Phe Met His Trp Tyr Gln Gln Lys Pro Gly Gln Pro Pro
         35                  40                  45

Lys Leu Leu Ile Tyr Arg Ala Ser Thr Arg Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Asp Pro Leu Thr Phe Gly Gly Gly Thr Lys Val Glu Ile Lys Arg
            100                 105                 110
```

```
<210> SEQ ID NO 298
<211> LENGTH: 220
<212> TYPE: PRT
<213> ORGANISM: Artificial Sequence
<220> FEATURE:
<223> OTHER INFORMATION: Ab256 Light Chain

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 299
<211> LENGTH: 222
<212> TYPE: PRT
<213> ORGANISM: Artificial Sequence
<220> FEATURE:
<223> OTHER INFORMATION: Ab256 Heavy Chain Knob

<400> SEQUENCE: 299

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95
```

```
Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
            115                 120                 125

Ser Arg Glu Glu Met Thr Lys Asn Gln Val Ser Leu Trp Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
            210                 215                 220
```

<210> SEQ ID NO 300
<211> LENGTH: 449
<212> TYPE: PRT
<213> ORGANISM: Artificial Sequence
<220> FEATURE:
<223> OTHER INFORMATION: Ab256 Heavy Chain Hole

<400> SEQUENCE: 300

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
        260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Ser
        355             360             365

Cys Ala Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Val Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

ANTI-MET ANTIBODIES AND METHODS OF USE THEREOF

This application is a divisional application of U.S. patent application Ser. No. 15/558,306, which is a U.S. national stage of International Patent Application No. PCT/US2016/022464, filed Mar. 15, 2016, which claims the benefit of U.S. Provisional Application No. 62/133,789, filed Mar. 16, 2015, and U.S. Provisional Application No. 62/149,465, filed Apr. 17, 2015; the foregoing applications are hereby incorporated by reference in their entireties.

REFERENCE TO SEQUENCE LISTING SUBMITTED ELECTRONICALLY

This application incorporates by reference a Sequence Listing submitted with this application as text file entitled "Sequence_Listing_12638_125_228.txt" created on Mar. 7, 2016 and having a size of 153,511 bytes.

1. FIELD

Provided herein are compositions, methods and uses involving antibodies that specifically bind to MET, a receptor tyrosine kinase, and modulate the expression and/or activity of MET for managing, treating, or preventing disorders, such as cancer.

2. BACKGROUND

The hepatocyte growth factor (HGF) receptor MET (also known as HGFR, c-MET) is a single-pass receptor tyrosine kinase encoded by the MET gene. The MET tyrosine kinase is a heterodimer comprising an extracellular α-subunit linked by a disulfide bond to a transmembrane β-subunit with an intracellular protein tyrosine kinase domain (see, e.g., Giordano, et al., Nature, 1989, 339:155-156). The extracellular region of MET is organized into three functional regions. The Sema domain, also found in the semaphorins and plexins, covers a conserved sequence of about 500 amino acids. It is necessary for ligand binding and receptor dimerization. The PSI domain (for domain found in plexin, semaphorin and integrins) covers approximately the next 50 residues from the N-terminus. Four IPT (for immunoglobulin-like fold shared by plexins and transcriptional factors) domains connect the PSI domain to the transmembrane helix. The MET intracellular segment harbors five key serine/tyrosine residues (Ser975, Tyr1234, Tyr1235, Tyr1349 and Tyr1356) that either regulate its enzymatic activity or form docking sites for adaptors and signal transducers (see, e.g., Trusolino and Comoglio, Nat. Rev. Cancer, 2002, 2:289-300; Kong-Beltran, et al., Cancer Cell, 2004, 6:75-84; Trusolino et al., Nat. Rev. Mol. Cell Biol., 2010, 11:834-848).

The human MET gene encoding the MET kinase has been cloned as described by Cooper et al., Nature, 1984, 311:29-33. Upon binding of the ligand HGF, MET kinase is activated by receptor dimerization and trans-phosphorylation of the catalytic tyrosine residues Tyr1234 and Tyr1235. Subsequent phosphorylation of Tyr1349 and Tyr1356 in the C-terminal tail provides docking sites for the recruitment of signal transduction adaptors and transducers. MET can also be activated by semaphorins in an HGF-independent manner when oligomerized with plexins, leading to stimulation of MET downstream effectors. Members of the MAPK (including ERK1/2, JNK and p38), PI3K-AKT, STAT and NF-κB signaling pathways have been shown to be downstream signal transducers of MET signaling (see, e.g., Ponzetto et al., Cell, 1994, 77:261-271; Trusolino et al., Nat. Rev. Mol. Cell Biol., 2010, 11:834-848).

MET function is required for various events in embryonic morphogenesis. Loss-of-function studies indicate that MET signaling supports the growth and survival of hepatocytes and placental trophoblast cells, and the proper wiring of the nervous system. Moreover, MET signaling plays an important role in wound healing and the regeneration of the liver and the kidney (see, e.g., Trusolino et al., Nat. Rev. Mol. Cell Biol., 2010, 11:834-848).

Aberrant MET activation, due to overexpression, mutations, or autocrine ligand production, has been implicated in connection with a number of cancers. Studies indicate that aberrant MET signaling is important not only for tumor growth but also for tumor metastasis.

There is a need for therapies modulating MET to manage, treat or prevent conditions involving MET and/or abnormal MET activity (e.g., MET signaling) or abnormal MET expression.

3. SUMMARY

In one aspect, provided herein are antibodies (e.g., monoclonal antibodies), including antigen-binding fragments thereof, which specifically bind to the extracellular domain (ECD) of MET such as human MET. In a specific aspect, such anti-MET antibodies, which specifically bind to an ECD of human MET (e.g., Sema/PSI domain of human MET-ECD), inhibit phosphorylation of MET and inhibit tumor cell proliferation or tumor growth better as an IgG$_2$ isotype as compared to as an IgG$_1$ isotype. Also provided herein are polynucleotides and vectors comprising sequences encoding such antibodies, cells (e.g., host cells) comprising such polynucleotides or vectors, and compositions, reagents and kits comprising such antibodies. In another aspect, provided herein are methods for modulating MET activity, e.g., inhibiting MET activity, or MET expression levels, diagnostic methods and uses, and therapeutic methods and uses of such anti-MET antibodies. In certain aspects, provided herein are methods for modulating ligand-dependent MET activity. In certain aspects, provided herein are methods for modulating MET-amplified (e.g., ligand-independent) MET activity.

In one aspect, provided herein is a monoclonal antibody or antigen-binding fragment thereof that binds to the Sema/PSI domain of human MET, wherein the antibody or antigen-binding fragment thereof:
  (a) inhibits MET activity in cells as determined by inhibition of phosphorylation of MET;
  (b) induces MET degradation in cells; and
  (c) inhibits tumor cell proliferation or tumor growth; and
wherein the antibody inhibits phosphorylation of MET, induces MET degradation, or inhibits tumor cell proliferation or tumor growth better as a human IgG$_2$ isotype as compared to as an IgG$_1$ isotype. In one aspect, the monoclonal antibody or antigen-binding fragment thereof binds to the Sema domain of human MET.

In certain aspects, the antibody or antigen-binding fragment thereof comprises:
  (a) a light chain variable region (VL) comprising VL complementary determining region 1 (CDR1), VL CDR2, and VL CDR3 of any one of antibodies Ab235-Ab237, Ab239, or Ab241-Ab255 as set forth in Table 1; and
  (b) a heavy chain variable region (VH) comprising VH complementary determining region 1 (CDR1), VH CDR2, and VH CDR3 of any one of antibodies Ab235-Ab237, Ab239, or Ab241-Ab255 as set forth in Table 2.

In certain embodiments, the VL CDR1, VL CDR2, and VL CDR3 of the antibody or antigen-binding fragment thereof comprise the amino acid sequences of SEQ ID NOS: 1, 2, and 3, respectively, and the VH CDR1, VH CDR2, and VH CDR3 of the antibody or antigen-binding fragment thereof comprise the amino acid sequences of SEQ ID NOS: 4, 5, and 6, respectively.

In certain embodiments, the VL CDR1, VL CDR2, and VL CDR3 of the antibody or antigen-binding fragment thereof comprise the amino acid sequences of SEQ ID NOS: 7, 8, and 9, respectively, and the VH CDR1, VH CDR2, and VH CDR3 of the antibody or antigen-binding fragment thereof comprise the amino acid sequences of SEQ ID NOS: 10, 11, and 12, respectively.

In certain embodiments, the VL CDR1, VL CDR2, and VL CDR3 of the antibody or antigen-binding fragment thereof comprise the amino acid sequences of SEQ ID NOS: 13, 14, and 15, respectively, and the VH CDR1, VH CDR2, and VH CDR3 of the antibody or antigen-binding fragment thereof comprise the amino acid sequences of SEQ ID NOS: 16, 17, and 18, respectively.

In certain embodiments, the VL CDR1, VL CDR2, and VL CDR3 of the antibody or antigen-binding fragment thereof comprise the amino acid sequences of SEQ ID NOS: 25, 26, and 27, respectively, and the VH CDR1, VH CDR2, and VH CDR3 of the antibody or antigen-binding fragment thereof comprise the amino acid sequences of SEQ ID NOS: 28, 17, and 29, respectively.

In certain embodiments, the VL CDR1, VL CDR2, and VL CDR3 of the antibody or antigen-binding fragment thereof comprise the amino acid sequences of SEQ ID NOS: 72, 14, and 15, respectively, and the VH CDR1, VH CDR2, and VH CDR3 of the antibody or antigen-binding fragment thereof comprise the amino acid sequences of SEQ ID NOS: 16, 73, and 18, respectively.

In certain embodiments, the antibody or antigen-binding fragment thereof comprises:
- (a) a VL comprising:
  - (i) a VL CDR1 comprising the amino acid sequence of SASSSVX$_7$YMF (SEQ ID NO:41), wherein X$_7$ is any amino acid, for example, N or S;
  - (ii) a VL CDR2 comprising the amino acid sequence of DTX$_{13}$X$_{14}$LAS (SEQ ID NO:43), wherein X$_{13}$ is any amino acid, for example, F or S and X$_{14}$ is any amino acid, for example, N or D;
  - (iii) a VL CDR3 comprising the amino acid sequence of QQWSX$_{15}$YPYT (SEQ ID NO:44), wherein X$_{15}$ is any amino acid, for example, I or N; and
- (b) a VH comprising:
  - (i) a VH CDR1 comprising the amino acid sequence X$_1$YWIEW (SEQ ID NO:36), wherein X$_1$ is any amino acid, for example, N or S;
  - (ii) a VH CDR2 comprising the amino acid sequence of EILPGSDX$_3$TKYX4EKFKGK (SEQ ID NO:38), wherein X$_3$ is any amino acid, for example, Y or F and X$_4$ is any amino acid, for example, N or S; and
  - (iii) a VH CDR3 comprising the amino acid sequence of PSTX$_6$PPDC (SEQ ID NO:40), wherein X$_6$ is any amino acid, for example, I or V.

In certain embodiments, the antibody or antigen-binding fragment thereof comprises a VL comprising the amino acid sequence of MGWSCIILFLVATATGVHSQIVLTQSPAIMSX$_{136}$SPGEKVTMTCSASSSVX$_{137}$YMFWYQ QKX$_{138}$GSSPRLLIYDTX$_{139}$X$_{140}$LASGVPVRFSGSGSGTSYSLTISRMEAEDAATYYCQQW SX$_{141}$IYPYTFGGGT-KLEIK (SEQ ID NO: 273), wherein X$_{136}$ is any amino acid, for example, T or A, X$_{137}$ is any amino acid, for example, N or S, X$_{138}$ is any amino acid, for example, A or P, X$_{139}$ is any amino acid, for example, F or S, X$_{140}$ is any amino acid, for example, N or D, and X$_{141}$ is any amino acid, for example, I or N.

In certain embodiments, the antibody or antigen-binding fragment thereof the antibody or antigen-binding fragment thereof comprises a VL comprising the amino acid sequence of QIVLTQSPAIMSX$_{43}$SPGEKVTMTCSASSSVX$_{44}$YMFWYQQKX$_{45}$GSSPRLLIYDTX$_{46}$X$_{47}$LA SGVPVRFSGSGSGTSYSLTISRMEAEDAATYYCQQWSX$_{48}$IYPYTFGGGTKLEIK (SEQ ID NO: 48), wherein X$_{43}$ is any amino acid, for example, T or A, X$_{44}$ is any amino acid, for example, N or S, X$_{45}$ is any amino acid, for example, A or P, X$_{46}$ is any amino acid, for example, F or S, X$_{47}$ is any amino acid, for example, N or D, and X$_{48}$ is any amino acid, for example, I or N.

In certain embodiments, the antibody or antigen-binding fragment thereof comprises a VH comprising the amino acid sequence of QX$_{57}$QLQQSGAELMKPGASVKISCKATGYX$_{58}$FSX$_{59}$YWIEWVKQRPGHGLEWIGEILPGS DX$_{60}$X$_{61}$KYX$_{62}$EKFKGKATFTADTSSNTAYMQLSX$_{63}$LTSEDSAVYYCARPSTX$_{64}$PPDCW GQGTTLTVSA (SEQ ID NO:50), wherein X$_{57}$ is any amino acid, for example, V or A, X$_{58}$ is any amino acid, for example, I or T, X$_{59}$ is any amino acid, for example, N or S, X$_{60}$ is any amino acid, for example, Y or F, X$_{61}$ is any amino acid, for example, T or I, X$_{62}$ is any amino acid, for example, N or S, X$_{63}$ is any amino acid, for example, S or N, and X$_{64}$ is any amino acid, for example, I or V.

In certain embodiments, the antibody or antigen-binding fragment thereof comprises:
- (a) a VL comprising the amino acid sequence of MGWSCIILFLVATATGVHSQIVLTQSPAIMSX$_{136}$SPGEKVTMTCSASSSVX$_{137}$YMF WYQQKX$_{138}$GSSPRLLIYDTX$_{139}$X$_{140}$LASGVPVRFSGSGSGTS-YSLTISRMEAEDAA TYYCQQWSX$_{141}$IYPYTFG-GGTKLEIK (SEQ ID NO: 273), wherein X$_{136}$ is any amino acid, for example, T or A, X$_{137}$ is any amino acid, for example, N or S, X$_{138}$ is any amino acid, for example, A or P, X$_{139}$ is any amino acid, for example, F or S, X$_{140}$ is any amino acid, for example, N or D, and X$_{141}$ is any amino acid, for example, I or N; and
- (b) a VH comprising the amino acid sequence of QX$_{57}$QLQQSGAELMKPGASVKISCKATGYX$_{58}$FSX$_{59}$YWIEWVKQRPGHGLEWIGEI LPGSDX$_{60}$X$_{61}$KYX$_{62}$EKFKGKATFTADTSSNTAYMQLSX$_{63}$LTSEDSAVYYCARPST X$_{64}$PPDCWGQGTTLTVSA (SEQ ID NO:50), wherein X$_{57}$ is any amino acid, for example, V or A, X$_{58}$ is any amino acid, for example, I or T, X$_{59}$ is any amino acid, for example, N or S, X$_{60}$ is any amino acid, for example, Y or F, X$_{61}$ is any amino acid, for example, T or I, X$_{62}$ is any amino acid, for example, N or S, X$_{63}$ is any amino acid, for example, S or N, and X$_{64}$ is any amino acid, for example, I or V.

In certain embodiments, the antibody or antigen-binding fragment thereof comprises:
- (a) a VL comprising the amino acid sequence of QIVLTQSPAIMSX$_{43}$SPGEKVTMTCSASSSVX$_{44}$YMFWYQQKX$_{45}$GSSPRLLIYDTX$_{46}$X$_{47}$LASGVP-VRFSGSGSGTSYSLTISRMEAEDAATYYCQQW-SX$_{48}$IYPYTFGGGTKL EIK (SEQ ID NO: 48), wherein X$_{43}$ is any amino acid, for example, T or A, X$_{44}$ is any amino acid, for example, N or S, X$_{45}$ is any amino acid, for example, A or P, X$_{46}$ is any amino acid, for example, F or S, $X_{47}$ is any amino acid, for example, N or D, and $X_{48}$ is any amino acid, for example, I or N; and (b) a VH comprising the amino acid sequence of QX$_{57}$QLQQSGAELMKPGASVKISCKATGYX$_{58}$ FSX$_{59}$YWIEWVKQRPGHGLEWIGE ILPGSDX$_{60}$ X$_{61}$KYX$_{62}$EKFKGKATFTADTSSNTAYMQLSX$_{63}$ LTSEDSAVYYCARPS TX$_{64}$PPDCWGQGTTLTVSA (SEQ ID NO:50), wherein $X_{57}$ is any amino acid, for example, V or A, $X_{58}$ is any amino acid, for example, I or T, $X_{59}$ is any amino acid, for example, N or S, $X_{60}$ is any amino acid, for example, Y or F, $X_{61}$ is any amino acid, for example, T or I, $X_{62}$ is any amino acid, for example, N or S, $X_{63}$ is any amino acid, for example, S or N, and $X_{64}$ is any amino acid, for example, I or V.

In certain embodiments, the antibody or antigen-binding fragment thereof comprises a VL comprising the amino acid sequence of SEQ ID NO:57.

In certain embodiments, the antibody or antigen-binding fragment thereof comprises a VH comprising the amino acid sequence of SEQ ID NO:66.

In certain embodiments, the antibody or antigen-binding fragment thereof comprises:
(a) a VL comprising the amino acid sequence of SEQ ID NO:57; and
(b) a VH comprising the amino acid sequence of SEQ ID NO:66.

In certain embodiments, the antibody or antigen-binding fragment thereof comprises a VL comprising the amino acid sequence of SEQ ID NO:58.

In certain embodiments, the antibody or antigen-binding fragment thereof comprises a VH comprising the amino acid sequence of SEQ ID NO:67.

In certain embodiments, the antibody or antigen-binding fragment thereof comprises:
(a) a VL comprising the amino acid sequence of SEQ ID NO:58; and
(b) a VH comprising the amino acid sequence of SEQ ID NO:67.

In certain embodiments, the antibody or antigen-binding fragment thereof comprises:
(a) a VL comprising:
  (i) a VL CDR1 comprising the amino acid sequence of SEQ ID NOS: 13 or 72;
  (ii) a VL CDR2 comprising the amino acid sequence of SEQ ID NO:14;
  (iii) a VL CDR3 comprising the amino acid sequence of SEQ ID NO:15; and
(b) a VH comprising:
(i) a VH CDR1 comprising the amino acid sequence of SEQ ID NOS: 16, 28, or DX$_2$YMA (SEQ ID NO:37), wherein $X_2$ is any amino acid, for example, S or C;
(ii) a VH CDR2 comprising the amino acid sequence of SEQ ID NOS: 17 or 46, or SIS-SDGGGTYYRDSVKGX$_5$ (SEQ ID NO:39), wherein $X_5$ is any amino acid, for example, R or is absent; and
(iii) a VH CDR3 comprising the amino acid sequence of SEQ ID NOS: 18 or 29, or EX$_{16}$X$_{17}$YX$_{18}$X$_{19}$X$_{20}$YYX$_{21}$X$_{22}$X$_{23}$FX$_{24}$X$_{25}$ (SEQ ID NO:45), wherein $X_{16}$ is any amino acid, for example, G or R, $X_{17}$ is any amino acid, for example, I or Y, $X_{18}$ is any amino acid, for example, T or D, $X_{19}$ is any amino acid, for example, T or G, $X_{20}$ is any amino acid, for example, D or T, $X_{21}$ is any amino acid, for example, P or G, $X_{22}$ is any amino acid, for example, C or W, $X_{23}$ is any amino acid, for example, Y or absent, $X_{24}$ is any amino acid, for example, N or D, and $X_{25}$ is any amino acid, for example, Y or F.

In certain embodiments, the antibody or antigen-binding fragment thereof comprises:
(a) a VL comprising:
  (i) a VL CDR1 comprising the amino acid sequence of SEQ ID NO:25;
  (ii) a VL CDR2 comprising the amino acid sequence of SEQ ID NO:26;
  (iii) a VL CDR3 comprising the amino acid sequence of SEQ ID NO:27; and
(b) a VH comprising:
  (i) a VH CDR1 comprising the amino acid sequence of SEQ ID NOS: 16, 28, or DX2YMA (SEQ ID NO:37), wherein $X_2$ is any amino acid, for example, S or C;
  (ii) a VH CDR2 comprising the amino acid sequence of SEQ ID NOS: 17 or 46, or SIS-SDGGGTYYRDSVKGX$_5$ (SEQ ID NO:39), wherein $X_5$ is any amino acid, for example, R or is absent; and
  (iii) a VH CDR3 comprising the amino acid sequence of SEQ ID NOS: 18 or 29, or EX$_{16}$X$_{17}$YX$_{18}$X$_{19}$X$_{20}$YYX$_{21}$X$_{22}$X$_{23}$FX$_{24}$X$_{25}$ (SE ID NO:45), wherein $X_{16}$ is any amino acid, for example, G or R, $X_{17}$ is any amino acid, for example, I or Y, $X_{18}$ is any amino acid, for example, T or D, $X_{19}$ is any amino acid, for example, T or G, $X_{20}$ is any amino acid, for example, D or T, $X_{21}$ is any amino acid, for example, P or G, $X_{22}$ is any amino acid, for example, C or W, $X_{23}$ is any amino acid, for example, Y or absent, $X_{24}$ is any amino acid, for example, N or D, and $X_{25}$ is any amino acid, for example, Y or F.

In certain embodiments, the antibody or antigen-binding fragment thereof comprises a VL comprising the amino acid sequence of DIQMTQSPX$_{26}$SLSASX$_{27}$GX$_{28}$X$_{29}$TIX$_{30}$ CLASADIHSNLAWYQQKPGX$_{31}$X$_{32}$PX$_{33}$LLIYGN NLNDGVPSRFSGX$_{34}$GX$_{35}$GTX$_{36}$X$_{37}$X$_{38}$LX$_{39}$IX$_{40}$ SLQX$_{41}$EDVX$_{42}$IYFCQQSYDSPPTFGQGT KLEIK (SEQ ID NO:47), wherein $X_{26}$ is any amino acid, for example, S or G, $X_{27}$ is any amino acid, for example, V or L, $X_{28}$ is any amino acid, for example, D or E, $X_{29}$ is any amino acid, for example, R or T, $X_{30}$ is any amino acid, for example, T or E, $X_{31}$ is any amino acid, for example, K or N, $X_{32}$ is any amino acid, for example, A or S, $X_{33}$ is any amino acid, for example, K or Q, $X_{34}$ is any amino acid, for example, F or S, $X_{35}$ is any amino acid, for example, F or S, $X_{36}$ is any amino acid, for example, D or Q, $X_{37}$ is any amino acid, for example, F or Y, $X_{38}$ is any amino acid, for example, T or S, $X_{39}$ is any amino acid, for example, T or K, $X_{40}$ is any amino acid, for example, S or N, $X_{41}$ is any amino acid, for example, P or S, and $X_{42}$ is any amino acid, for example, A or S.

In certain embodiments, the antibody or antigen-binding fragment thereof comprises a VH comprising the amino acid sequence of EVQLVESGGGLVQPGX$_{49}$SLKLSCAASG-FTFSDSYMAWVRQAPX$_{50}$KGLEWVASISSDG GGTYY-RDSVKGRFX$_{51}$ISRDNAKX$_{52}$SLYLQMDSLRX$_{53}$EDT-ATYYCTTEGIYTTDYYPYC FNYWGX$_{54}$GX$_{55}$MV-TVSX$_{56}$ (SEQ ID NO:49), wherein $X_{49}$ is any amino acid, for example, G or R, $X_{50}$ is any amino acid, for example, G or T, $X_{51}$ is any amino acid, for example, T or S, $X_{52}$ is any amino acid, for example, S or N, $X_{53}$ is any amino acid, for example, T or S, $X_{54}$ is any amino acid, for example, Q or H, $X_{55}$ is any amino acid, for example, V or T, and $X_{56}$ is any amino acid, for example, S or A.

In certain embodiments, the antibody or antigen-binding fragment thereof comprises:
(a) a VL comprising the amino acid sequence of DIQMTQSPX$_{26}$SLSASX$_{27}$GX$_{28}$X$_{29}$TIX$_{30}$CLASAD-IHSNLAWYQQKPGX$_{31}$X$_{32}$PX$_{33}$LLI YGNNLND-GVPSRFSGX$_{34}$GX$_{35}$GTX$_{36}$X$_{37}$X$_{38}$LX$_{39}$IX$_{40}$SLQX$_{41}$EDVX$_{42}$IYFCQQSYDS PPTFGQGTKLEIK (SEQ ID NO:47), wherein $X_{26}$ is S or G, $X_{27}$ is V or L, $X_{28}$ is D or E, $X_{29}$ is R or T, $X_{30}$ is T or E, $X_{31}$ is K or N, $X_{32}$ is A or S, $X_{33}$ is K or Q, $X_{34}$ is F or S, $X_{35}$ is F or S, $X_{36}$ is D or Q, $X_{37}$ is F or Y, $X_{38}$ is T or S, $X_{39}$ is T or K, $X_{40}$ is S or N, $X_{41}$ is P or S, and $X_{42}$ is A or S; and
(b) a VH comprising the amino acid sequence of EVQLVESGGGLVQPGX$_{49}$SLKLSCAASGFTF SDSYMAWVRQAPX$_{50}$KGLEWVASI SSDGGGT-YYRDSVKGRFX$_{51}$ISRDNAKX$_{52}$SLYLQMDSL-RX$_{53}$EDTATYYCTTEGIY TTDYYPYCFNYWGX$_{54}$GX$_{55}$MVTVSX$_{56}$ (SEQ ID NO:49, wherein $X_{49}$ is any amino acid, for example, G or R, $X_{50}$ is any amino acid, for example, G or T, $X_{51}$ is any amino acid, for example, T or S, $X_{52}$ is any amino acid, for example, S or N, $X_{53}$ is any amino acid, for example, T or S, $X_{54}$ is any amino acid, for example, Q or H, $X_{55}$ is any amino acid, for example, V or T, and $X_{56}$ is any amino acid, for example, S or A.

In certain embodiments, the antibody or antigen-binding fragment thereof comprises a VL comprising the amino acid sequence of SEQ ID NO:59.

In certain embodiments, the antibody or antigen-binding fragment thereof comprises a VL comprising the amino acid sequence of SEQ ID NO:52.

In certain embodiments, the antibody or antigen-binding fragment thereof comprises a VL comprising the amino acid sequence of SEQ ID NO:53.

In certain embodiments, the antibody or antigen-binding fragment thereof comprises a VL comprising the amino acid sequence of SEQ ID NO:54.

In certain embodiments, the antibody or antigen-binding fragment thereof comprises a VL comprising the amino acid sequence of SEQ ID NO:55.

In certain embodiments, the antibody or antigen-binding fragment thereof comprises a VL comprising the amino acid sequence of SEQ ID NO:56.

In certain embodiments, the antibody or antigen-binding fragment thereof comprises a VL comprising the amino acid sequence of SEQ ID NO:61.

In certain embodiments, the antibody or antigen-binding fragment thereof comprises a VH comprising the amino acid sequence of SEQ ID NO:68.

In certain embodiments, the antibody or antigen-binding fragment thereof comprises a VH comprising the amino acid sequence of SEQ ID NO:63.

In certain embodiments, the antibody or antigen-binding fragment thereof comprises a VH comprising the amino acid sequence of SEQ ID NO:64.

In certain embodiments, the antibody or antigen-binding fragment thereof comprises a VH comprising the amino acid sequence of SEQ ID NO:65.

In certain embodiments, the antibody or antigen-binding fragment thereof comprises a VH comprising the amino acid sequence of SEQ ID NO:70.

In certain embodiments, the antibody or antigen-binding fragment thereof comprises:
(a) a VL comprising the amino acid sequence of SEQ ID NO:59; and
(b) a VH comprising the amino acid sequence of SEQ ID NO:68.

In certain embodiments, the antibody or antigen-binding fragment thereof comprises:
(a) a VL comprising the amino acid sequence of SEQ ID NO:52; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:53; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:54; and
(a) a VH comprising the amino acid sequence of SEQ ID NO:63.

In certain embodiments, the antibody or antigen-binding fragment thereof comprises:
(a) a VL comprising the amino acid sequence of SEQ ID NO:55; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:56; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:52; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:53; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:54; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:55; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:56; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:52; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:53; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:54; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:55; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:56; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:61; and
(b) a VH comprising the amino acid sequence of SEQ ID NO:70.

In certain embodiments, the antibody or antigen-binding fragment thereof specifically binds to human MET and monkey MET, but not mouse MET or dog MET. In certain embodiments, the antibody or antigen-binding fragment thereof specifically binds to the SEMA domain of human MET and monkey MET, but not the SEMA domain of mouse MET or dog MET.

In certain embodiments, the inhibition of MET activity occurs in SNU-5 cells, A549 cells, and/or Hop92 cells. In certain embodiments, the IC50 for the inhibition of MET activity in SNU-5 cells is between about 100 pM to about 500 pM, about 25 pM to about 200 pM, or about 40 pM to about 160 pM, about 50 pM to about 125 pM, or about 5 pM to about 100 pM. In certain embodiments, the maximal percent inhibition of MET activity in SNU-5 cells that is at least about 10%, 20%, 30%, 40%, 45%, 50%, 55%, 60%, 65%, 70%, 75%, 80%, 85%, 90%, 95%, or 100%. In certain embodiments, the IgG$_2$ isotype has a maximal percent inhibition of MET activity in SNU-5 cells that is between 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold more than the maximal percent inhibition of MET activity of the IgG$_1$ isotype. In certain embodiments, the IC$_{50}$ for the inhibition of MET activity in A549 cells is between about 40 pM to about 250 pM, 100 pM to about 500 pM, about 25 pM to about 200 pM, or about 40 pM to about 160 pM, about 50 pM to about 125 pM, or about 5 pM to about 100 pM. In certain embodiments, the IC$_{50}$ for the inhibition of MET activity in Hop92 cells is between about 100 pM to about 500 pM, about 25 pM to about 200 pM, or about 40 pM to about 160 pM, about 50 pM to about 125 pM, or about 5 pM to about 100 pM. In certain embodiments, the IC50 for the inhibition of MET activity in Hop92 cells is between 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than a humanized anti-MET antibody that does not bind the SEMA domain, e.g., a human SEMA domain, or a bivalent, IgG$_4$ anti-MET antibody that binds to the SEMA domain, e.g., a human SEMA domain.

In certain embodiments, the phosphorylation of MET is determined at MET amino acid residues Tyr1234 and/or Tyr1235.

In certain embodiments, the induction of MET degradation occurs in SNU-5 cells, A549 cells, U87MG cells, H596 cells, Hop92 cells, or in tumor cells. In certain embodiments, the induction of MET degradation occurs in cells expressing MET comprising one or more mutations, e.g., deletions, in exon 14 (encoding, e.g., Leu964-Asp1010) of the human MET gene. In certain embodiments, the induction of MET degradation occurs in cells with amplified MET. In certain embodiments, the maximal percent induction of MET degradation in SNU-5 cells is at least about 10%, 20%, 30%, 40%, 45%, 50%, 55%, 60%, 65%, 70%, 75%, 80%, 85%, 90%, 95%, or 100%. In certain embodiments, the IgG$_2$ isotype maximal percent induction of MET degradation in the SNU-5 cells is between 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold more than the IgG$_1$ isotype maximal percent induction of MET degradation.

In certain embodiments, the inhibition of tumor cell proliferation occurs in SNU-5 tumor cells, EBC-1 tumor cells, U87MG tumor cells, A549 tumor cells, and/or H596 tumor cells. In certain embodiments, the inhibition of tumor cell proliferation occurs in cells expressing MET comprising one or more mutations, e.g., deletions, in exon 14 (encoding, e.g., Leu964-Asp1010) of the human MET gene. In certain embodiments, the inhibition of tumor cell proliferation occurs in cells with amplified MET. In certain embodiments, the maximal percent inhibition for the inhibition of the SNU-5 tumor cell proliferation is at least about 10%, 20%, 30%, 40%, 45%, 50%, 55%, 60%, 65%, 70%, 75%, 80%, 85%, 90%, 95%, or 100%. In certain embodiments, the IgG$_2$ isotype maximal percent inhibition for the inhibition of the SNU-5 tumor cell proliferation is between 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold higher than the IgG$_1$ maximal percent inhibition. In certain embodiments, the maximal percent inhibition for the inhibition of the EBC-1 tumor cell proliferation is at least about 10%, 20%, 30%, 40%, 45%, 50%, 55%, 60%, 65%, 70%, 75%, 80%, 85%, 90%, 95%, or 100%. In certain embodiments, the IgG$_2$ isotype maximal percent inhibition for the inhibition of the EBC-1 tumor cell proliferation is between 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold higher than the IgG$_1$ maximal percent inhibition. In certain embodiments, the IC50 for the inhibition of tumor cell proliferation in the U87MG tumor cells is between about 100 nM to about 500 nM, about 25 nM to about 200 nM, or about 40 nM to about 160 nM, about 50 nM to about 125 nM, or about 5 nM to about 100 nM. In certain embodiments, the IC50 for the inhibition of tumor cell proliferation in the A549 tumor cells is between about 100 nM to about 500 nM, about 25 nM to about 200 nM, or about 40 nM to about 160 nM, about 50 nM to about 125 nM, or about 5 nM to about 100 nM. In certain embodiments, the IC50 for the inhibition of tumor cell proliferation in the H596 tumor cells is between about 100 nM to about 500 nM, about 25 nM to about 200 nM, or about 40 nM to about 160 nM, about 50 nM to about 125 nM, or about 5 nM to about 100 nM.

In certain embodiments, the tumor growth is a U87 xenograft tumor model, a SNU15 xenograft tumor model, or a U87MG orthotopic tumor model.

In certain embodiments, the antibody or antigen binding fragment thereof inhibits the interaction between MET and hepatocyte growth factor (HGF) on cells. In certain embodiments, the cells are A549 cells. In certain embodiments, the IC50 for the inhibition of the interaction between MET and HGF on the A549 cells is between about 0.01 nM to 10,000 nM, 0.01 nM to 1,000 nM, 0.1 nM to 500 nM, 0.1 nM to 100 nM, or 0.1 nM to 50 nM.

In certain embodiments, the antibody or antigen-binding fragment thereof induces ubiquitination of MET in cells. In certain embodiments, the cells are A549 cells.

In certain embodiments, the antibody or antigen-binding fragment thereof inhibits MET signaling in cells. In certain embodiments, the cells are A549 cells. In certain embodiments, the MET signaling is HGF-dependent. In certain embodiments, the MET signaling is HGF-independent. In certain embodiments, the inhibition of MET signaling is identified as inhibition of AKT and/or MET phosphorylation.

In certain embodiments, the antibody or antigen-binding fragment thereof inhibits HGF-induced endothelial to mesenchymal transition (EMT). In certain embodiments, the inhibition of HGF-induced EMT is determined by DU145 cell scatter. In certain embodiments, the IC50 for the DU145 cell scatter is about 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM. In certain embodiments, the DU145 cell scatter is percent inhibition is about 5%, 10%, 15%, 20%, 25%, 30%, 35%, 40%, 45%, 50%, 55%, 60%, 65%, 70%, 75%, 80%, 85%, 90%, 95%, 98%, or 99%.

In certain embodiments, the $IgG_2$ isotype of the antibody alters MET dimer configuration as compared to the $IgG_1$ isotype of the antibody.

Also provided herein is a monoclonal antibody or antigen-binding fragment thereof that binds to the Sema/PSI domain of MET, wherein the antibody or antigen-binding fragment thereof comprises:
(a) a light chain variable region (VL) comprising VL complementary determining region 1 (CDR1), VL CDR2, and VL CDR3 of any one of antibodies Ab235-Ab255 as set forth in Table 1; and
(b) a heavy chain variable region (VH) comprising VH complementary determining region 1 (CDR1), VH CDR2, and VH CDR3 of any one of antibodies Ab235-Ab255 as set forth in Table 2.

In certain embodiments, the VL CDR1, VL CDR2, and VL CDR3 of the antibody or antigen-binding fragment thereof comprise the amino acid sequences of SEQ ID NOS: 1, 2, and 3, respectively, and the VH CDR1, VH CDR2, and VH CDR3 of the antibody or antigen-binding fragment thereof comprise the amino acid sequences of SEQ ID NOS: 265, 5, and 6, respectively.

In certain embodiments, the VL CDR1, VL CDR2, and VL CDR3 of the antibody or antigen-binding fragment thereof comprise the amino acid sequences of SEQ ID NOS: 7, 8, and 9, respectively, and the VH CDR1, VH CDR2, and VH CDR3 of the antibody or antigen-binding fragment thereof comprise the amino acid sequences of SEQ ID NOS: 266, 11, and 12, respectively.

In certain embodiments, the VL CDR1, VL CDR2, and VL CDR3 of the antibody or antigen-binding fragment thereof comprise the amino acid sequences of SEQ ID NOS: 13, 14, and 15, respectively, and the VH CDR1, VH CDR2, and VH CDR3 of the antibody or antigen-binding fragment thereof comprise the amino acid sequences of SEQ ID NOS: 16, 17, and 18, respectively.

In certain embodiments, the VL CDR1, VL CDR2, and VL CDR3 of the antibody or antigen-binding fragment thereof comprise the amino acid sequences of SEQ ID NOS: 19, 20, and 21, respectively, and the VH CDR1, VH CDR2, and VH CDR3 of the antibody or antigen-binding fragment thereof comprise the amino acid sequences of SEQ ID NOS: 267, 23, and 24, respectively.

In certain embodiments, the VL CDR1, VL CDR2, and VL CDR3 of the antibody or antigen-binding fragment thereof comprise the amino acid sequences of SEQ ID NOS: 25, 26, and 27, respectively, and the VH CDR1, VH CDR2, and VH CDR3 of the antibody or antigen-binding fragment thereof comprise the amino acid sequences of SEQ ID NOS: 28, 73, and 29, respectively.

In certain embodiments, the VL CDR1, VL CDR2, and VL CDR3 of the antibody or antigen-binding fragment thereof comprise the amino acid sequences of SEQ ID NOS: 72, 14, and 15, respectively, and the VH CDR1, VH CDR2, and VH CDR3 of the antibody or antigen-binding fragment thereof comprise the amino acid sequences of SEQ ID NOS: 16, 73, and 18, respectively.

In certain embodiments, the VL CDR1, VL CDR2, and VL CDR3 of the antibody or antigen-binding fragment thereof comprise the amino acid sequences of SEQ ID NOS: 30, 31, and 32, respectively, and the VH CDR1, VH CDR2, and VH CDR3 of the antibody or antigen-binding fragment thereof comprise the amino acid sequences of SEQ ID NOS: 33, 34, and 35, respectively.

In certain embodiments, the antibody or antigen-binding fragment thereof comprises:
(a) a VL comprising:
(i) a VL CDR1 comprising the amino acid sequence of SEQ ID NO: 13 or 72;
(ii) a VL CDR2 comprising the amino acid sequence of SEQ ID NO:14;
(iii) a VL CDR3 comprising the amino acid sequence of SEQ ID NO: 15; and
(b) a VH comprising:
(i) a VH CDR1 comprising the amino acid sequence of SEQ ID NOS: 16, 28, or $DX_2YMA$ (SEQ ID NO:37), wherein $X_2$ is any amino acid, for example, S or C;
(ii) a VH CDR2 comprising the amino acid sequence of SEQ ID NOS: 17 or 46, or SIS-SDGGGTYYRDSVKGX5 (SEQ ID NO:39), wherein $X_5$ is any amino acid, for example, R or is absent; and
(iii) a VH CDR3 comprising the amino acid sequence of SEQ ID NOS: 18 or 29, or $EX_{16}X_{17}YX_{18}X_{19}X_{20}YYX_{21}X_{22}X_{23}FX_{24}X_{25}$ (SE ID NO:45), wherein $X_{16}$ is any amino acid, for example, G or R, $X_{17}$ is any amino acid, for example, I or Y, $X_{18}$ is any amino acid, for example, T or D, $X_{19}$ is any amino acid, for example, T or G, $X_{20}$ is any amino acid, for example, D or T, $X_{21}$ is any amino acid, for example, P or G, $X_{22}$ is any amino acid, for example, C or W, $X_{23}$ is any amino acid, for example, Y or absent, $X_{24}$ is any amino acid, for example, N or D, and $X_{25}$ is any amino acid, for example, Y or F.

In certain embodiments, the antibody or antigen-binding fragment thereof comprises:

(a) a VL comprising:
(i) a VL CDR1 comprising the amino acid sequence of SEQ ID NO:25;
(ii) a VL CDR2 comprising the amino acid sequence of SEQ ID NO:26;
(iii) a VL CDR3 comprising the amino acid sequence of SEQ ID NO:27; and (b) a VH comprising:
(i) a VH CDR1 comprising the amino acid sequence of SEQ ID NOS: 16, 28, or DX$_2$YMA (SEQ ID NO:37), wherein $X_2$ is any amino acid, for example, S or C;
(ii) a VH CDR2 comprising the amino acid sequence of SEQ ID NOS: 17 or 46, or SIS-SDGGGTYYRDSVKGX$_5$ (SEQ ID NO:39), wherein $X_5$ is any amino acid, for example, R or is absent; and
(iii) a VH CDR3 comprising the amino acid sequence of SEQ ID NOS: 18 or 29, or EX$_{16}$X$_{17}$YX$_{18}$X$_{19}$X$_{20}$YYX$_{21}$X$_{22}$X$_{23}$FX$_{24}$X$_{25}$ (SE ID NO:45), wherein $X_{16}$ is any amino acid, for example, G or R, $X_{17}$ is any amino acid, for example, I or Y, $X_{18}$ is any amino acid, for example, T or D, $X_{19}$ is any amino acid, for example, T or G, $X_{20}$ is any amino acid, for example, D or T, $X_{21}$ is any amino acid, for example, P or G, $X_{22}$ is any amino acid, for example, C or W, $X_{23}$ is any amino acid, for example, Y or absent, $X_{24}$ is any amino acid, for example, N or D, and $X_{25}$ is any amino acid, for example, Y or F.

In certain embodiments, the antibody or antigen-binding fragment thereof comprises a VL comprising the amino acid sequence of DIQMTQSPX$_{26}$SLSASX$_{27}$GX$_{28}$X$_{29}$TIX$_{30}$CLASADIHSNLAWYQQKPGX$_{31}$X$_{32}$PX$_{33}$LLIYGN NLNDGVPSRFSGX$_{34}$GX$_{35}$GTX$_{36}$X$_{37}$X$_{38}$LX$_{39}$IX$_{40}$ SLQX$_{41}$EDVX$_{42}$IYFCQQSYDSPPTFGQGT KLEIK (SEQ ID NO:47), wherein $X_{26}$ is any amino acid, for example, S or G, $X_{27}$ is any amino acid, for example, V or L, $X_{28}$ is any amino acid, for example, D or E, $X_{29}$ is any amino acid, for example, R or T, $X_{30}$ is any amino acid, for example, T or E, $X_{31}$ is any amino acid, for example, K or N, $X_{32}$ is any amino acid, for example, A or S, $X_{33}$ is any amino acid, for example, K or Q, $X_{34}$ is any amino acid, for example, F or S, $X_{35}$ is any amino acid, for example, F or S, $X_{36}$ is any amino acid, for example, D or Q, $X_{37}$ is any amino acid, for example, F or Y, $X_{38}$ is any amino acid, for example, T or S, $X_{39}$ is any amino acid, for example, T or K, $X_{40}$ is any amino acid, for example, S or N, $X_{41}$ is any amino acid, for example, P or S, and $X_{42}$ is any amino acid, for example, A or S.

In certain embodiments, the antibody or antigen-binding fragment thereof comprises a VH comprising the amino acid sequence of EVQLVESGGGLVQPGX$_{49}$SLKLSCAASGFTFSDSYMAWVRQAPX$_{50}$KGLEWVASISSDG GGTY-YRDSVKGRFX$_{51}$ISRDNAKX$_{52}$SLYLQMDSLRX$_{53}$EDTATYYCTTEGIYTTDYYPYC FNYWGX$_{54}$GX$_{55}$MVTVSX$_{56}$ (SEQ ID NO:49), wherein $X_{49}$ is any amino acid, for example, G or R, $X_{50}$ is any amino acid, for example, T or S, $X_{52}$ is any amino acid, for example, S or N, $X_{53}$ is any amino acid, for example, T or S, $X_{54}$ is any amino acid, for example, Q or H, $X_{55}$ is any amino acid, for example, V or T, and $X_{56}$ is any amino acid, for example, S or A.

In certain embodiments, the antibody or antigen-binding fragment thereof comprises:

(a) a VL comprising the amino acid sequence of DIQMTQSPX$_{26}$SLSASX$_{27}$GX$_{28}$X$_{29}$TIX$_{30}$CLASA-DIHSNLAWYQQKPGX$_{31}$X$_{32}$PX$_{33}$LLI YGNNL-NDGVPSRFSGX$_{34}$GX$_{35}$GTX$_{36}$X$_{37}$X$_{38}$LX$_{39}$IX$_{40}$ SLQX$_{41}$EDVX$_{42}$IYFCQQSYDS PPTFGQGTKLEIK (SEQ ID NO:47), wherein $X_{26}$ is any amino acid, for example, S or G, $X_{27}$ is any amino acid, for example, V or L, $X_{28}$ is any amino acid, for example, D or E, $X_{29}$ is any amino acid, for example, R or T, $X_{30}$ is any amino acid, for example, T or E, $X_{31}$ is any amino acid, for example, K or N, $X_{32}$ is any amino acid, for example, A or S, $X_{33}$ is any amino acid, for example, K or Q, $X_{34}$ is any amino acid, for example, F or S, $X_{35}$ is any amino acid, for example, F or S, $X_{36}$ is any amino acid, for example, D or Q, $X_{37}$ is any amino acid, for example, F or Y, $X_{38}$ is any amino acid, for example, T or S, $X_{39}$ is any amino acid, for example, T or K, $X_{40}$ is any amino acid, for example, S or N, $X_{41}$ is any amino acid, for example, P or S, and $X_{42}$ is any amino acid, for example, A or S; and (b) a VH comprising the amino acid sequence of EVQLVESGGGLVQPGX$_{49}$SLKLSCAASGFTF SDSYMAWVRQAPX$_{50}$KGLEWVASI SSDGGGTY-YRDSVKGRFX$_{51}$ISRDNAKX$_{52}$SLYLQMDSLRX$_{53}$ EDTATYYCTTEGIY TTDYYPYCFNYWGX$_{54}$GX$_{55}$MVTVSX$_{56}$ (SEQ ID NO:49, wherein $X_{49}$ is any amino acid, for example, G or R, $X_{50}$ is any amino acid, for example, G or T, $X_{51}$ is any amino acid, for example, T or S, $X_{52}$ is any amino acid, for example, S or N, $X_{53}$ is any amino acid, for example, T or S, $X_{54}$ is any amino acid, for example, Q or H, $X_{55}$ is any amino acid, for example, V or T, and $X_{56}$ is any amino acid, for example, S or A.

In certain embodiments, the antibody or antigen-binding fragment thereof comprises a VL comprising the amino acid sequence of SEQ ID NO:59.

In certain embodiments, antibody or antigen-binding fragment thereof comprises a VL comprising the amino acid sequence of SEQ ID NO:52.

In certain embodiments, the antibody or antigen-binding fragment thereof comprises a VL comprising the amino acid sequence of SEQ ID NO:53.

In certain embodiments, the antibody or antigen-binding fragment thereof comprises a VL comprising the amino acid sequence of SEQ ID NO:54.

In certain embodiments, the antibody or antigen-binding fragment thereof comprises a VL comprising the amino acid sequence of SEQ ID NO:55.

In certain embodiments, the antibody or antigen-binding fragment thereof comprises a VL comprising the amino acid sequence of SEQ ID NO:56.

In certain embodiments, the antibody or antigen-binding fragment thereof comprises a VL comprising the amino acid sequence of SEQ ID NO:61.

In certain embodiments, the antibody or antigen-binding fragment thereof comprises a VH comprising the amino acid sequence of SEQ ID NO:68.

In certain embodiments, the antibody or antigen-binding fragment thereof comprises a VH comprising the amino acid sequence of SEQ ID NO:63.

In certain embodiments, the antibody or antigen-binding fragment thereof comprises a VH comprising the amino acid sequence of SEQ ID NO:64.

In certain embodiments, the antibody or antigen-binding fragment thereof comprises a VH comprising the amino acid sequence of SEQ ID NO:65.

In certain embodiments, the antibody or antigen-binding fragment thereof comprises a VH comprising the amino acid sequence of SEQ ID NO:70.

In certain embodiments, the antibody or antigen-binding fragment thereof comprises:
(a) a VL comprising the amino acid sequence of SEQ ID NO:59; and
(b) a VH comprising the amino acid sequence of SEQ ID NO:68.

In certain embodiments, the antibody or antigen-binding fragment thereof comprises:
(a) a VL comprising the amino acid sequence of SEQ ID NO:52; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:53; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:54; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:55; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:56; and
(b) a VH comprising the amino acid sequence of SEQ ID NO:63.

In certain embodiments, the antibody or antigen-binding fragment thereof comprises:
(a) a VL comprising the amino acid sequence of SEQ ID NO:52; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:53; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:54; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:55; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:56; and
(b) a VH comprising the amino acid sequence of SEQ ID NO:64.

In certain embodiments, the antibody or antigen-binding fragment thereof comprises:
(a) a VL comprising the amino acid sequence of SEQ ID NO:52; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:53; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:54; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:55; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:56; and
(b) a VH comprising the amino acid sequence of SEQ ID NO:65.

In certain embodiments, the antibody or antigen-binding fragment thereof comprises:
(a) a VL comprising the amino acid sequence of SEQ ID NO:61; and
(b) a VH comprising the amino acid sequence of SEQ ID NO:70.

In certain embodiments, the antibody or antigen-binding fragment thereof comprises:
(a) a VL comprising:
  (i) a VL CDR1 comprising the amino acid sequence of SASSSVX$_7$YMF (SEQ ID NO:41), wherein X$_7$ is any amino acid, for example, N or S;
  (ii) a VL CDR2 comprising the amino acid sequence of DTX$_{13}$X$_{14}$LAS (SEQ ID NO:43), wherein X$_{13}$ is any amino acid, for example, F or S and X$_{14}$ is any amino acid, for example, N or D;
  (iii) a VL CDR3 comprising the amino acid sequence of QQWSX$_{15}$YPYT (SEQ ID NO:44), wherein X$_{15}$ is any amino acid, for example, I or N; and
(b) a VH comprising:
  (i) a VH CDR1 comprising the amino acid sequence X$_1$YWIEW (SEQ ID NO:36), wherein X$_1$ is any amino acid, for example, N or S;
  (ii) a VH CDR2 comprising the amino acid sequence of EILPGSDX$_3$TKYX$_4$EKFKGK (SEQ ID NO:38), wherein X$_3$ is any amino acid, for example, Y or F and X$_4$ is any amino acid, for example, N or S; and
  (iii) a VH CDR3 comprising the amino acid sequence of PSTX$_6$PPDC (SEQ ID NO:40), wherein X$_6$ is any amino acid, for example, I or V.

In certain embodiments, the antibody or antigen-binding fragment thereof comprises a VL comprising the amino acid sequence of MGWSCIILFLVATATGVHSQIVLTQSP-AIMSX$_{136}$SPGEKVTMTCSASSSVX$_{137}$YMFWYQ QKX$_{138}$GSSPRLLIYDTX$_{139}$X$_{140}$LASGVPVRFSGSGS- GTSYSLTISRMEAEDAATYYCQQW SX$_{141}$IYPYTFGGGTKLEIK (SEQ ID NO: 273), wherein X$_{136}$ is any amino acid, for example, T or A, X$_{137}$ is any amino acid, for example, N or S, X$_{138}$ is any amino acid, for example, A or P, X$_{139}$ is any amino acid, for example, F or S, X$_{140}$ is any amino acid, for example, N or D, and X$_{141}$ is any amino acid, for example, I or N.

In certain embodiments, the antibody or antigen-binding fragment thereof comprises a VL comprising the amino acid sequence of QIVLTQSPAIMSX$_{43}$SPGEKVTMTCSASSSVX$_{44}$YMFWYQQKX$_{45}$GSSPRLLIYDTX$_{46}$X$_{47}$LASGVPVRFSGSGSGTSYSLTISRMEAEDAATYYCQQWSX$_{48}$IYPYTFGGGTKLEIK (SEQ ID NO: 48), wherein X$_{43}$ is any amino acid, for example, T or A, X$_{44}$ is any amino acid, for example, N or S, X$_{45}$ is any amino acid, for example, A or P, X$_{46}$ is any amino acid, for example, F or S, X$_{47}$ is any amino acid, for example, N or D, and X$_{48}$ is any amino acid, for example, I or N.

In certain embodiments, the antibody or antigen-binding fragment thereof comprises a VH comprising the amino acid sequence of QX$_{57}$QLQQSGAELMKPGASVKISCKATGYX$_{58}$FSX$_{59}$YWIEWVKQRPGHGLEWIGEILPGSDX$_{60}$X$_{61}$KYX$_{62}$EKFKGKATFTADTSSNTAYMQLSX$_{63}$LTSEDSAVYYCARPSTX$_{64}$PPDCW GQGTTLTVSA (SEQ ID NO:50), wherein X$_{57}$ is any amino acid, for example, V or A, X$_{58}$ is any amino acid, for example, I or T, X$_{59}$ is any amino acid, for example, N or S, X$_{60}$ is any amino acid, for example, Y or F, X$_{61}$ is any amino acid, for example, T or I, X$_{62}$ is any amino acid, for example, N or S, X$_{63}$ is any amino acid, for example, S or N, and X$_{64}$ is any amino acid, for example, I or V.

In certain embodiments, the antibody or antigen-binding fragment thereof comprises:
(a) a VL comprising the amino acid sequence of MGWSCIILFLVATATGVHSQIVLTQSPAIMSX$_{136}$SPGEKVTMTCSASSSVX$_{137}$YMF WYQQKX$_{138}$GSSPRLLIYDTX$_{139}$X$_{140}$LASGVPVRFSGSGSGTSYSLTISRMEAEDAA TYYCQQWSX$_{141}$IYPYTFGGGTKLEIK (SEQ ID NO: 273), wherein X$_{136}$ is any amino acid, for example, T or A, X$_{137}$ is any amino acid, for example, N or S, X$_{138}$ is any amino acid, for example, A or P, X$_{139}$ is any amino acid, for example, F or S, X$_{140}$ is any amino acid, for example, N or D, and X$_{141}$ is any amino acid, for example, I or N; and
(b) a VH comprising the amino acid sequence of QX$_{57}$QLQQSGAELMKPGASVKISCKATGYX$_{58}$FSX$_{59}$YWIEWVKQRPGHGLEWIGEI LPGSDX$_{60}$X$_{61}$KYX$_{62}$EKFKGKATFTADTSSNTAYMQLSX$_{63}$LTSEDSAVYYCARPST X$_{64}$PPDCWQGTTLTVSA (SEQ ID NO:50), wherein X$_{57}$ is any amino acid, for example, V or A, X$_{58}$ is any amino acid, for example, I or T, X$_{59}$ is any amino acid, for example, N or S, X$_{60}$ is any amino acid, for example, Y or F, X$_{61}$ is any amino acid, for example, T or I, X$_{62}$ is any amino acid, for example, N or S, X$_{63}$ is any amino acid, for example, S or N, and X$_{64}$ is any amino acid, for example, I or V.

In certain embodiments, the antibody or antigen-binding fragment thereof comprises:
(a) a VL comprising the amino acid sequence of QIVLTQSPAIMSX$_{43}$SPGEKVTMTCSASSSVX$_{44}$YMFWYQQKX$_{45}$GSSPRLLIYDTX$_{46}$X$_{47}$LASGVPVRFSGSGSGTSYSLTISRMEAEDAATYYCQQWSX$_{48}$IYPYTFGGGTKL EIK (SEQ ID NO: 48), wherein X$_{43}$ is any amino acid, for example, T or A, X$_{44}$ is any amino acid, for example, N or S, X$_{45}$ is any amino acid, for example, A or P, X$_{46}$ is any amino acid, for example, F or S, X$_{47}$ is any amino acid, for example, N or D, and X$_{48}$ is any amino acid, for example, I or N; and
(b) a VH comprising the amino acid sequence of QX$_{57}$QLQQSGAELMKPGASVKISCKATGYX$_{58}$FSX$_{59}$YWIEWVKQRPGHGLEWIGEI LPGSDX$_{60}$X$_{61}$KYX$_{62}$EKFKGKATFTADTSSNTAYMQLSX$_{63}$LTSEDSAVYYCARPST X$_{64}$PPDCWGQGTTLTVSA (SEQ ID NO:50), wherein X$_{57}$ is any amino acid, for example, V or A, X$_{58}$ is any amino acid, for example, I or T, X$_{59}$ is any amino acid, for example, N or S, X$_{60}$ is any amino acid, for example, Y or F, X$_{61}$ is any amino acid, for example, T or I, X$_{62}$ is any amino acid, for example, N or S, X$_{63}$ is any amino acid, for example, S or N, and X$_{64}$ is any amino acid, for example, I or V.

In certain embodiments, the antibody or antigen-binding fragment thereof comprises a VL comprising the amino acid sequence of SEQ ID NO:57.

In certain embodiments, the antibody or antigen-binding fragment thereof comprises a VH comprising the amino acid sequence of SEQ ID NO:66.

In certain embodiments, the antibody or antigen-binding fragment thereof comprises:
(a) a VL comprising the amino acid sequence of SEQ ID NO:57; and
(b) a VH comprising the amino acid sequence of SEQ ID NO:66.

In certain embodiments, the antibody or antigen-binding fragment thereof comprises a VL comprising the amino acid sequence of SEQ ID NO:58.

In certain embodiments, the antibody or antigen-binding fragment thereof comprises a VH comprising the amino acid sequence of SEQ ID NO:67.

In certain embodiments, the antibody or antigen-binding fragment thereof comprises:
(a) a VL comprising the amino acid sequence of SEQ ID NO:58; and
(b) a VH comprising the amino acid sequence of SEQ ID NO:67.

Also provided herein is an isolated antibody or antigen-binding fragment thereof that binds to the Sema domain of MET, wherein the antibody or antigen-binding fragment thereof comprises:
(a) a light chain variable region (VL) comprising VL complementary determining region 1 (CDR1), VL CDR2, and VL CDR3 of any one of antibodies Ab235-Ab255 as set forth in Table 5; and
(b) a heavy chain variable region (VH) comprising VH complementary determining region 1 (CDR1), VH CDR2, and VH CDR3 of any one of antibodies Ab235-Ab255 as set forth in Table 6.

Also provided herein is an isolated antibody or antigen-binding fragment thereof that binds to the Sema domain of MET, wherein the antibody or antigen-binding fragment thereof comprises:
(a) a light chain variable region (VL) comprising VL complementary determining region 1 (CDR1), VL CDR2, and VL CDR3 of any one of antibodies Ab235-Ab255 as set forth in Table 7; and
(b) a heavy chain variable region (VH) comprising VH complementary determining region 1 (CDR1), VH CDR2, and VH CDR3 of any one of antibodies Ab235-Ab255 as set forth in Table 8.

In certain embodiments, an antibody or antigen-binding fragment thereof provided herein inhibits metastasis.

In certain embodiments, an antibody or antigen-binding fragment thereof provided herein comprises a human IgG$_2$ Fc region.

In certain embodiments, an antibody or antigen-binding fragment thereof provided herein is a chimeric antibody or a humanized antibody. In certain aspects, the humanized antibody is a deimmunized antibody or a composite human antibody.

In certain embodiments, n antibody or antigen-binding fragment thereof provided herein is a bispecific antibody or antigen-binding fragment thereof.

In certain embodiments, an antibody or antigen-binding fragment thereof provided herein is fused to a heterologous polypeptide.

In certain embodiments, an antibody or antigen-binding fragment thereof provided herein is conjugated to an agent. In certain embodiments, the agent is suitable for imaging and therapy. In certain embodiments, the agent is a radioisotope, quantum dots, or other nano-particles. In certain embodiments, the agent is a toxin. In certain embodiments, the toxin is abrin, ricin A, *pseudomonas* exotoxin, cholera toxin, or diphtheria toxin.

Also provided herein is a composition comprising a therapeutically effective amount of an antibody or antigen-binding fragment provided herein. In certain embodiments, the composition further comprises a pharmaceutically acceptable carrier.

Also provided herein is a polynucleotide comprising nucleotide sequences encoding a VH chain region, a VL chain region, or both a VL chain region and a VH chain region, of an antibody provided herein.

Also provided herein is a polynucleotide comprising nucleotide sequences encoding a heavy chain, a light chain, or both heavy chain and a light chain of an antibody provided herein. In certain embodiments, the polynucleotide is operably linked to a promoter.

Also provided herein is a population of polynucleotides comprising (i) a first polynucleotide comprising nucleotide sequences encoding a VH or a heavy chain of an antibody provided herein, and (ii) a second polypeptide comprising nucleotide sequences encoding a VL or a light chain of an antibody provided herein. In certain embodiments, the first polynucleotide is operably linked to a first promoter, and the second polynucleotide is operably linked to a second promoter.

Also provided herein is a vector comprising a polynucleotide provided herein.

Also provided herein is a population of vectors comprising (i) a first vector comprising nucleotide sequences encoding a VH or a heavy chain of an antibody provided herein, and (ii) a second vector comprising nucleotide sequences encoding a VL or a light chain of an antibody provided herein.

Also provided herein is a population of vectors comprising (i) a first vector comprising nucleotide sequences encoding a VH or a heavy chain of an antibody provided herein, and (ii) a second vector comprising nucleotide sequences encoding a VL or a light chain of an antibody provided herein.

Also provided herein is a cell comprising a polynucleotide provided herein.

Also provided herein is a cell comprising a population of polynucleotides provided herein.

Also provided herein is a cell comprising a vector provided herein.

Also provided herein is an isolated cell producing an antibody or antigen-binding fragment provided herein.

Also provided herein is a population of cells comprising (i) a first host cell comprising a polynucleotide comprising nucleotide sequences encoding a VH or a heavy chain of an antibody provided herein, and (ii) a second host cell comprising a polynucleotide comprising nucleotide sequences encoding a VL or a light chain of an antibody provided herein.

Also provided herein is a population of cells comprising (i) a first host cell comprising a polynucleotide comprising nucleotide sequences encoding a VH or a heavy chain of an antibody provided herein operably linked to a first promoter, and (ii) a second host cell comprising a polynucleotide comprising nucleotide sequences encoding a VL or a light chain of an antibody provided herein.

Also provided herein is a kit comprising an antibody or antigen-binding fragment provided herein.

Also provided herein is a method of managing, protecting against, or treating cancer in a subject, comprising administering to a subject in need thereof a therapeutically effective amount of an antibody or antigen-binding fragment provided herein. In certain embodiments, the cancer is colorectal, gastric, lung, melanoma, uveal melanoma, non-small cell lung, stomach, esophagus, brain, liver, kidney, head and neck, thyroid, ovary, prostate, pancreas, breast, colon, oral, muscular, bone, glioma, or lymphoid cancer. In certain embodiments, the cancer comprises cancer cells expressing MET. In certain embodiments, the cancer comprises cancer cells expressing EGFR. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site. In certain embodiments, the cancer comprises cancer cells expressing with amplified MET. In certain embodiments, the cancer is non-small cell lung cancer (e.g., lung adenocarcinoma). In certain embodiments, the cancer is a brain glioma. In certain embodiments, the cancer is a gastric cancer.

Also provided herein is a method of managing, protecting against, or treating cancer in a subject, comprising administering to a subject in need thereof a therapeutically effective amount of a composition provided herein. In certain embodiments, the cancer is colorectal, gastric, lung, melanoma, uveal melanoma, non-small cell lung, stomach, esophagus, brain, liver, kidney, head and neck, thyroid, ovary, prostate, pancreas, breast, colon, oral, muscular, bone, glioma, or lymphoid cancer. In certain embodiments, the cancer comprises cancer cells expressing MET. In certain embodiments, the cancer comprises cancer cells expressing EGFR. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site. In certain embodiments, the cancer comprises cancer cells expressing with amplified MET. In certain embodiments, the cancer is non-small cell lung cancer (e.g., lung adenocarcinoma). In certain embodiments, the cancer is a brain glioma. In certain embodiments, the cancer is a gastric cancer.

Also provided herein is a method of managing, preventing, protecting against, or treating metastasis in a subject, comprising administering to a subject in need thereof a therapeutically effective amount of an antibody or antigen-binding fragment provided herein.

Also provided herein is a method of managing, preventing, protecting against, or treating metastasis in a subject, comprising administering to a subject in need thereof a therapeutically effective amount of a composition provided herein.

In certain embodiments, the subject treated according to a method provided herein expresses a MET comprising one or more deletions in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutate or remove the Tyr1003 site. In certain embodiments, the subject treated according to a method provided herein expresses a MET protein comprising an isoleucine amino acid substitution at MET amino acid residue Thr1010. In certain embodiments, the subject treated according to a method provided herein has cancer, or is being treated for cancer with an anti-cancer therapeutic.

In certain embodiments, the cancer comprises cancer cells expressing MET. In certain embodiments, the cancer comprises cancer cells expressing EGFR.

In certain embodiments, a method provided herein further comprises administering to the patient another agent. In certain embodiments, the agent is a chemotherapeutic agent.

Also provided herein is a method of making an antibody or an antigen-binding fragment thereof which specifically binds to the Sema domain of human MET, comprising culturing a cell provided herein to express the antibody or antigen-binding fragment.

Also provided herein is a method of making an antibody or an antigen-binding fragment thereof which specifically binds to the Sema domain of human MET, comprising expressing a polynucleotide provided herein.

4. BRIEF DESCRIPTION OF THE FIGURES

FIG. 1 depicts an exemplary amino acid sequence of human MET ECD, wherein amino acid residues 1-24 comprise the signal sequence FIG. 2 depicts a western blot of lysates from cells incubated with a control vector (1), HGF (2), or HGF in the presence of Ab237 (3), crizotinib (4), or a control chimeric IgG$_1$ anti-KLH antibody (5). The western blot was probed with antibodies for detecting phosphorylated MET ("pMet"), phosphorylated Akt ("pAkt"), tubulin, phosphorylated MAPK ("pMAPK"), MET, Akt, and MAPK.

Figure 3A:
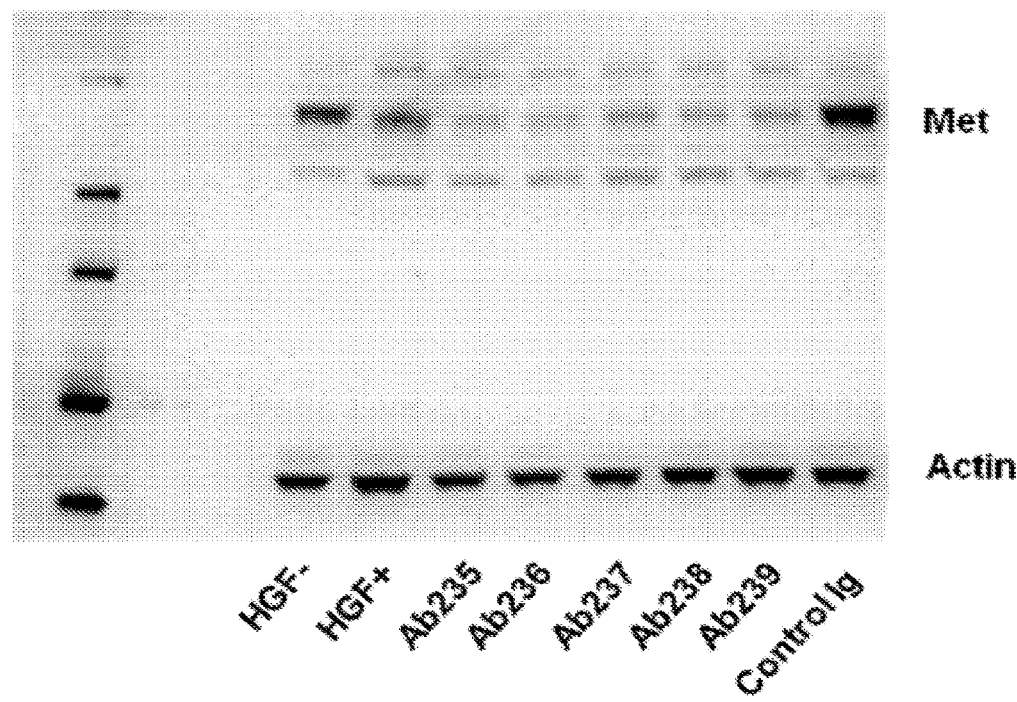
Figure 3B:
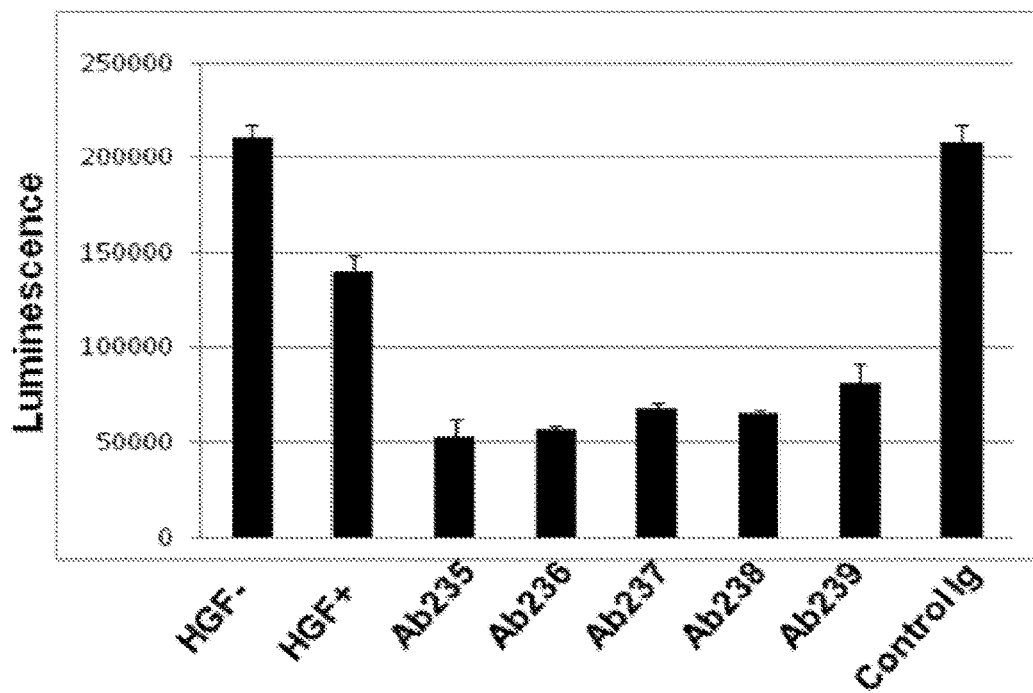
Figure 3C:
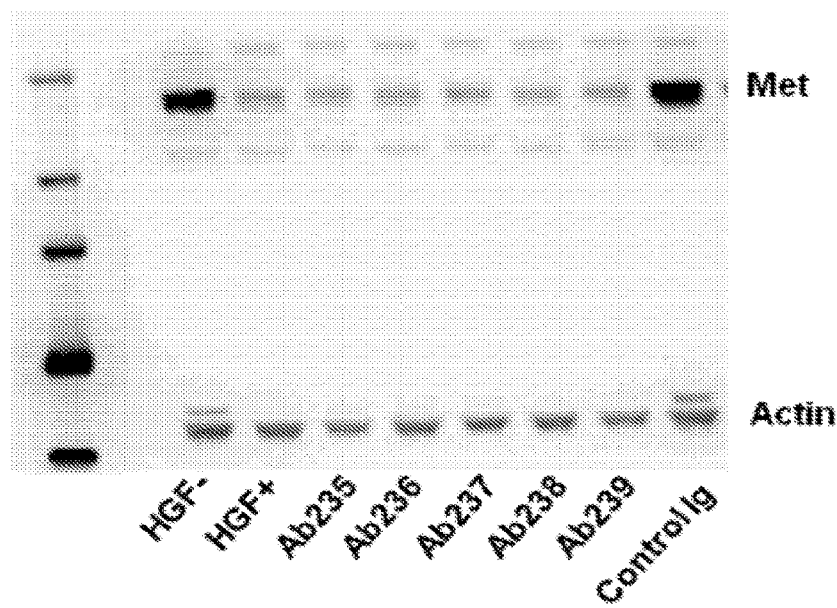
Figure 3D:
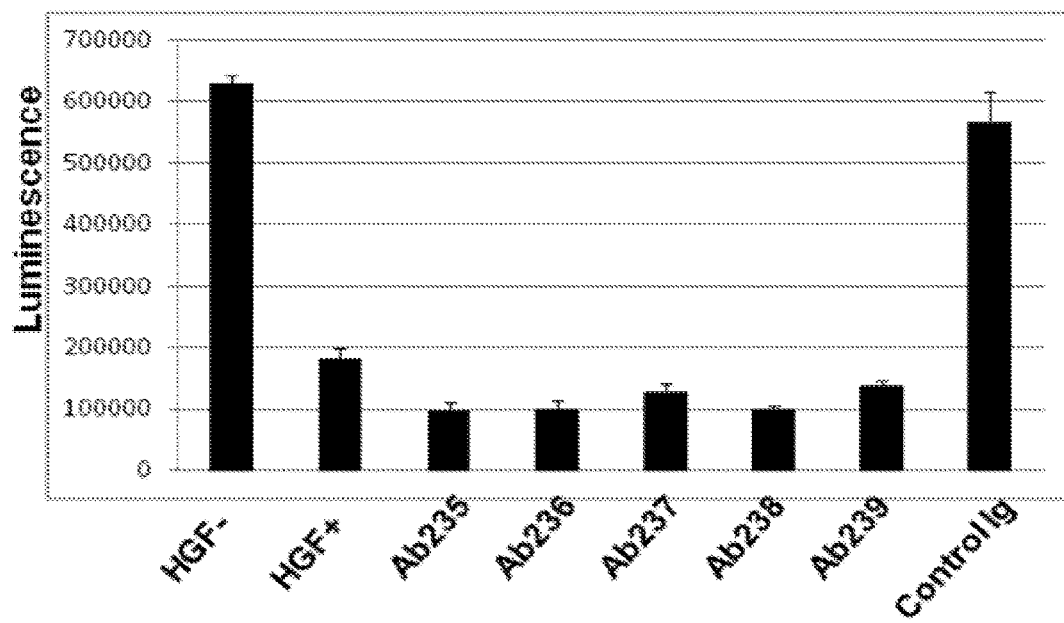
Figure 3E:
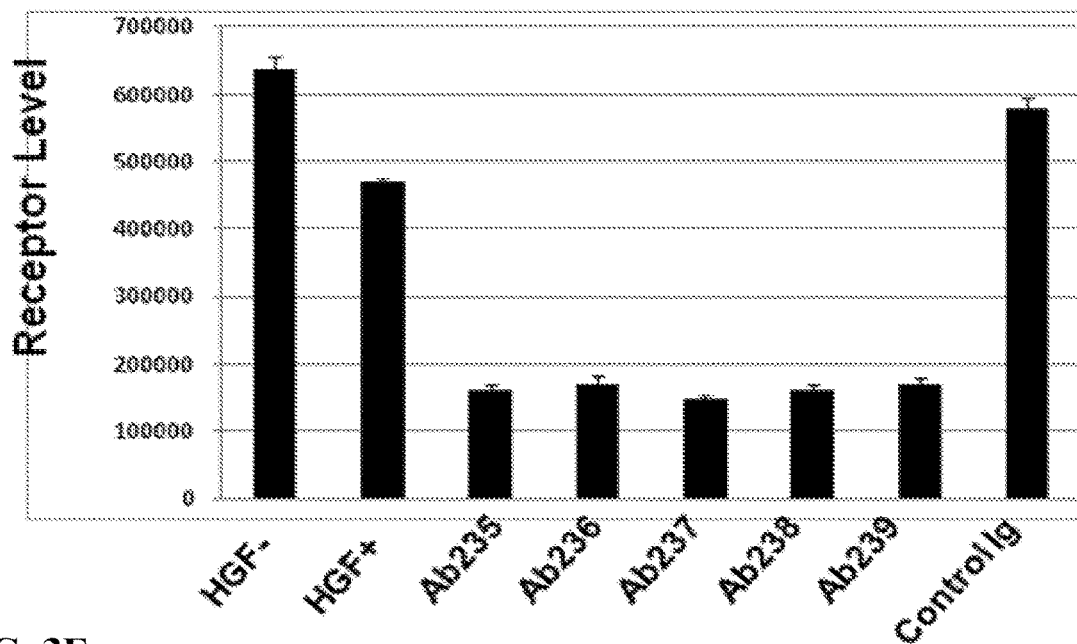
Figure 3F:
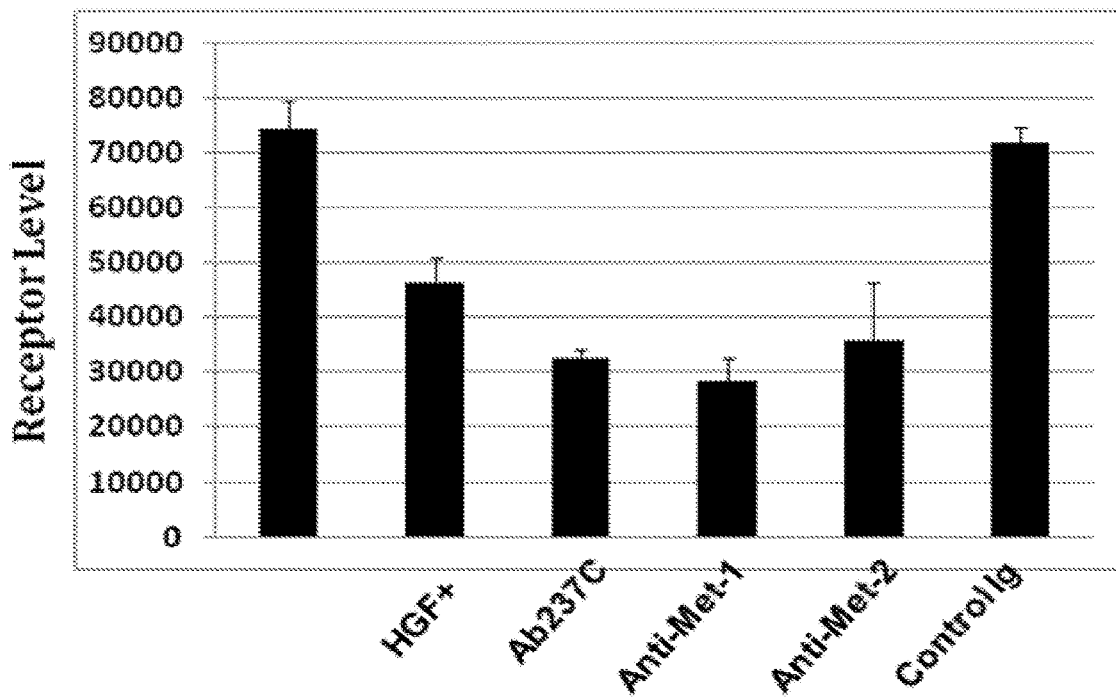

FIG. 3A depicts the degradation of MET in U87MG cells upon incubation with Ab235, Ab236, Ab237, Ab238, Ab239, or with a control chimeric IgG$_1$ anti-KLH antibody as determined by western blot analysis. FIG. 3B depicts the degradation of MET in U87MG cells upon incubation with Ab235, Ab236, Ab237, Ab238, Ab239, or with a control chimeric IgG$_1$ anti-KLH antibody as determined by ELISA. FIG. 3C depicts the degradation of MET in A549 cells upon incubation with Ab235, Ab236, Ab237, Ab238, Ab239, or with a control chimeric IgG$_1$ anti-KLH antibody as determined by western blot analysis. FIG. 3D depicts the degradation of MET in A549 cells upon incubation with Ab235, Ab236, Ab237, Ab238, Ab239, or with a control chimeric IgG$_1$ anti-KLH antibody as determined by ELISA. FIG. 3E depicts the degradation of MET in H596 cells upon incubation with Ab237C, anti-MET-1, anti-MET-2, or with a control chimeric IgG$_1$ anti-KLH antibody as determined by ELISA. FIG. 3F depicts the degradation of MET in Hop92 cells upon incubation with Ab235, Ab236, Ab237, Ab238, Ab239, or with a control chimeric IgG$_1$ anti-KLH antibody as determined by ELISA.

Figure 4A:
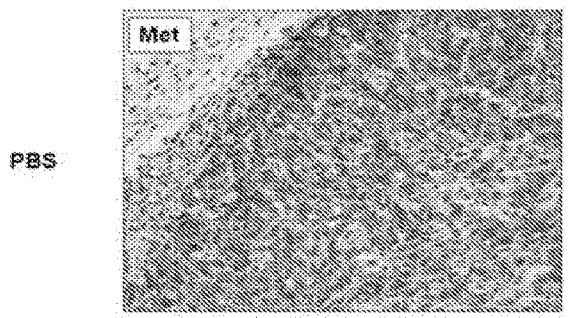
Figure 4B:
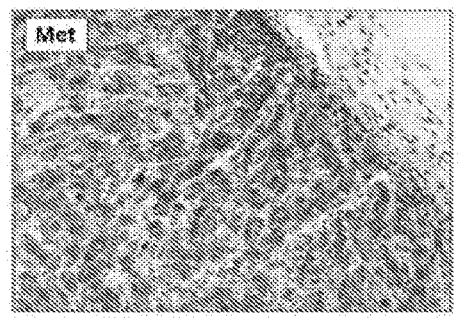
Figure 4C:
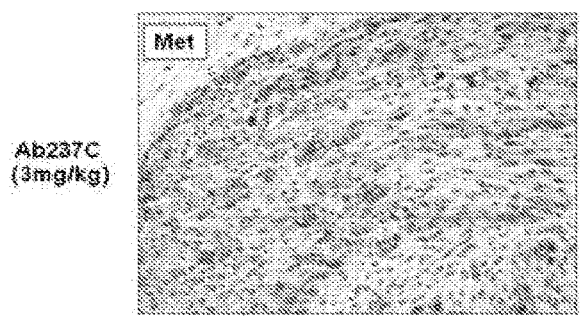
Figure 4D:
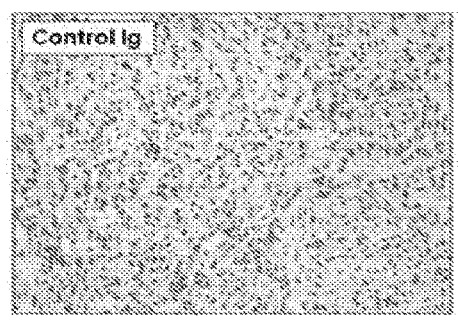

FIG. 4A depicts immunohistochemistry of MET levels in tumor samples of a U87MG subcutaneous tumor model at day 4 post two intraperitoneal injections with PBS. FIG. 4B depicts immunohistochemistry of MET levels in tumor samples of a U87MG subcutaneous tumor model at day 4 post two intraperitoneal injections with a control chimeric IgG$_1$ anti-KLH antibody. FIG. 4C depicts immunohistochemistry of MET levels in tumor samples of a U87MG subcutaneous tumor model at day 4 post two intraperitoneal injections with Ab240. FIG. 4D depicts immunohistochemistry of control Ig levels in tumor samples of a U87MG subcutaneous tumor model at day 4 post two intraperitoneal injections with a control chimeric IgG$_1$ anti-KLH antibody.

Figure 5:
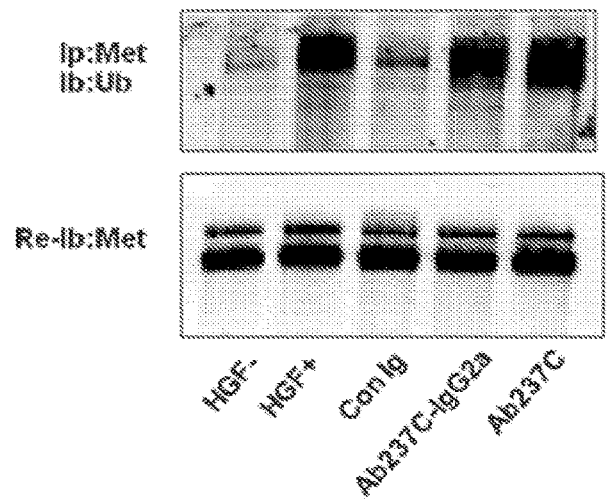

FIG. 5 depicts the ubiquitination of MET in A549 cells upon incubation with a control chimeric IgG$_1$ anti-KLH antibody, Ab237C-IgG$_{2a}$, or Ab237C as determined by immunoblot for ubiquitin on protein lysates immunoprecipitated with an anti-MET antibody.

Figure 6A:
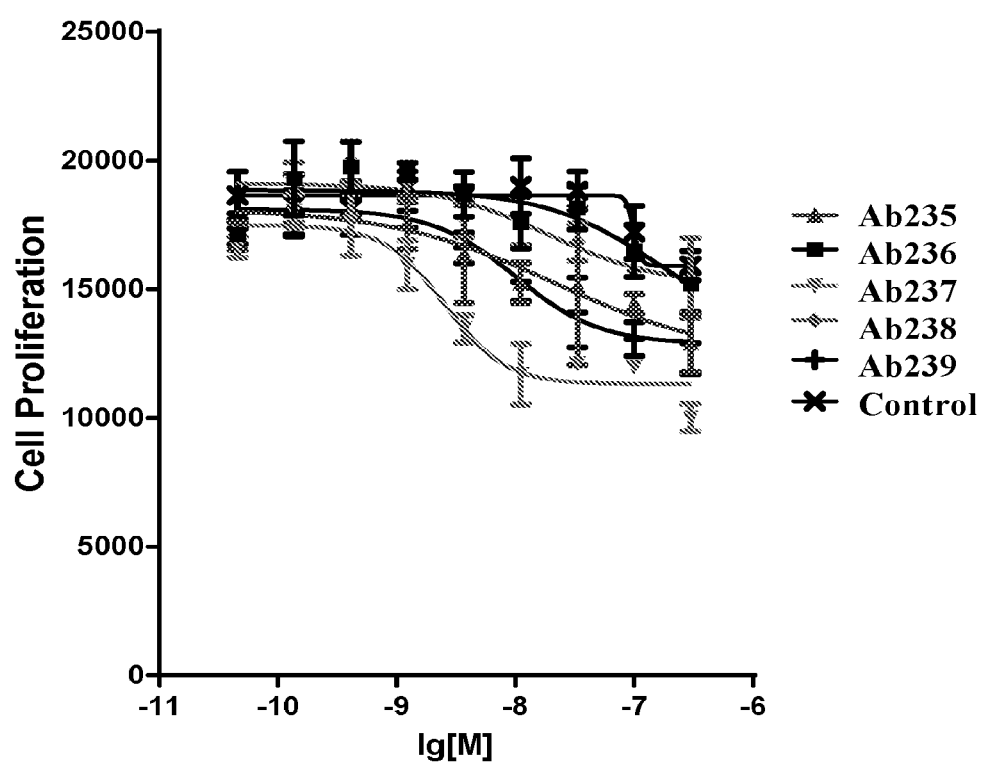
Figure 6C:
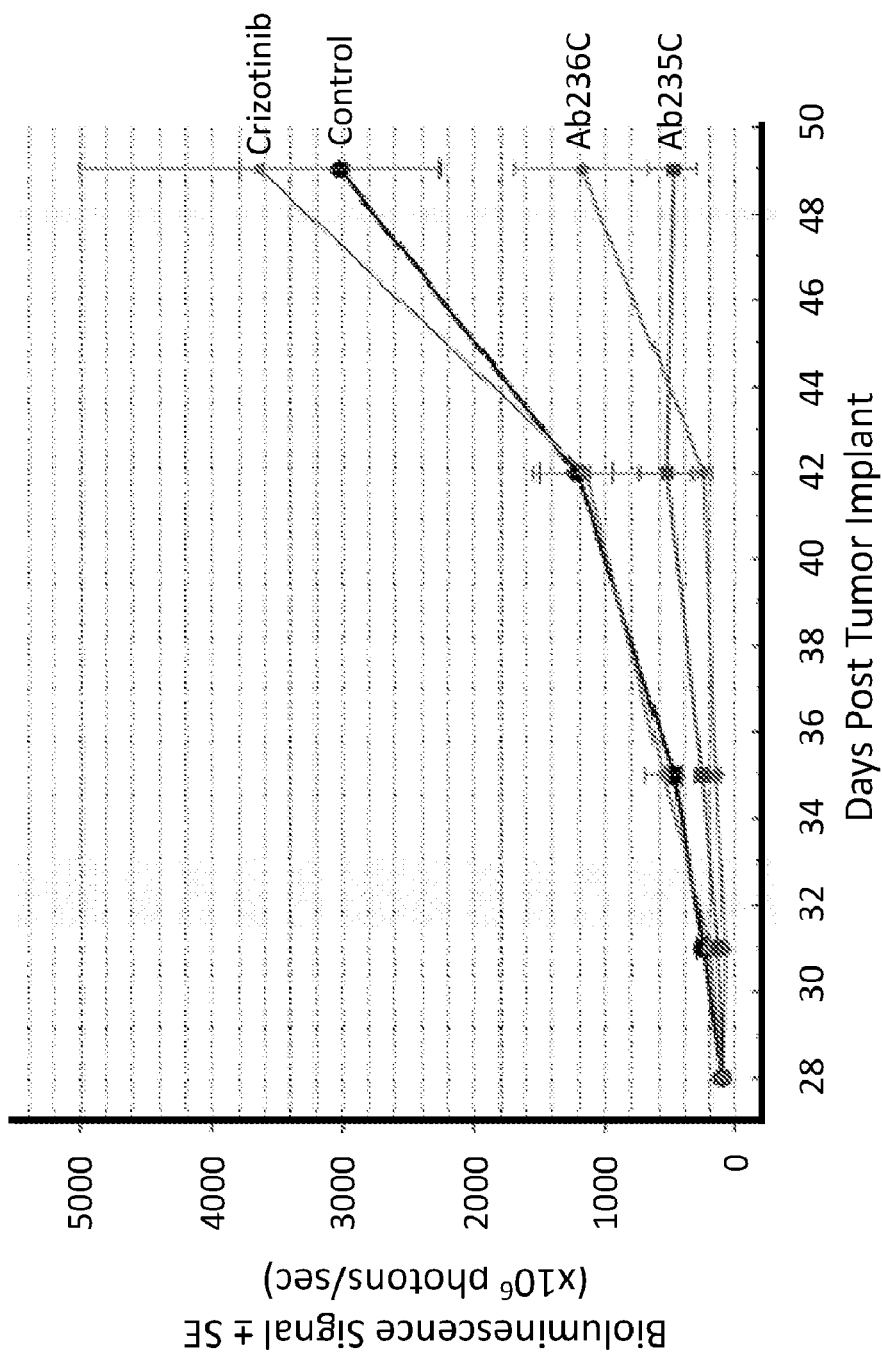

FIG. 6A depicts proliferation of U87MG cells in the absence of HGF, upon treatment with Ab235 (triangles, point up), Ab236 (squares), Ab237 (triangles, point down), Ab238 (diamonds), Ab239 (vertical lines), or control (x). FIG. 6B depicts bioluminescence signals observed in mice of U87MG orthotopic tumor models in vivo upon treatment with a control chimeric IgG$_1$ anti-KLH antibody, crizotinib, Ab235C, or Ab236C at the indicated days (e.g., days 28, 31, 35, 42 and 49) post tumor implant. FIG. 6C depicts a graphical representation of the bioluminescence signals in FIG. 6B for mice treated with a control chimeric IgG$_1$ anti-KLH antibody (circles), crizotinib (triangles), Ab235C (squares), or Ab236C (diamonds).

Figure 7A:
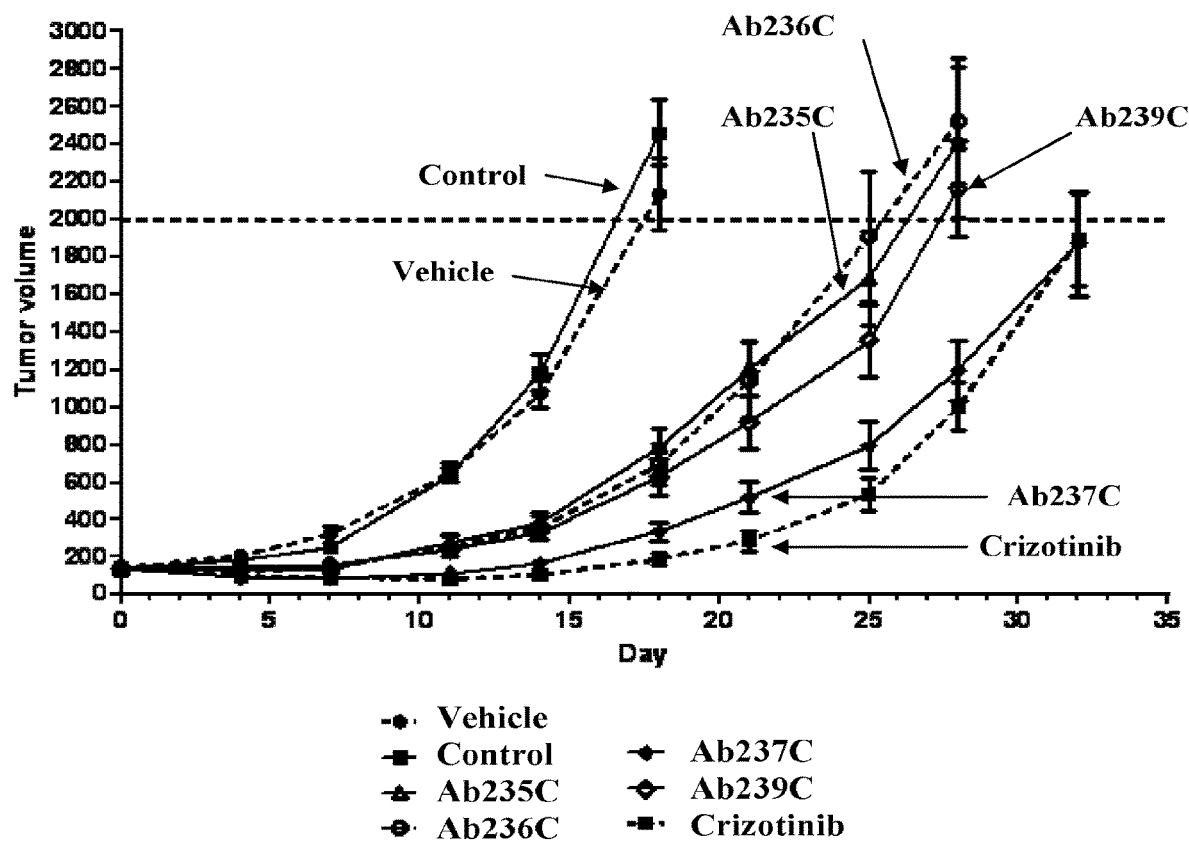
Figure 7B:
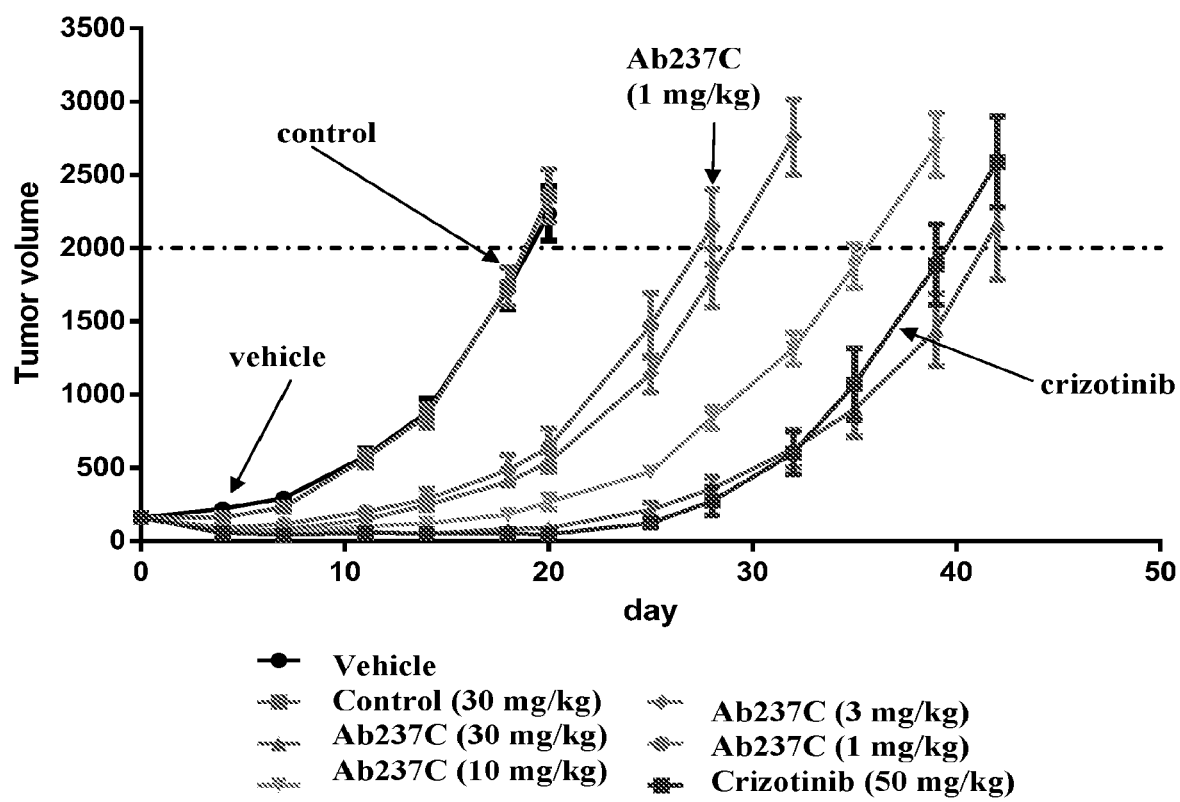

FIG. 7A depicts the tumor volume at various days post tumor implant in a U87MG subcutaneous tumor model upon treatment with control ("vehicle", dashed line, closed circles), control chimeric IgG$_1$ anti-KLH antibody (solid line, squares), Ab235C (solid line, open triangles), Ab236C (dashed line, solid circles), Ab237C (solid line, solid diamonds), Ab239C (solid line, open diamonds), or crizotinib (dashed line, squares) (50 mg/kg). FIG. 7B depicts the tumor volume at various days post tumor implant in a U87MG subcutaneous tumor model upon treatment with control ("vehicle", circles and indicated with arrow), 30 mg/kg of control chimeric IgG$_1$ anti-KLH antibody (squares and indicated with arrow), 30 mg/kg of Ab237C (triangles, point up), 10 mg/kg of Ab237C (triangles, point down), 3 mg/kg of Ab237C (diamonds), 1 mg/kg of Ab237C (circles and indicated with arrow), or 50 mg/kg of crizotinib (squares and indicated with arrow). The dashed line represents the endpoint.

Figure 8A:
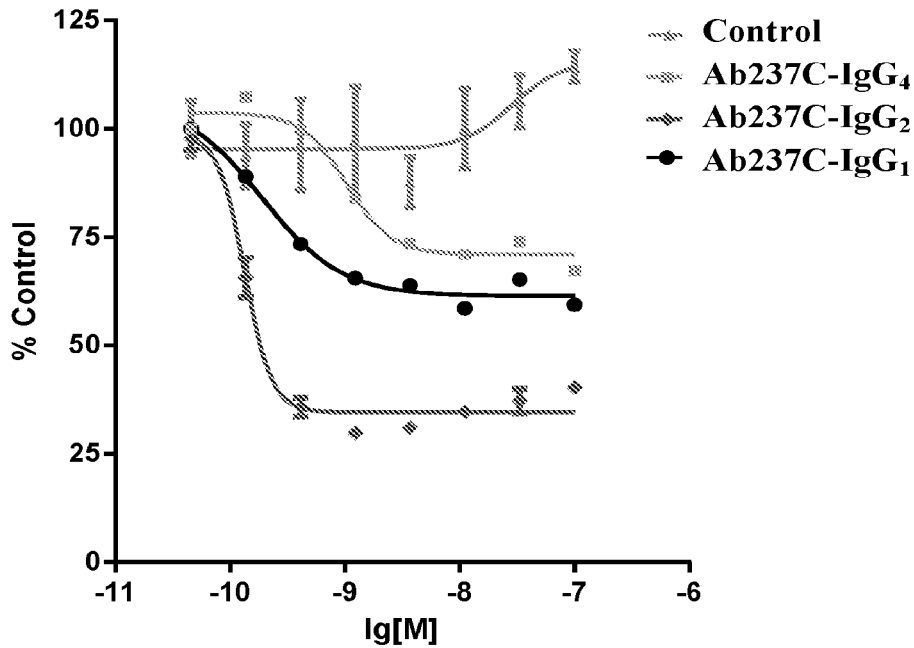
Figure 8B:
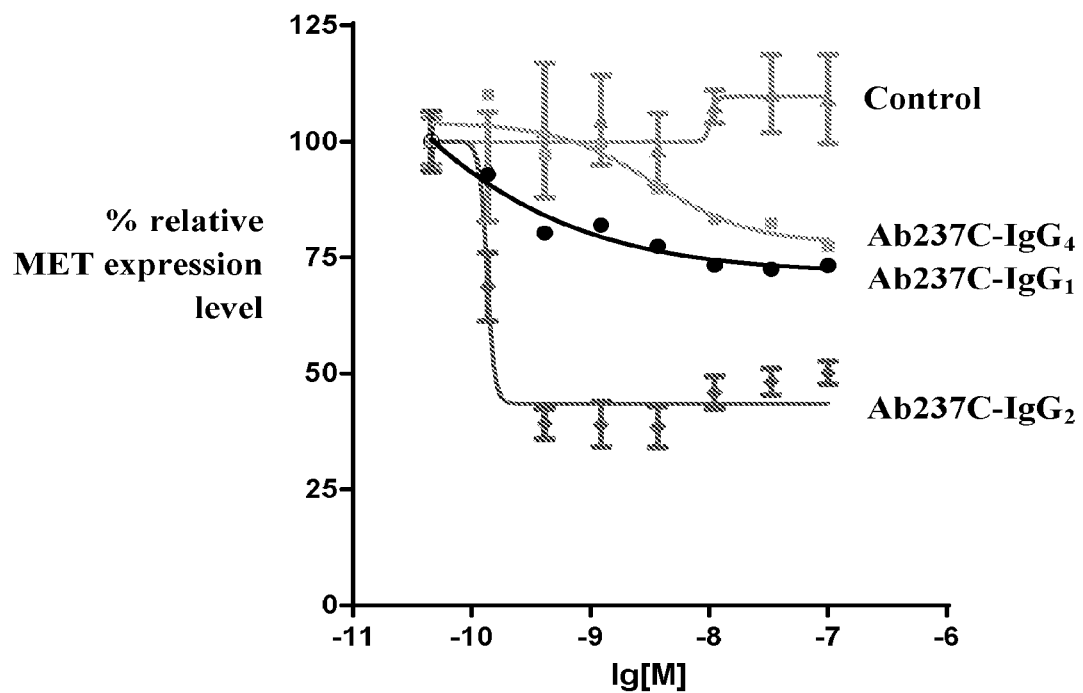
Figure 8C:
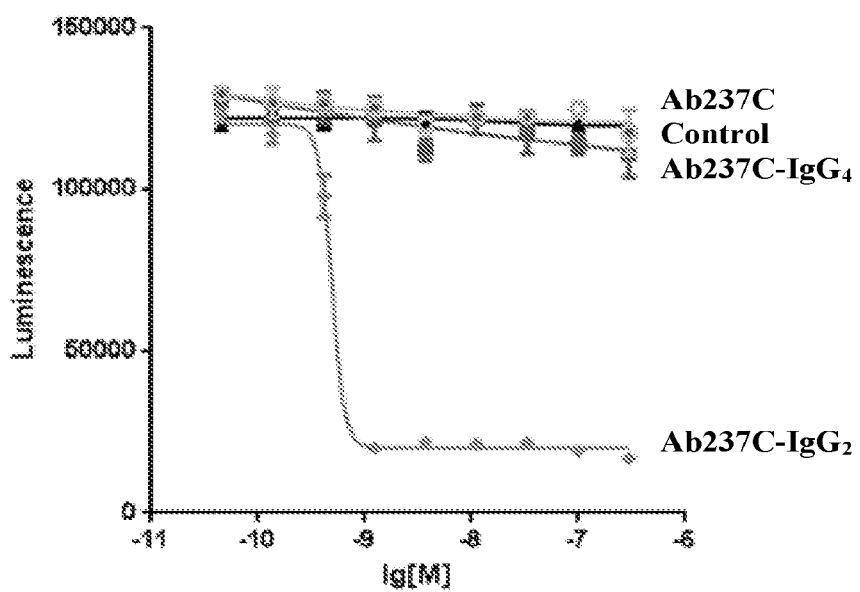
Figure 8D:
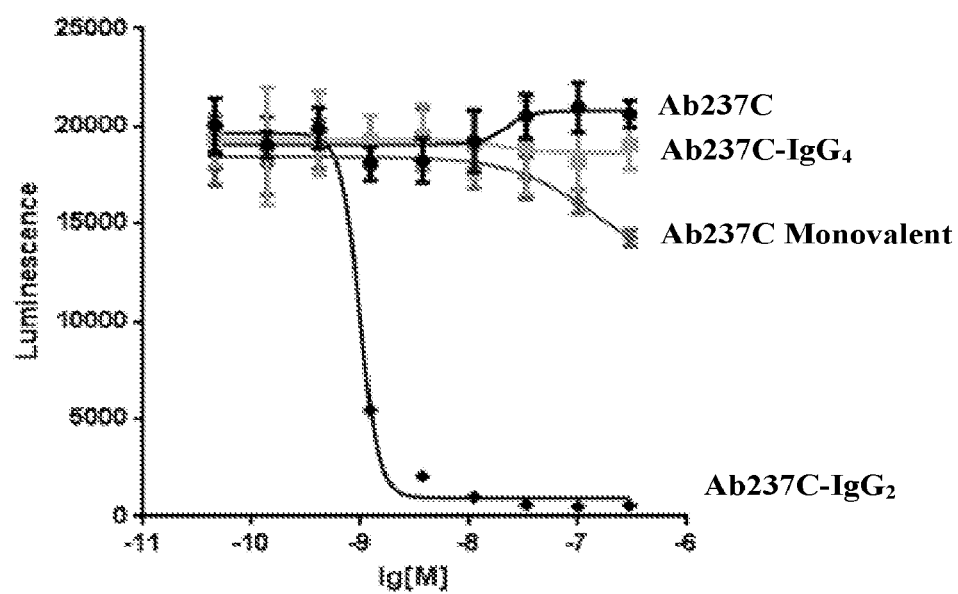
Figure 8E:
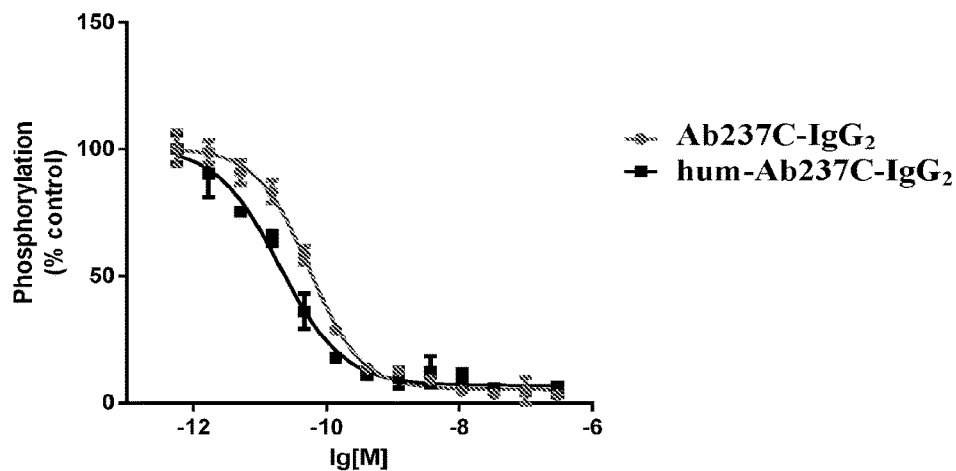
Figure 8F:
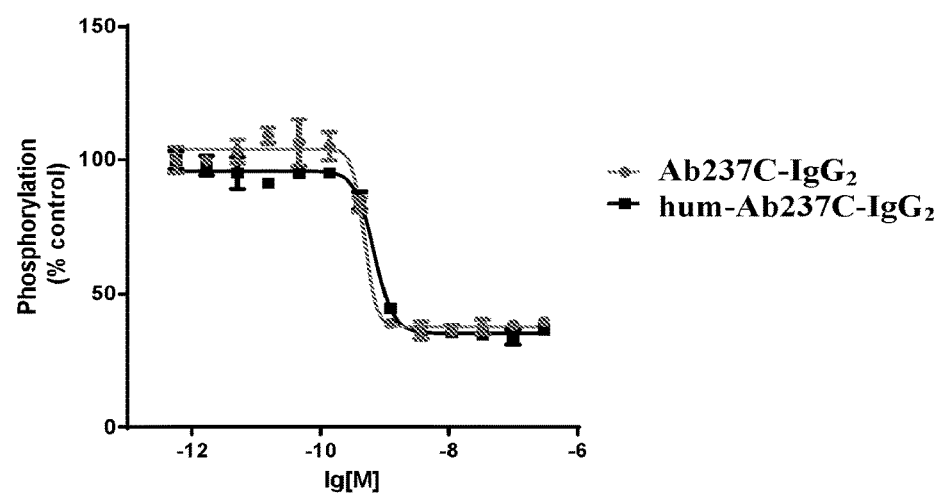
Figure 8G:
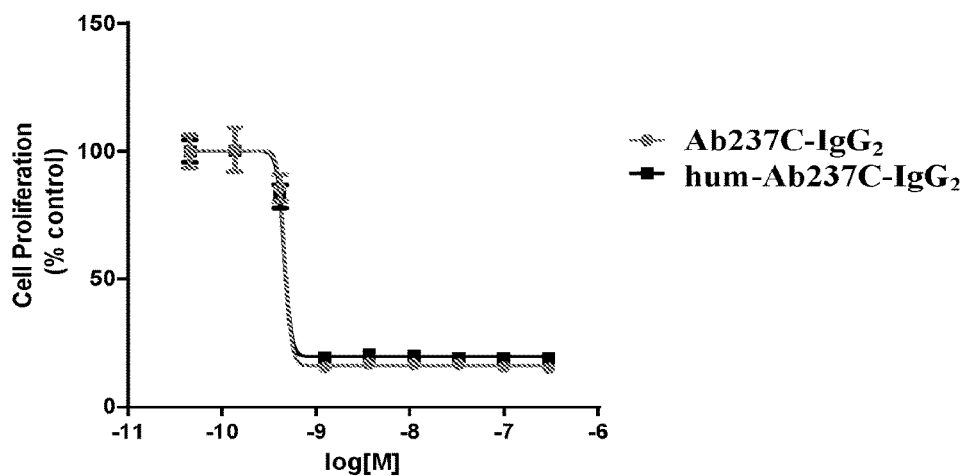

FIG. 8A depicts the percent of MET phosphorylation (relative to control) in SNU-5 cells treated with control chimeric IgG$_1$ anti-KLH antibody ("control", triangles, point up) or with Ab237C comprising a human IgG$_1$ constant region ("Ab237C-IgG$_1$", circles), Ab237C comprising a human IgG$_2$ constant region ("Ab237C-IgG$_2$", diamonds), or Ab237C comprising a human IgG$_4$ constant region ("Ab237C-IgG$_4$", squares). FIG. 8B depicts the % relative MET expression level (relative to no treatment) in SNU-5 cells treated with control chimeric IgG$_1$ anti-KLH antibody ("control", triangles, point up) or with Ab237C comprising a human IgG$_1$ human constant region ("Ab237C-IgG$_1$", circles), Ab237C-IgG$_2$ (diamonds), or Ab237C-IgG$_4$ (squares). FIG. 8C depicts the impact of treatment with control chimeric IgG$_1$ anti-KLH antibody (triangles) or with Ab237C (open circles), Ab237C-IgG$_2$ (diamonds), or Ab237C-IgG$_4$ (squares) on SNU-5 cell proliferation. FIG. 8D depicts the impact of treatment with Ab237C (circles), Ab237C-IgG$_2$ (diamonds), Ab237C-IgG$_4$ (squares), or a monovalent form of Ab237 (triangles) on EBC-1 cell proliferation. FIG. 8E depicts the percent of MET phosphorylation (relative to control) in A549 cells treated with Ab237C comprising a human IgG$_2$ constant region ("Ab237C-IgG$_2$", circles), or a humanized version of Ab237 comprising a human IgG$_2$ constant region ("hum-Ab237C-IgG$_2$", squares). FIG. 8F depicts the percent of MET phosphorylation (relative to control) in SNU-5 cells treated with Ab237C comprising a human IgG$_2$ constant region ("Ab237C-IgG$_2$", circles), or a humanized version of Ab237 comprising a human IgG$_2$ constant region ("hum-Ab237C-IgG$_2$", squares). FIG. 8G depicts the percent of cell proliferation (relative to control) in SNU-5 cells treated with Ab237C comprising a human IgG$_2$ constant region ("Ab237C-IgG$_2$", circles), or a humanized version of Ab237 comprising a human IgG$_2$ constant region ("hum-Ab237C-IgG$_2$", squares).

Figure 9A:
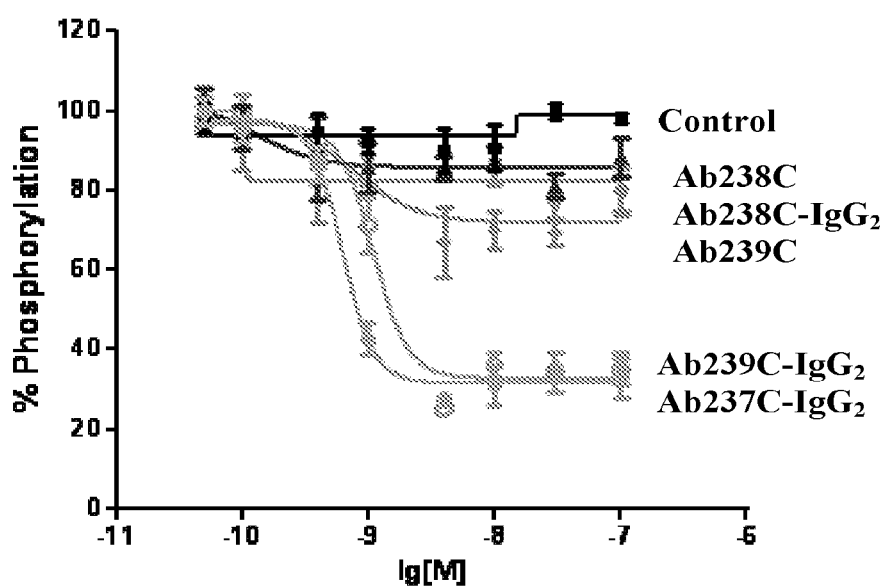
Figure 9B:
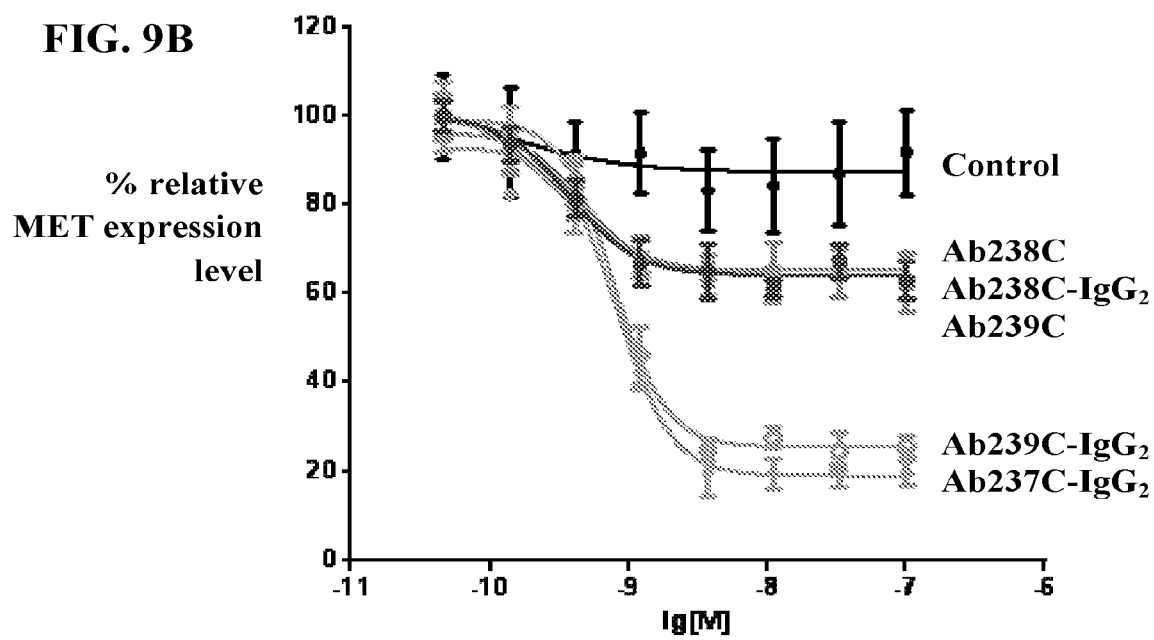
Figure 9C:
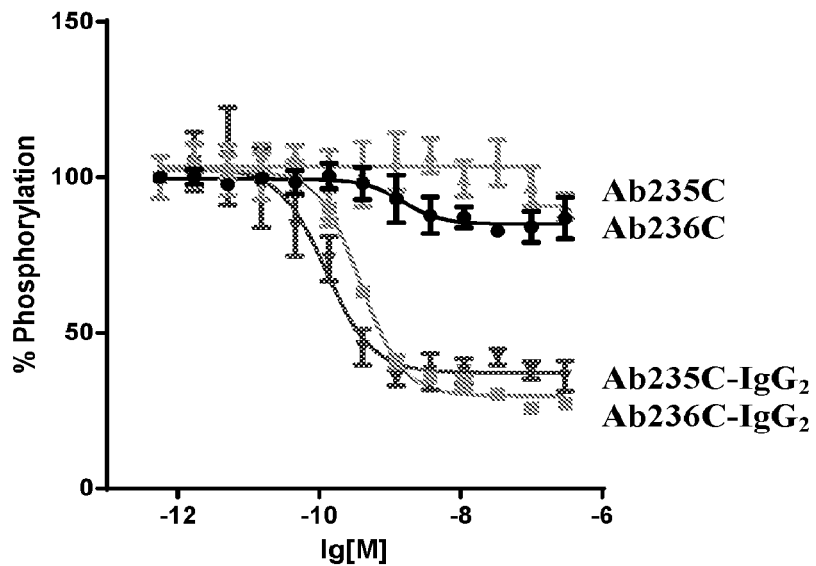
Figure 9D:
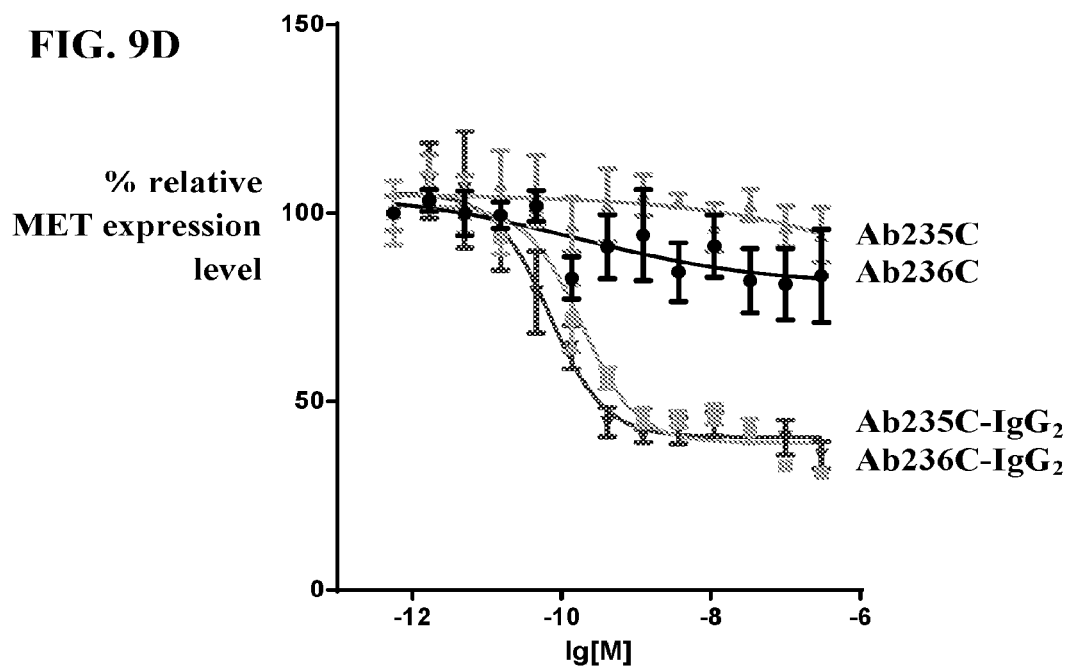

FIG. 9A depicts the percent of MET phosphorylation (relative to control) in SNU-5 cells treated with control chimeric IgG$_1$ anti-KLH antibody (squares), Ab237C-IgG$_2$ (filled circles), Ab238C (which comprises an IgG$_1$ framework; triangles, point up), Ab238C comprising a human IgG$_2$ framework ("Ab238C-IgG$_2$"; triangles, point down), Ab239C (which comprises an IgG$_1$ framework; diamonds), or Ab239C comprising a human IgG$_2$ framework ("Ab239C-IgG$_2$"; open circles). FIG. 9B depicts the % relative MET expression level (relative to no treatment) in SNU-5 cells treated with control chimeric IgG$_1$ anti-KLH antibody (diamonds), Ab237C-IgG$_2$ (diamonds), Ab238C (circles), Ab238C-IgG$_2$ (triangles, point up), Ab239C (diamonds), or Ab239C-IgG$_2$ (open circles). FIG. 9C depicts the percent of MET phosphorylation (relative to control) in SNU-5 cells treated with Ab235C (which comprises an IgG$_1$ framework; circles), Ab235C comprising a human IgG$_2$ framework ("Ab235C-IgG$_2$"; squares), Ab236C (which comprises an IgG$_1$ framework; diamonds), or Ab236C comprising a human IgG$_2$ framework ("Ab236C-IgG$_2$"; triangles). FIG. 9D depicts the % relative MET expression level in SNU-5 cells treated with Ab236C (which comprises an IgG$_1$ framework; circles), Ab236C comprising a human IgG$_2$ framework ("Ab236C-IgG$_2$"; squares), Ab235C (which comprises an IgG$_1$ framework; diamonds), or Ab235C comprising a human IgG$_2$ framework ("Ab235C-IgG$_2$"; triangles).

Figure 10A:
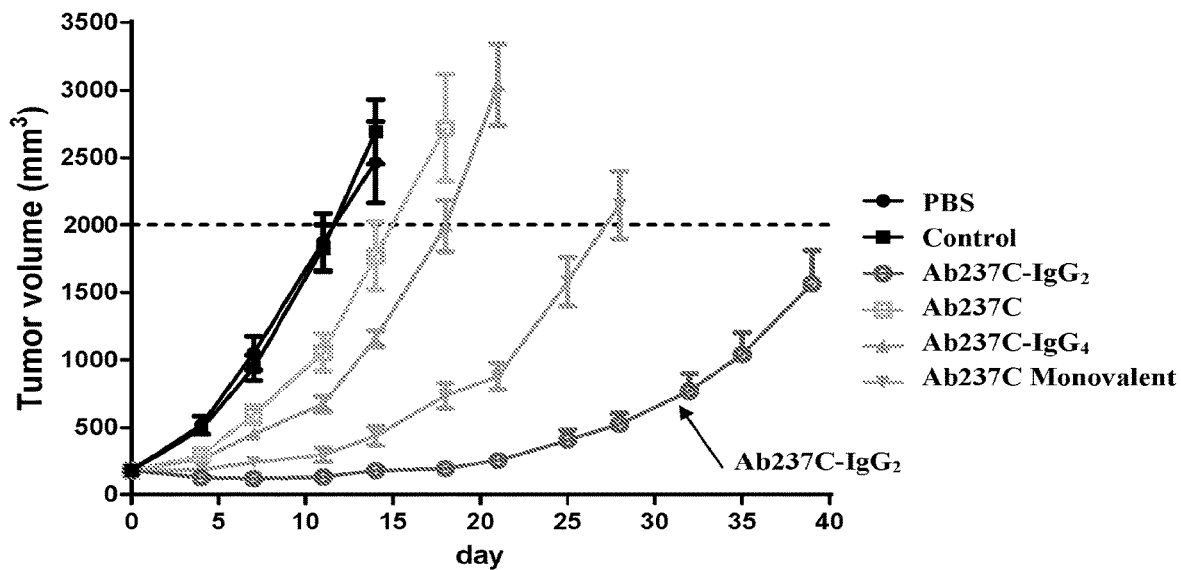
Figure 10B:
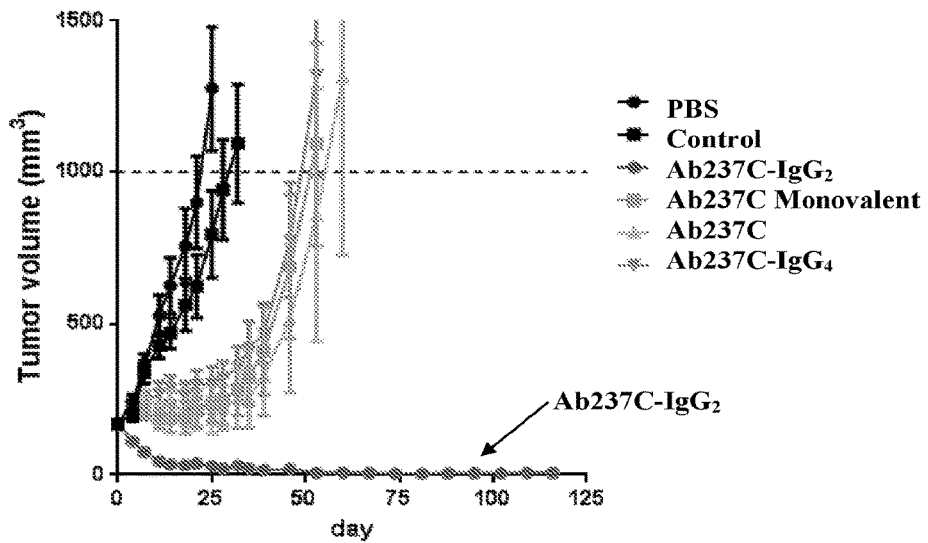

FIG. 10A depicts the effect of treatment with PBS (filled circles), control chimeric IgG$_1$ anti-KLH antibody (filled squares), Ab237C (open squares), Ab237C-IgG$_2$ (open circles), Ab237C-IgG$_4$ (triangle, point up), or a monovalent anti-MET antibody (triangle, point down) on tumor volume at the indicated days post tumor implant in a U87 xenograft mouse model. FIG. 10B depicts the effect of treatment with PBS (filled circles), control chimeric IgG$_1$ anti-KLH antibody (filled squares), Ab237C (triangle, point up), Ab237C-IgG$_2$ (open circles), Ab237C-IgG$_4$ (triangle, point down), or a monovalent anti-MET antibody (open squares) on tumor volume at the indicated days post tumor implant in a SNU-5 xenograft mouse model.

Figure 11A:
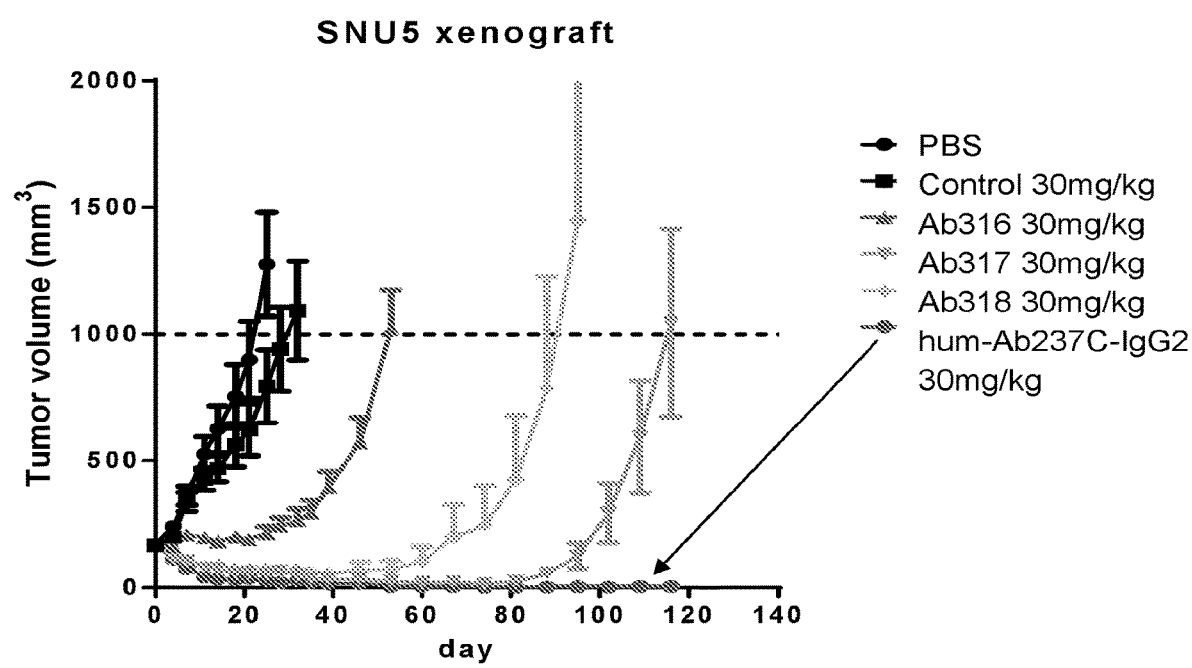
Figure 11B:
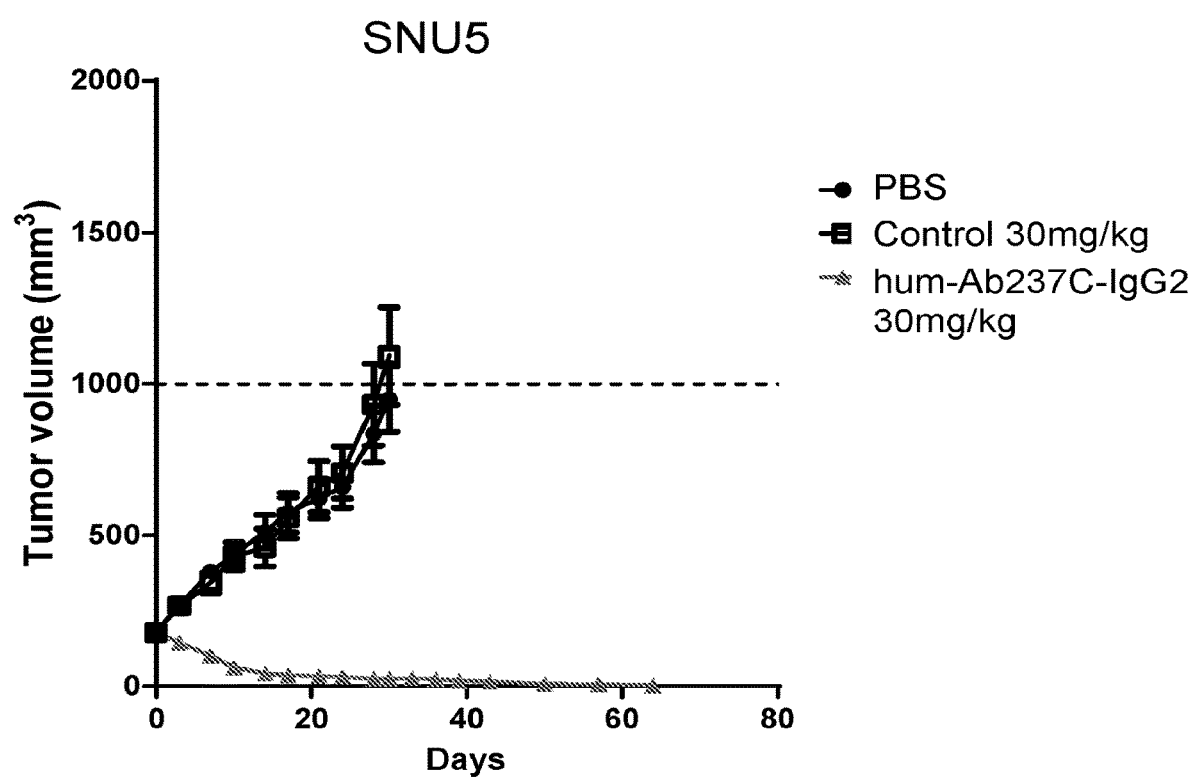
Figure 11C:
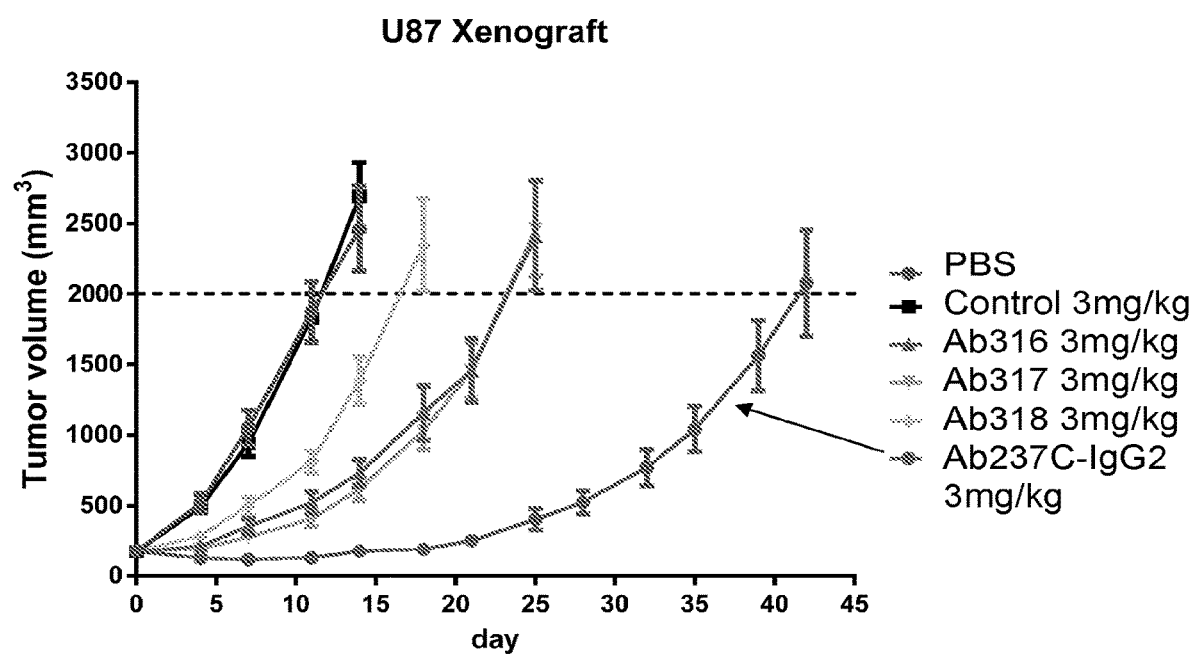
Figure 11D:
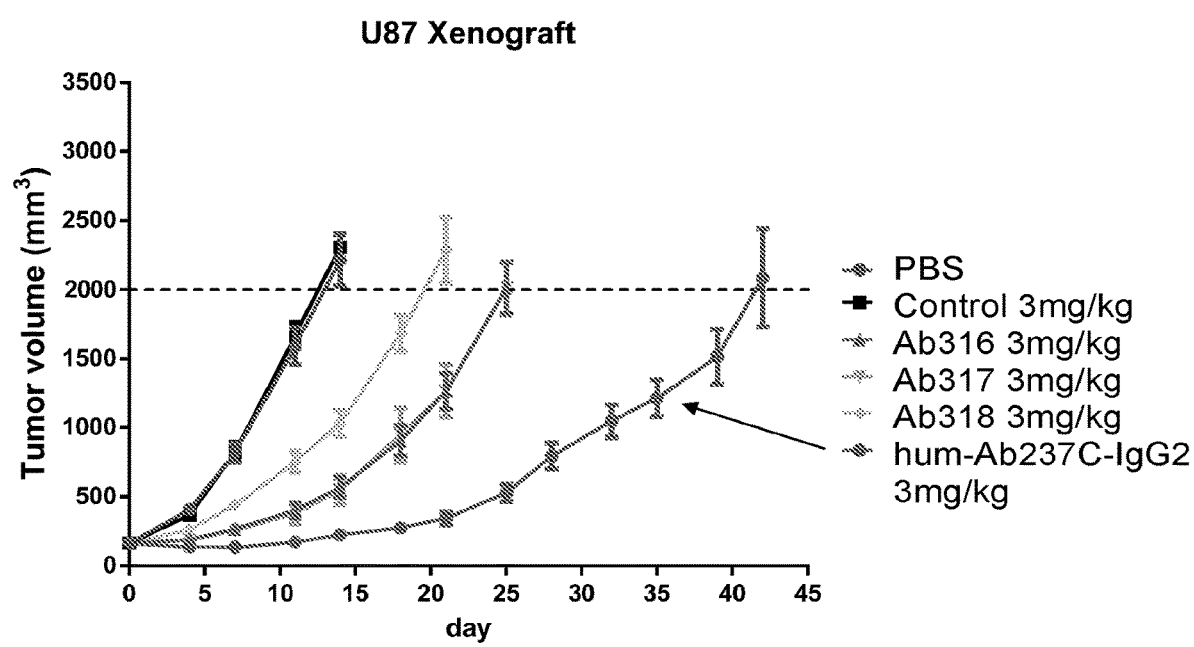

FIG. 11A depicts the effect of treatment with PBS (black circles), control chimeric IgG$_1$ anti-KLH antibody (black squares), Ab316 (triangles, point up), Ab317 (triangles, point down), Ab318 (diamonds), or Ab237C-IgG$_2$ (grey circles, and indicated with arrow) on tumor volume at the indicated days post tumor implant in a SNU5 xenograft mouse model at the indicated antibody doses. FIG. 11B depicts the effect of treatment with PBS (black circles), control chimeric IgG$_1$ anti-KLH antibody (squares), or hum-Ab237C-IgG$_2$ (triangles) on tumor volume at the indicated days post tumor implant in a SNU5 xenograft mouse model at the indicated antibody doses. FIG. 11C depicts the effect of treatment with PBS (grey circles), control chimeric IgG$_1$ anti-KLH antibody (squares), Ab316 (triangles, point up), Ab317 (triangles, point down), Ab318 (diamonds), or Ab237C-IgG$_2$ (circles, and indicated with arrow) on tumor volume at the indicated days post tumor implant in a U87 xenograft mouse model at the indicated antibody doses. FIG. 11D depicts the effect of treatment with PBS (grey circles), control chimeric IgG$_1$ anti-KLH antibody (squares), Ab316 (triangles, point up), Ab317 (triangles, point down), Ab318 (diamonds), or hum-Ab237C-IgG$_2$ (circles, and indicated with arrow) on tumor volume at the indicated days post tumor implant in a U87 xenograft mouse model at the indicated antibody doses.

Figure 12A:
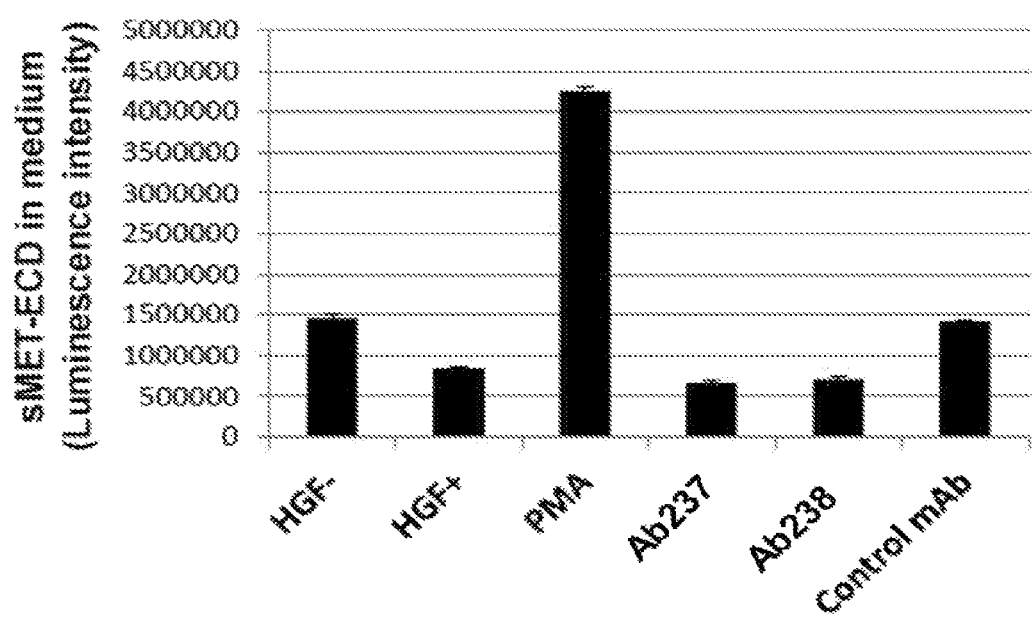
Figure 12B:
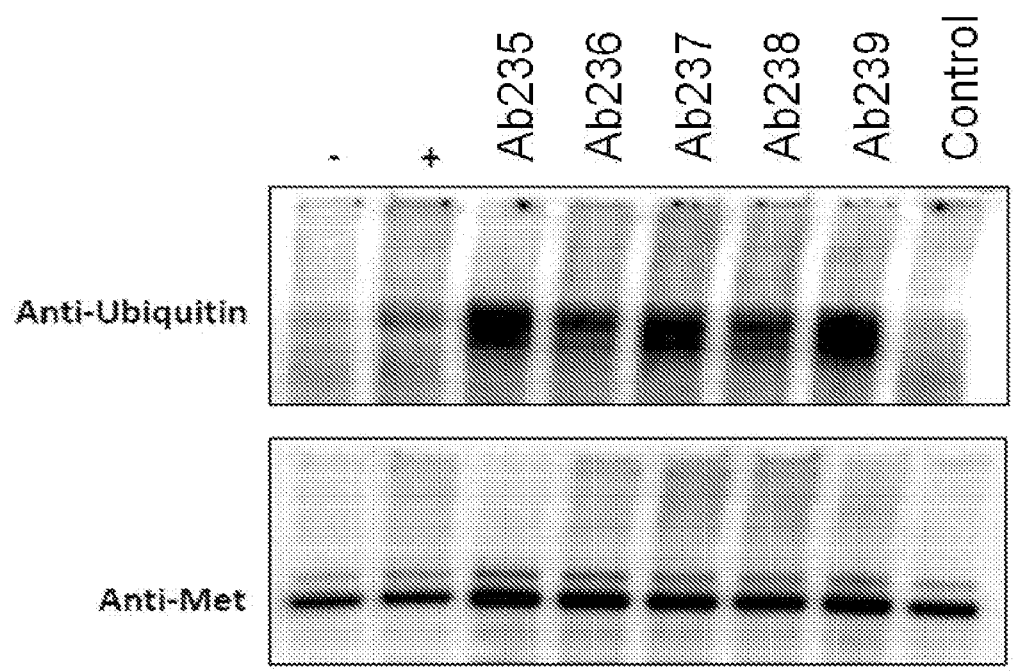

FIG. 12A depicts that the anti-MET antibodies demonstrated no effect on MET shedding. A549 cells were treated with PMA, HGF or anti-MET antibodies for 24 hrs. Cell culture medium was collected at the end of incubation and sMET-ECD levels were measured by ELISA using capture and detection antibodies against MET-ECD. FIG. 12B depicts that the anti-MET antibodies induced MET ubiquitination. A549 cells were treated with 1 nM of HGF or 1 nM of anti-MET antibodies for 15 min. Cell lysates were immunoprecipitated with anti-ubiquitin antibody conjugated agarose (Santa Cruz) and immunoblotted with anti-MET antibody (Cell Signaling Technology). Total cell lysates from the same samples were immunoblotted with anti-MET antibody to show total MET protein level.

Figure 13A:
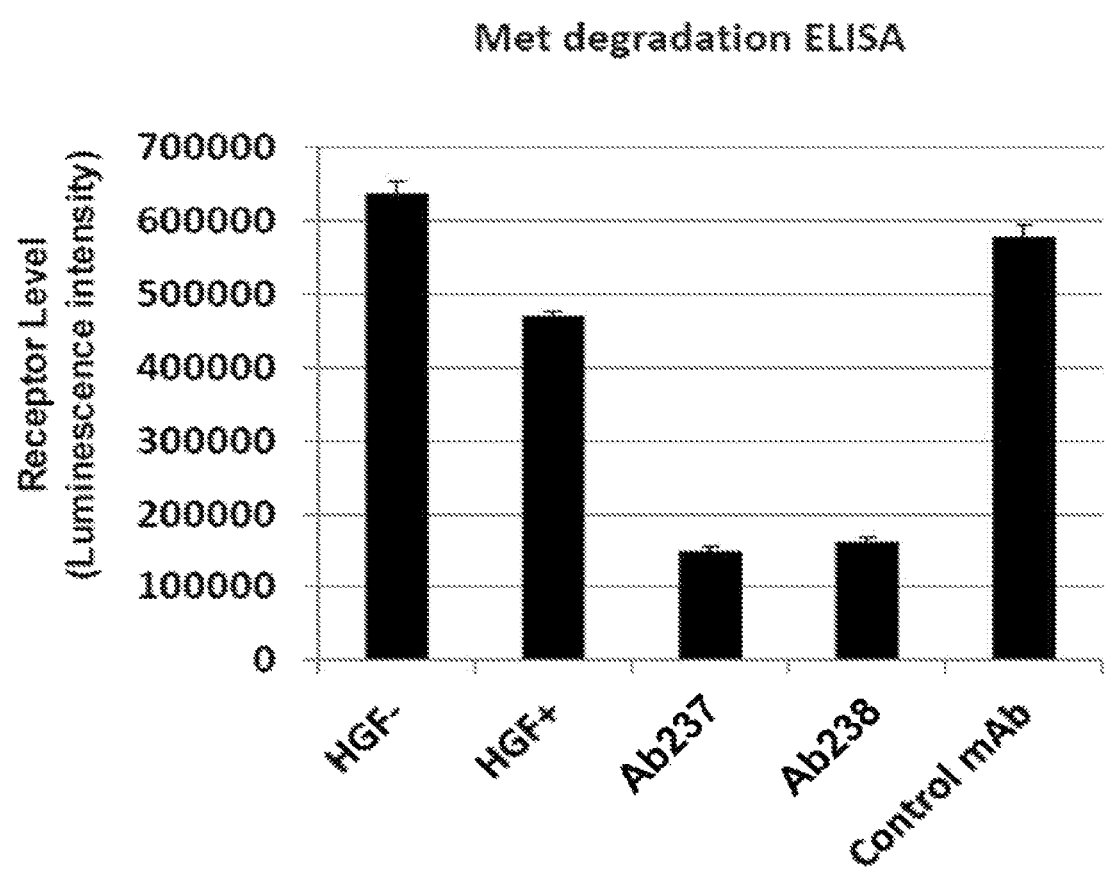
Figure 13B:
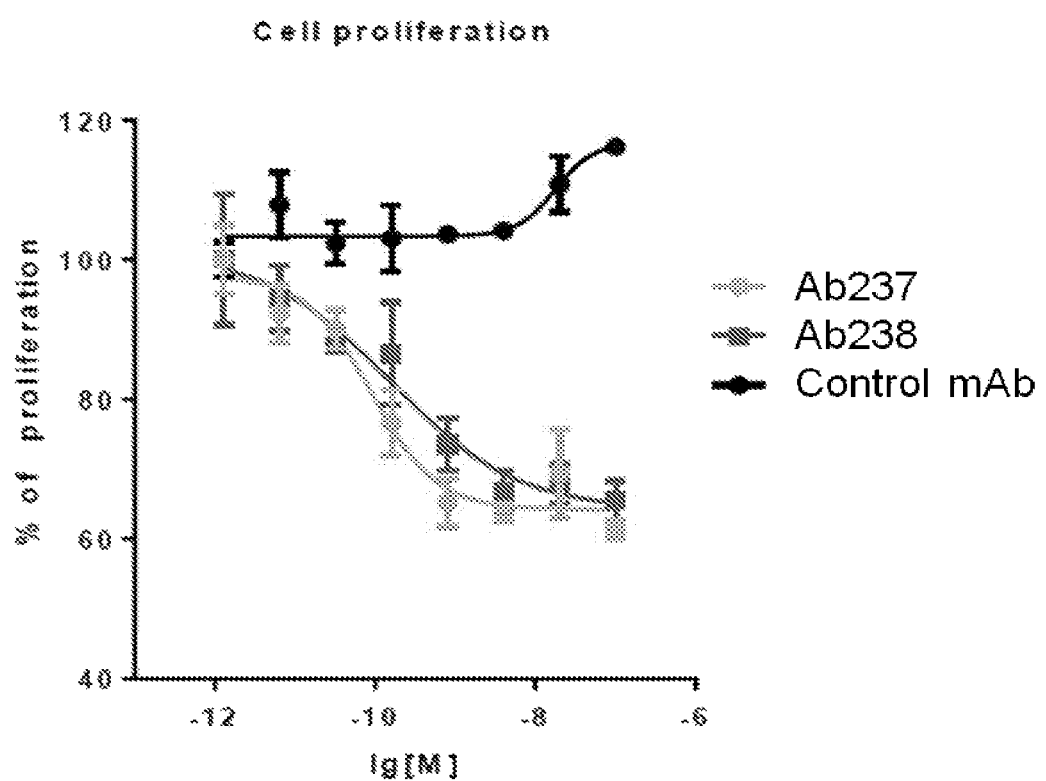

FIG. 13A depicts that the anti-MET antibodies induce MET degradation in cells with exon 14 deletion mutation. H596 cells with MET an exon 14 mutation were incubated with 1 nM of HGF or 1 nM of antibody for 24 hrs. MET protein levels were detected by ELISA. FIG. 13B depicts that the anti-MET antibodies inhibit proliferation of cells with exon 14 deletion mutation. H596 cells were serum-starved and treated with indicated antibody for 5 days in the presence of HGF followed by measurement of cell proliferation by CellTiter-Glo.

Figure 14:
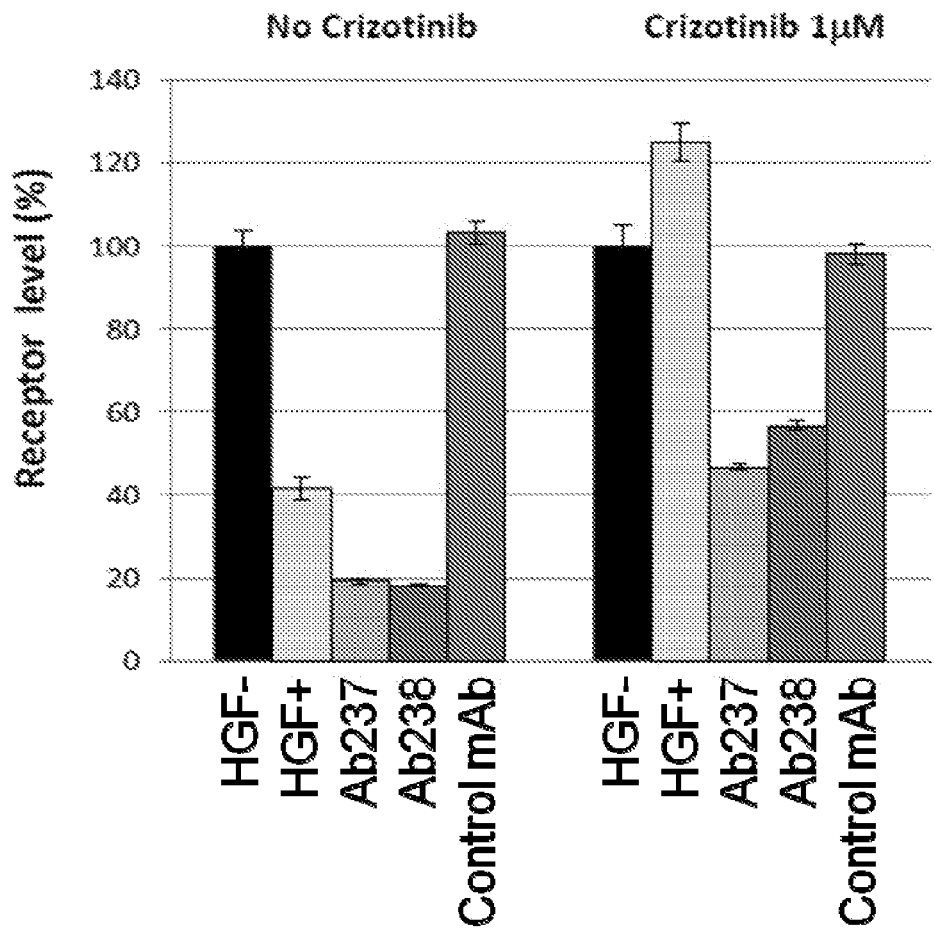

FIG. 14 depicts that the anti-MET antibody induced MET degradation was partially inhibited by crizotinib. A549 cells were either pre-incubated with 1 µM of crizotinib for 1 hr or without. Cells were then treated with 1 nM of HGF or 1 nM of antibody for 24 hrs after which MET protein level was quantified by ELISA.

5. DETAILED DESCRIPTION

In one aspect, provided herein are antibodies (e.g., monoclonal antibodies), and antigen-binding fragments thereof, that specifically bind to a MET polypeptide (e.g., an ECD of human MET) and modulate MET activity (e.g., MET signaling) and/or MET expression. The antibodies provided herein display potent inhibition of tumor growth in preclinical models where MET has been implicated in tumor growth. In certain aspects, provided herein are antibodies that modulate ligand-dependent MET activity. In certain aspects, provided herein are antibodies that modulate MET-amplified (e.g., ligand-independent) MET activity. In a specific embodiment, such antibodies, which specifically bind to an ECD of human MET (e.g., Sema/PSI domain, for example, a Sema domain or one or more amino acid residues thereof, such as one or more of amino acid residues Q328, R331, S336, L337, and N338 of human MET-ECD), inhibits MET activity (e.g., inhibits phosphorylation of MET, induces MET degradation, and/or inhibits tumor cell proliferation or tumor growth) better as an $IgG_2$ isotype as compared to as an $IgG_1$ isotype. Also provided are isolated nucleic acids (polynucleotides), such as complementary DNA (cDNA), encoding such antibodies, and antigen-binding fragments thereof. Further provided are vectors (e.g., expression vectors) and cells (e.g., host cells) comprising nucleic acids (polynucleotides) encoding such antibodies or antigen-binding fragments thereof. Also provided are methods of making such antibodies and cells, e.g., host cells. In other aspects, provided herein are methods and uses for modulating MET expression or MET activity (e.g., inhibiting MET expression or MET activity), or treating or managing certain conditions or disorders described herein, such as treating or managing cancer. Related compositions (e.g., pharmaceutical compositions), kits, and diagnostic methods are also provided.

As used herein, the terms "c-Met" or "MET" or "MET receptor" or "MET polypeptide" refer to the MET receptor tyrosine kinase protein as described in Park et al., 1987, Proc. Natl. Sci., 84:6379-6383, and Trusolino et al., 2010, Nat. Rev. Mol. Cell Biol., 11:834-848). GenBank™ accession numbers NM_001127500.1 and NM_000245.2 provide an exemplary human MET nucleic acid sequence. GenBank™ accession numbers NP_001120972.1 and NP_000236.2 provide exemplary human MET amino acid sequences. Native MET comprises an extracellular domain, which comprises an alpha chain and a beta chain, and an intracellular domain, which comprises a portion of the beta chain. The extracellular MET domain comprises a Sema domain, a PSI domain, and four IPT domains (see, e.g., Trusolino et al., 2010, Nat. Rev. Mol. Cell Biol., 11:834-848). An exemplary amino acid sequence of an ECD of human MET is provided in FIG. 1.

5.1 Antibodies

In a specific aspect, provided herein are antibodies (e.g., monoclonal antibodies, such as chimeric or humanized, for example, composite human, antibodies) which specifically bind to an extracellular domain (ECD) of human MET (e.g., Sema/PSI domain, for example, a Sema domain, of human MET) and modulate MET expression and/or MET activity. In certain aspects, provided herein are antibodies that bind to a Sema/PSI domain of human MET. In certain aspects, provided herein are antibodies that bind to a Sema domain of human MET. In certain aspects, provided herein are antibodies that bind to one or more of amino acid residues Q328, R331, S336, L337, and N338 of human MET. In certain aspects, said antibodies modulate ligand-dependent MET activity. In certain aspects, said antibodies modulate MET-amplified (e.g., ligand-independent) MET activity. In certain embodiments, an anti-MET antibody described herein, or an antigen-binding fragment thereof, inhibits MET activity (e.g., ligand-dependent MET activity and/or MET-amplified (e.g., ligand-independent) MET activity) in a cell, for example, as determined by inhibition of phosphorylation of MET, cell proliferation, and/or cell scatter. In certain embodiments, an anti-MET antibody described herein or an antigen-binding fragment thereof inhibits MET ligand (e.g., hepatocyte growth factor (HGF)) binding to MET receptor. In certain embodiments, an anti-MET antibody described herein or an antigen-binding fragment thereof induces MET receptor degradation. In certain embodiments, an anti-MET antibody described herein or an antigen-binding fragment thereof induces HGF-induced receptor degradation of a MET receptor comprising one or more mutations, e.g., deletions, in exon 14 (encoding, e.g., Leu964-Asp1010) of the human MET gene. In certain embodiments, an anti-MET antibody described herein or an antigen-binding fragment thereof blocks MET ligand (e.g., hepatocyte growth factor (HGF)) binding to MET receptor and induces MET receptor degradation. In certain embodiments, an anti-MET antibody described herein or an antigen-binding fragment thereof inhibits MET ligand (e.g., hepatocyte growth factor (HGF)) binding to MET receptor and induces MET receptor degradation better as an $IgG_2$ isotype as compared to as an $IgG_1$ isotype. In certain embodiments, an anti-MET antibody described herein or an antigen-binding fragment thereof inhibits tumor cell proliferation or tumor growth. In certain embodiments, an anti-MET antibody described herein or an antigen-binding fragment thereof inhibits tumor cell proliferation or tumor growth better as an $IgG_2$ isotype as compared to as an $IgG_1$ isotype. In a specific aspect, antibodies provided herein, which specifically bind to an ECD of human MET (e.g., Sema/PSI domain, for example, a Sema domain, of human MET-ECD), inhibit MET activity (e.g., inhibit phosphorylation of MET, induce MET degradation, or inhibit tumor cell proliferation or tumor growth) better as an $IgG_2$ isotype (e.g., human $IgG_2$ isotype) as compared to as an $IgG_1$ isotype (e.g., human $IgG_1$ isotype) in cells (e.g., EBC-1 cells and SNU-5 cells) having ligand-independent MET activity, for example, in cells having MET amplification or MET mutant, e.g., constitutively active MET mutant. In certain embodiments, an anti-MET antibody described herein or an antigen-binding fragment thereof specifically binds to human MET and monkey MET, but not mouse MET or dog MET. In certain embodiments, the antibody or antigen-binding fragment thereof specifically binds to the SEMA domain of human MET and monkey MET, but not the SEMA domain of mouse MET or dog MET. In certain embodiments, provided herein are antibodies that bind to one or more of amino acid residues Q328, R331, S336, L337, and N338 of human MET. In certain embodiments, antibodies or antigen-binding fragments described herein can comprise sequences that do not naturally exist within the antibody germline repertoire of an animal or mammal (e.g., human) in vivo.

As used herein and unless otherwise specified, the terms "about" or "approximately" mean within plus or minus 10% of a given value or range. In instances where an integer is required, the terms mean within plus or minus 10% of a given value or range, rounded either up or down to the nearest integer.

As used herein, the terms "antibody" and "immunoglobulin" and "Ig" are terms of art and can be used interchangeably herein and refer to a molecule with an antigen binding site that specifically binds an antigen.

Antibodies can include, for example, monoclonal antibodies, recombinantly produced antibodies, monospecific antibodies, multispecific antibodies (including bispecific antibodies), human antibodies, humanized antibodies, such as composite human antibodies or deimmunized antibodies, murine antibodies (e.g., mouse or rat antibodies), chimeric antibodies, synthetic antibodies, and tetrameric antibodies comprising two heavy chain and two light chain molecules. In specific embodiments, antibodies can include, but are not limited to an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, and monovalent antibodies. In a specific embodiment, antibodies can include antigen-binding fragments or epitope binding fragments such as, but not limited to, single chain antibodies or single-chain Fvs (scFv) (e.g., including monospecific, bispecific, etc.), camelized antibodies, affybodies, Fab fragments, F(ab') fragments, F(ab')$_2$ fragments, and disulfide-linked Fvs (sdFv). In certain embodiments, antibodies described herein refer to polyclonal antibody populations.

Antibodies can be of any type (e.g., IgG, IgE, IgM, IgD, IgA or IgY), any class, (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$, IgG$_2$, or IgG$_4$) or subclass thereof. In certain embodiments, antibodies described herein are IgG$_2$ antibodies (e.g., human IgG$_2$) or a subclass thereof (e.g., human IgG$_{2a}$ or human IgG$_{2b}$, or a mixture thereof). In certain embodiments, antibodies described herein (e.g., Ab235, Ab236, Ab237, Ab238, Ab239, and Ab241-Ab255) are IgG$_1$ antibodies (e.g., human IgG$_1$) or a subclass thereof. In certain embodiments, IgG$_1$ antibodies described herein (e.g., Ab235, Ab236, Ab237, Ab239, and Ab241-Ab255) comprise one or more amino acid substitutions and/or deletions in the constant region such that the antibody functions more like an IgG$_2$ (e.g., human IgG$_2$, human IgG$_{2a}$, human IgG$_{2b}$, or a mixture thereof).

As used herein, an "antigen" is a moiety or molecule that contains an epitope to which an antibody can specifically bind. As such, an antigen is also specifically bound by an antibody. In a specific embodiment, the antigen to which an antibody described herein binds, is human MET, or a fragment thereof, for example, an extracellular domain of human MET. In another specific embodiment, the antigen to which an antibody described herein binds, is the SEMA/PSI domain of human MET. The SEMA/PSI domain of human MET refers to a polypeptide comprising the SEMA and PSI domains. An exemplary SEMA/PSI domain corresponds to amino acids 25 to 562 of a human MET sequence provided in FIG. 1A.

As used herein, an "epitope" is a term in the art and refers to a localized region of an antigen to which an antibody can specifically bind. An epitope can be a linear epitope or a conformational, non-linear, or discontinuous, epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, an anti-MET antibody described herein binds to a group of amino acids regardless of whether they are folded in a natural three dimensional protein structure. In other embodiments, an anti-MET antibody described herein does not recognize the individual amino acid residues making up the epitope, and require a particular conformation (e.g., bend, twist, turn or fold) in order to recognize and bind the epitope.

As used herein, the terms "immunospecifically binds," "immunospecifically recognizes," "specifically binds," and "specifically recognizes" are analogous terms in the context of antibodies and refer to molecules that bind to an antigen/epitope as such binding is understood by one skilled in the art. For example, a molecule that specifically binds to an antigen may bind to other peptides or polypeptides, generally with lower affinity as determined by, e.g., immunoassays, surface plasmon resonance assays, for example, Biacore™, KinExA platform (Sapidyne Instruments, Boise, ID), or other assays known in the art. In a specific embodiment, molecules that specifically bind to an antigen bind to the antigen with a K$_a$ that is at least 2 logs, 2.5 logs, 3 logs, 4 logs or greater than the K$_a$ when the molecules bind to another antigen. In another specific embodiment, molecules that specifically bind to an antigen do not cross react with other proteins. In another specific embodiment, molecules that specifically bind to an antigen do not cross react with other non-MET proteins.

As used herein, the term "monoclonal antibody" is a well known term of art that refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell or cell line wherein the antibody immunospecifically binds to a MET epitope (e.g., an epitope of the extracellular domain of human MET) as determined, e.g., by ELISA or other antigen-binding or competitive binding assay known in the art or in the Examples provided herein. In particular embodiments, a monoclonal antibody can be a chimeric antibody or a humanized antibody. In particular embodiments, a monoclonal antibody can be a composite human antibody. In particular embodiments, a monoclonal antibody can be a deimmunized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody).

As used herein, the term "polyclonal antibodies" refers to an antibody population that includes a variety of different antibodies that immunospecifically bind to the same and/or to different epitopes within an antigen or antigens.

As used herein, the terms "variable region" or "variable domain" refer to a portion of an antibody, generally, a portion of an antibody light or heavy chain, typically about the amino-terminal 110 to 120 amino acids in a mature heavy chain and about the amino-terminal 90 to 100 amino acids in a mature light chain. Variable regions comprise complementarity determining regions (CDRs) flanked by framework regions (FRs). Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242. In certain embodiments, the variable region is a human variable region. In certain embodiments, the variable region comprises murine (e.g., mouse or rat) CDRs and human framework regions (FRs). In particular embodiments, the variable region is a primate (e.g., human or non-human primate) variable region. In certain embodiments, the variable region comprises murine (e.g., mouse or rat) CDRs and primate (e.g., human or non-human primate) framework regions (FRs). As a non-limiting example, a variable region described herein is obtained from assembling two or more fragments of human sequences into a composite human sequence.

In certain aspects, the CDRs of an antibody can be determined according to (i) the Kabat numbering system (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al., 1999, Nucleic Acids Res., 27:209-212 ("IMGT CDRs"); or (iv) MacCallum et al., 1996, J. Mol. Biol., 262:732-745. See also, e.g., Martin, A., "Protein Sequence and Structure Analysis of Antibody Variable Domains," in *Antibody Engineering*, Kontermann and Dühel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

Antibodies provided herein can be of any type (e.g., IgG, IgE, IgM, IgD, IgA or IgY), any class, (e.g., $IgG_1$, $IgG_2$, $IgG_3$, $IgG_4$, $IgA_1$ or $IgA_2$), or any subclass (e.g., $IgG_{2a}$ or $IgG_{2b}$, or a mixture thereof) of immunoglobulin molecule. In certain embodiments, antibodies described herein are IgG antibodies (e.g., human IgG), or a class (e.g., human $IgG_1$ or $IgG_4$) or subclass thereof. In a specific embodiment, an antibody provided herein comprises $IgG_2$ constant region, e.g., human $IgG_2$ constant region, for example, an $IgG_{2a}$ or $IgG_{2b}$ antibody. Without being bound by any theory, $IgG_{2a}$ and $IgG_{2b}$ (e.g., human $IgG_{2a}$ and human $IgG_{2b}$, respectively) comprise the same amino acid sequence, but differ in disulfide bond conformation. See, e.g., Dillon, 2008, JBC, 2 83(23):16206-15. Accordingly, in certain embodiments, an antibody provided herein comprises a mixture of an $IgG_{2a}$ and an $IgG_{2b}$ (e.g., human $IgG_{2a}$ and human $IgG_{2b}$, respectively) constant region.

In a specific embodiment, an anti-MET antibody provided herein or an antigen-binding fragment thereof comprises CDRs of a VL region and CDRs of a VH region of any one of antibodies Ab235-Ab255 described herein, and specifically binds MET. For example, provided herein are antibodies, and antigen-binding fragments thereof, that specifically bind MET and comprise CDRs of a VL domain in Table 9, below, and CDRs of a VH domain in Table 10, below. In a specific embodiment, an anti-MET antibody provided herein, or an antigen-binding fragment thereof, comprises a VL region and a VH region of any one of antibodies Ab235-Ab255 described herein. For example, provided herein are antibodies, and antigen-binding fragments thereof, that specifically bind MET and comprise a VL domain in Table 9, below, and VH domain in Table 10, below.

In certain embodiments, an antibody described herein comprises a VL domain as described herein, wherein the VL domain does not comprise a signal sequence. In certain embodiments, an antibody described herein comprises a VH domain as described herein, wherein the VH domain does not comprise a signal sequence. In certain embodiments, an antibody described herein comprises a VL domain and a VH domain, wherein the VL domain does not comprise a signal sequence, and wherein the VH domain does not comprise a signal sequence. In certain embodiments, an antibody described herein comprises a VL domain, wherein the VL domain comprises a signal sequence. In certain embodiments, an antibody described herein comprises a VH domain, wherein the VH domain comprises a signal sequence. In certain embodiments, an antibody described herein comprises a VL domain and a VH domain, wherein the VL domain comprises a signal sequence, and wherein the VH domain comprises a signal sequence.

In a specific embodiment, an anti-MET antibody described herein or an antigen-binding fragment thereof comprises a VL region comprising SEQ ID NO: 57 and a VH region comprising SEQ ID NO: 66 (e.g., antibody Ab235). In a specific embodiment, an anti-MET antibody described herein or an antigen-binding fragment thereof comprises a VL region comprising SEQ ID NO: 58 and a VH region comprising SEQ ID NO: 67 (e.g., antibody Ab236). In a specific embodiment, an anti-MET antibody described herein or an antigen-binding fragment thereof comprises a VL region comprising SEQ ID NO: 59 and a VH region comprising SEQ ID NO: 68 (e.g., antibody Ab237). In a specific embodiment, an anti-MET antibody described herein or an antigen-binding fragment thereof comprises a VL region comprising SEQ ID NO: 60 and a VH region comprising SEQ ID NO: 69 (e.g., antibody Ab238). In a specific embodiment, an anti-MET antibody described herein or an antigen-binding fragment thereof comprises a VL region comprising SEQ ID NO: 61 and a VH region comprising SEQ ID NO: 70 (e.g., antibody Ab239). In a specific embodiment, an anti-MET antibody described herein or an antigen-binding fragment thereof comprises a VL region comprising SEQ ID NO: 62 and a VH region comprising SEQ ID NO: 71 (e.g., antibody Ab240). In a specific embodiment, an anti-MET antibody described herein or an antigen-binding fragment thereof comprises a VL region comprising SEQ ID NO: 52 and a VH region comprising SEQ ID NO: 63 (e.g., antibody Ab241). In a specific embodiment, an anti-MET antibody described herein or an antigen-binding fragment thereof comprises a VL region comprising SEQ ID NO: 53 and a VH region comprising SEQ ID NO: 63 (e.g., antibody Ab242). In a specific embodiment, an anti-MET antibody described herein or an antigen-binding fragment thereof comprises a VL region comprising SEQ ID NO: 54 and a VH region comprising SEQ ID NO: 63 (e.g., antibody Ab243). In a specific embodiment, an anti-MET antibody described herein or an antigen-binding fragment thereof comprises a VL region comprising SEQ ID NO: 55 and a VH region comprising SEQ ID NO: 63 (e.g., antibody Ab244). In a specific embodiment, an anti-MET antibody described herein or an antigen-binding fragment thereof comprises a VL region comprising SEQ ID NO: 56 and a VH region comprising SEQ ID NO: 63 (e.g., antibody Ab246). In a specific embodiment, an anti-MET antibody described herein or an antigen-binding fragment thereof comprises a VL region comprising SEQ ID NO: 52 and a VH region comprising SEQ ID NO: 64 (e.g., antibody Ab246). In a specific embodiment, an anti-MET antibody described herein or an antigen-binding fragment thereof comprises a VL region comprising SEQ ID NO: 53 and a VH region comprising SEQ ID NO: 64 (e.g., antibody Ab247). In a specific embodiment, an anti-MET antibody described herein or an antigen-binding fragment thereof comprises a VL region comprising SEQ ID NO: 54 and a VH region comprising SEQ ID NO: 64 (e.g., antibody Ab248). In a specific embodiment, an anti-MET antibody described herein or an antigen-binding fragment thereof comprises a VL region comprising SEQ ID NO: 55 and a VH region comprising SEQ ID NO: 64 (e.g., antibody Ab249). In a specific embodiment, an anti-MET antibody described herein or an antigen-binding fragment thereof comprises a VL region comprising SEQ ID NO: 56 and a VH region comprising SEQ ID NO: 64 (e.g., antibody Ab250). In a specific embodiment, an anti-MET antibody described herein or an antigen-binding fragment thereof comprises a VL region comprising SEQ ID NO: 52 and a VH region comprising SEQ ID NO: 65 (e.g., antibody Ab251). In a specific embodiment, an anti-MET antibody described herein or an antigen-binding fragment thereof comprises a VL region comprising SEQ ID NO: 53 and a VH region comprising SEQ ID NO: 65 (e.g., antibody Ab252). In a specific embodiment, an anti-MET antibody described herein or an antigen-binding fragment thereof comprises a VL region comprising SEQ ID NO: 54 and a VH region comprising SEQ ID NO: 65 (e.g., antibody Ab253). In a specific embodiment, an anti-MET antibody described herein or an antigen-binding fragment thereof comprises a VL region comprising SEQ ID NO: 55 and a VH region comprising SEQ ID NO: 65 (e.g., antibody Ab254). In a specific embodiment, an anti-MET antibody described herein or an antigen-binding fragment thereof comprises a VL region comprising SEQ ID NO: 56 and a VH region comprising SEQ ID NO: 65 (e.g., antibody Ab255).

In a specific embodiment, an anti-MET antibody described herein or an antigen-binding fragment thereof comprises a VL region comprising SEQ ID NO: 57 (e.g., the VL region of antibody Ab235). In a specific embodiment, an anti-MET antibody described herein or an antigen-binding fragment thereof comprises a VL region comprising SEQ ID NO: 58 (e.g., the VL region of antibody Ab236). In a specific embodiment, an anti-MET antibody described herein or an antigen-binding fragment thereof comprises a VL region comprising SEQ ID NO: 59 (e.g., the VL region of antibody Ab237). In a specific embodiment, an anti-MET antibody described herein or an antigen-binding fragment thereof comprises a VL region comprising SEQ ID NO: 60 (e.g., the VL region of antibody Ab238). In a specific embodiment, an anti-MET antibody described herein or an antigen-binding fragment thereof comprises a VL region comprising SEQ ID NO: 61 (e.g., the VL region of antibody Ab239). In a specific embodiment, an anti-MET antibody described herein or an antigen-binding fragment thereof comprises a VL region comprising SEQ ID NO: 62 (e.g., the VL region of antibody Ab240). In a specific embodiment, an anti-MET antibody described herein or an antigen-binding fragment thereof comprises a VL region comprising SEQ ID NO: 52 (e.g., the VL region of antibody Ab241). In a specific embodiment, an anti-MET antibody described herein or an antigen-binding fragment thereof comprises a VL region comprising SEQ ID NO: 53 (e.g., the VL region of antibody Ab242). In a specific embodiment, an anti-MET antibody described herein or an antigen-binding fragment thereof comprises a VL region comprising SEQ ID NO: 54 (e.g., the VL region of antibody Ab243). In a specific embodiment, an anti-MET antibody described herein or an antigen-binding fragment thereof comprises a VL region comprising SEQ ID NO: 55 (e.g., the VL region of antibody Ab244). In a specific embodiment, an anti-MET antibody described herein or an antigen-binding fragment thereof comprises a VL region comprising SEQ ID NO: 56 (e.g., the VL region of antibody Ab245). In a specific embodiment, an anti-MET antibody described herein or an antigen-binding fragment thereof comprises a VL region comprising SEQ ID NO: 52 (e.g., the VL region of antibody Ab246). In a specific embodiment, an anti-MET antibody described herein or an antigen-binding fragment thereof comprises a VL region comprising SEQ ID NO: 53 (e.g., the VL region of antibody Ab247). In a specific embodiment, an anti-MET antibody described herein or an antigen-binding fragment thereof comprises a VL region comprising SEQ ID NO: 54 (e.g., the VL region of antibody Ab248). In a specific embodiment, an anti-MET antibody described herein or an antigen-binding fragment thereof comprises a VL region comprising SEQ ID NO: 55 (e.g., the VL region of antibody Ab249). In a specific embodiment, an anti-MET antibody described herein or an antigen-binding fragment thereof comprises a VL region comprising SEQ ID NO: 56 (e.g., the VL region of antibody Ab250). In a specific embodiment, an anti-MET antibody described herein or an antigen-binding fragment thereof comprises a VL region comprising SEQ ID NO: 52 (e.g., the VL region of antibody Ab251). In a specific embodiment, an anti-MET antibody described herein or an antigen-binding fragment thereof comprises a VL region comprising SEQ ID NO: 53 (e.g., the VL region of antibody Ab252). In a specific embodiment, an anti-MET antibody described herein or an antigen-binding fragment thereof comprises a VL region comprising SEQ ID NO: 54 (e.g., the VL region of antibody Ab253). In a specific embodiment, an anti-MET antibody described herein or an antigen-binding fragment thereof comprises a VL region comprising SEQ ID NO: 55 (e.g., the VL region of antibody Ab254). In a specific embodiment, an anti-MET antibody described herein or an antigen-binding fragment thereof comprises a VL region comprising SEQ ID NO: 56 (e.g., the VL region of antibody Ab255).

In a specific embodiment, an anti-MET antibody described herein or an antigen-binding fragment thereof comprises a VH region comprising SEQ ID NO: 66 (e.g., the VH region of antibody Ab235). In a specific embodiment, an anti-MET antibody described herein or an antigen-binding fragment thereof comprises a VH region comprising SEQ ID NO: 67 (e.g., the VH region of antibody Ab236). In a specific embodiment, an anti-MET antibody described herein or an antigen-binding fragment thereof comprises a VH region comprising SEQ ID NO: 68 (e.g., the VH region of antibody Ab237). In a specific embodiment, an anti-MET antibody described herein or an antigen-binding fragment thereof comprises a VH region comprising SEQ ID NO: 69 (e.g., the VH region of antibody Ab238). In a specific embodiment, an anti-MET antibody described herein or an antigen-binding fragment thereof comprises a VH region comprising SEQ ID NO: 70 (e.g., the VH region of antibody Ab239). In a specific embodiment, an anti-MET antibody described herein or an antigen-binding fragment thereof comprises a VH region comprising SEQ ID NO: 71 (e.g., the VH region of antibody Ab240). In a specific embodiment, an anti-MET antibody described herein or an antigen-binding fragment thereof comprises a VH region comprising SEQ ID NO: 63 (e.g., the VH region of antibody Ab241). In a specific embodiment, an anti-MET antibody described herein or an antigen-binding fragment thereof comprises VH region comprising SEQ ID NO: 63 (e.g., the VH region of antibody Ab242). In a specific embodiment, an anti-MET antibody described herein or an antigen-binding fragment thereof comprises a VH region comprising SEQ ID NO: 63 (e.g., the VH region of antibody Ab243). In a specific embodiment, an anti-MET antibody described herein or an antigen-binding fragment thereof comprises a VH region comprising SEQ ID NO: 63 (e.g., the VH region of antibody Ab244). In a specific embodiment, an anti-MET antibody described herein or an antigen-binding fragment thereof comprises a VH region comprising SEQ ID NO: 63 (e.g., the VH region of antibody Ab245). In a specific embodiment, an anti-MET antibody described herein or an antigen-binding fragment thereof comprises a VH region comprising SEQ ID NO: 64 (e.g., the VH region of antibody Ab246). In a specific embodiment, an anti-MET antibody described herein or an antigen-binding fragment thereof comprises a VH region comprising SEQ ID NO: 64 (e.g., the VH region of antibody Ab247). In a specific embodiment, an anti-MET antibody described herein or an antigen-binding fragment thereof comprises a VH region comprising SEQ ID NO: 64 (e.g., the VH region of antibody Ab248). In a specific embodiment, an anti-MET antibody described herein or an antigen-binding fragment thereof comprises a VH region comprising SEQ ID NO: 64 (e.g., the VH region of antibody Ab249). In a specific embodiment, an anti-MET antibody described herein or an antigen-binding fragment thereof comprises a VH region comprising SEQ ID NO: 64 (e.g., the VH region of antibody Ab250). In a specific embodiment, an anti-MET antibody described herein or an antigen-binding fragment thereof comprises a VH region comprising SEQ ID NO: 65 (e.g., the VH region of antibody Ab251). In a specific embodiment, an anti-MET antibody described herein or an antigen-binding fragment thereof comprises a VH region comprising SEQ ID NO: 65 (e.g., the VH region of antibody Ab252). In a specific embodiment, an anti-MET antibody described herein or an antigen-binding fragment thereof comprises a VH region comprising SEQ ID NO: 65 (e.g., the VH region of antibody Ab253). In a specific embodiment, an anti-MET antibody described herein or an antigen-binding fragment thereof comprises a VH region comprising SEQ ID NO: 65 (e.g., the VH region of antibody Ab254). In a specific embodiment, an anti-MET antibody described herein or an antigen-binding fragment thereof comprises a VH region comprising SEQ ID NO: 65 (e.g., the VH region of antibody Ab255).

In certain embodiments, provided herein is an anti-MET antibody or an antigen-binding fragment thereof which specifically binds to an ECD of human MET and comprises VL CDRs (e.g., Kabat CDRs, Chothia CDRs, or IMGT CDRs) of a VL comprising the amino acid sequence as set forth in Table 9 and VH CDRs (e.g., Kabat CDRs, Chothia CDRs, or IMGT CDRs) of a VH comprising the amino acid sequence as set forth in Table 10.

In certain embodiments, provided herein is an antibody or an antigen-binding fragment thereof which specifically binds to an ECD of human MET and comprises VL and VH CDRs of any of the anti-MET antibodies provided herein, for example as set forth in Tables 1 and 2.

TABLE 1

| VL CDR Amino Acid Sequences (Kabat) | | | |
|---|---|---|---|
| Antibody | VL CDR1 (SEQ ID NO:) | VL CDR2 (SEQ ID NO:) | VL CDR3 (SEQ ID NO:) |
| Ab235 | SASSSVNYMF (SEQ ID NO: 1) | DTFNLAS (SEQ ID NO: 2) | QQWSIYPYT (SEQ ID NO: 3) |
| Ab236 | SASSSVSYMF (SEQ ID NO: 7) | DTSDLAS (SEQ ID NO: 8) | QQWSNYPYT (SEQ ID NO: 9) |
| Ab237 | LASADIHSNLA (SEQ ID NO: 13) | YGNNLND (SEQ ID NO: 14) | QQSYDSPPT (SEQ ID NO: 15) |
| Ab238 | LASEDIYSDLA (SEQ ID NO: 19) | NANTLQN (SEQ ID NO: 20) | QQYNNYPPT (SEQ ID NO: 21) |
| Ab239 | VRSSGDIGDRYVS (SEQ ID NO: 25) | AADQRPS (SEQ ID NO: 26) | QSYDSNIDIV (SEQ ID NO: 27) |
| Ab240 | RASQGISKYLN (SEQ ID NO: 30) | YTSNLQS (SEQ ID NO: 31) | QQYDSSPFT (SEQ ID NO: 32) |
| Ab241 | LASADIHSNLA (SEQ ID NO: 72) | YGNNLND (SEQ ID NO: 14) | QQSYDSPPT (SEQ ID NO: 15) |
| Ab242 | LASADIHSNLA (SEQ ID NO: 72) | YGNNLND (SEQ ID NO: 14) | QQSYDSPPT (SEQ ID NO: 15) |
| Ab243 | LASADIHSNLA (SEQ ID NO: 72) | YGNNLND (SEQ ID NO: 14) | QQSYDSPPT (SEQ ID NO: 15) |
| Ab244 | LASADIHSNLA (SEQ ID NO: 72) | YGNNLND (SEQ ID NO: 14) | QQSYDSPPT (SEQ ID NO: 15) |

TABLE 1-continued

VL CDR Amino Acid Sequences (Kabat)

| Antibody | VL CDR1 (SEQ ID NO:) | VL CDR2 (SEQ ID NO:) | VL CDR3 (SEQ ID NO:) |
| --- | --- | --- | --- |
| Ab245 | LASADIHSNLA (SEQ ID NO: 72) | YGNNLND (SEQ ID NO: 14) | QQSYDSPPT (SEQ ID NO: 15) |
| Ab246 | LASADIHSNLA (SEQ ID NO: 72) | YGNNLND (SEQ ID NO: 14) | QQSYDSPPT (SEQ ID NO: 15) |
| Ab247 | LASADIHSNLA (SEQ ID NO: 72) | YGNNLND (SEQ ID NO: 14) | QQSYDSPPT (SEQ ID NO: 15) |
| Ab248 | LASADIHSNLA (SEQ ID NO: 72) | YGNNLND (SEQ ID NO: 14) | QQSYDSPPT (SEQ ID NO: 15) |
| Ab249 | LASADIHSNLA (SEQ ID NO: 72) | YGNNLND (SEQ ID NO: 14) | QQSYDSPPT (SEQ ID NO: 15) |
| Ab250 | LASADIHSNLA (SEQ ID NO: 72) | YGNNLND (SEQ ID NO: 14) | QQSYDSPPT (SEQ ID NO: 15) |
| Ab251 | LASADIHSNLA (SEQ ID NO: 72) | YGNNLND (SEQ ID NO: 14) | QQSYDSPPT (SEQ ID NO: 15) |
| Ab252 | LASADIHSNLA (SEQ ID NO: 72) | YGNNLND (SEQ ID NO: 14) | QQSYDSPPT (SEQ ID NO: 15) |
| Ab253 | LASADIHSNLA (SEQ ID NO: 72) | YGNNLND (SEQ ID NO: 14) | QQSYDSPPT (SEQ ID NO: 15) |
| Ab254 | LASADIHSNLA (SEQ ID NO: 72) | YGNNLND (SEQ ID NO: 14) | QQSYDSPPT (SEQ ID NO: 15) |
| Ab255 | LASADIHSNLA (SEQ ID NO: 72) | YGNNLND (SEQ ID NO: 14) | QQSYDSPPT (SEQ ID NO: 15) |
| Ab256-Ab270 | SASSSVNYMF (SEQ ID NO: 1) | DTFNLAS (SEQ ID NO: 2) | QQWSIYPYT (SEQ ID NO: 3) |
| Ab271-Ab285 | SASSSVSYMF (SEQ ID NO: 7) | DTSDLAS (SEQ ID NO: 8) | QQWSNYPYT (SEQ ID NO: 9) |
| Ab286-Ab300 | LASEDIYSDLA (SEQ ID NO: 19) | NANTLQN (SEQ ID NO: 20) | QQYNNYPPT (SEQ ID NO: 21) |
| Ab301-Ab315 | VRSSGDIGDRYVS (SEQ ID NO: 25) | AADQRPS (SEQ ID NO: 26) | QSYDSNIDIV (SEQ ID NO: 27) |

TABLE 2

VH CDR Amino Acid Sequences (Kabat)

| Antibody | VH CDR1 (SEQ ID NO:) | VH CDR2 (SEQ ID NO:) | VH CDR3 (SEQ ID NO:) |
| --- | --- | --- | --- |
| Ab235 | NYWIE (SEQ ID NO: 265) | EILPGSDYTKYNEKFKG (SEQ ID NO: 5) | PSTIPPDC (SEQ ID NO: 6) |
| Ab236 | SYWIE (SEQ ID NO: 266) | EILPGSDFIKYSEKFKG (SEQ ID NO: 11) | PSTVPPDC (SEQ ID NO: 12) |
| Ab237 | DSYMA (SEQ ID NO: 16) | SISSDGGGTYYRDSVKG (SEQ ID NO: 17) | EGIYTTDYYPYCFNY (SEQ ID NO: 18) |
| Ab238 | TYGMGVA (SEQ ID NO: 267) | NIWWDDVNYSNPSLKN (SEQ ID NO: 23) | IGTSHIVDA (SEQ ID NO: 24) |
| Ab239 | DCYMA (SEQ ID NO: 28) | SISSDGGGTYYRDSVKG (SEQ ID NO: 73) | ERYYDGTYYGWYFDF (SEQ ID NO: 29) |
| Ab240 | TNSVH (SEQ ID NO: 33) | VIWGDGSTDYNSALKS (SEQ ID NO: 34) | DPYQNYFDY (SEQ ID NO: 35) |
| Ab241 | DSYMA (SEQ ID NO: 16) | SISSDGGGTYYRDSVKG (SEQ ID NO: 73) | EGIYTTDYYPYCFNY (SEQ ID NO: 18) |

TABLE 2-continued

VH CDR Amino Acid Sequences (Kabat)

| Antibody | VH CDR1 (SEQ ID NO:) | VH CDR2 (SEQ ID NO:) | VH CDR3 (SEQ ID NO:) |
|---|---|---|---|
| Ab242 | DSYMA (SEQ ID NO: 16) | SISSDGGGTYYRDSVKG (SEQ ID NO: 73) | EGIYTTDYYPYCFNY (SEQ ID NO: 18) |
| Ab243 | DSYMA (SEQ ID NO: 16) | SISSDGGGTYYRDSVKG (SEQ ID NO: 73) | EGIYTTDYYPYCFNY (SEQ ID NO: 18) |
| Ab244 | DSYMA (SEQ ID NO: 16) | SISSDGGGTYYRDSVKG (SEQ ID NO: 73) | EGIYTTDYYPYCFNY (SEQ ID NO: 18) |
| Ab245 | DSYMA (SEQ ID NO: 16) | SISSDGGGTYYRDSVKG (SEQ ID NO: 73) | EGIYTTDYYPYCFNY (SEQ ID NO: 18) |
| Ab246 | DSYMA (SEQ ID NO: 16) | SISSDGGGTYYRDSVKG (SEQ ID NO: 73) | EGIYTTDYYPYCFNY (SEQ ID NO: 18) |
| Ab247 | DSYMA (SEQ ID NO: 16) | SISSDGGGTYYRDSVKG (SEQ ID NO: 73) | EGIYTTDYYPYCFNY (SEQ ID NO: 18) |
| Ab248 | DSYMA (SEQ ID NO: 16) | SISSDGGGTYYRDSVKG (SEQ ID NO: 73) | EGIYTTDYYPYCFNY (SEQ ID NO: 18) |
| Ab249 | DSYMA (SEQ ID NO: 16) | SISSDGGGTYYRDSVKG (SEQ ID NO: 73) | EGIYTTDYYPYCFNY (SEQ ID NO: 18) |
| Ab250 | DSYMA (SEQ ID NO: 16) | SISSDGGGTYYRDSVKG (SEQ ID NO: 73) | EGIYTTDYYPYCFNY (SEQ ID NO: 18) |
| Ab251 | DSYMA (SEQ ID NO: 16) | SISSDGGGTYYRDSVKG (SEQ ID NO: 73) | EGIYTTDYYPYCFNY (SEQ ID NO: 18) |
| Ab252 | DSYMA (SEQ ID NO: 16) | SISSDGGGTYYRDSVKG (SEQ ID NO: 73) | EGIYTTDYYPYCFNY (SEQ ID NO: 18) |
| Ab253 | DSYMA (SEQ ID NO: 16) | SISSDGGGTYYRDSVKG (SEQ ID NO: 73) | EGIYTTDYYPYCFNY (SEQ ID NO: 18) |
| Ab254 | DSYMA (SEQ ID NO: 16) | SISSDGGGTYYRDSVKG (SEQ ID NO: 73) | EGIYTTDYYPYCFNY (SEQ ID NO: 18) |
| Ab255 | DSYMA (SEQ ID NO: 16) | SISSDGGGTYYRDSVKG (SEQ ID NO: 73) | EGIYTTDYYPYCFNY (SEQ ID NO: 18) |
| Ab256-Ab270 | NYWIE (SEQ ID NO: 265) | EILPGSDYTKYNEKFKG (SEQ ID NO: 5) | PSTIPPDC (SEQ ID NO: 6) |
| Ab271-Ab285 | SYWIE (SEQ ID NO: 266) | EILPGSDFIKYSEKFKG (SEQ ID NO: 11) | PSTVPPDC (SEQ ID NO: 12) |
| Ab286-Ab300 | TYGMGVA (SEQ ID NO: 267) | NIWWDDVNYSNPSLKN (SEQ ID NO: 23) | IGTSHIVDA (SEQ ID NO: 24) |
| Ab301-Ab315 | DCYMA (SEQ ID NO: 28) | SISSDGGGTYYRDSVKG (SEQ ID NO: 73) | ERYYDGTYYGWYFDF (SEQ ID NO: 29) |

TABLE 3

VL FR Amino Acid Sequences (Kabat)

| Antibody | VL FR1 (SEQ ID NO:) | VL FR2 (SEQ ID NO;) | VL FR3 (SEQ ID NO:) | VL FR4 (SEQ ID NO:) |
|---|---|---|---|---|
| Ab235 | QIVLTQSPAIMSTSPGEKVTMTC (SEQ ID NO: 103) | WYQQKAGSSPRLLIY (SEQ ID NO: 111) | GVPVRFSGSGSGTSYSLTISRMEAEDAATYYC (SEQ ID NO: 122) | FGGGTKLEIKR (SEQ ID NO: 128) |
| Ab236 | QIVLTQSPAIMSASPGEKVTMTC (SEQ ID NO: 104) | WYQQKPGSSPRLLIY (SEQ ID NO: 112) | GVPVRFSGSGSGTSYSLTISRMEAEDAATYYC (SEQ ID NO: 122) | FGGGTKLEIKR (SEQ ID NO: 128) |
| Ab237 | DIQMTQSPGSLSASLGETVTIEC (SEQ ID NO: 105) | WYQQKPGNSPQLLIY (SEQ ID NO: 113) | GVPSRFSGSGSGTQYSLKINSLQSEDVSIYFC (SEQ ID NO: 123) | FGQGTKLEIKR (SEQ ID NO: 127) |

TABLE 3-continued

VL FR Amino Acid Sequences (Kabat)

| Antibody | VL FR1 (SEQ ID NO:) | VL FR2 (SEQ ID NO;) | VL FR3 (SEQ ID NO:) | VL FR4 (SEQ ID NO:) |
|---|---|---|---|---|
| Ab238 | DIRMTQSPASLSASLGETVNIEC (SEQ ID NO: 106) | WYQQKPGKSPQLLIY (SEQ ID NO: 114) | GVPSVFSGSGSGTQYSLKINNLHSEDVATYFC (SEQ ID NO: 124) | FGGGTKLEIKR (SEQ ID NO: 128) |
| Ab239 | GQFTLTQPKSVSGSLRSTITIPC (SEQ ID NO: 107) | WYQQRLGRPPLNVIY (SEQ ID NO: 115) | EVSDRFSGSIDSSSNSASLTITDLQMDDEADYFC (SEQ ID NO: 125) | FGGGTKLEIKR (SEQ ID NO: 128) |
| Ab240 | DIQMTQTPFYMPASLGERVTISC (SEQ ID NO: 108) | WYQQKPDGTIKTLIY (SEQ ID NO: 116) | GVPSRFSGSGSGTDYSLTISGLEPEDFAVYYC (SEQ ID NO: 126) | FGSGTKLEIKR (SEQ ID NO: 129) |
| Ab241, Ab256, Ab271, Ab286, Ab301 | DIQMTQSPSSLSASVGDRVTITC (SEQ ID NO: 102) | WYQQKPGKAPQLLIY (SEQ ID NO: 109) | GVPSRFSGSGSGTDYTLKINSLQSEDVAIYFC (SEQ ID NO: 117) | FGQGTKLEIKR (SEQ ID NO: 127) |
| Ab242, Ab257, Ab272, Ab287, Ab302 | DIQMTQSPSSLSASVGDRVTITC (SEQ ID NO: 102) | WYQQKPGKAPKLLIY (SEQ ID NO: 110) | GVPSRFSGFGFGTDYTLTISSLQSEDVAIYFC (SEQ ID NO: 118) | FGQGTKLEIKR (SEQ ID NO: 127) |
| Ab243, Ab258, Ab273, Ab288, Ab303 | DIQMTQSPSSLSASVGDRVTITC (SEQ ID NO: 102) | WYQQKPGKAPKLLIY (SEQ ID NO: 110) | GVPSRFSGSGSGTDYTLTISSLQPEDVAIYFC (SEQ ID NO: 119) | FGQGTKLEIKR (SEQ ID NO: 127) |
| Ab244, Ab259, Ab274, Ab289, Ab304 | DIQMTQSPSSLSASVGDRVTITC (SEQ ID NO: 102) | WYQQKPGKAPKLLIY (SEQ ID NO: 110) | GVPSRFSGSGSGTDFTLTISSLQPEDVAIYFC (SEQ ID NO: 120) | FGQGTKLEIKR (SEQ ID NO: 127) |
| Ab245, Ab260, Ab275, Ab290, Ab305 | DIQMTQSPSSLSASVGDRVTITC (SEQ ID NO: 102) | WYQQKPGKAPKLLIY (SEQ ID NO: 110) | GVPSRFSGSGSGTDFTLTISSLQPEDVATYFC (SEQ ID NO: 121) | FGQGTKLEIKR (SEQ ID NO: 127) |
| Ab246, Ab261, Ab276, Ab291, Ab306 | DIQMTQSPSSLSASVGDRVTITC (SEQ ID NO: 102) | WYQQKPGKAPQLLIY (SEQ ID NO: 109) | GVPSRFSGSGSGTDYTLKINSLQSEDVAIYFC (SEQ ID NO: 117) | FGQGTKLEIKR (SEQ ID NO: 127) |
| Ab247, Ab262, Ab277, Ab292, Ab307 | DIQMTQSPSSLSASVGDRVTITC (SEQ ID NO: 102) | WYQQKPGKAPKLLIY (SEQ ID NO: 110) | GVPSRFSGFGFGTDYTLTISSLQSEDVAIYFC (SEQ ID NO: 118) | FGQGTKLEIKR (SEQ ID NO: 127) |
| Ab248, Ab263, Ab278, Ab293, Ab308 | DIQMTQSPSSLSASVGDRVTITC (SEQ ID NO: 102) | WYQQKPGKAPKLLIY (SEQ ID NO: 110) | GVPSRFSGSGSGTDYTLTISSLQPEDVAIYFC (SEQ ID NO: 119) | FGQGTKLEIKR (SEQ ID NO: 127) |
| Ab249, Ab264, Ab279, Ab294, Ab309 | DIQMTQSPSSLSASVGDRVTITC (SEQ ID NO: 102) | WYQQKPGKAPKLLIY (SEQ ID NO: 110) | GVPSRFSGSGSGTDFTLTISSLQPEDVAIYFC (SEQ ID NO: 120) | FGQGTKLEIKR (SEQ ID NO: 127) |
| Ab250, Ab265, Ab280, Ab295, Ab310 | DIQMTQSPSSLSASVGDRVTITC (SEQ ID NO: 102) | WYQQKPGKAPKLLIY (SEQ ID NO: 110) | GVPSRFSGSGSGTDFTLTISSLQPEDVATYFC (SEQ ID NO: 121) | FGQGTKLEIKR (SEQ ID NO: 127) |

TABLE 3-continued

VL FR Amino Acid Sequences (Kabat)

| Antibody | VL FR1 (SEQ ID NO:) | VL FR2 (SEQ ID NO;) | VL FR3 (SEQ ID NO:) | VL FR4 (SEQ ID NO:) |
|---|---|---|---|---|
| Ab251, Ab266, Ab281, Ab296, Ab311 | DIQMTQSPSSLSASV GDRVTITC (SEQ ID NO: 102) | WYQQKPGKAPQLLI Y (SEQ ID NO: 109) | GVPSRFSGSGSGTDYT LKINSLQSEDVAIYFC (SEQ ID NO: 117) | FGQGTKLEIKR (SEQ ID NO: 127) |
| Ab252, Ab267, Ab282, Ab297, Ab312 | DIQMTQSPSSLSASV GDRVTITC (SEQ ID NO: 102) | WYQQKPGKAPKLLI Y (SEQ ID NO: 110) | GVPSRFSGFGFGTDYT LTISSLQSEDVAIYFC (SEQ ID NO: 118) | FGQGTKLEIKR (SEQ ID NO: 127) |
| Ab253, Ab268, Ab283, Ab298, Ab313 | DIQMTQSPSSLSASV GDRVTITC (SEQ ID NO: 102) | WYQQKPGKAPKLLI Y (SEQ ID NO: 110) | GVPSRFSGSGSGTDYT LTISSLQPEDVAIYFC (SEQ ID NO: 119) | FGQGTKLEIKR (SEQ ID NO: 127) |
| Ab254, Ab269, Ab284, Ab299, Ab314 | DIQMTQSPSSLSASV GDRVTITC (SEQ ID NO: 102) | WYQQKPGKAPKLLI Y (SEQ ID NO: 110) | GVPSRFSGSGSGTDFT LTISSLQPEDVAIYFC (SEQ ID NO: 120) | FGQGTKLEIKR (SEQ ID NO: 127) |
| Ab255, Ab270, Ab285, Ab300, Ab315 | DIQMTQSPSSLSASV GDRVTITC (SEQ ID NO: 102) | WYQQKPGKAPKLLI Y (SEQ ID NO: 110) | GVPSRFSGSGSGTDFT LTISSLQPEDVATYFC (SEQ ID NO: 121) | FGQGTKLEIKR (SEQ ID NO: 127) |

TABLE 4

VH FR Amino Acid Sequences (Kabat)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab235 | QVQLQQSGAELMKP GASVKISCKATGYTF S (SEQ ID NO: 75) | WVKQRPGHGLEW IG (SEQ ID NO: 82) | KATFTADTSSNTAYMQL SSLTSEDSAVYYCAR (SEQ ID NO: 268) | WGQGTTLTVS A (SEQ ID NO: 97) |
| Ab236 | QAQLQQSGAELMKP GASVKISCKATGYIF S (SEQ ID NO: 76) | WVKQRPGHGLEW IG (SEQ ID NO: 82) | KATFTADTSSNTAYMQL SNLTSEDSAVYYCAR (SEQ ID NO: 269) | WGQGTTLTVS A (SEQ ID NO: 97) |
| Ab237 | EVQLVESGGGLVQP GRSLKLSCAASGFTF S (SEQ ID NO: 77) | WVRQAPTKGLEW VA (SEQ ID NO: 83) | RFSISRDNAKSSLYLQM DSLRSEDTATYYCTT (SEQ ID NO: 270) | WGHGVMVTV SA (SEQ ID NO: 98) |
| Ab238 | QVTLKESGPGILQPS QTLSLTCTFSGFSLS (SEQ ID NO: 78) | WIRQPSGKDLEWL A (SEQ ID NO: 271) | RLTISKDTSNNQVFLQIT NVDTAETATYYCAR (SEQ ID NO: 92) | WGQGASVTVS A (SEQ ID NO: 99) |
| Ab239 | EVQLVESGGGLVQP GRSLKLSCAASGFSF T (SEQ ID NO: 79) | WVRQAPTKGLEW VA (SEQ ID NO: 83) | FTISRDNARSSLYLEMDS LRSEDTATYYCTT (SEQ ID NO: 93) | WGPGTMVTV SA (SEQ ID NO: 100) |
| Ab240 | QVQLKESGPGLVQP SQTLSLTCSVSGLSL T (SEQ ID NO: 80) | AWIRQPSGKDLE WLA (SEQ ID NO: 84) | RLTISRDTSRSQVFLKMN SLQTDDTAIYFCAR (SEQ ID NO: 94) | WGQGVKVTV SS (SEQ ID NO: 101) |
| Ab241, Ab256, Ab271, Ab286, Ab301 | EVQLVESGGGLVQP GGSLKLSCAASGFTF S (SEQ ID NO: 74) | WVRQAPGKGLEW VA (SEQ ID NO: 81) | RFTISRDNAKSSLYLQM DSLRIEDTATYYCTT (SEQ ID NO: 86) | WGQGVMVTV SS (SEQ ID NO: 95) |

TABLE 4-continued

VH FR Amino Acid Sequences (Kabat)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab242, Ab257, Ab272, Ab287, Ab302 | EVQLVESGGGLVQPGGSLKLSCAASGFTFS (SEQ ID NO: 74) | WVRQAPGKGLEWVA (SEQ ID NO: 81) | RFTISRDNAKSSLYLQMDSLRIEDTATYYCTT (SEQ ID NO: 86) | WGQGVMVTVSS (SEQ ID NO: 95) |
| Ab243, Ab258, Ab273, Ab288, Ab303 | EVQLVESGGGLVQPGGSLKLSCAASGFTFS (SEQ ID NO: 74) | WVRQAPGKGLEWVA (SEQ ID NO: 81) | RFTISRDNAKSSLYLQMDSLRIEDTATYYCTT (SEQ ID NO: 86) | WGQGVMVTVSS (SEQ ID NO: 95) |
| Ab244, Ab259, Ab274, Ab289, Ab304 | EVQLVESGGGLVQPGGSLKLSCAASGFTFS (SEQ ID NO: 74) | WVRQAPGKGLEWVA (SEQ ID NO: 81) | RFTISRDNAKSSLYLQMDSLRIEDTATYYCTT (SEQ ID NO: 86) | WGQGVMVTVSS (SEQ ID NO: 95) |
| Ab245, Ab260, Ab275, Ab290, Ab305 | EVQLVESGGGLVQPGGSLKLSCAASGFTFS (SEQ ID NO: 74) | WVRQAPGKGLEWVA (SEQ ID NO: 81) | RFTISRDNAKSSLYLQMDSLRIEDTATYYCTT (SEQ ID NO: 86) | WGQGVMVTVSS (SEQ ID NO: 95) |
| Ab246, Ab261, Ab276, Ab291, Ab306 | EVQLVESGGGLVQPGGSLKLSCAASGFTFS (SEQ ID NO: 74) | WVRQAPGKGLEWVA (SEQ ID NO: 81) | RFTISRDNAKSSLYLQMNSLR IEDTATYYCTT (SEQ ID NO: 87) | WGQGVMVTVSS (SEQ ID NO: 95) |
| Ab247, Ab262, Ab277, Ab292, Ab307 | EVQLVESGGGLVQPGGSLKLSCAASGFTFS (SEQ ID NO: 74) | WVRQAPGKGLEWVA (SEQ ID NO: 81) | RFTISRDNAKSSLYLQMNSLRIEDTATYYCTT (SEQ ID NO: 87) | WGQGVMVTVSS (SEQ ID NO: 95) |
| Ab248, Ab263, Ab278, Ab293, Ab308 | EVQLVESGGGLVQPGGSLKLSCAASGFTFS (SEQ ID NO: 74) | WVRQAPGKGLEWVA (SEQ ID NO: 81) | RFTISRDNAKSSLYLQMNSLRIEDTATYYCTT (SEQ ID NO: 87) | WGQGVMVTVSS (SEQ ID NO: 95) |
| Ab249, Ab264, Ab279, Ab294, Ab309 | EVQLVESGGGLVQPGGSLKLSCAASGFTFS (SEQ ID NO: 74) | WVRQAPGKGLEWVA (SEQ ID NO: 81) | RFTISRDNAKSSLYLQMNSLRIEDTATYYCTT (SEQ ID NO: 87) | WGQGVMVTVSS (SEQ ID NO: 95) |
| Ab250, Ab265, Ab280, Ab295, Ab310 | EVQLVESGGGLVQPGGSLKLSCAASGFTFS (SEQ ID NO: 74) | WVRQAPGKGLEWVA (SEQ ID NO: 81) | RFTISRDNAKSSLYLQMNSLRIEDTATYYCTT (SEQ ID NO: 87) | WGQGVMVTVSS (SEQ ID NO: 95) |
| Ab251, Ab266, Ab281, Ab296, Ab311 | EVQLVESGGGLVQPGGSLKLSCAASGFTFS (SEQ ID NO: 74) | WVRQAPGKGLEWVA (SEQ ID NO: 81) | RFTISRDNAKNSLYLQMNSLRIEDTATYYCTT (SEQ ID NO: 88) | WGQGTMVTVSS (SEQ ID NO: 96) |
| Ab252, Ab267, Ab282, Ab297, Ab312 | EVQLVESGGGLVQPGGSLKLSCAASGFTFS (SEQ ID NO: 74) | WVRQAPGKGLEWVA (SEQ ID NO: 81) | RFTISRDNAKNSLYLQMNSLRIEDTATYYCTT (SEQ ID NO: 88) | WGQGTMVTVSS (SEQ ID NO: 96) |
| Ab253, Ab268, Ab283, Ab298, Ab313 | EVQLVESGGGLVQPGGSLKLSCAASGFTFS (SEQ ID NO: 74) | WVRQAPGKGLEWVA (SEQ ID NO: 81) | RFTISRDNAKNSLYLQMNSLRIEDTATYYCTT (SEQ ID NO: 88) | WGQGTMVTVSS (SEQ ID NO: 96) |

TABLE 4-continued

VH FR Amino Acid Sequences (Kabat)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab254, Ab269, Ab284, Ab299, Ab314 | EVQLVESGGGLVQP GGSLKLSCAASGFTF S (SEQ ID NO: 74) | WVRQAPGKGLEW VA (SEQ ID NO: 81) | RFTISRDNAKNSLYLQM NSLRIEDTATYYCTT (SEQ ID NO: 88) | WGQGTMVTV SS (SEQ ID NO: 96) |
| Ab255, Ab270, Ab285, Ab300, Ab315 | EVQLVESGGGLVQP GGSLKLSCAASGFTF S (SEQ ID NO: 74) | WVRQAPGKGLEW VA (SEQ ID NO: 81) | RFTISRDNAKNSLYLQM NSLRIEDTATYYCTT (SEQ ID NO: 88) | WGQGTMVTV SS (SEQ ID NO: 96) |

In a particular embodiment, an antibody described herein, or an antigen-binding fragment thereof, which specifically binds to an ECD of MET, comprises a light chain variable region (VL) comprising:
  (a) a VL CDR1 comprising the amino acid sequence of SASSSVX$_7$YMF (SEQ ID NO:41), wherein X$_7$ is any amino acid, for example, an amino acid with an uncharged polar side chain, e.g., N or S;
  (b) a VL CDR2 comprising the amino acid sequence of DTX$_{13}$X$_{14}$LAS (SEQ ID NO:43), wherein X$_{13}$ is any amino acid, for example, F or S and X$_{14}$ is any amino acid, for example, N or D; and
  (c) a VL CDR3 comprising the amino acid sequence of QQWSX$_{15}$YPYT (SEQ ID NO:44), wherein X$_{15}$ is any amino acid, for example, I or N. In certain embodiments, any one of X$_7$ and X$_{13}$-X$_{15}$ is any amino acid sequence. In specific embodiments, X$_7$ is a conservative substitution of N or S, X$_{13}$ is a conservative substitution of F or S, X$_{14}$ is a conservative substitution of N or D, and X$_{15}$ is a conservative substitution of I or N.

As used herein, a "conservative amino acid substitution" is one in which the amino acid residue is replaced with an amino acid residue having a side chain with a similar charge. Families of amino acid residues having side chains with similar charges have been defined in the art. These families include amino acids with charged side chains (e.g., lysine, arginine, histidine, aspartic acid, glutamic acid), acidic side chains (e.g., aspartic acid, glutamic acid), basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In a particular embodiment, an antibody described herein, or an antigen-binding fragment thereof, which specifically binds to an ECD of MET, comprises a light chain variable region (VL) comprising:
  (a) a VL CDR1 comprising the amino acid sequence of SEQ ID NOS: 13 or 72;
  (b) a VL CDR2 comprising the amino acid sequence of SEQ ID NO:14; and
  (c) a VL CDR3 comprising the amino acid sequence of SEQ ID NO:15.

In a particular embodiment, an antibody described herein, or an antigen-binding fragment thereof, comprises the VL CDR1, VL CDR2, and VL CDR3 of Ab235, for example, the VL CDR1, VL CDR2, and VL CDR3 of Ab235 as set forth in Table 1 (SEQ ID NOS: 1, 2, and 3, respectively).

In a particular embodiment, an antibody described herein, or an antigen-binding fragment thereof, comprises the VL CDR1, VL CDR2, and VL CDR3 of Ab236, for example, the VL CDR1, VL CDR2, and VL CDR3 of Ab236 as set forth in Table 1 (SEQ ID NOS: 7, 8, and 9, respectively).

In a particular embodiment, an antibody described herein, or an antigen-binding fragment thereof, comprises the VL CDR1, VL CDR2, and VL CDR3 of Ab237, for example, the VL CDR1, VL CDR2, and VL CDR3 of Ab237 as set forth in Table 1 (SEQ ID NOS: 13, 14, and 15, respectively).

In a particular embodiment, an antibody described herein, or an antigen-binding fragment thereof, comprises the VL CDR1, VL CDR2, and VL CDR3 of Ab238, for example, the VL CDR1, VL CDR2, and VL CDR3 of Ab238 as set forth in Table 1 (SEQ ID NOS: 19, 20, and 21, respectively).

In a particular embodiment, an antibody described herein, or an antigen-binding fragment thereof, comprises the VL CDR1, VL CDR2, and VL CDR3 of Ab239, for example, the VL CDR1, VL CDR2, and VL CDR3 of Ab239 as set forth in Table 1 (SEQ ID NOS: 25, 26, and 27, respectively).

In a particular embodiment, an antibody described herein, or an antigen-binding fragment thereof, comprises the VL CDR1, VL CDR2, and VL CDR3 of Ab240, for example, the VL CDR1, VL CDR2, and VL CDR3 of Ab240 as set forth in Table 1 (SEQ ID NOS: 30, 31, and 32, respectively).

In a particular embodiment, an antibody described herein, or an antigen-binding fragment thereof, comprises the VL CDR1, VL CDR2, and VL CDR3 of any one of Ab241-Ab255, for example, the VL CDR1, VL CDR2, and VL CDR3 of Ab241 as set forth in Table 1 (SEQ ID NOS: 72, 14, and 15, respectively).

In a particular embodiment, an antibody described herein, or an antigen-binding fragment thereof, which specifically binds to an ECD of MET, comprises a heavy chain variable region (VH) comprising:
  (a) a VH CDR1 comprising the amino acid sequence X$_1$YWIEW (SEQ ID NO:36), wherein X$_1$ is any amino acid, for example, an amino acid with an uncharged polar side chain, e.g., N or S;
  (b) a VH CDR2 comprising the amino acid sequence of EILPGSDX$_3$TKYX$_4$EKFKGK (SEQ ID NO:38), wherein X$_3$ is any amino acid, for example, an amino acid with an aromatic side chain, e.g., Y or F, and X$_4$ is any amino acid, for example, an amino acid with an uncharged polar side chain, e.g., N or S; and (c) a VH CDR3 comprising the amino acid sequence of PSTX$_6$PPDC (SEQ ID NO:40), wherein X$_6$ is any amino acid, for example, an amino acid with a nonpolar side chain, e.g., I or V. In certain embodiments, any one of X$_1$, X$_3$, X$_4$ and X$_6$ is any amino acid sequence. In specific embodiments, X$_1$ is a conservative substitution of N or S, X$_3$ is a conservative substitution of Y or F, X$_4$ is a conservative substitution of N or S, and X$_6$ is a conservative substitution of I or V.

In a particular embodiment, an antibody described herein, or an antigen-binding fragment thereof, which specifically binds to an ECD of MET, comprises a heavy chain variable region (VH) comprising:

(a) a VH CDR1 comprising the amino acid sequence of SEQ ID NOS: 16, 28, or DX$_2$YMA (SEQ ID NO:37), wherein X$_2$ is any amino acid, for example, an amino acid with an uncharged polar side chain, e.g., S or C;

(b) a VH CDR2 comprising the amino acid sequence of SISSDGGGTYYRDSVKG (SEQ ID NO: 17); and (c) a VH CDR3 comprising the amino acid sequence of SEQ ID NOS: 18 or 29, or EX$_{16}$X$_{17}$YX$_{18}$X$_{19}$X$_{20}$YYX$_{21}$X$_{22}$X$_{23}$FX$_{24}$X$_{25}$ (SE ID NO:45), wherein X$_{16}$ is any amino acid, for example, G or R, X$_{17}$ is any amino acid, for example, I or Y, X$_{18}$ is any amino acid, for example, T or D, X$_{19}$ is any amino acid, for example, an amino acid with an uncharged polar side chain, e.g., T or G, X$_{20}$ is any amino acid, for example, D or T, X$_{21}$ is any amino acid, for example, P or G, X$_{22}$ is any amino acid, for example, C or W, X$_{23}$ is any amino acid, for example, Y, or absent, X$_{24}$ is any amino acid, for example, N or D, and X$_{25}$ is any amino acid, for example, an amino acid with an aromatic side chain, e.g., Y or F. In certain embodiments, any one of X$_2$, and X$_{16}$ to X$_{25}$ is any amino acid sequence. In specific embodiments, X$_2$ is a conservative substitution of S or C, X$_{16}$ is a conservative substitution of G or R, X$_{17}$ is a conservative substitution of I or Y, X$_{18}$ is a conservative substitution of D or T, X$_{19}$ is a conservative substitution of T or G, X$_{20}$ is a conservative substitution of D or T, X$_{21}$ is a conservative substitution of P or G, X$_{22}$ is a conservative substitution of C or W, X$_{23}$ is a conservative substitution of Y or absent, X$_{24}$ is a conservative substitution of N or D, and X$_{25}$ is a conservative substitution of Y or F.

In a particular embodiment, an antibody described herein, or an antigen-binding fragment thereof, comprises the VH CDR1, VH CDR2, and VH CDR3 of Ab235, for example, the VH CDR1, VH CDR2, and VH CDR3 of Ab235 as set forth in Table 2 (SEQ ID NOS: 265, 5, and 6, respectively). In a particular embodiment, an antibody described herein, or an antigen-binding fragment thereof, comprises the VH CDR1, VH CDR2, and VH CDR3 of Ab235, for example, the VH CDR1, VH CDR2, and VH CDR3 of as set forth in SEQ ID NOS: 4, 5, and 6, respectively.

In a particular embodiment, an antibody described herein, or an antigen-binding fragment thereof, comprises the VH CDR1, VH CDR2, and VH CDR3 of Ab236, for example, the VH CDR1, VH CDR2, and VH CDR3 of Ab236 as set forth in Table 2 (SEQ ID NOS: 266, 11, and 12, respectively). In a particular embodiment, an antibody described herein, or an antigen-binding fragment thereof, comprises the VH CDR1, VH CDR2, and VH CDR3 of Ab236, for example, the VH CDR1, VH CDR2, and VH CDR3 as set forth in SEQ ID NOS: 10, 11, and 12, respectively.

In a particular embodiment, an antibody described herein, or an antigen-binding fragment thereof, comprises the VH CDR1, VH CDR2, and VH CDR3 of Ab237, for example, the VH CDR1, VH CDR2, and VH CDR3 of Ab237 as set forth in Table 2 (SEQ ID NOS: 16, 17, and 18, respectively).

In a particular embodiment, an antibody described herein, or an antigen-binding fragment thereof, comprises the VH CDR1, VH CDR2, and VH CDR3 of Ab238, for example, the VH CDR1, VH CDR2, and VH CDR3 of Ab238 as set forth in Table 2 (SEQ ID NOS: 267, 23, and 24, respectively). In a particular embodiment, an antibody described herein, or an antigen-binding fragment thereof, comprises the VH CDR1, VH CDR2, and VH CDR3 of Ab238, for example, the VH CDR1, VH CDR2, and VH CDR3 as set forth in SEQ ID NOS: 22, 23, and 24, respectively.

In a particular embodiment, an antibody described herein, or an antigen-binding fragment thereof, comprises the VH CDR1, VH CDR2, and VH CDR3 of Ab239, for example, the VH CDR1, VH CDR2, and VH CDR3 of Ab239 as set forth in Table 2 (SEQ ID NOS: 28, 73, and 29, respectively).

In a particular embodiment, an antibody described herein, or an antigen-binding fragment thereof, comprises the VH CDR1, VH CDR2, and VH CDR3 of Ab240, for example, the VH CDR1, VH CDR2, and VH CDR3 of Ab240 as set forth in Table 2 (SEQ ID NOS: 33, 34, and 35, respectively).

In a particular embodiment, an antibody described herein, or an antigen-binding fragment thereof, comprises the VH CDR1, VH CDR2, and VH CDR3 of any one of Ab241-Ab255, for example, the VH CDR1, VH CDR2, and VH CDR3 of Ab241 as set forth in Table 2 (SEQ ID NOS: 16, 73, and 18, respectively).

In a specific embodiment, an anti-MET antibody described herein or an antigen-binding fragment thereof comprises (i) the VH CDR1, VH CDR2, and VH CDR3 of Ab235, for example, the VH CDR1, VH CDR2, and VH CDR3 of Ab235 as set forth in Table 2 (SEQ ID NOS: 265, 5, and 6, respectively); and (ii) the VL CDR1, VL CDR2, and VL CDR3 of Ab235, for example, the VL CDR1, VL CDR2, and VL CDR3 of Ab235 as set forth in Table 1 (SEQ ID NOS: 1, 2, and 3, respectively). In a specific embodiment, an anti-MET antibody described herein or an antigen-binding fragment thereof comprises (i) the VH CDR1, VH CDR2, and VH CDR3 as set forth in SEQ ID NOS: 4, 5, and 6, respectively; and (ii) the VL CDR1, VL CDR2, and VL CDR3 of Ab235, for example, the VL CDR1, VL CDR2, and VL CDR3 of Ab235 as set forth in Table 1 (SEQ ID NOS: 1, 2, and 3, respectively). In a specific embodiment, an anti-MET antibody described herein or an antigen-binding fragment thereof comprises (i) the VH CDR1, VH CDR2, and VH CDR3 of Ab236, for example, the VH CDR1, VH CDR2, and VH CDR3 of Ab236 as set forth in Table 2 (SEQ ID NOS: 266, 11, and 12, respectively); and (ii) the VL CDR1, VL CDR2, and VL CDR3 of Ab236, for example, the VL CDR1, VL CDR2, and VL CDR3 of Ab236 as set forth in Table 1 (SEQ ID NOS: 7, 8, and 9, respectively). In a specific embodiment, an anti-MET antibody described herein or an antigen-binding fragment thereof comprises (i) the VH CDR1, VH CDR2, and VH CDR3 as set forth in SEQ ID NOS: 10, 11, and 12, respectively; and (ii) the VL CDR1, VL CDR2, and VL CDR3 of Ab236, for example, the VL CDR1, VL CDR2, and VL CDR3 of Ab236 as set forth in Table 1 (SEQ ID NOS: 7, 8, and 9, respectively). In a specific embodiment, an anti-MET antibody described herein or an antigen-binding fragment thereof comprises (i) the VH CDR1, VH CDR2, and VH CDR3 of Ab237, for example, the VH CDR1, VH CDR2, and VH CDR3 of Ab237 as set forth in Table 2 (SEQ ID NOS: 16, 17, and 18, respectively); and (ii) the VL CDR1, VL CDR2, and VL CDR3 of Ab237, for example, the VL CDR1, VL CDR2, and VL CDR3 of Ab237 as set forth in Table 1 (SEQ ID NOS:

13, 14, and 15, respectively). In a specific embodiment, an anti-MET antibody described herein or an antigen-binding fragment thereof comprises (i) the VH CDR1, VH CDR2, and VH CDR3 of Ab238, for example, the VH CDR1, VH CDR2, and VH CDR3 of Ab238 as set forth in Table 2 (SEQ ID NOS: 267, 23, and 24, respectively); and (ii) the VL CDR1, VL CDR2, and VL CDR3 of Ab238, for example, the VL CDR1, VL CDR2, and VL CDR3 of Ab238 as set forth in Table 1 (SEQ ID NOS: 19, 20, and 21, respectively). In a specific embodiment, an anti-MET antibody described herein or an antigen-binding fragment thereof comprises (i) the VH CDR1, VH CDR2, and VH CDR3 as set forth in SEQ ID NOS: 22, 23, and 24, respectively; and (ii) the VL CDR1, VL CDR2, and VL CDR3 of Ab238, for example, the VL CDR1, VL CDR2, and VL CDR3 of Ab238 as set forth in Table 1 (SEQ ID NOS: 19, 20, and 21, respectively). In a specific embodiment, an anti-MET antibody described herein or an antigen-binding fragment thereof comprises (i) the VH CDR1, VH CDR2, and VH CDR3 of Ab239, for example, the VH CDR1, VH CDR2, and VH CDR3 of Ab239 as set forth in Table 2 (SEQ ID NOS: 28, 29, and 30, respectively); and (ii) the VL CDR1, VL CDR2, and VL CDR3 of Ab239, for example, the VL CDR1, VL CDR2, and VL CDR3 of Ab239 as set forth in Table 1 (SEQ ID NOS: 25, 26, and 27, respectively). In a specific embodiment, an anti-MET antibody described herein or an antigen-binding fragment thereof comprises (i) the VH CDR1, VH CDR2, and VH CDR3 of Ab240, for example, the VH CDR1, VH CDR2, and VH CDR3 of Ab240 as set forth in Table 2 (SEQ ID NOS: 33, 34, and 35, respectively); and (ii) the VL CDR1, VL CDR2, and VL CDR3 of Ab240, for example, the VL CDR1, VL CDR2, and VL CDR3 of Ab240 as set forth in Table 1 (SEQ ID NOS: 30, 31, and 32, respectively). In a specific embodiment, an anti-MET antibody described herein or an antigen-binding fragment thereof comprises (i) the VH CDR1, VH CDR2, and VH CDR3 of any of Ab241-Ab255, for example, the VH CDR1, VH CDR2, and VH CDR3 of any of Ab241-Ab255 as set forth in Table 2 (SEQ ID NOS: 16, 73, and 18, respectively); and (ii) the VL CDR1, VL CDR2, and VL CDR3 of any of Ab241-Ab255, for example, the VL CDR1, VL CDR2, and VL CDR3 of any of Ab241-Ab255 as set forth in Table 1 (SEQ ID NOS: 72, 14, and 15, respectively).

In certain embodiments, an antibody described herein or an antigen-binding fragment thereof comprising Kabat VL and VH CDRS (e.g., Kabat VL CDR 1, 2, and 3, and Kabat VH CDR 1, 2, and 3 for any of antibodies Ab235-Ab255 as described in Tables 1 and 2, respectively) further comprises framework regions surrounding the CDRs in the variable region (e.g., variable region in Tables 9 and 10) in the format, from the N-terminus to C-terminus: FR1-CDR1-FR2-CDR2-FR3-CDR3-FR4.

In certain embodiments, an anti-MET antibody, or antigen-binding fragment thereof, described herein comprises CDRs of any of antibodies Ab235-Ab255, as determined by the IMGT (Immunogenetics) numbering system; see, e.g., Lefranc, M.-P., 1999, The Immunologist, 7:132-136 and Lefranc, M.-P. et al., 1999, Nucleic Acids Res., 27:209-212), both of which are incorporated herein by reference in their entirety. Using the IMGT numbering system, CDRs within an antibody heavy chain molecule are typically present at amino acid positions 26 to 35 (CDR1), amino acid positions 51 to 57 (CDR2), and amino acid positions 93 to 102 (CDR3). Using the IMGT numbering system, CDRs within an antibody light chain molecule are typically present at amino acid positions 27 to 32 (CDR1), amino acid positions 50 to 52 (CDR2), and amino acid positions 89 to 97 (CDR3).

In certain embodiments, provided herein is an antibody or antigen-binding fragment thereof, which specifically binds to an ECD of human MET and comprises VL and VH CDRs of any of Ab235-Ab255, for example as set forth in Tables 5 and 6.

TABLE 5

VL CDR Amino Acid Sequences (IMGT)

| Antibody | VL CDR1 (SEQ ID NO:) | VL CDR2 (SEQ ID NO:) | VL CDR3 (SEQ ID NO:) |
|---|---|---|---|
| Ab235 | SSVNY (SEQ ID NO: 163) | DTF (SEQ ID NO: 164) | QQWSIYPYT (SEQ ID NO: 165) |
| Ab236 | SSVSY (SEQ ID NO: 169) | DTS (SEQ ID NO: 170) | QQWSNYPYT (SEQ ID NO: 171) |
| Ab237 | ADHISN (SEQ ID NO: 175) | YGN (SEQ ID NO: 176) | QQSYDSPPT (SEQ ID NO: 177) |
| Ab238 | EDIYSD (SEQ ID NO: 181) | NAN (SEQ ID NO: 182) | QQYNNYPPT (SEQ ID NO: 183) |
| Ab239 | SGDIGDRY (SEQ ID NO: 187) | AAD (SEQ ID NO: 188) | QSYDSNIDIV (SEQ ID NO: 189) |
| Ab241 | ADHISN (SEQ ID NO: 175) | YGN (SEQ ID NO: 176) | QQSYDSPPT (SEQ ID NO: 177) |
| Ab242 | ADHISN (SEQ ID NO: 175) | YGN (SEQ ID NO: 176) | QQSYDSPPT (SEQ ID NO: 177) |
| Ab243 | ADHISN (SEQ ID NO: 175) | YGN (SEQ ID NO: 176) | QQSYDSPPT (SEQ ID NO: 177) |
| Ab244 | ADHISN (SEQ ID NO: 175) | YGN (SEQ ID NO: 176) | QQSYDSPPT (SEQ ID NO: 177) |
| Ab245 | ADHISN (SEQ ID NO: 175) | YGN (SEQ ID NO: 176) | QQSYDSPPT (SEQ ID NO: 177) |
| Ab246 | ADHISN (SEQ ID NO: 175) | YGN (SEQ ID NO: 176) | QQSYDSPPT (SEQ ID NO: 177) |
| Ab247 | ADHISN (SEQ ID NO: 175) | YGN (SEQ ID NO: 176) | QQSYDSPPT (SEQ ID NO: 177) |
| Ab248 | ADHISN (SEQ ID NO: 175) | YGN (SEQ ID NO: 176) | QQSYDSPPT (SEQ ID NO: 177) |
| Ab249 | ADHISN (SEQ ID NO: 175) | YGN (SEQ ID NO: 176) | QQSYDSPPT (SEQ ID NO: 177) |
| Ab250 | ADHISN (SEQ ID NO: 175) | YGN (SEQ ID NO: 176) | QQSYDSPPT (SEQ ID NO: 177) |

TABLE 5-continued

VL CDR Amino Acid Sequences (IMGT)

| Antibody | VL CDR1 (SEQ ID NO:) | VL CDR2 (SEQ ID NO:) | VL CDR3 (SEQ ID NO:) |
|---|---|---|---|
| Ab251 | ADHISN (SEQ ID NO: 175) | YGN (SEQ ID NO: 176) | QQSYDSPPT (SEQ ID NO: 177) |
| Ab252 | ADHISN (SEQ ID NO: 175) | YGN (SEQ ID NO: 176) | QQSYDSPPT (SEQ ID NO: 177) |
| Ab253 | ADHISN (SEQ ID NO: 175) | YGN (SEQ ID NO: 176) | QQSYDSPPT (SEQ ID NO: 177) |
| Ab254 | ADHISN (SEQ ID NO: 175) | YGN (SEQ ID NO: 176) | QQSYDSPPT (SEQ ID NO: 177) |
| Ab255 | ADHISN (SEQ ID NO: 175) | YGN (SEQ ID NO: 176) | QQSYDSPPT (SEQ ID NO: 177) |
| Ab256-Ab270 | SSVNY (SEQ ID NO: 163) | DTF (SEQ ID NO: 164) | QQWSIYPYT (SEQ ID NO: 165) |
| Ab271-Ab285 | SSVSY (SEQ ID NO: 169) | DTS (SEQ ID NO: 170) | QQWSNYPYT (SEQ ID NO: 171) |
| Ab286-Ab300 | EDIYSD (SEQ ID NO: 181) | NAN (SEQ ID NO: 182) | QQYNNYPPT (SEQ ID NO: 183) |
| Ab301-Ab315 | SGDIGDRY (SEQ ID NO: 187) | AAD (SEQ ID NO: 188) | QSYDSNIDIV (SEQ ID NO: 189) |

TABLE 6

VH CDR Amino Acid Sequences (IMGT)

| Antibody | VH CDR1 (SEQ ID NO:) | VH CDR2 (SEQ ID NO:) | VH CDR3 (SEQ ID NO:) |
|---|---|---|---|
| Ab235 | GYTFSNYW (SEQ ID NO: 160) | ILPGSDYT (SEQ ID NO: 161) | ARPSTIPPDC (SEQ ID NO: 162) |
| Ab236 | GYIFSSYW (SEQ ID NO: 166) | ILPGSDFI (SEQ ID NO: 167) | ARPSTVPPDC (SEQ ID NO: 168) |
| Ab237 | GFTFSDSY (SEQ ID NO: 172) | ISSDGGGT (SEQ ID NO: 173) | TTEGIYTTDYYPYCFNY (SEQ ID NO: 174) |
| Ab238 | FSGFSLSTYGMG (SEQ ID NO: 178) | IWWDDVN (SEQ ID NO: 179) | ARIGTSHIVDA (SEQ ID NO: 180) |
| Ab239 | GFSFTDCYI (SEQ ID NO: 184) | ISSDGGGT (SEQ ID NO: 185) | TTERYYDGTYYGY (SEQ ID NO: 186) |
| Ab241 | GFTFSDSY (SEQ ID NO: 172) | ISSDGGGT (SEQ ID NO: 173) | TTEGIYTTDYYPYCFNY (SEQ ID NO: 174) |
| Ab242 | GFTFSDSY (SEQ ID NO: 172) | ISSDGGGT (SEQ ID NO: 173) | TTEGIYTTDYYPYCFNY (SEQ ID NO: 174) |
| Ab243 | GFTFSDSY (SEQ ID NO: 172) | ISSDGGGT (SEQ ID NO: 173) | TTEGIYTTDYYPYCFNY (SEQ ID NO: 174) |
| Ab244 | GFTFSDSY (SEQ ID NO: 172) | ISSDGGGT (SEQ ID NO: 173) | TTEGIYTTDYYPYCFNY (SEQ ID NO: 174) |
| Ab245 | GFTFSDSY (SEQ ID NO: 172) | ISSDGGGT (SEQ ID NO: 173) | TTEGIYTTDYYPYCFNY (SEQ ID NO: 174) |
| Ab246 | GFTFSDSY (SEQ ID NO: 172) | ISSDGGGT (SEQ ID NO: 173) | TTEGIYTTDYYPYCFNY (SEQ ID NO: 174) |
| Ab247 | GFTFSDSY (SEQ ID NO: 172) | ISSDGGGT (SEQ ID NO: 173) | TTEGIYTTDYYPYCFNY (SEQ ID NO: 174) |
| Ab248 | GFTFSDSY (SEQ ID NO: 172) | ISSDGGGT (SEQ ID NO: 173) | TTEGIYTTDYYPYCFNY (SEQ ID NO: 174) |
| Ab249 | GFTFSDSY (SEQ ID NO: 172) | ISSDGGGT (SEQ ID NO: 173) | TTEGIYTTDYYPYCFNY (SEQ ID NO: 174) |
| Ab250 | GFTFSDSY (SEQ ID NO: 172) | ISSDGGGT (SEQ ID NO: 173) | TTEGIYTTDYYPYCFNY (SEQ ID NO: 174) |

TABLE 6-continued

VH CDR Amino Acid Sequences (IMGT)

| Antibody | VH CDR1 (SEQ ID NO:) | VH CDR2 (SEQ ID NO:) | VH CDR3 (SEQ ID NO:) |
|---|---|---|---|
| Ab251 | GFTFSDSY (SEQ ID NO: 172) | ISSDGGGT (SEQ ID NO: 173) | TTEGIYTTDYYPYCFNY (SEQ ID NO: 174) |
| Ab252 | GFTFSDSY (SEQ ID NO: 172) | ISSDGGGT (SEQ ID NO: 173) | TTEGIYTTDYYPYCFNY (SEQ ID NO: 174) |
| Ab253 | GFTFSDSY (SEQ ID NO: 172) | ISSDGGGT (SEQ ID NO: 173) | TTEGIYTTDYYPYCFNY (SEQ ID NO: 174) |
| Ab254 | GFTFSDSY (SEQ ID NO: 172) | ISSDGGGT (SEQ ID NO: 173) | TTEGIYTTDYYPYCFNY (SEQ ID NO: 174) |
| Ab255 | GFTFSDSY (SEQ ID NO: 172) | ISSDGGGT (SEQ ID NO: 173) | TTEGIYTTDYYPYCFNY (SEQ ID NO: 174) |
| Ab256-Ab270 | GYTFSNYW (SEQ ID NO: 160) | ILPGSDYT (SEQ ID NO: 161) | ARPSTIPPDC (SEQ ID NO: 162) |
| Ab271-Ab285 | GYIFSSYW (SEQ ID NO: 166) | ILPGSDFI (SEQ ID NO: 167) | ARPSTVPPDC (SEQ ID NO: 168) |
| Ab286-Ab300 | FSGFSLSTYGMG (SEQ ID NO: 178) | IWWDDVN (SEQ ID NO: 179) | ARIGTSHIVDA (SEQ ID NO: 180) |
| Ab301-Ab315 | GFSFTDCYI (SEQ ID NO: 184) | ISSDGGGT (SEQ ID NO: 185) | TTERYYDGTYYGY (SEQ ID NO: 186) |

In a particular embodiment, an antibody described herein, or an antigen-binding fragment thereof, which specifically binds to an ECD of MET, comprises a light chain variable region (VL) comprising:
  (a) a VL CDR1 comprising SSVX$_{113}$Y, wherein X$_{113}$ is any amino acid, for example, an amino acid with an uncharged polar side chain, e.g., N or S;
  (b) a VL CDR2 comprising DTX$_{114}$, wherein X$_{114}$ is any amino acid, for example, F or S; and
  (c) a VL CDR3 comprising QQWSX$_{115}$YPYT, wherein X$_{115}$ is any amino acid, for example, I or N. In certain embodiments, any one of X$_{113}$ to X$_{115}$ is any amino acid sequence. In specific embodiments, X$_{113}$ is a conservative substitution of N or S, X$_{114}$ is a conservative substitution of F or S, and X$_{115}$ is a conservative substitution of F or S.

In a particular embodiment, an antibody described herein, or an antigen-binding fragment thereof, comprises the VL CDR1, VL CDR2, and VL CDR3 of Ab235, for example, the VL CDR1, VL CDR2, and VL CDR3 of Ab235 as set forth in Table 5 (SEQ ID NOS: 163, 164, and 165, respectively).

In a particular embodiment, an antibody described herein, or an antigen-binding fragment thereof, comprises the VL CDR1, VL CDR2, and VL CDR3 of Ab236, for example, the VL CDR1, VL CDR2, and VL CDR3 of Ab236 as set forth in Table 5 (SEQ ID NOS: 169, 170, and 171, respectively).

In a particular embodiment, an antibody described herein, or an antigen-binding fragment thereof, comprises the VL CDR1, VL CDR2, and VL CDR3 of Ab237, for example, the VL CDR1, VL CDR2, and VL CDR3 of Ab237 as set forth in Table 5 (SEQ ID NOS: 175, 176, and 177, respectively).

In a particular embodiment, an antibody described herein, or an antigen-binding fragment thereof, comprises the VL CDR1, VL CDR2, and VL CDR3 of Ab238, for example, the VL CDR1, VL CDR2, and VL CDR3 of Ab238 as set forth in Table 5 (SEQ ID NOS: 178, 179, and 180, respectively).

In a particular embodiment, an antibody described herein, or an antigen-binding fragment thereof, comprises the VL CDR1, VL CDR2, and VL CDR3 of Ab239, for example, the VL CDR1, VL CDR2, and VL CDR3 of Ab239 as set forth in Table 5 (SEQ ID NOS: 184, 185, and 186, respectively).

In a particular embodiment, an antibody described herein, or an antigen-binding fragment thereof, comprises the VL CDR1, VL CDR2, and VL CDR3 of any one of Ab241-Ab255, for example, the VL CDR1, VL CDR2, and VL CDR3 of Ab241 as set forth in Table 5 (SEQ ID NOS: 175, 176, and 177, respectively).

In a particular embodiment, an antibody described herein, or an antigen-binding fragment thereof, which specifically binds to an ECD of MET, comprises a heavy chain variable region (VH) comprising:
  (a) a VH CDR1 comprising GYX$_{116}$FSX$_{117}$YW (SEQ ID NO: 259), wherein X$_{116}$ is any amino acid, for example, an amino acid with a beta-branched side chain, e.g., T or I and X$_{117}$ is any amino acid, for example, an amino acid with an uncharged polar side chain, e.g., N or S;
  (b) a VH CDR2 comprising ILPGSDX$_{118}$X$_{119}$ (SEQ ID NO: 260), wherein X$_{118}$ is any amino acid, for example, an amino acid with an aromatic side chain, e.g., Y or F and X$_{119}$ is any amino acid, for example, an amino acid with a beta-branched side chain, e.g., I or T; and
  (c) a VH CDR3 comprising ARPSTX$_{120}$PPDC (SEQ ID NO: 261), wherein X$_{120}$ is any amino acid, for example, an amino acid with an nonpolar side chain, e.g., I or V. In certain embodiments, any one of X$_{116}$ to X$_{120}$ is any amino acid. In specific embodiments, X$_{116}$ is a conservative substitution of T or I, X$_{117}$ is a conservative substitution of N or S, X$_{118}$ is a conservative substitution of Y or F, X$_{119}$ is a conservative substitution of I or T, and X$_{120}$ is a conservative substitution of I or V.

In a particular embodiment, an antibody described herein, or an antigen-binding fragment thereof, which specifically binds to an ECD of MET, comprises a heavy chain variable region (VH) comprising:
  (a) a VH CDR1 comprising GFX$_{121}$FX$_{122}$DX$_{123}$YX$_{124}$, wherein X$_{121}$ is any amino acid, for example, an amino acid with an uncharged polar side chain, e.g., S or T, $X_{122}$ is any amino acid, for example, an amino acid with an uncharged polar side chain, e.g., T or S, $X_{123}$ is any amino acid, for example, an amino acid with an uncharged polar side chain, e.g., C or S, and $X_{124}$ is any amino acid, for example, I or absent;

(b) a VH CDR2 comprising SEQ ID NO: 173; and (C) a VH CDR3 comprising TTEX$_{125}$X$_{126}$YX$_{127}$X$_{128}$X$_{129}$YYX$_{130}$YX$_{131}$X$_{132}$X$_{133}$X$_{134}$X$_{135}$, wherein $X_{125}$ is any amino acid, for example, R or G, $X_{126}$ is any amino acid, for example, I or Y, $X_{127}$ is any amino acid, for example, T or D, $X_{128}$ is any amino acid, for example, an amino acid with an uncharged polar side chain, e.g., G or T, $X_{129}$ is any amino acid, for example, T or D, $X_{130}$ is any amino acid, for example, T or D, $X_{131}$ is any amino acid, for example, P or G, $X_{132}$ is any amino acid, for example, C or absent, $X_{133}$ is any amino acid, for example, F or absent, $X_{134}$ is any amino acid, for example, N or absent, and $X_{135}$ is any amino acid, for example, Y or absent. In certain embodiments, any one of $X_{121}$ to $X_{135}$ is any amino acid sequence. In specific embodiments, $X_{121}$ is a conservative substitution of S or T, $X_{122}$ is a conservative substitution of S or T, $X_{123}$ is a conservative substitution of C or S, $X_{124}$ is a conservative substitution of I or absent, $X_{125}$ is a conservative substitution of R or G, $X_{126}$ is a conservative substitution of I or Y, $X_{127}$ is a conservative substitution of T or D, $X_{128}$ is a conservative substitution of G or T, $X_{129}$ is a conservative substitution of T or D, $X_{130}$ is a conservative substitution of T or D, $X_{131}$ is a conservative substitution of P or G, $X_{132}$ is a conservative substitution of C or absent, $X_{133}$ is a conservative substitution of F or absent, $X_{134}$ is a conservative substitution of N or absent, and $X_{135}$ is a conservative substitution of Y or absent.

In a particular embodiment, an antibody described herein, or an antigen-binding fragment thereof, comprises the VH CDR1, VH CDR2, and VH CDR3 of Ab235, for example, the VH CDR1, VH CDR2, and VH CDR3 of Ab235 as set forth in Table 6 (SEQ ID NOS: 160, 161, and 162, respectively).

In a particular embodiment, an antibody described herein, or an antigen-binding fragment thereof, comprises the VH CDR1, VH CDR2, and VH CDR3 of Ab236, for example, the VH CDR1, VH CDR2, and VH CDR3 of Ab236 as set forth in Table 6 (SEQ ID NOS: 166, 167, and 168, respectively).

In a particular embodiment, an antibody described herein, or an antigen-binding fragment thereof, comprises the VH CDR1, VH CDR2, and VH CDR3 of Ab237, for example, the VH CDR1, VH CDR2, and VH CDR3 of Ab237 as set forth in Table 6 (SEQ ID NOS: 172, 173, and 174, respectively).

In a particular embodiment, an antibody described herein, or an antigen-binding fragment thereof, comprises the VH CDR1, VH CDR2, and VH CDR3 of Ab238, for example, the VH CDR1, VH CDR2, and VH CDR3 of Ab238 as set forth in Table 6 (SEQ ID NOS: 178, 179, and 180, respectively).

In a particular embodiment, an antibody described herein, or an antigen-binding fragment thereof, comprises the VH CDR1, VH CDR2, and VH CDR3 of Ab239, for example, the VH CDR1, VH CDR2, and VH CDR3 of Ab239 as set forth in Table 6 (SEQ ID NOS: 184, 185, and 186, respectively).

In a particular embodiment, an antibody described herein, or an antigen-binding fragment thereof, comprises the VH CDR1, VH CDR2, and VH CDR3 of any one of Ab241-Ab255, for example, the VH CDR1, VH CDR2, and VH CDR3 of Ab241 as set forth in Table 6 (SEQ ID NOS: 172, 173, and 174, respectively).

In certain embodiments, an antibody described herein or an antigen-binding fragment thereof comprising IMGT VL and VH CDRS (e.g., IMGT VL CDR 1, 2, and 3, and IMGT VH CDR 1, 2, and 3 for any of antibodies Ab235-Ab255 as described in Tables 5 and 6, respectively) further comprises framework regions surrounding the CDRs in the variable region (e.g., variable region in Tables 9 and 10) in the format, from the N-terminus to C-terminus: FR1-CDR1-FR2-CDR2-FR3-CDR3-FR4.

In certain aspects, the CDRs of an antibody described herein are Chothia CDRs (see, e.g., Chothia and Lesk, 1987, J. Mol. Biol., 196:901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in *Antibody Engineering*, Kontermann and Dübel, eds., Chapter 31, pp. 422-439, Springer-Verlag, Berlin (2001)). Using the Kabat numbering system of numbering amino acid residues in the VH region and VL region, Chothia CDRs within an antibody heavy chain molecule are typically present at amino acid positions 26 to 32 (CDR1), amino acid positions 53 to 55 (CDR2), and amino acid positions 96 to 101 (CDR3). Using the Kabat numbering system of numbering amino acid residues in the VH region and VL region, Chothia CDRs within an antibody light chain molecule are typically present at amino acid positions 26 to 33 (CDR1), amino acid positions 50 to 52 (CDR2), and amino acid positions 91 to 96 (CDR3). In a specific embodiment, using the Kabat numbering system of numbering amino acid residues in the VH chain region and VL chain region, the Chothia CDRs within an antibody heavy chain molecule are at amino acid positions 26 to 32 or 34 (CDR1), amino acid positions 52 to 56 (CDR2; in one embodiment, CDR2 is at positions 52A-56, wherein 52A follows position 52), and amino acid positions 95 to 102 (CDR3; in one embodiment, there is no amino acid at positions numbered 96-100); and the Chothia CDRs within an antibody light chain molecule are at amino acid positions 24 to 34 (CDR1), amino acid positions 50 to 56 (CDR2), and amino acid positions 89 to 97 (CDR3). These Chothia CDR positions may vary depending on the antibody, and may be determined according to methods known in the art.

In certain aspects, also described herein are antibodies that immunospecifically bind to a MET polypeptide that comprise one or more Chothia VL CDRs of a VL of any one of antibodies Ab235-Ab255 (see, Table 7 and/or one or more Chothia VH CDRs of a VH of any one of antibodies Ab235-Ab255 (see, Table 8). In certain embodiments, antibodies described herein that immunospecifically bind to a MET polypeptide comprise one or more CDRs, in which the Chothia and Kabat CDRs have the same amino acid sequence. In certain embodiments, provided herein are antibodies that immunospecifically bind to a MET polypeptide and which comprise combinations of Kabat CDRs and Chothia CDRs.

TABLE 7

VL CDR Amino Acid Sequences (Chothia)

| Antibody | VL CDR1 (SEQ ID NO:) | VL CDR2 (SEQ ID NO:) | VL CDR3 (SEQ ID NO:) |
|---|---|---|---|
| Ab235 | SASSSVNYMF (SEQ ID NO: 133) | DTFNLAS (SEQ ID NO: 134) | QQWSYPYT (SEQ ID NO: 135) |
| Ab236 | SASSSVSYMF (SEQ ID NO: 139) | DTSDLAS (SEQ ID NO: 140) | QQWSNYPYT (SEQ ID NO: 141) |
| Ab237 | LASADIHSNLA (SEQ ID NO: 145) | NNLND (SEQ ID NO: 146) | PPTFGAGT (SEQ ID NO: 147) |
| Ab238 | LASEDIYSDLA (SEQ ID NO: 151) | NANTLQN (SEQ ID NO: 152) | QQYNNYPPT (SEQ ID NO: 153) |
| Ab239 | VRSSGDIGDRYVS (SEQ ID NO: 157) | AADQRPS (SEQ ID NO: 158) | QSYDSNIDIV (SEQ ID NO: 159) |
| Ab241 | LASADIHSNLA (SEQ ID NO: 145) | NNLND (SEQ ID NO: 146) | PPTFGQGT (SEQ ID NO: 264) |
| Ab242 | LASADIHSNLA (SEQ ID NO: 145) | NNLND (SEQ ID NO: 146) | PPTFGQGT (SEQ ID NO: 264) |
| Ab243 | LASADIHSNLA (SEQ ID NO: 145) | NNLND (SEQ ID NO: 146) | PPTFGQGT (SEQ ID NO: 264) |
| Ab244 | LASADIHSNLA (SEQ ID NO: 145) | NNLND (SEQ ID NO: 146) | PPTFGQGT (SEQ ID NO: 264) |
| Ab245 | LASADIHSNLA (SEQ ID NO: 145) | NNLND (SEQ ID NO: 146) | PPTFGQGT (SEQ ID NO: 264) |
| Ab246 | LASADIHSNLA (SEQ ID NO: 145) | NNLND (SEQ ID NO: 146) | PPTFGQGT (SEQ ID NO: 264) |
| Ab247 | LASADIHSNLA (SEQ ID NO: 145) | NNLND (SEQ ID NO: 146) | PPTFGQGT (SEQ ID NO: 264) |
| Ab248 | LASADIHSNLA (SEQ ID NO: 145) | NNLND (SEQ ID NO: 146) | PPTFGQGT (SEQ ID NO: 264) |
| Ab249 | LASADIHSNLA (SEQ ID NO: 145) | NNLND (SEQ ID NO: 146) | PPTFGQGT (SEQ ID NO: 264) |
| Ab250 | LASADIHSNLA (SEQ ID NO: 145) | NNLND (SEQ ID NO: 146) | PPTFGQGT (SEQ ID NO: 264) |
| Ab251 | LASADIHSNLA (SEQ ID NO: 145) | NNLND (SEQ ID NO: 146) | PPTFGQGT (SEQ ID NO: 264) |
| Ab252 | LASADIHSNLA (SEQ ID NO: 145) | NNLND (SEQ ID NO: 146) | PPTFGQGT (SEQ ID NO: 264) |
| Ab253 | LASADIHSNLA (SEQ ID NO: 145) | NNLND (SEQ ID NO: 146) | PPTFGQGT (SEQ ID NO: 264) |
| Ab254 | LASADIHSNLA (SEQ ID NO: 145) | NNLND (SEQ ID NO: 146) | PPTFGQGT (SEQ ID NO: 264) |
| Ab255 | LASADIHSNLA (SEQ ID NO: 145) | NNLND (SEQ ID NO: 146) | PPTFGQGT (SEQ ID NO: 264) |
| Ab256-Ab270 | SASSSVNYMF (SEQ ID NO: 133) | DTFNLAS (SEQ ID NO: 134) | QQWSYPYT (SEQ ID NO: 135) |
| Ab271-Ab285 | SASSSVSYMF (SEQ ID NO: 139) | DTSDLAS (SEQ ID NO: 140) | QQWSNYPYT (SEQ ID NO: 141) |
| Ab286-Ab300 | LASEDIYSDLA (SEQ ID NO: 151) | NANTLQN (SEQ ID NO: 152) | QQYNNYPPT (SEQ ID NO: 153) |
| Ab301-Ab315 | VRSSGDIGDRYVS (SEQ ID NO: 157) | AADQRPS (SEQ ID NO: 158) | QSYDSNIDIV (SEQ ID NO: 159) |

TABLE 8

VH CDR Amino Acid Sequences (Chothia)

| Antibody | VH CDR1 (SEQ ID NO:) | VH CDR2 (SEQ ID NO:) | VH CDR3 (SEQ ID NO:) |
|---|---|---|---|
| Ab235 | GYTFSNY (SEQ ID NO: 130) | LPGSDY (SEQ ID NO: 131) | PSTIPPDC (SEQ ID NO: 132) |
| Ab236 | GYIFSSY (SEQ ID NO: 136) | LPGSDF (SEQ ID NO: 137) | PSTVPPDC (SEQ ID NO: 138) |
| Ab237 | GFTFSDS (SEQ ID NO: 142) | SSDGGG (SEQ ID NO: 143) | EGIYTTDYYPYCFNY (SEQ ID NO: 144) |
| Ab238 | GFSLSTYGM (SEQ ID NO: 148) | WVVDDV (SEQ ID NO: 149) | IGTSHIVDA (SEQ ID NO: 150) |
| Ab239 | GFSFTDC (SEQ ID NO: 154) | SSDGGG (SEQ ID NO: 155) | ERYYDGTYYGYWYFDF (SEQ ID NO: 156) |
| Ab241 | GFTFSDS (SEQ ID NO: 142) | SSDGGG (SEQ ID NO: 143) | EGIYTTDYYPYCFNY (SEQ ID NO: 144) |

TABLE 8-continued

VH CDR Amino Acid Sequences (Chothia)

| Antibody | VH CDR1 (SEQ ID NO:) | VH CDR2 (SEQ ID NO:) | VH CDR3 (SEQ ID NO:) |
|---|---|---|---|
| Ab242 | GFTFSDS (SEQ ID NO: 142) | SSDGGG (SEQ ID NO: 143) | EGIYTTDYYPYCFNY (SEQ ID NO: 144) |
| Ab243 | GFTFSDS (SEQ ID NO: 142) | SSDGGG (SEQ ID NO: 143) | EGIYTTDYYPYCFNY (SEQ ID NO: 144) |
| Ab244 | GFTFSDS (SEQ ID NO: 142) | SSDGGG (SEQ ID NO: 143) | EGIYTTDYYPYCFNY (SEQ ID NO: 144) |
| Ab245 | GFTFSDS (SEQ ID NO: 142) | SSDGGG (SEQ ID NO: 143) | EGIYTTDYYPYCFNY (SEQ ID NO: 144) |
| Ab246 | GFTFSDS (SEQ ID NO: 142) | SSDGGG (SEQ ID NO: 143) | EGIYTTDYYPYCFNY (SEQ ID NO: 144) |
| Ab247 | GFTFSDS (SEQ ID NO: 142) | SSDGGG (SEQ ID NO: 143) | EGIYTTDYYPYCFNY (SEQ ID NO: 144) |
| Ab248 | GFTFSDS (SEQ ID NO: 142) | SSDGGG (SEQ ID NO: 143) | EGIYTTDYYPYCFNY (SEQ ID NO: 144) |
| Ab249 | GFTFSDS (SEQ ID NO: 142) | SSDGGG (SEQ ID NO: 143) | EGIYTTDYYPYCFNY (SEQ ID NO: 144) |
| Ab250 | GFTFSDS (SEQ ID NO: 142) | SSDGGG (SEQ ID NO: 143) | EGIYTTDYYPYCFNY (SEQ ID NO: 144) |
| Ab251 | GFTFSDS (SEQ ID NO: 142) | SSDGGG (SEQ ID NO: 143) | EGIYTTDYYPYCFNY (SEQ ID NO: 144) |
| Ab252 | GFTFSDS (SEQ ID NO: 142) | SSDGGG (SEQ ID NO: 143) | EGIYTTDYYPYCFNY (SEQ ID NO: 144) |
| Ab253 | GFTFSDS (SEQ ID NO: 142) | SSDGGG (SEQ ID NO: 143) | EGIYTTDYYPYCFNY (SEQ ID NO: 144) |
| Ab254 | GFTFSDS (SEQ ID NO: 142) | SSDGGG (SEQ ID NO: 143) | EGIYTTDYYPYCFNY (SEQ ID NO: 144) |
| Ab255 | GFTFSDS (SEQ ID NO: 142) | SSDGGG (SEQ ID NO: 143) | EGIYTTDYYPYCFNY (SEQ ID NO: 144) |
| Ab256-Ab270 | GYTFSNY (SEQ ID NO: 130) | LPGSDY (SEQ ID NO: 131) | PSTIPPDC (SEQ ID NO: 132) |
| Ab271-Ab285 | GYIFSSY (SEQ ID NO: 136) | LPGSDF (SEQ ID NO: 137) | PSTVPPDC (SEQ ID NO: 138) |
| Ab286-Ab300 | GFSLSTYGM (SEQ ID NO: 148) | WVVDDV (SEQ ID NO: 149) | IGTSHIVDA (SEQ ID NO: 150) |
| Ab301-Ab315 | GFSFTDC (SEQ ID NO: 154) | SSDGGG (SEQ ID NO: 155) | ERYYDGTYYGWYFDF (SEQ ID NO: 156) |

In a particular embodiment, an antibody described herein, or an antigen-binding fragment thereof, which specifically binds to an ECD of MET, comprises a light chain variable region (VL) comprising:
(a) a VL CDR1 comprising SASSSVX$_{90}$YMF (SEQ ID NO: 248), wherein X$_{90}$ is any amino acid, for example, an amino acid with an uncharged polar side chain, e.g., S or N;
(b) a VL CDR2 comprising DX$_{91}$X$_{92}$X$_{93}$LAS (SEQ ID NO: 249), wherein X$_{91}$ is any amino acid, for example, Y or D, X$_{92}$ is any amino acid, for example, F or S, and X$_{93}$ is any amino acid, for example, N or D; and
(c) a VL CDR3 comprising QQWSX$_{94}$X$_{95}$PYT (SEQ ID NO: 250), wherein X$_{94}$ is any amino acid, for example, an amino acid with an uncharged polar side chain, e.g., Y or N, and X$_{95}$ is any amino acid, for example, Y or absent. In certain embodiments, any one of X$_{90}$ to X$_{95}$ is any amino acid sequence. In specific embodiments, X$_{90}$ is a conservative substitution of S or N, X$_{91}$ is a conservative substitution of Y or D, X$_{92}$ is a conservative substitution of F or S, X$_{93}$ is a conservative substitution of N or D, X$_{94}$ is a conservative substitution of Y or N, and X$_{95}$ is a conservative substitution of Y or absent.

In a particular embodiment, an antibody described herein, or an antigen-binding fragment thereof, comprises the VL CDR1, VL CDR2, and VL CDR3 of Ab235, for example, the VL CDR1, VL CDR2, and VL CDR3 of Ab235 as set forth in Table 7 (SEQ ID NOS: 133, 134, and 135, respectively).

In a particular embodiment, an antibody described herein, or an antigen-binding fragment thereof, comprises the VL CDR1, VL CDR2, and VL CDR3 of Ab236, for example, the VL CDR1, VL CDR2, and VL CDR3 of Ab236 as set forth in Table 7 (SEQ ID NOS: 139, 140, and 141, respectively).

In a particular embodiment, an antibody described herein, or an antigen-binding fragment thereof, comprises the VL CDR1, VL CDR2, and VL CDR3 of Ab237, for example, the VL CDR1, VL CDR2, and VL CDR3 of Ab237 as set forth in Table 7 (SEQ ID NOS: 145, 146, and 147, respectively).

In a particular embodiment, an antibody described herein, or an antigen-binding fragment thereof, comprises the VL CDR1, VL CDR2, and VL CDR3 of Ab238, for example, the VL CDR1, VL CDR2, and VL CDR3 of Ab238 as set forth in Table 7 (SEQ ID NOS: 151, 152, and 153, respectively).

In a particular embodiment, an antibody described herein, or an antigen-binding fragment thereof, comprises the VL CDR1, VL CDR2, and VL CDR3 of Ab239, for example, the VL CDR1, VL CDR2, and VL CDR3 of Ab239 as set forth in Table 7 (SEQ ID NOS: 157, 158, and 159, respectively).

In a particular embodiment, an antibody described herein, or an antigen-binding fragment thereof, comprises the VL CDR1, VL CDR2, and VL CDR3 of any one of Ab241-Ab255, for example, the VL CDR1, VL CDR2, and VL CDR3 of Ab241 as set forth in Table 7 (SEQ ID NOS: 145, 146, and 264, respectively). In a particular embodiment, an antibody described herein, or an antigen-binding fragment thereof, comprises the VL CDR1, VL CDR2, and VL CDR3 as set forth in SEQ ID NOS: 145, 146, and 147, respectively. In a particular embodiment, an antibody described herein, or an antigen-binding fragment thereof, comprises the VL CDR1 and VL CDR2 as set forth in SEQ ID NOS: 145 and 146, respectively, and the VL CDR3 as set forth in SEQ ID NOS: 147 or 264. In a particular embodiment, an antibody described herein, or an antigen-binding fragment thereof, comprises the VL CDR1 and VL CDR2 as set forth in SEQ ID NOS: 145 and 146, respectively, and the VL CDR3 as set forth in PPTFGX$_{136}$GT (SEQ ID NO: 272), wherein X$_{136}$ is any amino acid, for example, A or Q.

In a particular embodiment, an antibody described herein, or an antigen-binding fragment thereof, which specifically binds to an ECD of MET, comprises a heavy chain variable region (VH) comprising:
(a) a VH CDR1 comprising GYX$_{96}$FSX$_{97}$Y (SEQ ID NO: 251), wherein X$_{96}$ is any amino acid, for example, an amino acid with a beta-branched side chain, e.g., I or T and X$_{97}$ is any amino acid, for example, an amino acid with an uncharged polar side chain, e.g., S or N;
(b) a VH CDR2 comprising LPGSDX$_{98}$ (SEQ ID NO: 252), wherein X$_{98}$ is any amino acid, for example, an amino acid with an aromatic side chain, e.g., Y or F; and
(c) a VH CDR3 comprising PSTX$_{99}$PPDC, wherein X$_{99}$ is any amino acid, for example, an amino acid with an nonpolar side chain, e.g., I or V. In certain embodiments, any one of X$_{96}$ to X$_{99}$ is any amino acid sequence. In specific embodiments, X$_{96}$ is a conservative substitution of I or T, X$_{97}$ is a conservative substitution of S or N, X$_{98}$ is a conservative substitution of Y or F, and X$_{99}$ is a conservative substitution of I or V.

In a particular embodiment, an antibody described herein, or an antigen-binding fragment thereof, which specifically binds to an ECD of MET, comprises a heavy chain variable region (VH) comprising:
(a) a VH CDR1 comprising GFX$_{100}$FX$_{101}$DX$_{102}$ (SEQ ID NO: 254), wherein X$_{100}$ is any amino acid, for example, an amino acid with an uncharged polar side chain, e.g., T or S, X$_{101}$ is any amino acid, for example, an amino acid with an uncharged polar side chain, e.g., S or T, and X$_{102}$ is any amino acid, for example, an amino acid with an uncharged polar side chain, e.g., S or C;
(b) a VH CDR2 comprising SEQ ID NO: 143; and
(c) a VH CDR3 comprising EX$_{103}$X$_{104}$YX$_{105}$X$_{106}$X$_{107}$YYX$_{108}$YX$_{109}$X$_{110}$FX$_{111}$X$_{112}$ (SEQ ID NO: 255), wherein X$_{103}$ is any amino acid, for example, G or R, X$_{104}$ is any amino acid, for example, I or Y, X$_{105}$ is any amino acid, for example, T or D, X$_{106}$ is any amino acid, for example, an amino acid with an uncharged polar side chain, e.g., T or G, X$_{107}$ is any amino acid, for example, D or T, X$_{108}$ is any amino acid, for example, P or G, X$_{109}$ is any amino acid, for example, C or W, X$_{110}$ is any amino acid, for example, Y or absent, Xiii is any amino acid, for example, N or D, and X$_{112}$ is any amino acid, for example, an amino acid with an aromatic side chain, e.g., Y or F. In certain embodiments, any one of X$_{100}$ to X$_{112}$ is any amino acid. In specific embodiments, X$_{100}$ is a conservative substitution of T or S, X$_{101}$ is a conservative substitution of S or T, X$_{102}$ is a conservative substitution of S or C, X$_{103}$ is a conservative substitution of G or R, X$_{104}$ is a conservative substitution of I or Y, X$_{105}$ is a conservative substitution of T or D, X$_{106}$ is a conservative substitution of T or G, X$_{107}$ is a conservative substitution of T or D, X$_{108}$ is a conservative substitution of P or G, X$_{109}$ is a conservative substitution of C or W, X$_{110}$ is a conservative substitution of Y or absent, X$_{111}$ is a conservative substitution of N or D, and X$_{112}$ is a conservative substitution of Y or F.

In a particular embodiment, an antibody described herein, or an antigen-binding fragment thereof, comprises the VH CDR1, VH CDR2, and VH CDR3 of Ab235, for example, the VH CDR1, VH CDR2, and VH CDR3 of Ab235 as set forth in Table 8 (SEQ ID NOS: 130, 131, and 132, respectively).

In a particular embodiment, an antibody described herein, or an antigen-binding fragment thereof, comprises the VH CDR1, VH CDR2, and VH CDR3 of Ab236, for example, the VH CDR1, VH CDR2, and VH CDR3 of Ab236 as set forth in Table 8 (SEQ ID NOS: 136, 137, and 138, respectively).

In a particular embodiment, an antibody described herein, or an antigen-binding fragment thereof, comprises the VH CDR1, VH CDR2, and VH CDR3 of Ab237, for example, the VH CDR1, VH CDR2, and VH CDR3 of Ab237 as set forth in Table 8 (SEQ ID NOS: 142, 143, and 144, respectively).

In a particular embodiment, an antibody described herein, or an antigen-binding fragment thereof, comprises the VH CDR1, VH CDR2, and VH CDR3 of Ab238, for example, the VH CDR1, VH CDR2, and VH CDR3 of Ab238 as set forth in Table 8 (SEQ ID NOS: 148, 149, and 150, respectively).

In a particular embodiment, an antibody described herein, or an antigen-binding fragment thereof, comprises the VH CDR1, VH CDR2, and VH CDR3 of Ab239, for example, the VH CDR1, VH CDR2, and VH CDR3 of Ab239 as set forth in Table 8 (SEQ ID NOS: 154, 155, and 156, respectively).

In a particular embodiment, an antibody described herein, or an antigen-binding fragment thereof, comprises the VH CDR1, VH CDR2, and VH CDR3 of any one of Ab241-Ab255, for example, the VH CDR1, VH CDR2, and VH CDR3 of Ab241 as set forth in Table 8 (SEQ ID NOS: 142, 143, and 144, respectively).

In certain embodiments, an antibody described herein or an antigen-binding fragment thereof comprising Chothia VL and VH CDRS (e.g., Chothia VL CDR 1, 2, and 3, and Chothia VH CDR 1, 2, and 3 for any of antibodies Ab235-Ab255 as described in Tables 7 and 8, respectively) further comprises framework regions surrounding the CDRs in the variable region (e.g., variable region in Tables 10 and 11) in the format, from the N-terminus to C-terminus: FR1-CDR1-FR2-CDR2-FR3-CDR3-FR4.

In a specific embodiment, an anti-MET antibody described herein comprises a VL region comprising DIQMTQSPX$_{26}$SLSASX$_{27}$GX$_{28}$X$_{29}$TIX$_{30}$CLASADIHSNLAWYQQKPGX$_{31}$X$_{32}$PX$_{33}$LLIYGN NLNDGVPSRFSGX$_{34}$GX$_{35}$GTX$_{36}$X$_{37}$X$_{38}$LX$_{39}$IX$_{40}$SLQX$_{41}$EDVX$_{42}$IYFCQQSYDSPPTFGQGT KLEIK (SEQ ID NO:47), wherein X$_{26}$ is any amino acid, for example, an amino acid with an uncharged polar side chain, e.g., S or G, X$_{27}$ is any amino acid, for example, an amino acid with an nonpolar side chain, e.g., V or L, X$_{28}$ is any amino acid, for example, an amino acid with an charged side chain, for example, an acidic side chain, e.g., D or E, X$_{29}$ is any amino acid, for example, R or T, X$_{30}$ is any amino acid, for example, T or E, X$_{31}$ is any amino acid, for example, K or N, X$_{32}$ is any amino acid, for example, A or S, X$_{33}$ is any amino acid, for example, K or Q, X$_{34}$ is any amino acid, for example, F or S, X$_{35}$ is any amino acid, for example, F or S, X$_{36}$ is any amino acid, for example, D or Q, X$_{37}$ is any amino acid, for example, an amino acid with an aromatic side chain, e.g., F or Y, X$_{38}$ is any amino acid, for example, an amino acid with an uncharged polar side chain, e.g., T or S, X$_{39}$ is any amino acid, for example, T or K, X$_{40}$ is any amino acid, for example, an amino acid with an uncharged polar side chain, e.g., S or N, X$_{41}$ is any amino acid, for example, P or S, and X$_{42}$ is any amino acid, for example, A or S. In certain embodiments, any one of X$_{26}$ to X$_{42}$ is any amino acid. In specific embodiments, X$_{26}$ is a conservative substitution of S or G, X$_{27}$ is a conservative substitution of V or L, X$_{28}$ is a conservative substitution of D or E, X$_{29}$ is a conservative substitution of R or T, X$_{30}$ is a conservative substitution of T or E, X$_{31}$ is a conservative substitution of K or N, X$_{32}$ is a conservative substitution of A or S, X$_{33}$ is a conservative substitution of K or Q, X$_{34}$ is a conservative substitution of F or S, X$_{35}$ is a conservative substitution of F or S, X$_{36}$ is a conservative substitution of D or Q, X$_{37}$ is a conservative substitution of F or Y, X$_{38}$ is a conservative substitution of T or S, X$_{39}$ is a conservative substitution of T or K, X$_{40}$ is a conservative substitution of S or N, X$_{41}$ is a conservative substitution of P or S, and X$_{42}$ is a conservative substitution of A or S.

In a specific embodiment, an anti-MET antibody described herein comprises a VH region comprising EVQLVESGGGLVQPGX$_{49}$SLKLSCAASGFTFSDSYMAWVRQAPX$_{50}$KGLEWVASISSDG GGTYYRDSVKGRFX$_{51}$ISRDNAKX$_{52}$SLYLQMDSLRX$_{53}$EDTATYYCTTEGIYTTDYYPYC FNYWGX$_{54}$GX$_{55}$MVTVSX$_{56}$ (SEQ ID NO:49, wherein X$_{49}$ is any amino acid, for example, G or R, X$_{50}$ is any amino acid, for example, an amino acid with an uncharged polar side chain, e.g., G or T, X$_{51}$ is any amino acid, for example, an amino acid with an uncharged polar side chain, e.g., T or S, X$_{52}$ is any amino acid, for example, an amino acid with an uncharged polar side chain, e.g., S or N, X$_{53}$ is any amino acid, for example, an amino acid with an uncharged polar side chain, e.g., T or S, X$_{54}$ is any amino acid, for example, Q or H, X$_{55}$ is any amino acid, for example, V or T, and X$_{56}$ is any amino acid, for example, S or A. In certain embodiments, any one of X$_{49}$ to X$_{56}$ is any amino acid sequence. In specific embodiments, X$_{49}$ is a conservative substitution of G or R, X$_{50}$ is a conservative substitution of G or T, X$_{51}$ is a conservative substitution of T or S, X$_{52}$ is a conservative substitution of S or N, X$_{53}$ is a conservative substitution of T or S, X$_{54}$ is a conservative substitution of Q or H, X$_{55}$ is a conservative substitution of V or T, and X$_{56}$ is a conservative substitution of S or A.

In a specific embodiment, an anti-MET antibody described herein comprises (a) a VL region comprising DIQMTQSPX$_{26}$SLSASX$_{27}$GX$_{28}$X$_{29}$TIX$_{30}$CLASADIHSNLAWYQQKPGX$_{31}$X$_{32}$PX$_{33}$LLIYGNN LNDGVPSRFSGX$_{34}$GX$_{35}$GTX$_{36}$X$_{37}$X$_{38}$LX$_{39}$IX$_{40}$SLQX$_{41}$EDVX$_{42}$IYFCQQSYDSPPTFGQGTK LEIK (SEQ ID NO:47), wherein X$_{26}$ is any amino acid, for example, an amino acid with an uncharged polar side chain, e.g., S or G, X$_{27}$ is any amino acid, for example, an amino acid with an nonpolar side chain, e.g., V or L, X$_{28}$ is any amino acid, for example, an amino acid with a charged side chain, for example, an acidic side chain, e.g., D or E, X$_{28}$ is any amino acid, for example, R or T, X$_{30}$ is any amino acid, for example, T or E, X$_{31}$ is any amino acid, for example, K or N, X$_{32}$ is any amino acid, for example, an amino acid with an uncharged polar side chain, e.g., A or S, X$_{33}$ is any amino acid, for example, K or Q, X$_{34}$ is any amino acid, for example, F or S, X$_{35}$ is any amino acid, for example, F or S, X$_{36}$ is any amino acid, for example, D or Q, X$_{37}$ is any amino acid, for example, an amino acid with an aromatic side chain, e.g., F or Y, X$_{38}$ is any amino acid, for example, an amino acid with an uncharged polar side chain, e.g., T or S, X$_{39}$ is any amino acid, for example, T or K, X$_{40}$ is any amino acid, for example, an amino acid with an uncharged polar side chain, e.g., S or N, X$_{41}$ is any amino acid, for example, P or S, and X$_{42}$ is any amino acid, for example, A or S; and (b) a VH region comprising EVQLVESGGGLVQPGX$_{49}$SLKLSCAASGFTF SDSYMAWVRQAPX$_{50}$KGLEWVASISSDGG GTYYRDSVKGRFX$_{51}$ISRDNAKX$_{52}$SLYLQMDSLRX$_{53}$EDTATYYCTTEGIYTTDYYPYCF NYWGX$_{54}$GX$_{55}$MVTVSX$_{56}$ (SEQ ID NO:49, wherein X$_{49}$ is any amino acid, for example, G or R, X$_{50}$ is any amino acid, for example, an amino acid with an uncharged polar side chain, e.g., G or T, X$_{51}$ is any amino acid, for example, an amino acid with an uncharged polar side chain, e.g., T or S, X$_{52}$ is any amino acid, for example, an amino acid with an uncharged polar side chain, e.g., S or N, X$_{53}$ is any amino acid, for example, an amino acid with an uncharged polar side chain, e.g., T or S, X$_{54}$ is any amino acid, for example, Q or H, X$_{55}$ is any amino acid, for example, V or T, and X$_{56}$ is any amino acid, for example, S or A. In certain embodiments, any one of X$_{26}$ to X$_{42}$ and X$_{49}$ to X$_{56}$ is any amino acid. In specific embodiments, X$_{26}$ is a conservative substitution of S or G, X$_{27}$ is a conservative substitution of V or L, X$_{28}$ is a conservative substitution of D or E, X$_{29}$ is a conservative substitution of R or T, X$_{30}$ is a conservative substitution of T or E, X$_{31}$ is a conservative substitution of K or N, X$_{32}$ is a conservative substitution of A or S, X$_{33}$ is a conservative substitution of K or Q, X$_{34}$ is a conservative substitution of F or S, X$_{35}$ is a conservative substitution of F or S, X$_{36}$ is a conservative substitution of D or Q, X$_{37}$ is a conservative substitution of F or Y, X$_{38}$ is a conservative substitution of T or S, X$_{39}$ is a conservative substitution of T or K, X$_{40}$ is a conservative substitution of S or N, $X_{41}$ is a conservative substitution of P or S, $X_{42}$ is a conservative substitution of A or S, $X_{49}$ is a conservative substitution of G or R, $X_{50}$ is a conservative substitution of G or T, $X_{51}$ is a conservative substitution of T or S, $X_{52}$ is a conservative substitution of S or N, $X_{53}$ is a conservative substitution of T or S, $X_{54}$ is a conservative substitution of Q or H, $X_{55}$ is a conservative substitution of V or T, and $X_{56}$ is a conservative substitution of S or A.

In a specific embodiment, an anti-MET antibody described herein comprises a VL region comprising DIQMTQSPSSLSASVGDRVTITCLASADIHSNLAWYQQKPGKAPX$_{68}$LLIYYGNNLNDGV PSRFSGX$_{69}$GX$_{70}$GTDX$_{71}$TLX$_{72}$IX$_{73}$SLQX$_{74}$EDVAX$_{75}$YFCQQSYDSPPTFGQGTKLEIK (SEQ ID NO: 238), wherein $X_{68}$ is any amino acid, for example, K or Q, $X_{69}$ is any amino acid, for example, S or F, $X_{70}$ is any amino acid, for example, S or F, $X_{71}$ is any amino acid, for example, an amino acid with an aromatic side chain, e.g., Y or F, $X_{72}$ is any amino acid, for example, T or K, $X_{73}$ is any amino acid, for example, an amino acid with an uncharged polar side chain, e.g., S or N, $X_{74}$ is any amino acid, for example, P or S, and $X_{75}$ is any amino acid, for example, I or T. In certain embodiments, any one of $X_{68}$ to $X_{75}$ is any amino acid. In specific embodiments, $X_{43}$ is a conservative substitution of T or A, $X_{68}$ is a conservative substitution of K or Q, $X_{69}$ is a conservative substitution of S or F, $X_{70}$ is a conservative substitution of S or F, $X_{71}$ is a conservative substitution of Y or F, $X_{72}$ is a conservative substitution of T or K, $X_{73}$ is a conservative substitution of S or N, $X_{74}$ is a conservative substitution of P or S, and $X_{75}$ is a conservative substitution of I or T.

In a specific embodiment, an anti-MET antibody described herein comprises a VH region comprising EVQLVESGGGLVQPGGSLKLSCAASGFTF SDSYMAWVRQAPGKGLEWVASISSDGGG TYYRDSVKGRFTISRDNAKX$_{76}$SLYLQMX$_{77}$SLRTEDTATYYCTTEGIYTTDYYPYCFNY WGQGX$_{78}$MV (SEQ ID NO: 239), wherein $X_{76}$ is any amino acid, for example, an amino acid with an uncharged polar side chain, e.g., S or N, $X_{77}$ is any amino acid, for example, D or N, and $X_{78}$ is any amino acid, for example, T or V. In certain embodiments, any one of $X_{76}$ to $X_{78}$ is any amino acid sequence. In specific embodiments, $X_{76}$ is a conservative substitution of S or N, $X_{77}$ is a conservative substitution of D or N, and $X_{78}$ is a conservative substitution of T or V.

In a specific embodiment, an anti-MET antibody described herein comprises
(a) a VL region comprising DIQMTQSPSSLSASVGDRVTITCLASADIHSNLAWYQQKPGKAPX$_{68}$ LLIYYGNNLNDGV PSRFSGX$_{69}$GX$_{70}$GTDX$_{71}$ TLX$_{72}$IX$_{73}$SLQX$_{74}$EDVAX$_{75}$YFCQQSYDSPPTFGQGTKLEIK (SEQ ID NO: 238), wherein $X_{68}$ is any amino acid, for example, K or Q, $X_{69}$ is any amino acid, for example, S or F, $X_{70}$ is any amino acid, for example, S or F, $X_{71}$ is any amino acid, for example, an amino acid with an aromatic side chain, e.g., Y or F, $X_{72}$ is any amino acid, for example, T or K, $X_{73}$ is any amino acid, for example, an amino acid with an uncharged polar side chain, e.g., S or N, $X_{74}$ is any amino acid, for example, P or S, and $X_{75}$ is any amino acid, for example, I or T; and
(b) a VH region comprising EVQLVESGGGLVQPGGSLKLSCAASGFTF SDSYMAWVRQAPGKGLEWVASISSDGGG TYYRDSVKGRFTISRDNAKX$_{76}$SLYLQMX$_{77}$SLRTEDTATYYCTTEGIYTTDYYPYCFNY WGQGX$_{78}$MV (SEQ ID NO: 239), wherein $X_{76}$ is any amino acid, for example, an amino acid with an uncharged polar side chain, e.g., S or N, $X_{77}$ is any amino acid, for example, D or N, and $X_{78}$ is any amino acid, for example, T or V. In certain embodiments, any one of $X_{68}$ to $X_{78}$ is any amino acid. In specific embodiments, $X_{43}$ is a conservative substitution of T or A, $X_{68}$ is a conservative substitution of K or Q, $X_{69}$ is a conservative substitution of S or F, $X_{70}$ is a conservative substitution of S or F, $X_{71}$ is a conservative substitution of Y or F, $X_{72}$ is a conservative substitution of T or K, $X_{73}$ is a conservative substitution of S or N, $X_{74}$ is a conservative substitution of P or S, $X_{75}$ is a conservative substitution of I or T, $X_{76}$ is a conservative substitution of S or N, $X_{77}$ is a conservative substitution of D or N, and $X_{78}$ is a conservative substitution of T or V.

In a specific embodiment, an anti-MET antibody described herein comprises a VL region comprising MGWSCIILFLVATATGVHSQIVLTQSPAIMSX$_{136}$SPGEKVTMTCSASSSVX$_{137}$YMFWYQ QKX$_{138}$GSSPRLLIYDTX$_{139}$X$_{140}$LASGVPVRFSGSGSGTSYSLTISRMEAEDAATYYCQQW SX$_{141}$IYPYTFGGGTKLEIK (SEQ ID NO: 273), wherein $X_{136}$ is any amino acid, for example, T or A, $X_{137}$ is any amino acid, for example, an amino acid with an uncharged polar side chain, e.g., N or S, $X_{138}$ is any amino acid, for example, A or P, $X_{139}$ is any amino acid, for example, F or S, $X_{140}$ is any amino acid, for example, N or D, and $X_{141}$ is any amino acid, for example, I or N. In certain embodiments, any one of $X_{136}$ to $X_{141}$ is any amino acid sequence. In specific embodiments, $X_{136}$ is a conservative substitution of T or A, $X_{137}$ is a conservative substitution of N or S, $X_{138}$ is a conservative substitution of A or P, $X_{139}$ is a conservative substitution of F or S, $X_{140}$ is a conservative substitution of N or D, and $X_{141}$ is a conservative substitution of I or N.

In a specific embodiment, an anti-MET antibody described herein comprises a VL region comprising QIVLTQSPAIMSX$_{43}$SPGEKVTMTCSASSSVX$_{44}$YMFWYQQKX$_{45}$GSSPRLLIYDTX$_{46}$X$_{47}$LA SGVPVRFSGSGSGTSYSLTISRMEAEDAATYYCQQWSX$_{48}$IYPYTFGGGTKLEIK (SEQ ID NO: 48), wherein $X_{43}$ is any amino acid, for example, T or A, $X_{44}$ is any amino acid, for example, an amino acid with an uncharged polar side chain, e.g., N or S, $X_{45}$ is any amino acid, for example, A or P, $X_{46}$ is any amino acid, for example, F or S, $X_{47}$ is any amino acid, for example, N or D, and $X_{48}$ is any amino acid, for example, I or N. In certain embodiments, any one of $X_{43}$ to $X_{48}$ is any amino acid sequence. In specific embodiments, $X_{43}$ is a conservative substitution of T or A, $X_{44}$ is a conservative substitution of N or S, $X_{45}$ is a conservative substitution of A or P, $X_{46}$ is a conservative substitution of F or S, $X_{47}$ is a conservative substitution of N or D, and $X_{48}$ is a conservative substitution of I or N.

In a specific embodiment, an anti-MET antibody described herein comprises a VH region comprising QX$_{57}$QLQQSGAELMKPGASVKISCKATGYX$_{58}$FSX$_{59}$ YWIEWVKQRPGHGLEWIGEILPGS DX$_{60}$X$_{61}$KYX$_{62}$ EKFKGKATFTADTSSNTAYMQLSX$_{63}$LTSEDSAVYYCARPSTX$_{64}$PPDCW GQGTTLTVSA (SEQ ID NO:50), wherein $X_{57}$ is any amino acid, for example, an amino acid with an nonpolar side chain, e.g., V or A, $X_{58}$ is any amino acid, for example, I or T, $X_{59}$ is any amino acid, for example, an amino acid with an uncharged polar side chain, e.g., N or S, $X_{60}$ is any amino acid, for example, an amino acid with an aromatic side chain, e.g., Y or F, $X_{61}$ is any amino acid, for example, T or I, $X_{62}$ is any amino acid, for example, an amino acid with an uncharged polar side chain, e.g., N or S, $X_{63}$ is any amino acid, for example, an amino acid with an uncharged polar side chain, e.g., S or N, and $X_{64}$ is any amino acid, for example, an amino acid with a nonpolar side chain, e.g., I or V. In certain embodiments, any one of $X_{57}$ to $X_{64}$ is any amino acid sequence. In specific embodiments, $X_{57}$ is a conservative substitution of V or A, $X_{58}$ is a conservative substitution of I or T, $X_{59}$ is a conservative substitution of N or S, $X_{60}$ is a conservative substitution of Y or F, $X_{61}$ is a conservative substitution of T or I, $X_{62}$ is a conservative substitution of N or S, $X_{63}$ is a conservative substitution of S or N, and $X_{64}$ is a conservative substitution of I or V.

In a specific embodiment, an anti-MET antibody described herein comprises (a) a VL region comprising MGWSCIILFLVATATGV-HSQIVLTQSPAIMSX$_{136}$SPGEKVTMTCSASSS-VX$_{137}$YMFWYQQ KX$_{138}$GSSPRLLIYDTX$_{139}$X$_{140}$LASGVPVRFSGSGSGTSYSLTISRMEAEDA-ATYYCQQWSX$_{141}$IYPYTFGGGTKLEIK (SEQ ID NO: 273), wherein X$_{136}$ is any amino acid, for example, T or A, X$_{137}$ is any amino acid, for example, an amino acid with an uncharged polar side chain, e.g., N or S, X$_{138}$ is any amino acid, for example, A or P, X$_{139}$ is any amino acid, for example, F or S, X$_{140}$ is any amino acid, for example, N or D, and X$_{141}$ is any amino acid, for example, I or N; and (b) a VH region comprising QX$_{57}$QLQQSGAELMK-PGASVKISCKATGYX$_{58}$FSX$_{59}$YWIEWVKQRPG-HGLEWIGEILPGS DX$_{60}$X$_{61}$KYX$_{62}$EKFKGKAT-FTADTSSNTAYMQLSX$_{63}$LTSEDSAVYYCARPS-TX$_{64}$PPDCWG QGTTLTVSA (SEQ ID NO:50), wherein X$_{57}$ is any amino acid, for example, an amino acid with a nonpolar side chain, e.g., V or A, X$_{58}$ is any amino acid, for example, I or T, X$_{59}$ is any amino acid, for example, an amino acid with an uncharged polar side chain, e.g., N or S, X$_{60}$ is any amino acid, for example, an amino acid with an aromatic side chain, e.g., Y or F, X$_{61}$ is any amino acid, for example, T or I, X$_{62}$ is any amino acid, for example, an amino acid with an uncharged polar side chain, e.g., N or S, X$_{63}$ is any amino acid, for example, an amino acid with an uncharged polar side chain, e.g., S or N, and X$_{64}$ is any amino acid, for example, an amino acid with a nonpolar side chain, e.g., I or V. In certain embodiments, any one of X$_{43}$ to X$_{48}$ and X$_{57}$ to X$_{64}$ is any amino acid sequence. In specific embodiments, X$_{136}$ is a conservative substitution of T or A, X$_{137}$ is a conservative substitution of N or S, X$_{138}$ is a conservative substitution of A or P, X$_{139}$ is a conservative substitution of F or S, X$_1$ is a conservative substitution of N or D, X$_{141}$ is a conservative substitution of I or N, X$_{57}$ is a conservative substitution of V or A, X$_{58}$ is a conservative substitution of I or T, X$_{59}$ is a conservative substitution of N or S, X$_{60}$ is a conservative substitution of Y or F, X$_{61}$ is a conservative substitution of T or I, X$_{62}$ is a conservative substitution of N or S, X$_{63}$ is a conservative substitution of S or N, and X$_{64}$ is a conservative substitution of I or V.

In a specific embodiment, an anti-MET antibody described herein comprises (a) a VL region comprising QIVLTQSPAIMSX$_{43}$SPGE-KVTMTCSASSSVX$_{44}$YMFWYQQKX$_{45}$GSSPRLL-IYDTX$_{46}$X$_{47}$LA SGVPVRFSGSGSGTSYSLTI-SRMEAEDAATYYCQQWSX$_{48}$IYPYTFGGGTKL-EIK (SEQ ID NO: 48), wherein X$_{43}$ is any amino acid, for example, T or A, X$_{44}$ is any amino acid, for example, an amino acid with an uncharged polar side chain, e.g., N or S, X$_{45}$ is any amino acid, for example, A or P, X$_{46}$ is any amino acid, for example, F or S, X$_{47}$ is any amino acid, for example, N or D, and X$_{48}$ is any amino acid, for example, I or N; and (b) a VH region comprising QX$_{57}$QLQQSGAELMKPG-ASVKISCKATGYX$_{58}$FSX$_{59}$YWIEWVKQRPGHG-LEWIGEILPGS DX$_{60}$X$_{61}$KYX$_{62}$EKFKGKATFT-ADTSSNTAYMQLSX$_{63}$LTSEDSAVYYCARPSTX$_{64}$PPDCW GQGTTLTVSA (SEQ ID NO:50), wherein X$_{57}$ is any amino acid, for example, an amino acid with a nonpolar side chain, e.g., V or A, X$_{58}$ is any amino acid, for example, I or T, X$_{59}$ is any amino acid, for example, an amino acid with an uncharged polar side chain, e.g., N or S, X$_{60}$ is any amino acid, for example, an amino acid with an aromatic side chain, e.g., Y or F, X$_{61}$ is any amino acid, for example, T or I, X$_{62}$ is any amino acid, for example, an amino acid with an uncharged polar side chain, e.g., N or S, X$_{63}$ is any amino acid, for example, an amino acid with an uncharged polar side chain, e.g., S or N, and X$_{64}$ is any amino acid, for example, an amino acid with a nonpolar side chain, e.g., I or V. In certain embodiments, any one of X$_{43}$ to X$_{48}$ and X$_{57}$ to X$_{64}$ is any amino acid sequence. In specific embodiments, X$_{43}$ is a conservative substitution of T or A, X$_{44}$ is a conservative substitution of N or S, X$_{45}$ is a conservative substitution of A or P, X$_{46}$ is a conservative substitution of F or S, X$_{47}$ is a conservative substitution of N or D, X$_{48}$ is a conservative substitution of I or N, X$_{57}$ is a conservative substitution of V or A, X$_{58}$ is a conservative substitution of I or T, X$_{59}$ is a conservative substitution of N or S, X$_{60}$ is a conservative substitution of Y or F, X$_{61}$ is a conservative substitution of T or I, X$_{62}$ is a conservative substitution of N or S, X$_{63}$ is a conservative substitution of S or N, and X$_{64}$ is a conservative substitution of I or V.

In a specific embodiment, an anti-MET antibody described herein or an antigen-binding fragment thereof comprises a VL as described in Table 9. In a specific embodiment, an anti-MET antibody described herein or an antigen-binding fragment thereof comprises a VH as described in Table 10.

TABLE 9

| VL Domain Amino Acid Sequences | |
|---|---|
| Antibody | VL (SEQ ID NO:) |
| Ab235 | QIVLTQSPAIMSTSPGEKVTMTCSASSSVNYMFWYQQKAGSSPRLLIYDTFNLASGVPVRFSG SGSGTSYSLTISRMEAEDAATYYCQQWSIYPYTFGGGTKLEIKR (SEQ ID NO: 57) |
| Ab236 | QIVLTQSPAIMSASPGEKVTMTCSASSSVSYMFWYQQKPGSSPRLLIYDTSDLASGVPVRFSGS GSGTSYSLTISRMEAEDAATYYCQQWSNYPYTFGGGTKLEIKR (SEQ ID NO :58) |
| Ab237 | DIQMTQSPGSLSASLGETVTIECLASADIHSNLAWYQQKPGNSPQLLIYYGNNLNDGVPSRFS GSGSGTQYSLKINSLQSEDVSIYFCQQSYDSPPTFGAGTKLEIKR (SEQ ID NO: 59) |

TABLE 9-continued

VL Domain Amino Acid Sequences

| Antibody | VL (SEQ ID NO:) |
|---|---|
| Ab238 | DIRMTQSPASLSASLGETVNIECLASEDIYSDLAWYQQKPGKSPQLLIYNANTLQNGVPSVFSG SGSGTQYSLKINNLHSEDVATYFCQQYNNYPPTFGGGTKLEIKR (SEQ ID NO: 60) |
| Ab239 | GQFTLTQPKSVSGSLRSTITIPCVRSSGDIGDRYVSWYQQRLGRPPLNVIYAADQRPSEVSDRF SGSIDSSSNSASLTITDLQMDDEADYFCQSYDSNIDIVFGGGTKLEIKR (SEQ ID NO: 61) |
| Ab240 | DIQMTQTPFYMPASLGERVTISCRASQGISKYLNWYQQKPDGTIKTLIYYTSNLQSGVPSSALK SRLTISRDTSRSQVFLKMNSLQTDDTAIYFCARDPYQNYFDYWGQGVKVTVSS (SEQ ID NO: 62) |
| Ab241 | DIQMTQSPSSLSASVGDRVTITCLASADIHSNLAWYQQKPGKAPQLLIYYGNNLNDGVPSRFS GSGSGTDYTLKINSLQSEDVAIYFCQQSYDSPPTFGQGTKLEIKR (SEQ ID NO: 52) |
| Ab242 | DIQMTQSPSSLSASVGDRVTITCLASADIHSNLAWYQQKPGKAPKLLIYYGNNLNDGVPSRFS GFGFGTDYTLTISSLQSEDVAIYFCQQSYDSPPTFGQGTKLEIKR (SEQ ID NO: 53) |
| Ab243 | DIQMTQSPSSLSASVGDRVTITCLASADIHSNLAWYQQKPGKAPKLLIYYGNNLNDGVPSRFS GSGSGTDYTLTISSLQPEDVAIYFCQQSYDSPPTFGQGTKLEIKR (SEQ ID NO: 54) |
| Ab244 | DIQMTQSPSSLSASVGDRVTITCLASADIHSNLAWYQQKPGKAPKLLIYYGNNLNDGVPSRFS GSGSGTDFTLTISSLQPEDVAIYFCQQSYDSPPTFGQGTKLEIKR (SEQ ID NO: 55) |
| Ab245 | DIQMTQSPSSLSASVGDRVTITCLASADIHSNLAWYQQKPGKAPKLLIYYGNNLNDGVPSRFS GSGSGTDFTLTISSLQPEDVATYFCQQSYDSPPTFGQGTKLEIKR (SEQ ID NO: 56) |
| Ab246 | DIQMTQSPSSLSASVGDRVTITCLASADIHSNLAWYQQKPGKAPQLLIYYGNNLNDGVPSRFS GSGSGTDYTLKINSLQSEDVAIYFCQQSYDSPPTFGQGTKLEIKR (SEQ ID NO: 52) |
| Ab247 | DIQMTQSPSSLSASVGDRVTITCLASADIHSNLAWYQQKPGKAPKLLIYYGNNLNDGVPSRFS GFGFGTDYTLTISSLQSEDVAIYFCQQSYDSPPTFGQGTKLEIKR (SEQ ID NO: 53) |
| Ab248 | DIQMTQSPSSLSASVGDRVTITCLASADIHSNLAWYQQKPGKAPKLLIYYGNNLNDGVPSRFS GSGSGTDYTLTISSLQPEDVAIYFCQQSYDSPPTFGQGTKLEIKR (SEQ ID NO: 54) |
| Ab249 | DIQMTQSPSSLSASVGDRVTITCLASADIHSNLAWYQQKPGKAPKLLIYYGNNLNDGVPSRFS GSGSGTDFTLTISSLQPEDVAIYFCQQSYDSPPTFGQGTKLEIKR (SEQ ID NO: 55) |
| Ab250 | DIQMTQSPSSLSASVGDRVTITCLASADIHSNLAWYQQKPGKAPKLLIYYGNNLNDGVPSRFS GSGSGTDFTLTISSLQPEDVATYFCQQSYDSPPTFGQGTKLEIKR (SEQ ID NO: 56) |
| Ab251 | DIQMTQSPSSLSASVGDRVTITCLASADIHSNLAWYQQKPGKAPQLLIYYGNNLNDGVPSRFS GSGSGTDYTLKINSLQSEDVAIYFCQQSYDSPPTFGQGTKLEIKR (SEQ ID NO: 52) |
| Ab252 | DIQMTQSPSSLSASVGDRVTITCLASADIHSNLAWYQQKPGKAPKLLIYYGNNLNDGVPSRFS GFGFGTDYTLTISSLQSEDVAIYFCQQSYDSPPTFGQGTKLEIKR (SEQ ID NO: 53) |
| Ab253 | DIQMTQSPSSLSASVGDRVTITCLASADIHSNLAWYQQKPGKAPKLLIYYGNNLNDGVPSRFS GSGSGTDYTLTISSLQPEDVAIYFCQQSYDSPPTFGQGTKLEIKR (SEQ ID NO: 54) |
| Ab254 | DIQMTQSPSSLSASVGDRVTITCLASADIHSNLAWYQQKPGKAPKLLIYYGNNLNDGVPSRFS GSGSGTDFTLTISSLQPEDVAIYFCQQSYDSPPTFGQGTKLEIKR (SEQ ID NO: 55) |
| Ab255 | DIQMTQSPSSLSASVGDRVTITCLASADIHSNLAWYQQKPGKAPKLLIYYGNNLNDGVPSRFS GSGSGTDFTLTISSLQPEDVATYFCQQSYDSPPTFGQGTKLEIKR (SEQ ID NO: 56) |

TABLE 10

VH Domain Amino Acid Sequences

| Antibody | VH (SEQ ID NO:) |
|---|---|
| Ab235 | QVQLQQSGAELMKPGASVKISCKATGYTFSNYWIEWVKQRPGHGLEWIGEILPGSDYTKYNE KFKGKATFTADTSSNTAYMQLSSLTSEDSAVYYCARPSTIPPDCWGQGTTLTVSS (SEQ ID NO: 66) |
| Ab236 | QAQLQQSGAELMKPGASVKISCKATGYIFSSYWIEWVKQRPGHGLEWIGEILPGSDFIKYSEK FKGKATFTADTSSNTAYMQLSNLTSEDSAVYYCARPSTVPPDCWGQGTTLTVSS (SEQ ID NO: 67) |
| Ab237 | EVQLVESGGGLVQPGRSLKLSCAASGFTFSDSYMAWVRQAPTKGLEWVASISSDGGGTYYR DSVKGRFSISRDNAKSSLYLQMDSLRSEDTATYYCTTEGIYTTDYYPYCFNYWGHGVMVTVS S (SEQ ID NO: 68) |

TABLE 10-continued

VH Domain Amino Acid Sequences

| Antibody | VH (SEQ ID NO:) |
|---|---|
| Ab238 | QVTLKESGPGILQPSQTLSLTCTFSGFSLSTYGMGVAWIRQPSGKDLEWLANIWWDDVNYSN PSLKNRLTISKDTSNNQVFLQITNVDTAETATYYCARIGTSHIVDAWGQGASVTVSS (SEQ ID NO: 69) |
| Ab239 | EVQLVESGGGLVQPGRSLKLSCAASGFSFTDCYMAWVRQAPTKGLEWVASISSDGGGTYYR DSVKGRFTISRDNARSSLYLEMDSLRSEDTATYYCTTERYYDGTYYGYWYFDFWGPGTMVT VSS (SEQ ID NO: 70) |
| Ab240 | QVQLKESGPGLVQPSQTLSLTCSVSGLSLTTNSVHWIRQPPGRGLEWMGVIWGDGSTDYNSA LKSRLTISRDTSRSQVFLKMNSLQTDDTAIYFCARDPYQNYFDYWGQGVKVTVSS (SEQ ID NO: 71) |
| Ab241 | EVQLVESGGGLVQPGGSLKLSCAASGFTFSDSYMAWVRQAPGKGLEWVASISSDGGGTYYR DSVKGRFTISRDNAKSSLYLQMDSLRTEDTATYYCTTEGIYTTDYYPYCFNYWGQGVMVTV SS (SEQ ID NO: 63) |
| Ab242 | EVQLVESGGGLVQPGGSLKLSCAASGFTFSDSYMAWVRQAPGKGLEWVASISSDGGGTYYR DSVKGRFTISRDNAKSSLYLQMDSLRTEDTATYYCTTEGIYTTDYYPYCFNYWGQGVMVTV SS (SEQ ID NO: 63) |
| Ab243 | EVQLVESGGGLVQPGGSLKLSCAASGFTFSDSYMAWVRQAPGKGLEWVASISSDGGGTYYR DSVKGRFTISRDNAKSSLYLQMDSLRTEDTATYYCTTEGIYTTDYYPYCFNYWGQGVMVTV SS (SEQ ID NO: 63) |
| Ab244 | EVQLVESGGGLVQPGGSLKLSCAASGFTFSDSYMAWVRQAPGKGLEWVASISSDGGGTYYR DSVKGRFTISRDNAKSSLYLQMDSLRTEDTATYYCTTEGIYTTDYYPYCFNYWGQGVMVTV SS (SEQ ID NO: 63) |
| Ab245 | EVQLVESGGGLVQPGGSLKLSCAASGFTFSDSYMAWVRQAPGKGLEWVASISSDGGGTYYR DSVKGRFTISRDNAKSSLYLQMDSLRTEDTATYYCTTEGIYTTDYYPYCFNYWGQGVMVTV SS (SEQ ID NO: 63) |
| Ab246 | EVQLVESGGGLVQPGGSLKLSCAASGFTFSDSYMAWVRQAPGKGLEWVASISSDGGGTYYR DSVKGRFTISRDNAKSSLYLQMNSLRTEDTATYYCTTEGIYTTDYYPYCFNYWGQGVMVTV SS (SEQ ID NO: 64) |
| Ab247 | EVQLVESGGGLVQPGGSLKLSCAASGFTFSDSYMAWVRQAPGKGLEWVASISSDGGGTYYR DSVKGRFTISRDNAKSSLYLQMNSLRTEDTATYYCTTEGIYTTDYYPYCFNYWGQGVMVTV SS (SEQ ID NO: 64) |
| Ab248 | EVQLVESGGGLVQPGGSLKLSCAASGFTFSDSYMAWVRQAPGKGLEWVASISSDGGGTYYR DSVKGRFTISRDNAKSSLYLQMNSLRTEDTATYYCTTEGIYTTDYYPYCFNYWGQGVMVTV SS (SEQ ID NO: 64) |
| Ab249 | EVQLVESGGGLVQPGGSLKLSCAASGFTFSDSYMAWVRQAPGKGLEWVASISSDGGGTYYR DSVKGRFTISRDNAKSSLYLQMNSLRTEDTATYYCTTEGIYTTDYYPYCFNYWGQGVMVTV SS (SEQ ID NO: 64) |
| Ab250 | EVQLVESGGGLVQPGGSLKLSCAASGFTFSDSYMAWVRQAPGKGLEWVASISSDGGGTYYR DSVKGRFTISRDNAKSSLYLQMNSLRTEDTATYYCTTEGIYTTDYYPYCFNYWGQGVMVTV SS (SEQ ID NO: 64) |
| Ab251 | EVQLVESGGGLVQPGGSLKLSCAASGFTFSDSYMAWVRQAPGKGLEWVASISSDGGGTYYR DSVKGRFTISRDNAKNSLYLQMNSLRTEDTATYYCTTEGIYTTDYYPYCFNYWGQGTMVTV SS (SEQ ID NO: 65) |
| Ab252 | EVQLVESGGGLVQPGGSLKLSCAASGFTFSDSYMAWVRQAPGKGLEWVASISSDGGGTYYR DSVKGRFTISRDNAKNSLYLQMNSLRTEDTATYYCTTEGIYTTDYYPYCFNYWGQGTMVTV SS (SEQ ID NO: 65) |
| Ab253 | EVQLVESGGGLVQPGGSLKLSCAASGFTFSDSYMAWVRQAPGKGLEWVASISSDGGGTYYR DSVKGRFTISRDNAKNSLYLQMNSLRTEDTATYYCTTEGIYTTDYYPYCFNYWGQGTMVTV SS (SEQ ID NO: 65) |
| Ab254 | EVQLVESGGGLVQPGGSLKLSCAASGFTFSDSYMAWVRQAPGKGLEWVASISSDGGGTYYR DSVKGRFTISRDNAKNSLYLQMNSLRTEDTATYYCTTEGIYTTDYYPYCFNYWGQGTMVTV SS (SEQ ID NO: 65) |
| Ab255 | EVQLVESGGGLVQPGGSLKLSCAASGFTFSDSYMAWVRQAPGKGLEWVASISSDGGGTYYR DSVKGRFTISRDNAKNSLYLQMNSLRTEDTATYYCTTEGIYTTDYYPYCFNYWGQGTMVTV SS (SEQ ID NO: 65) |

In certain aspects, an antibody described herein may be described by its VL region alone, or its VH region alone, or by its 3 VL CDRs alone, or its 3 VH CDRs alone. See, for example, Rader et al., 1998, Proc. Natl. Acad. Sci. USA, 95:

8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson et al., 1991, Nature 352:624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also, Kim & Hong, 2007, J. Microbiol. 45:572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In a specific embodiment, the position of one or more CDRs along the VH (e.g., CDR1, CDR2, or CDR3) and/or VL (e.g., CDR1, CDR2, or CDR3) region of an antibody described herein may vary by one, two, three, four, five, or six amino acid positions so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). For example, in one embodiment, the position defining a CDR of any of antibody Ab235-Ab255 may vary by shifting the N-terminal and/or C-terminal boundary of the CDR by one, two, three, four, five, or six amino acids, relative to the CDR position in the VL or VH (see, e.g., Tables 9 or 10, respectively), so long as immunospecific binding to MET (e.g., human MET) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody described herein may vary (e.g., be shorter or longer) by one, two, three, four, five, or more amino acids, so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). For example, in one embodiment, a VH and/or VL CDR1, CDR2, and/or CDR3 described herein may be one, two, three, four, five or more amino acids shorter than one or more of the CDRs described by SEQ ID NO: 1-35, so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). In another embodiment, a VH and/or VL CDR1, CDR2, and/or CDR3 described herein may be one, two, three, four, five or more amino acids longer than one or more of the CDRs described by SEQ ID NOS: 1-35, so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). In another embodiment, the amino terminus of a VH and/or VL CDR1, CDR2, and/or CDR3 described herein may be extended by one, two, three, four, five or more amino acids compared to one or more of the CDRs described by SEQ ID NOS: 1-25, so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). In another embodiment, the carboxy terminus of a VH and/or VL CDR1, CDR2, and/or CDR3 described herein may be extended by one, two, three, four, five or more amino acids compared to one or more of the CDRs described by SEQ ID NOS: 1-35, so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). In another embodiment, the amino terminus of a VH and/or VL CDR1, CDR2, and/or CDR3 described herein may be shortened by one, two, three, four, five or more amino acids compared to one or more of the CDRs described by SEQ ID NOS: 1-35, so long as immunospecific binding to MET (e.g., human MET, e.g., SEQ ID NO:190) is maintained (e.g., substantially maintained, for example, at least 50%, at least 60%, at least 70%, at least 80%, at least 90%, at least 95%). In one embodiment, the carboxy terminus of a VH and/or VL CDR1, CDR2, and/or CDR3 described herein may be shortened by one, two, three, four, five or more amino acids compared to one or more of the CDRs described by SEQ ID NOS: 1-35, so long as immunospecific binding to MET (e.g., human MET ECD, e.g., SEQ ID NO:190) is maintained (e.g., substantially maintained, for example, at least 50%, at least 60%, at least 70%, at least 80%, at least 90%, at least 95%). Any method known in the art can be used to ascertain whether immunospecific binding to MET (e.g., human MET ECD, e.g., SEQ ID NO:190) is maintained, for example, the binding assays and conditions described in the "Examples" section (Section 6) provided herein. For example, Section 6 provided herein describes an ELISA assay for measuring binding to an ECD of human MET. Briefly, ELISA plates are coated with 100 μL/well 1 μg/mL hu-MET-ECD in borate buffer at 4° C. overnight; then various concentrations of anti-MET antibodies were added to the coated ELISA plates and incubated in TBST (50 mM Tris pH 7.4, 150 mM NaCl, 0.1% Tween-20) for one hour at room temperature to allow binding of anti-MET antibodies to the ECD of human MET. Also, Section 6 provided herein describes FACS binding assays with A549 cells for ascertaining whether immunospecific binding of an anti-MET antibody to MET (e.g., human MET ECD, e.g., SEQ ID NO:190) is maintained.

In specific aspects, provided herein is an antibody comprising an antibody light chain and heavy chain, e.g., a separate light chain and heavy chain. With respect to the light chain, in a specific embodiment, the light chain of an antibody described herein is a kappa (κ) light chain. In another specific embodiment, the light chain of an antibody described herein is a lambda (λ) light chain. In another embodiment, light chain is a mixed sequence, e.g., the variable portion of the light chain comprises kappa light chain sequences and the constant region of the light chain comprises lambda light chain sequences, or vice versa. In certain embodiments, the light chain of an antibody described herein is a human kappa light chain or a human lambda light chain. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a particular embodiment, an antibody described herein, which immunospecifically binds to a MET polypeptide (e.g., an ECD of MET, for example human MET) comprises a light chain wherein the amino acid sequence of the VL chain region comprises any amino acid sequence described herein (e.g., SEQ ID NOS: 52-62), and wherein the constant region of the light chain comprises the amino acid sequence of a human kappa light chain constant region. In another particular embodiment, an antibody described herein, which immunospecifically binds a MET polypeptide (e.g., an ECD of MET, for example human MET) comprises a light chain wherein the amino acid sequence of the VL chain region can comprise any amino acid sequence described herein (e.g., SEQ ID NOS:52-62), and wherein the constant region of the light chain comprises the amino acid sequence of a human lambda light chain constant region.

With respect to the heavy chain, in a specific embodiment, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In a particular embodiment, an antibody described herein, which immunospecifically binds to a MET polypeptide (e.g., an ECD of MET, for example human MET), comprises a heavy chain wherein the amino acid sequence of the VH chain region can comprise any amino acid sequence described herein (e.g., any of SEQ ID NOs: 63-71), and wherein the constant region of the heavy chain comprises the amino acid sequence of a human gamma (γ) heavy chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific embodiment, an antibody described herein, which immunospecifically binds to a MET polypeptide (e.g., an ECD of MET, for example human MET) comprises a VL chain region and a VH chain region comprising any amino acid sequences described herein, and wherein the constant regions comprise amino acid sequences of constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which immunospecifically binds to a MET polypeptide (e.g., an ECD of MET, for example human MET) comprises a VL chain region and a VH chain region comprising any amino acid sequences described herein, and wherein the constant regions comprise amino acid sequences of constant regions of an IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_{2a}$ and $IgG_{2b}$, or a mixture thereof) of immunoglobulin molecule. In a particular embodiment, the constant regions comprise the amino acid sequences of the constant regions of a human IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_{2a}$ and $IgG_{2b}$, or a mixture thereof) of immunoglobulin molecule. In certain embodiments, an antibody described herein, which immunospecifically binds to a MET polypeptide (e.g., an ECD of MET, for example, human MET) comprises a VL chain region and a VH chain region comprising any amino acid sequences described herein, and wherein the constant regions comprise the amino acid sequences of the constant regions of an $IgG_2$. In certain embodiments, the $IgG_2$ is a human $IgG_2$. In certain embodiments, the $IgG_2$ (e.g., human $IgG_2$) is $IgG_{2a}$ (e.g., human $IgG_2a$). In certain embodiments, the $IgG_2$ (e.g., human $IgG_2$) is $IgG_{2b}$ (e.g., human $IgG_{2b}$). In certain embodiments, the $IgG_2$ (e.g., human $IgG_2$) is a mixture of $IgG_{2a}$ (e.g., human $IgG_2a$) and $IgG_{2b}$ (e.g., human $IgG_{2b}$).

In yet another specific embodiment, an antibody described herein, which immunospecifically binds to a MET polypeptide (e.g., an ECD of MET, for example human MET), comprises a VL chain region and a VH chain region comprising any amino acid sequences described herein, and wherein the constant regions comprise the amino acid sequences of the constant regions of a human $IgG_1$ (e.g., isotype a, z, or f) or human $IgG_4$. In a particular embodiment, an antibody described herein, which immunospecifically binds to a MET polypeptide (e.g., an ECD of MET, for example human MET) comprises a VL chain region and a VH chain region comprising any amino acid sequences described herein, and wherein the constant regions comprise the amino acid sequences of the constant region of a human $IgG_1$ (isotype f). Non-limiting examples of human constant regions are described in the art, e.g., see Kabat et al. (1991) *Sequences of Proteins of Immunological Interest*, Fifth Edition, U.S. Department of Health and Human Services, NIH Publication No. 91-3242.

In yet another specific embodiment, an antibody described herein, which immunospecifically binds to a MET polypeptide (e.g., an ECD of MET, for example human MET), comprises a VL chain region and a VH chain region comprising any amino acid sequences described herein (e.g., VL and VH of Ab235, Ab236, Ab237, Ab239, and Ab241-Ab255), and wherein the constant regions comprise the amino acid sequences of the constant regions of a human $IgG_2$ (e.g., $IgG_{2a}$ or $IgG_{2b}$, or a mixture thereof). In a particular embodiment, an antibody described herein, which immunospecifically binds to a MET polypeptide (e.g., an ECD of MET, for example human MET) comprises a VL chain region and a VH chain region comprising any amino acid sequences described herein (e.g., VL and VH of Ab235, Ab236, Ab237, Ab239, and Ab241-Ab255), and wherein the constant regions comprise the amino acid sequences of the constant region of a human $IgG_2$ (isotype $IgG_2a$). In a particular embodiment, an antibody described herein, which immunospecifically binds to a MET polypeptide (e.g., an ECD of MET, for example human MET) comprises a VL chain region and a VH chain region comprising any amino acid sequences described herein (e.g., VL and VH of Ab235, Ab236, Ab237, Ab239, and Ab241-Ab255), and wherein the constant regions comprise the amino acid sequences of the constant region of a human $IgG_2$ (isotype $IgG_{2b}$). In a particular embodiment, an antibody described herein, which immunospecifically binds to a MET polypeptide (e.g., an ECD of MET, for example human MET) comprises a VL chain region and a VH chain region comprising any amino acid sequences described herein, and wherein the constant regions comprise the amino acid sequence of the constant region of human $IgG_2$ isotype (e.g., human $IgG_2$ isotype where a mixture of $IgG_{2a}$ and $IgG_{2b}$ isotypes are present). In a particular embodiment, an antibody described herein, which immunospecifically binds to a MET polypeptide (e.g., an ECD of MET, for example human MET) comprises a VL chain region and a VH chain region comprising any amino acid sequences described herein (e.g., VL and VH of Ab235, Ab236, Ab237, Ab239, and Ab241-Ab255), and wherein the constant regions comprise the amino acid sequences of the constant region of a human $IgG_2$, for example, as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 having the amino acid sequences of any one of Ab235-Ab255 (e.g., those listed in Tables 1, 5, and 7); (ii) the heavy chain comprises a VH chain region comprising a VH CDR1, VH CDR2, and VH CDR3 having the amino acid sequences of any one of Ab235-Ab255 (e.g., those listed in Tables 2, 6, and 8); (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the IgG$_2$ (e.g., human IgG$_2$) comprises a mixture of IgG$_{2a}$ (e.g., human IgG$_2$a) and IgG$_{2b}$ (e.g., human IgG$_{2b}$).

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 of Ab235 (e.g., the VL CDR1, VL CDR2 and VL CDR3 listed in any one of Tables 1, 5, and 7); (ii) the heavy chain comprises a VH chain region comprising a VH CDR1, VH CDR2, and VH CDR3 of Ab235 (e.g., the VH CDR1, VH CDR2 and VH CDR3 listed in any one of Tables 2, 6, and 8); (iii) the light chain further comprises a human constant light chain domain; and (iv) the heavy chain further comprises a constant heavy chain domain comprising a constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 of Ab236 (e.g., the VL CDR1, VL CDR2 and VL CDR3 listed in any one of Tables 1, 5, and 7); (ii) the heavy chain comprises a VH chain region comprising a VH CDR1, VH CDR2, and VH CDR3 of Ab236 (e.g., the VH CDR1, VH CDR2 and VH CDR3 listed in any one of Tables 2, 6, and 8); (iii) the light chain further comprises a human constant light chain domain; and (iv) the heavy chain further comprises a constant heavy chain domain comprising a constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 of Ab237 (e.g., the VL CDR1, VL CDR2 and VL CDR3 listed in any one of Tables 1, 5, and 7); (ii) the heavy chain comprises a VH chain region comprising a VH CDR1, VH CDR2, and VH CDR3 of Ab237 (e.g., the VH CDR1, VH CDR2 and VH CDR3 listed in any one of Tables 2, 6, and 8); (iii) the light chain further comprises a human constant light chain domain; and (iv) the heavy chain further comprises a constant heavy chain domain comprising a constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 of Ab238 (e.g., the VL CDR1, VL CDR2 and VL CDR3 listed in any one of Tables 1, 5, and 7); (ii) the heavy chain comprises a VH chain region comprising a VH CDR1, VH CDR2, and VH CDR3 of Ab238 (e.g., the VH CDR1, VH CDR2 and VH CDR3 listed in any one of Tables 2, 6, and 8); (iii) the light chain further comprises a human constant light chain domain; and (iv) the heavy chain further comprises a constant heavy chain domain comprising a constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 of Ab239 (e.g., the VL CDR1, VL CDR2 and VL CDR3 listed in any one of Tables 1, 5, and 7); (ii) the heavy chain comprises a VH chain region comprising a VH CDR1, VH CDR2, and VH CDR3 of Ab239 (e.g., the VH CDR1, VH CDR2 and VH CDR3 listed in any one of Tables 2, 6, and 8); (iii) the light chain further comprises a human constant light chain domain; and (iv) the heavy chain further comprises a constant heavy chain domain comprising a constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 of Ab240 (e.g., the VL CDR1, VL CDR2 and VL CDR3 listed in any one of Tables 1, 5, and 7); (ii) the heavy chain comprises a VH chain region comprising a VH CDR1, VH CDR2, and VH CDR3 of Ab240 (e.g., the VH CDR1, VH CDR2 and VH CDR3 listed in any one of Tables 2, 6, and 8); (iii) the light chain further comprises a human constant light chain domain; and (iv) the heavy chain further comprises a constant heavy chain domain comprising a constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab235 (SEQ ID NOs: 57 and 66, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab236 (SEQ ID NOs: 58 and 67, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab237 (SEQ ID NOs: 59 and 68, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab238 (SEQ ID NOs: 60 and 69, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab239 (SEQ ID NOs: 61 and 70, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab240 (SEQ ID NOs: 62 and 71, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab241 (SEQ ID NOs: 52 and 63, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab242 (SEQ ID NOs: 53 and 63, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab243 (SEQ ID NOs: 54 and 63, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab244 (SEQ ID NOs: 55 and 63, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

In a particular embodiment, an antibody described herein, which immunospecifically binds to a MET polypeptide (e.g., an ECD of MET, for example human MET) comprises a VL chain region and a VH chain region of Ab245 (SEQ ID NOs: 56 and 63, respectively); wherein the light chain further comprises a human constant light chain domain and the heavy chain further comprises a constant heavy chain domain comprising the constant domain of a human $IgG_2$ heavy chain. In certain embodiments, the human $IgG_2$ is human $IgG_{2a}$. In certain embodiments, the human $IgG_2$ is human $IgG_{2b}$. In certain embodiments, the antibody is present as a mixture of the above human $IgG_{2a}$-containing antibodies and the above human $IgG_{2b}$-containing antibodies. In certain embodiments, the human $IgG_2$ heavy chain comprises the amino acid sequence as set forth below:

(SEQ ID NO: 191)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab246 (SEQ ID NOs: 52 and 64, respectively); wherein the light chain further comprises a human constant light chain domain and the heavy chain further comprises a constant heavy chain domain comprising the constant domain of a human $IgG_2$ heavy chain. In certain embodiments, the human $IgG_2$ is human $IgG_{2a}$. In certain embodiments, the human $IgG_2$ is human $IgG_{2b}$. In certain embodiments, the antibody is present as a mixture of the above human $IgG_{2a}$-containing antibodies and the above human $IgG_{2b}$-containing antibodies. In certain embodiments, the human $IgG_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab247 (SEQ ID NOs: 53 and 64, respectively); wherein the light chain further comprises a human constant light chain domain and the heavy chain further comprises a constant heavy chain domain comprising the constant domain of a human $IgG_2$ heavy chain. In certain embodiments, the human $IgG_2$ is human $IgG_{2a}$. In certain embodiments, the human $IgG_2$ is human $IgG_{2b}$. In certain embodiments, the antibody is present as a mixture of the above human $IgG_{2a}$-containing antibodies and the above human $IgG_{2b}$-containing antibodies. In certain embodiments, the human $IgG_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab248 (SEQ ID NOs: 54 and 64, respectively); wherein the light chain further comprises a human constant light chain domain and the heavy chain further comprises a constant heavy chain domain comprising the constant domain of a human $IgG_2$ heavy chain. In certain embodiments, the human $IgG_2$ is human $IgG_{2a}$. In certain embodiments, the human $IgG_2$ is human $IgG_{2b}$. In certain embodiments, the antibody is present as a mixture of the above human $IgG_{2a}$-containing antibodies and the above human $IgG_{2b}$-containing antibodies. In certain embodiments, the human $IgG_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab249 (SEQ ID NOs:

55 and 64, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab250 (SEQ ID NOs: 56 and 64, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab251 (SEQ ID NOs: 52 and 65, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab252 (SEQ ID NOs: 53 and 65, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.

In a particular embodiment, an antibody described herein, which immunospecifically binds to a MET polypeptide (e.g., an ECD of MET, for example human MET) comprises a VL chain region and a VH chain region of Ab253 (SEQ ID NOs: 54 and 65, respectively); wherein the light chain further comprises a human constant light chain domain and the heavy chain further comprises a constant heavy chain domain comprising the constant domain of a human IgG$_2$ heavy chain. In certain embodiments, the human IgG$_2$ is human IgG$_{2a}$. In certain embodiments, the human IgG$_2$ is human IgG$_{2b}$. In certain embodiments, the antibody is present as a mixture of the above human IgG$_{2a}$-containing antibodies and the above human IgG$_{2b}$-containing antibodies. In certain embodiments, the human IgG$_2$ heavy chain comprises the amino acid sequence as set forth below:

(SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

```
                                            (SEQ ID NO: 191 continued)
CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.
```

In a particular embodiment, an antibody described herein, which immunospecifically binds to a MET polypeptide (e.g., an ECD of MET, for example human MET) comprises a VL chain region and a VH chain region of Ab254 (SEQ ID NOs: 55 and 65, respectively); wherein the light chain further comprises a human constant light chain domain and the heavy chain further comprises a constant heavy chain domain comprising the constant domain of a human $IgG_2$ heavy chain. In certain embodiments, the human $IgG_2$ is human $IgG_{2a}$. In certain embodiments, the human $IgG_2$ is human $IgG_{2b}$. In certain embodiments, the antibody is present as a mixture of the above human $IgG_{2a}$-containing antibodies and the above human $IgG_{2b}$-containing antibodies. In certain embodiments, the human $IgG_2$ heavy chain comprises the amino acid sequence as set forth below:

```
                                            (SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.
```

In a particular embodiment, an antibody described herein, which immunospecifically binds to a MET polypeptide (e.g., an ECD of MET, for example human MET) comprises a VL chain region and a VH chain region of Ab255 (SEQ ID NOs: 56 and 65, respectively); wherein the light chain further comprises a human constant light chain domain and the heavy chain further comprises a constant heavy chain domain comprising the constant domain of a human $IgG_2$ heavy chain. In certain embodiments, the human $IgG_2$ is human $IgG_{2a}$. In certain embodiments, the human $IgG_2$ is human $IgG_{2b}$. In certain embodiments, the antibody is present as a mixture of the above human $IgG_{2a}$-containing antibodies and the above human $IgG_{2b}$-containing antibodies. In certain embodiments, the human $IgG_2$ heavy chain comprises the amino acid sequence as set forth below:

```
                                            (SEQ ID NO: 191)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSV

MHEALHNHYTQKSLSLSPGK.
```

In another particular embodiment, an antibody described herein, which immunospecifically binds to a MET polypeptide (e.g., an ECD of MET, for example human MET), comprises a light chain and a heavy chain, wherein (i) the light chain comprises a VL chain region comprising a VL CDR1, VL CDR2, and VL CDR3 having the amino acid sequences of any one of Ab235-Ab255 (e.g., those listed in Tables 1, 5, and 7); (ii) the heavy chain comprises a VH chain region comprising a VH CDR1, VH CDR2, and VH CDR3 having the amino acid sequences of any one of Ab235-Ab255 (e.g., those listed in Tables 2, 6, and 8); (iii) the light chain further comprises a constant light chain domain comprising the amino acid sequence of the constant domain of a human kappa light chain, for example, comprising the amino acid sequence TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 192; and (iv) the heavy chain further comprises a constant heavy chain domain comprising the amino acid sequence of the constant domain of a human $IgG_2$ heavy chain, for example, comprising the amino acid sequence of SEQ ID NO: 191. In certain embodiments, the human $IgG_2$ is human $IgG_{2a}$. In certain embodiments, the human $IgG_2$ is human $IgG_{2b}$. In certain embodiments, the $IgG_2$ (e.g., human $IgG_2$) is a mixture of $IgG_{2a}$ (e.g., human $IgG_2$a) and $IgG_{2b}$ (e.g., human $IgG_{2b}$).

In another particular embodiment, an antibody described herein, which immunospecifically binds to a MET polypeptide (e.g., an ECD of MET, for example human MET), comprises a light chain and a heavy chain, wherein (i) the light chain comprises the amino acid sequence:

```
                                            (SEQ ID NO: 193)
DIQMTQSPGSLSASLGETVTIECLASADIHSNLAWYQQKPGNSPQLLIYYG

NNLNDGVPSRFSGSGSGTQYSLKINSLQSEDVSIYFCQQSYDSPPTFGAGT

KLELKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;
``` and (ii) the heavy chain comprises the amino acid sequence:

```
                                            (SEQ ID NO: 194)
EVQLVESGGGLVQPGRSLKLSCAASGFTFSDSYMAWVRQAPTKGLEWVASI

SSDGGGTYYRDSVKGRFSISRDNAKSSLYLQMDSLRSEDTATYYCTTEGIY

TTDYYPYCFNYWGHGVMVTVSSASTKGPSVFPLAPCSRSTSESTAALGCLV

KDYFPEPVTVSWNSGALTSGVHTFPAVLQSSGLYSLSSVVTVPSSNFGTQT

YTCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRVV

SVLTVVHQDWLNGKEYKCKVSNKGLPAPIEKTISKTKGQPREPQVYTLPPS

REEMTKNQVSLTCLVKGFYPSDIAVEWESNGQPENNYKTTPPMLDSDGSFF

LYSKLTVDKSRWQQGNVFSCSVMHEALHNHYTQKSLSLSPGK.
```

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In certain embodiments, an antibody described herein comprises one or more VL framework regions (FRs) having the amino acid sequence described herein for any one of antibodies Ab235-Ab255 (e.g., see Table 3), wherein the antibody immunospecifically binds to MET, e.g., human MET ECD (e.g., SEQ ID NO:190). In specific aspects, VL FRs are in the following positions relative to VL CDRs in a VL sequence: FR1-CDR1-FR2-CDR2-FR3-CDR3-FR4. In specific aspects, VH FRs are in the following positions relative to VH CDRs in a VH sequence: FR1-CDR1-FR2-CDR2-FR3-CDR3-FR4. In certain embodiments, an antibody described herein comprises one or more VL framework regions (FRs) having the amino acid sequence described herein for Ab235 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 103, and VL CDRs of Ab235. In some embodiments, the VL FR2 has the amino acid sequence of SEQ ID NO: 111, and VL CDRs of Ab235. In some embodiments, the VL FR3 has the amino acid sequence of SEQ ID NO: 122, and VL CDRs of Ab235. In some embodiments, the VL FR4 has the amino acid sequence of SEQ ID NO: 128, and VL CDRs of Ab235. In certain embodiments, the an antibody described herein comprises one or more of the VL FR1 having the amino acid sequence of SEQ ID NO: 103, the VL FR 2 having the amino acid sequence of SEQ ID NO: 111, the VL FR3 having the amino acid sequence of SEQ ID NO: 122, and the VL FR4 having the amino acid sequence of SEQ ID NO: 128, and VL CDRs of Ab235.

In certain embodiments, an antibody described herein comprises one or more VL framework regions (FRs) having the amino acid sequence described herein for Ab236 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 104 and VL CDRs of Ab236. In some embodiments, the VL FR2 has the amino acid sequence of SEQ ID NO: 112 and VL CDRs of Ab236. In some embodiments, the VL FR3 has the amino acid sequence of SEQ ID NO: 122 and VL CDRs of Ab236. In some embodiments, the VL FR4 has the amino acid sequence of SEQ ID NO: 128 and VL CDRs of Ab236. In certain embodiments, the an antibody described herein comprises one or more of the VL FR1 having the amino acid sequence of SEQ ID NO: 104, the VL FR 2 having the amino acid sequence of SEQ ID NO: 112, the VL FR3 having the amino acid sequence of SEQ ID NO: 122, and the VL FR4 having the amino acid sequence of SEQ ID NO: 128 and VL CDRs of Ab236.

In certain embodiments, an antibody described herein comprises one or more VL framework regions (FRs) having the amino acid sequence described herein for Ab237 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 105 and VL CDRs of Ab237. In some embodiments, the VL FR2 has the amino acid sequence of SEQ ID NO: 113 and VL CDRs of Ab237. In some embodiments, the VL FR3 has the amino acid sequence of SEQ ID NO: 123 and VL CDRs of Ab237. In some embodiments, the VL FR4 has the amino acid sequence of SEQ ID NO: 127 and VL CDRs of Ab237. In certain embodiments, the an antibody described herein comprises one or more of the VL FR1 having the amino acid sequence of SEQ ID NO: 105, the VL FR 2 having the amino acid sequence of SEQ ID NO: 113, the VL FR3 having the amino acid sequence of SEQ ID NO: 123, and the VL FR4 having the amino acid sequence of SEQ ID NO: 127 and VL CDRs of Ab237.

In certain embodiments, an antibody described herein comprises one or more VL framework regions (FRs) having the amino acid sequence described herein for Ab238 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 106 and VL CDRs of Ab238. In some embodiments, the VL FR2 has the amino acid sequence of SEQ ID NO: 114 and VL CDRs of Ab238. In some embodiments, the VL FR3 has the amino acid sequence of SEQ ID NO: 124 and VL CDRs of Ab238. In some embodiments, the VL FR4 has the amino acid sequence of SEQ ID NO: 128 and VL CDRs of Ab238. In certain embodiments, the an antibody described herein comprises one or more of the VL FR1 having the amino acid sequence of SEQ ID NO: 106, the VL FR 2 having the amino acid sequence of SEQ ID NO: 114, the VL FR3 having the amino acid sequence of SEQ ID NO: 124, and the VL FR4 having the amino acid sequence of SEQ ID NO: 128 and VL CDRs of Ab238.

In certain embodiments, an antibody described herein comprises one or more VL framework regions (FRs) having the amino acid sequence described herein for Ab239 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 107 and VL CDRs of Ab239. In some embodiments, the VL FR2 has the amino acid sequence of SEQ ID NO: 115 and VL CDRs of Ab239. In some embodiments, the VL FR3 has the amino acid sequence of SEQ ID NO: 125 and VL CDRs of Ab239. In some embodiments, the VL FR4 has the amino acid sequence of SEQ ID NO: 128 and VL CDRs of Ab239. In certain embodiments, the an antibody described herein comprises one or more of the VL FR1 having the amino acid sequence of SEQ ID NO: 107, the VL FR 2 having the amino acid sequence of SEQ ID NO: 115, the VL FR3 having the amino acid sequence of SEQ ID NO: 125, and the VL FR4 having the amino acid sequence of SEQ ID NO: 128 and VL CDRs of Ab239.

In certain embodiments, an antibody described herein comprises one or more VL framework regions (FRs) having the amino acid sequence described herein for Ab240 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 103 and VL CDRs of Ab240. In some embodiments, the VL FR2 has the amino acid sequence of SEQ ID NO: 111 and VL CDRs of Ab240. In some embodiments, the VL FR3 has the amino acid sequence of SEQ ID NO: 122 and VL CDRs of Ab240. In some embodiments, the VL FR4 has the amino acid sequence of SEQ ID NO: 128 and VL CDRs of Ab240. In certain embodiments, the an antibody described herein comprises one or more of the VL FR1 having the amino acid sequence of SEQ ID NO: 103, the VL FR 2 having the amino acid sequence of SEQ ID NO: 111, the VL FR3 having the amino acid sequence of SEQ ID NO: 122, and the VL FR4 having the amino acid sequence of SEQ ID NO: 128 and VL CDRs of Ab240.

In certain embodiments, an antibody described herein comprises one or more VL framework regions (FRs) having the amino acid sequence described herein for Ab241 (e.g., see Table 3), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab241. In some embodiments, the VL FR2 has the amino acid sequence of SEQ ID NO: 109 and VL CDRs of Ab241. In some embodiments, the VL FR3 has the amino acid sequence of SEQ ID NO: 117 and VL CDRs of Ab241. In some embodiments, the VL FR4 has the amino acid sequence of SEQ ID NO: 127 and VL CDRs of Ab241. In certain embodiments, the an antibody described herein comprises one or more of the VL FR1 having the amino acid sequence of SEQ ID NO: 102, the VL FR 2 having the amino acid sequence of SEQ ID NO: 109, the VL FR3 having the amino acid sequence of SEQ ID NO: 117, and the VL FR4 having the amino acid sequence of SEQ ID NO: 127 and VL CDRs of Ab241.

In certain embodiments, an antibody described herein comprises one or more VL framework regions (FRs) having the amino acid sequence described herein for Ab242 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab242. In some embodiments, the VL FR2 has the amino acid sequence of SEQ ID NO: 110 and VL CDRs of Ab242. In some embodiments, the VL FR3 has the amino acid sequence of SEQ ID NO: 118 and VL CDRs of Ab242. In some embodiments, the VL FR4 has the amino acid sequence of SEQ ID NO: 127 and VL CDRs of Ab242. In certain embodiments, the an antibody described herein comprises one or more of the VL FR1 having the amino acid sequence of SEQ ID NO: 103, the VL FR 2 having the amino acid sequence of SEQ ID NO: 111, the VL FR3 having the amino acid sequence of SEQ ID NO: 122, and the VL FR4 having the amino acid sequence of SEQ ID NO: 128 and VL CDRs of Ab242.

In certain embodiments, an antibody described herein comprises one or more VL framework regions (FRs) having the amino acid sequence described herein for Ab243 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab243. In some embodiments, the VL FR2 has the amino acid sequence of SEQ ID NO: 110 and VL CDRs of Ab243. In some embodiments, the VL FR3 has the amino acid sequence of SEQ ID NO: 119 and VL CDRs of Ab243. In some embodiments, the VL FR4 has the amino acid sequence of SEQ ID NO: 127 and VL CDRs of Ab243. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 119, and the VL FR4 having the amino acid sequence of SEQ ID NO: 127 and VL CDRs of Ab243.

In certain embodiments, an antibody described herein comprises one or more VL framework regions (FRs) having the amino acid sequence described herein for Ab244 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab244. In some embodiments, the VL FR2 has the amino acid sequence of SEQ ID NO: 110 and VL CDRs of Ab244. In some embodiments, the VL FR3 has the amino acid sequence of SEQ ID NO: 120 and VL CDRs of Ab244. In some embodiments, the VL FR4 has the amino acid sequence of SEQ ID NO: 127 and VL CDRs of Ab244. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 120, and the VL FR4 having the amino acid sequence of SEQ ID NO: 127 and VL CDRs of Ab244.

In certain embodiments, an antibody described herein comprises one or more VL framework regions (FRs) having the amino acid sequence described herein for Ab245 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab245. In some embodiments, the VL FR2 has the amino acid sequence of SEQ ID NO: 110 and VL CDRs of Ab245. In some embodiments, the VL FR3 has the amino acid sequence of SEQ ID NO: 121 and VL CDRs of Ab245. In some embodiments, the VL FR4 has the amino acid sequence of SEQ ID NO: 127 and VL CDRs of Ab245. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 121, and the VL FR4 having the amino acid sequence of SEQ ID NO: 1278 and VL CDRs of Ab245.

In certain embodiments, an antibody described herein comprises one or more VL framework regions (FRs) having the amino acid sequence described herein for Ab246 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab246. In some embodiments, the VL FR2 has the amino acid sequence of SEQ ID NO: 109 and VL CDRs of Ab246. In some embodiments, the VL FR3 has the amino acid sequence of SEQ ID NO: 117 and VL CDRs of Ab246. In some embodiments, the VL FR4 has the amino acid sequence of SEQ ID NO: 127 and VL CDRs of Ab246. In certain embodiments, the an antibody described herein comprises one or more of the VL FR1 having the amino acid sequence of SEQ ID NO: 102, the VL FR 2 having the amino acid sequence of SEQ ID NO: 109, the VL FR3 having the amino acid sequence of SEQ ID NO: 117, and the VL FR4 having the amino acid sequence of SEQ ID NO: 127 and VL CDRs of Ab246.

In certain embodiments, an antibody described herein comprises one or more VL framework regions (FRs) having the amino acid sequence described herein for Ab247 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab247. In some embodiments, the VL FR2 has the amino acid sequence of SEQ ID NO: 110 and VL CDRs of Ab247. In some embodiments, the VL FR3 has the amino acid sequence of SEQ ID NO: 118 and VL CDRs of Ab247. In some embodiments, the VL FR4 has the amino acid sequence of SEQ ID NO: 127 and VL CDRs of Ab247. In certain embodiments, the an antibody described herein comprises one or more of the VL FR1 having the amino acid sequence of SEQ ID NO: 103, the VL FR 2 having the amino acid sequence of SEQ ID NO: 111, the VL FR3 having the amino acid sequence of SEQ ID NO: 122, and the VL FR4 having the amino acid sequence of SEQ ID NO: 128 and VL CDRs of Ab247.

In certain embodiments, an antibody described herein comprises one or more VL framework regions (FRs) having the amino acid sequence described herein for Ab248 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab248. In some embodiments, the VL FR2 has the amino acid sequence of SEQ ID NO: 110 and VL CDRs of Ab248. In some embodiments, the VL FR3 has the amino acid sequence of SEQ ID NO: 119 and VL CDRs of Ab248. In some embodiments, the VL FR4 has the amino acid sequence of SEQ ID NO: 127 and VL CDRs of Ab248. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 119, and the VL FR4 having the amino acid sequence of SEQ ID NO: 127 and VL CDRs of Ab248.

In certain embodiments, an antibody described herein comprises one or more VL framework regions (FRs) having the amino acid sequence described herein for Ab249 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab249. In some embodiments, the VL FR2 has the amino acid sequence of SEQ ID NO: 110 and VL CDRs of Ab249. In some embodiments, the VL FR3 has the amino acid sequence of SEQ ID NO: 120 and VL CDRs of Ab249. In some embodiments, the VL FR4 has the amino acid sequence of SEQ ID NO: 127 and VL CDRs of Ab249. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 120, and the VL FR4 having the amino acid sequence of SEQ ID NO: 127 and VL CDRs of Ab249.

In certain embodiments, an antibody described herein comprises one or more VL framework regions (FRs) having the amino acid sequence described herein for Ab2550 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab250. In some embodiments, the VL FR2 has the amino acid sequence of SEQ ID NO: 110 and VL CDRs of Ab250. In some embodiments, the VL FR3 has the amino acid sequence of SEQ ID NO: 121 and VL CDRs of Ab250. In some embodiments, the VL FR4 has the amino acid sequence of SEQ ID NO: 127 and VL CDRs of Ab250. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 121, and the VL FR4 having the amino acid sequence of SEQ ID NO: 1278 and VL CDRs of Ab250.

In certain embodiments, an antibody described herein comprises one or more VL framework regions (FRs) having the amino acid sequence described herein for Ab251 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab251. In some embodiments, the VL FR2 has the amino acid sequence of SEQ ID NO: 109 and VL CDRs of Ab251. In some embodiments, the VL FR3 has the amino acid sequence of SEQ ID NO: 117 and VL CDRs of Ab251. In some embodiments, the VL FR4 has the amino acid sequence of SEQ ID NO: 127 and VL CDRs of Ab251. In certain embodiments, the an antibody described herein comprises one or more of the VL FR1 having the amino acid sequence of SEQ ID NO: 102, the VL FR 2 having the amino acid sequence of SEQ ID NO: 109, the VL FR3 having the amino acid sequence of SEQ ID NO: 117, and the VL FR4 having the amino acid sequence of SEQ ID NO: 127 and VL CDRs of Ab251.

In certain embodiments, an antibody described herein comprises one or more VL framework regions (FRs) having the amino acid sequence described herein for Ab252 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab252. In some embodiments, the VL FR2 has the amino acid sequence of SEQ ID NO: 110 and VL CDRs of Ab252. In some embodiments, the VL FR3 has the amino acid sequence of SEQ ID NO: 118 and VL CDRs of Ab252. In some embodiments, the VL FR4 has the amino acid sequence of SEQ ID NO: 127 and VL CDRs of Ab252. In certain embodiments, the an antibody described herein comprises one or more of the VL FR1 having the amino acid sequence of SEQ ID NO: 103, the VL FR 2 having the amino acid sequence of SEQ ID NO: 111, the VL FR3 having the amino acid sequence of SEQ ID NO: 122, and the VL FR4 having the amino acid sequence of SEQ ID NO: 128 and VL CDRs of Ab252.

In certain embodiments, an antibody described herein comprises one or more VL framework regions (FRs) having the amino acid sequence described herein for Ab253 (e.g., see Table 3), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab253. In some embodiments, the VL FR2 has the amino acid sequence of SEQ ID NO: 110 and VL CDRs of Ab253. In some embodiments, the VL FR3 has the amino acid sequence of SEQ ID NO: 119 and VL CDRs of Ab253. In some embodiments, the VL FR4 has the amino acid sequence of SEQ ID NO: 127 and VL CDRs of Ab253. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 119, and the VL FR4 having the amino acid sequence of SEQ ID NO: 127 and VL CDRs of Ab253.

In certain embodiments, an antibody described herein comprises one or more VL framework regions (FRs) having the amino acid sequence described herein for Ab254 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab254. In some embodiments, the VL FR2 has the amino acid sequence of SEQ ID NO: 110 and VL CDRs of Ab254. In some embodiments, the VL FR3 has the amino acid sequence of SEQ ID NO: 120 and VL CDRs of Ab254. In some embodiments, the VL FR4 has the amino acid sequence of SEQ ID NO: 127 and VL CDRs of Ab254. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 120, and the VL FR4 having the amino acid sequence of SEQ ID NO: 127 and VL CDRs of Ab254.

In certain embodiments, an antibody described herein comprises one or more VL framework regions (FRs) having the amino acid sequence described herein for Ab255 (e.g., see Table 3), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 102 and VL CDRs of Ab255. In some embodiments, the VL FR2 has the amino acid sequence of SEQ ID NO: 110 and VL CDRs of Ab255. In some embodiments, the VL FR3 has the amino acid sequence of SEQ ID NO: 121 and VL CDRs of Ab255. In some embodiments, the VL FR4 has the amino acid sequence of SEQ ID NO: 127 and VL CDRs of Ab255. In certain embodiments, the an antibody described herein comprises one or more of the VL FR1 having the amino acid sequence of SEQ ID NO: 102, the VL FR 2 having the amino acid sequence of SEQ ID NO: 110, the VL FR3 having the amino acid sequence of SEQ ID NO: 121, and the VL FR4 having the amino acid sequence of SEQ ID NO: 1278.

In certain embodiments, an antibody described herein comprises one or more VL framework regions (FRs) having the amino acid sequence of (a) SEQ ID NO:240; (b) WYQQKPGKAPX$_{79}$LLIY (SEQ ID NO: 241), wherein X$_{79}$ is any amino acid, for example, K or Q; (c) GVPSRFSGX$_{80}$GX$_{81}$GTDX$_{82}$TLX$_{83}$IX$_{84}$SLQX$_{85}$EDVAX$_{86}$YFC, wherein X$_{80}$ is any amino acid, for example, S or F, X$_{81}$ is any amino acid, for example, S or F, X$_{82}$ is any amino acid, for example, an amino acid with an aromatic side chain, e.g., Y or F, X$_{83}$ is any amino acid, for example, T or K, X$_{84}$ is any amino acid, for example, an amino acid with an uncharged polar side chain, e.g., S or N, X$_{85}$ is any amino acid, for example, P or S, and X$_{86}$ is any amino acid, for example, I or T; and (d) SEQ ID NO: 243, wherein the antibody immunospecifically binds to MET, e.g., human MET ECD (e.g., SEQ ID NO:190). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 240 and VL CDRs of any one of Ab235-Ab255. In some embodiments, the VL FR2 has the amino acid sequence of WYQQKPGKAPX$_{79}$LLIY (SEQ ID NO: 241), wherein X$_{79}$ is any amino acid, for example, K or Q and VL CDRs of any of Ab235-Ab255. In some embodiments, the VL FR3 has the amino acid sequence of GVPSRFSGX$_{80}$GX$_{81}$GTDX$_{82}$TLX$_{83}$IX$_{84}$SLQX$_{85}$EDVAX$_{86}$YFC, wherein $X_{80}$ is any amino acid, for example, S or F, $X_{81}$ is any amino acid, for example, S or F, $X_{82}$ is any amino acid, for example, an amino acid with an aromatic side chain, e.g., Y or F, $X_{83}$ is any amino acid, for example, T or K, $X_{84}$ is any amino acid, for example, an amino acid with an uncharged polar side chain, e.g., S or N, $X_{85}$ is any amino acid, for example, P or S, and $X_{86}$ is any amino acid, for example, an amino acid with a nonpolar side chain, e.g., I or T and VL CDRs of any of Ab235-Ab255. In some embodiments, the VL FR4 has the amino acid sequence of SEQ ID NO: 243 and VL CDRs of any of Ab235-Ab255. In certain embodiments, the an antibody described herein comprises one or more of the VL FR1 having the amino acid sequence of SEQ ID NO: 240, the VL FR 2 having the amino acid sequence of WYQQKPGKAPX$_{79}$LLIY (SEQ ID NO: 241), wherein $X_{79}$ is any amino acid, for example, K or Q, the VL FR3 having the amino acid sequence of GVPSRFSGX$_{80}$GX$_{81}$GTDX$_{82}$TLX$_{83}$IX$_{84}$SLQX$_{85}$EDVAX$_{86}$YFC, wherein $X_{80}$ is any amino acid, for example, S or F, $X_{81}$ is any amino acid, for example, S or F, $X_{82}$ is any amino acid, for example, an amino acid with an aromatic side chain, e.g., Y or F, $X_{83}$ is any amino acid, for example, T or K, $X_{84}$ is any amino acid, for example, an amino acid with an uncharged polar side chain, e.g., S or N, $X_{85}$ is any amino acid, for example, P or S, and $X_{86}$ is any amino acid, for example, an amino acid with a nonpolar side chain, e.g., I or T, and the VL FR4 having the amino acid sequence of SEQ ID NO: 243. In certain embodiments, any one of $X_{79}$ to $X_{86}$ is any amino acid sequence. In specific embodiments, $X_{79}$ is a conservative substitution of K or Q, $X_{80}$ is a conservative substitution of S or F, $X_{81}$ is a conservative substitution of S or F, $X_{82}$ is a conservative substitution of Y or F, $X_{83}$ is a conservative substitution of T or K, $X_{84}$ is a conservative substitution of S or N, $X_{85}$ is a conservative substitution of P or S, and $X_{86}$ is a conservative substitution of I or T.

In certain embodiments, an antibody described herein comprises one or more VH framework regions (FRs) having the amino acid sequence described herein for Ab235 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 75 and VH CDRs of Ab235. In some embodiments, the VH FR2 has the amino acid sequence of SEQ ID NO: 82 and VH CDRs of Ab235. In some embodiments, the VH FR3 has the amino acid sequence of SEQ ID NO: 89 and VH CDRs of Ab235. In some embodiments, the VH FR3 has the amino acid sequence of SEQ ID NO: 268 and VH CDRs of Ab235. In some embodiments, the VH FR4 has the amino acid sequence of SEQ ID NO: 97 and VH CDRs of Ab235. In certain embodiments, the an antibody described herein comprises one or more of the VH FR1 having the amino acid sequence of SEQ ID NO: 75, the VH FR 2 having the amino acid sequence of SEQ ID NO: 82, the VH FR3 having the amino acid sequence of SEQ ID NO: 89, and the VH FR4 having the amino acid sequence of SEQ ID NO: 97. In certain embodiments, the an antibody described herein comprises one or more of the VH FR1 having the amino acid sequence of SEQ ID NO: 75, the VH FR 2 having the amino acid sequence of SEQ ID NO: 82, the VH FR3 having the amino acid sequence of SEQ ID NO: 268 and the VH FR4 having the amino acid sequence of SEQ ID NO: 97.

In certain embodiments, an antibody described herein comprises one or more VH framework regions (FRs) having the amino acid sequence described herein for Ab236 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 76 and VH CDRs of Ab236. In some embodiments, the VH FR2 has the amino acid sequence of SEQ ID NO: 82 and VH CDRs of Ab236. In some embodiments, the VH FR3 has the amino acid sequence of SEQ ID NO: 90 and VH CDRs of Ab236. In some embodiments, the VH FR3 has the amino acid sequence of SEQ ID NO: 269 and VH CDRs of Ab236. In some embodiments, the VH FR4 has the amino acid sequence of SEQ ID NO: 97 and VH CDRs of Ab236. In certain embodiments, the an antibody described herein comprises one or more of the VH FR1 having the amino acid sequence of SEQ ID NO: 76, the VH FR 2 having the amino acid sequence of SEQ ID NO: 82, the VH FR3 having the amino acid sequence of SEQ ID NO: 90, and the VH FR4 having the amino acid sequence of SEQ ID NO: 97 and VH CDRs of Ab236. In certain embodiments, the an antibody described herein comprises one or more of the VH FR1 having the amino acid sequence of SEQ ID NO: 76, the VH FR 2 having the amino acid sequence of SEQ ID NO: 82, the VH FR3 having the amino acid sequence of SEQ ID NO: 269, and the VH FR4 having the amino acid sequence of SEQ ID NO: 97 and VH CDRs of Ab236.

In certain embodiments, an antibody described herein comprises one or more VH framework regions (FRs) having the amino acid sequence described herein for Ab237 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 77 and VH CDRs of Ab237. In some embodiments, the VH FR2 has the amino acid sequence of SEQ ID NO: 83 and VH CDRs of Ab237. In some embodiments, the VH FR3 has the amino acid sequence of SEQ ID NO: 91 and VH CDRs of Ab237. In some embodiments, the VH FR3 has the amino acid sequence of SEQ ID NO: 270 and VH CDRs of Ab237. In some embodiments, the VH FR4 has the amino acid sequence of SEQ ID NO: 98 and VH CDRs of Ab237. In certain embodiments, the an antibody described herein comprises one or more of the VH FR1 having the amino acid sequence of SEQ ID NO: 77, the VH FR 2 having the amino acid sequence of SEQ ID NO: 83, the VH FR3 having the amino acid sequence of SEQ ID NO: 91, and the VH FR4 having the amino acid sequence of SEQ ID NO: 98 and VH CDRs of Ab237. In certain embodiments, the an antibody described herein comprises one or more of the VH FR1 having the amino acid sequence of SEQ ID NO: 77, the VH FR 2 having the amino acid sequence of SEQ ID NO: 83, the VH FR3 having the amino acid sequence of SEQ ID NO: 270, and the VH FR4 having the amino acid sequence of SEQ ID NO: 98 and VH CDRs of Ab237.

In certain embodiments, an antibody described herein comprises one or more VH framework regions (FRs) having the amino acid sequence described herein for Ab238 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 78 and VH CDRs of Ab238. In some embodiments, the VH FR2 has the amino acid sequence of SEQ ID NO: 84 and VH CDRs of Ab238. In some embodiments, the VH FR2 has the amino acid sequence of SEQ ID NO: 271 and VH CDRs of Ab238. In some embodiments, the VH FR3 has the amino acid sequence of SEQ ID NO: 92 and VH CDRs of Ab238. In some embodiments, the VH FR4 has the amino acid sequence of SEQ ID NO: 99 and VH CDRs of Ab238. In certain embodiments, the an antibody described herein comprises one or more of the VH FR1 having the amino acid sequence of SEQ ID NO: 78, the VH FR 2 having the amino acid sequence of SEQ ID NO: 84, the VH FR3 having the amino acid sequence of SEQ ID NO: 92, and the VH FR4 having the amino acid sequence of SEQ ID NO: 99 and VH CDRs of Ab238. In certain embodiments, the an antibody described herein comprises one or more of the VH FR1 having the amino acid sequence of SEQ ID NO: 78, the VH FR 2 having the amino acid sequence of SEQ ID NO: 271, the VH FR3 having the amino acid sequence of SEQ ID NO: 92, and the VH FR4 having the amino acid sequence of SEQ ID NO: 99 and VH CDRs of Ab238.

In certain embodiments, an antibody described herein comprises one or more VH framework regions (FRs) having the amino acid sequence described herein for Ab239 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 79 and VH CDRs of Ab239. In some embodiments, the VH FR2 has the amino acid sequence of SEQ ID NO: 83 and VH CDRs of Ab239. In some embodiments, the VH FR3 has the amino acid sequence of SEQ ID NO: 93 and VH CDRs of Ab239. In some embodiments, the VH FR4 has the amino acid sequence of SEQ ID NO: 100 and VH CDRs of Ab239. In certain embodiments, the an antibody described herein comprises one or more of the VH FR1 having the amino acid sequence of SEQ ID NO: 79, the VH FR 2 having the amino acid sequence of SEQ ID NO: 83, the VH FR3 having the amino acid sequence of SEQ ID NO: 93, and the VH FR4 having the amino acid sequence of SEQ ID NO: 100 and VH CDRs of Ab239.

In certain embodiments, an antibody described herein comprises one or more VH framework regions (FRs) having the amino acid sequence described herein for Ab240 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 80 and VH CDRs of Ab240. In some embodiments, the VH FR2 has the amino acid sequence of SEQ ID NO: 84 and VH CDRs of Ab240. In some embodiments, the VH FR3 has the amino acid sequence of SEQ ID NO: 94 and VH CDRs of Ab240. In some embodiments, the VH FR4 has the amino acid sequence of SEQ ID NO: 101 and VH CDRs of Ab240. In certain embodiments, the an antibody described herein comprises one or more of the VH FR1 having the amino acid sequence of SEQ ID NO: 80, the VH FR 2 having the amino acid sequence of SEQ ID NO: 84, the VH FR3 having the amino acid sequence of SEQ ID NO: 94, and the VH FR4 having the amino acid sequence of SEQ ID NO: 101 and VH CDRs of Ab240.

In certain embodiments, an antibody described herein comprises one or more VH framework regions (FRs) having the amino acid sequence described herein for Ab241 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab241. In some embodiments, the VH FR2 has the amino acid sequence of SEQ ID NO: 81 and VH CDRs of Ab241. In some embodiments, the VH FR3 has the amino acid sequence of SEQ ID NO: 86 and VH CDRs of Ab241. In some embodiments, the VH FR4 has the amino acid sequence of SEQ ID NO: 95 and VH CDRs of Ab241. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 86, and the VH FR4 having the amino acid sequence of SEQ ID NO: 95 and VH CDRs of Ab241.

In certain embodiments, an antibody described herein comprises one or more VH framework regions (FRs) having the amino acid sequence described herein for Ab242 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab242. In some embodiments, the VH FR2 has the amino acid sequence of SEQ ID NO: 81 and VH CDRs of Ab242. In some embodiments, the VH FR3 has the amino acid sequence of SEQ ID NO: 86 and VH CDRs of Ab242. In some embodiments, the VH FR4 has the amino acid sequence of SEQ ID NO: 95 and VH CDRs of Ab242. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 86, and the VH FR4 having the amino acid sequence of SEQ ID NO: 95 and VH CDRs of Ab242.

In certain embodiments, an antibody described herein comprises one or more VH framework regions (FRs) having the amino acid sequence described herein for Ab243 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab243. In some embodiments, the VH FR2 has the amino acid sequence of SEQ ID NO: 81 and VH CDRs of Ab243. In some embodiments, the VH FR3 has the amino acid sequence of SEQ ID NO: 86 and VH CDRs of Ab243. In some embodiments, the VH FR4 has the amino acid sequence of SEQ ID NO: 95 and VH CDRs of Ab243. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 86, and the VH FR4 having the amino acid sequence of SEQ ID NO: 95 and VH CDRs of Ab243.

In certain embodiments, an antibody described herein comprises one or more VH framework regions (FRs) having the amino acid sequence described herein for Ab244 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab244. In some embodiments, the VH FR2 has the amino acid sequence of SEQ ID NO: 81 and VH CDRs of Ab244. In some embodiments, the VH FR3 has the amino acid sequence of SEQ ID NO: 86 and VH CDRs of Ab244. In some embodiments, the VH FR4 has the amino acid sequence of SEQ ID NO: 95 and VH CDRs of Ab244. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 86, and the VH FR4 having the amino acid sequence of SEQ ID NO: 95 and VH CDRs of Ab244.

In certain embodiments, an antibody described herein comprises one or more VH framework regions (FRs) having the amino acid sequence described herein for Ab245 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab245. In some embodiments, the VH FR2 has the amino acid sequence of SEQ ID NO: 81 and VH CDRs of Ab245. In some embodiments, the VH FR3 has the amino acid sequence of SEQ ID NO: 86 and VH CDRs of Ab245. In some embodiments, the VH FR4 has the amino acid sequence of SEQ ID NO: 95 and VH CDRs of Ab245. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 86, and the VH FR4 having the amino acid sequence of SEQ ID NO: 95 and VH CDRs of Ab245

In certain embodiments, an antibody described herein comprises one or more VH framework regions (FRs) having the amino acid sequence described herein for Ab246 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab246. In some embodiments, the VH FR2 has the amino acid sequence of SEQ ID NO: 81 and VH CDRs of Ab246. In some embodiments, the VH FR3 has the amino acid sequence of SEQ ID NO: 87 and VH CDRs of Ab246. In some embodiments, the VH FR4 has the amino acid sequence of SEQ ID NO: 95 and VH CDRs of Ab246. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 87, and the VH FR4 having the amino acid sequence of SEQ ID NO: 95 and VH CDRs of Ab246.

In certain embodiments, an antibody described herein comprises one or more VH framework regions (FRs) having the amino acid sequence described herein for Ab247 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab247. In some embodiments, the VH FR2 has the amino acid sequence of SEQ ID NO: 81 and VH CDRs of Ab247. In some embodiments, the VH FR3 has the amino acid sequence of SEQ ID NO: 87 and VH CDRs of Ab247. In some embodiments, the VH FR4 has the amino acid sequence of SEQ ID NO: 95 and VH CDRs of Ab247. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 87, and the VH FR4 having the amino acid sequence of SEQ ID NO: 95 and VH CDRs of Ab247.

In certain embodiments, an antibody described herein comprises one or more VH framework regions (FRs) having the amino acid sequence described herein for Ab248 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab248. In some embodiments, the VH FR2 has the amino acid sequence of SEQ ID NO: 81 and VH CDRs of Ab248. In some embodiments, the VH FR3 has the amino acid sequence of SEQ ID NO: 87 and VH CDRs of Ab248. In some embodiments, the VH FR4 has the amino acid sequence of SEQ ID NO: 95 and VH CDRs of Ab248. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 87, and the VH FR4 having the amino acid sequence of SEQ ID NO: 95 and VH CDRs of Ab248.

In certain embodiments, an antibody described herein comprises one or more VH framework regions (FRs) having the amino acid sequence described herein for Ab249 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab249. In some embodiments, the VH FR2 has the amino acid sequence of SEQ ID NO: 81 and VH CDRs of Ab249. In some embodiments, the VH FR3 has the amino acid sequence of SEQ ID NO: 87 and VH CDRs of Ab249.

In some embodiments, the VH FR4 has the amino acid sequence of SEQ ID NO: 95 and VH CDRs of Ab249. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 87, and the VH FR4 having the amino acid sequence of SEQ ID NO: 95 and VH CDRs of Ab249.

In certain embodiments, an antibody described herein comprises one or more VH framework regions (FRs) having the amino acid sequence described herein for Ab250 (e.g., see Table 4), wherein the antibody immunospecifically binds to MET, e.g., human MET ECD (e.g., SEQ ID NO:190). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab250. In some embodiments, the VH FR2 has the amino acid sequence of SEQ ID NO: 81 and VH CDRs of Ab250. In some embodiments, the VH FR3 has the amino acid sequence of SEQ ID NO: 87 and VH CDRs of Ab250. In some embodiments, the VH FR4 has the amino acid sequence of SEQ ID NO: 95 and VH CDRs of Ab250. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 87, and the VH FR4 having the amino acid sequence of SEQ ID NO: 95 and VH CDRs of Ab250.

In certain embodiments, an antibody described herein comprises one or more VH framework regions (FRs) having the amino acid sequence described herein for Ab251 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab251. In some embodiments, the VH FR2 has the amino acid sequence of SEQ ID NO: 81 and VH CDRs of Ab251. In some embodiments, the VH FR3 has the amino acid sequence of SEQ ID NO: 88 and VH CDRs of Ab251. In some embodiments, the VH FR4 has the amino acid sequence of SEQ ID NO: 96 and VH CDRs of Ab251. In certain embodiments, the an antibody described herein comprises one or more of the VH FR1 having the amino acid sequence of SEQ ID NO: 74, the VH FR2 having the amino acid sequence of SEQ ID NO: 81, the VH FR3 having the amino acid sequence of SEQ ID NO: 88, and the VH FR4 having the amino acid sequence of SEQ ID NO: 96 and VH CDRs of Ab251.

In certain embodiments, an antibody described herein comprises one or more VH framework regions (FRs) having the amino acid sequence described herein for Ab252 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab252. In some embodiments, the VH FR2 has the amino acid sequence of SEQ ID NO: 81 and VH CDRs of Ab252. In some embodiments, the VH FR3 has the amino acid sequence of SEQ ID NO: 88 and VH CDRs of Ab252. In some embodiments, the VH FR4 has the amino acid sequence of SEQ ID NO: 96 and VH CDRs of Ab252. In certain embodiments, the an antibody described herein comprises one or more of the VH FR1 having the amino acid sequence of SEQ ID NO: 74, the VH FR2 having the amino acid sequence of SEQ ID NO: 81, the VH FR3 having the amino acid sequence of SEQ ID NO: 88, and the VH FR4 having the amino acid sequence of SEQ ID NO: 96 and VH CDRs of Ab252.

In certain embodiments, an antibody described herein comprises one or more VH framework regions (FRs) having the amino acid sequence described herein for Ab253 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab253. In some embodiments, the VH FR2 has the amino acid sequence of SEQ ID NO: 81 and VH CDRs of Ab253. In some embodiments, the VH FR3 has the amino acid sequence of SEQ ID NO: 88 and VH CDRs of Ab253. In some embodiments, the VH FR4 has the amino acid sequence of SEQ ID NO: 96 and VH CDRs of Ab253. In certain embodiments, the an antibody described herein comprises one or more of the VH FR1 having the amino acid sequence of SEQ ID NO: 74, the VH FR2 having the amino acid sequence of SEQ ID NO: 81, the VH FR3 having the amino acid sequence of SEQ ID NO: 88, and the VH FR4 having the amino acid sequence of SEQ ID NO: 96 and VH CDRs of Ab253.

In certain embodiments, an antibody described herein comprises one or more VH framework regions (FRs) having the amino acid sequence described herein for Ab254 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab254. In some embodiments, the VH FR2 has the amino acid sequence of SEQ ID NO: 81 and VH CDRs of Ab254. In some embodiments, the VH FR3 has the amino acid sequence of SEQ ID NO: 88 and VH CDRs of Ab254. In some embodiments, the VH FR4 has the amino acid sequence of SEQ ID NO: 96 and VH CDRs of Ab254. In certain embodiments, the an antibody described herein comprises one or more of the VH FR1 having the amino acid sequence of SEQ ID NO: 74, the VH FR 2 having the amino acid sequence of SEQ ID NO: 81, the VH FR3 having the amino acid sequence of SEQ ID NO: 88, and the VH FR4 having the amino acid sequence of SEQ ID NO: 96 and VH CDRs of Ab254.

In certain embodiments, an antibody described herein comprises one or more VH framework regions (FRs) having the amino acid sequence described herein for Ab255 (e.g., see Table 4), wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 74 and VH CDRs of Ab255. In some embodiments, the VH FR2 has the amino acid sequence of SEQ ID NO: 81 and VH CDRs of Ab255. In some embodiments, the VH FR3 has the amino acid sequence of SEQ ID NO: 88 and VH CDRs of Ab255. In some embodiments, the VH FR4 has the amino acid sequence of SEQ ID NO: 96 and VH CDRs of Ab255. In certain embodiments, the an antibody described herein comprises one or more of the VH FR1 having the amino acid sequence of SEQ ID NO: 74, the VH FR2 having the amino acid sequence of SEQ ID NO: 81, the VH FR3 having the amino acid sequence of SEQ ID NO: 88, and the VH FR4 having the amino acid sequence of SEQ ID NO: 96 and VH CDRs of Ab255. In certain embodiments, an antibody described herein comprises one or more VH framework regions (FRs) having the amino acid sequence of (a) SEQ ID NO:244; (b) SEQ ID NO: 245; (c) RFTISRDNAKX$_{87}$SLYLQMX$_{88}$SLRTEDTATYYCTT (SEQ ID NO: 246), wherein X$_{87}$ is any amino acid, for example, an amino acid with an uncharged polar side chain, e.g., S or N, and X$_{88}$ is any amino acid, for example, D or N; and (d) WGQGX$_{89}$MV (SEQ ID NO: 247), wherein X$_{89}$ is any amino acid, for example, T or V, wherein the antibody immunospecifically binds to MET, e.g., human MET ECD (e.g., SEQ ID NO:190). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 244 and VH CDRs of any one of Ab235-Ab255. In some embodiments, the VH FR2 has the amino acid sequence of SEQ ID NO: 245 and VH CDRs of any of Ab235-Ab255. In some embodiments, the VH FR3 has the amino acid sequence of RFTISRDNAKX$_{87}$SLYLQMX$_{88}$SLRTEDTATYYCTT (SEQ ID NO: 246), wherein X$_{87}$ is any amino acid, for example, an amino acid with an uncharged polar side chain, e.g., S or N, and X$_{88}$ is any amino acid, for example, D or N and VH CDRs of any of Ab235-Ab255. In some embodiments, the VH FR4 has the amino acid sequence of WGQGX$_{89}$MV (SEQ ID NO: 247), wherein X$_{89}$ is any amino acid, for example, T or V and VH CDRs of any of Ab235-Ab255. In certain embodiments, the an antibody described herein comprises one or more of the VH FR1 having the amino acid sequence of SEQ ID NO: 244, the VH FR 2 having the amino acid sequence of SEQ ID NO: 245, wherein X$_{79}$ is any amino acid, for example, K or Q, the VH FR3 having the amino acid sequence of RFTISRDNAKX$_{87}$SLYLQMX$_{88}$SLRTEDTATYYCTT (SEQ ID NO: 246), wherein X$_{87}$ is any amino acid, for example, an amino acid with an uncharged polar side chain, e.g., S or N, and X$_{88}$ is any amino acid, for example, D or N, and the VH FR4 having the amino acid sequence of WGQGX$_{89}$MV (SEQ ID NO: 247), wherein X$_{89}$ is any amino acid, for example, T or V. In certain embodiments, any one of X$_{87}$ to X$_{89}$ is any amino acid sequence. In specific embodiments, X$_{87}$ is a conservative substitution of S or N, X$_{88}$ is a conservative substitution of D or N, and X$_{89}$ is a conservative substitution of T or V.

In specific embodiments, an antibody described herein, which immunospecifically binds to MET, e.g., human MET ECD (e.g., SEQ ID NO:190), comprises framework regions (e.g., framework regions of the VL domain and/or VH domain) that are human framework regions or derived from human framework regions. Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiment, an antibody described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), are grafted onto homologous human or non-human primate acceptor frameworks. In one embodiment, the non-human primate acceptor frameworks are from Old World apes. In a specific embodiment, the Old World ape acceptor framework is from *Pan troglodytes, Pan paniscus* or *Gorilla gorilla*. In a particular embodiment, the non-human primate acceptor frameworks are from the chimpanzee Pan troglodytes. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are is derived from the cynomolgus monkey *Macaca* cynomolgus. Non-human primate framework sequences are described in U.S. Patent Application Publication No. US 2005/0208625.

In specific aspects, a composite human antibody can be generated using, for example, Composite Human Antibody™ technology (Antitope Ltd., Cambridge, United Kingdom). For example, composite human antibodies can be generated by fusing together segments of unrelated human antibody variable regions, which are subsequently evaluated for their avoidance of T cell epitope inclusion (see, e.g., Baker et al., 2010, Self Nonself., 1(4):314-322; and Bryson et al., 2010, BioDrugs, 24(1):1-8), for example, deimmunization (see, e.g., Jones et al., 2009, Methods Mol Biol., 525:405-23).

In certain aspects, antibodies described herein are deimmunized antibodies. Deimmunization is a technology for location and removal of T-cell epitopes through the combined use of immunological and molecular biology techniques (see, e.g., Jones et al., 2009, Methods Mol Biol., 525:405-23; and Perry et al., 2008, Drugs R D., 9(6):385-96). For example, mutations to remove T-cell epitopes can generally be introduced, for example in the constant region, VL and/or VH regions, without significantly reducing the binding affinity of an antibody. In certain embodiments, mutations to remove T-cell epitopes are introduced in one or more VL CDRs and/or VH CDRs without significantly reducing the binding affinity of an antibody. In specific embodiments, mutations to remove T-cell epitopes are not introduced in VL CDRs and/or VH CDRs of an antibody. In certain embodiments, mutations to remove T-cell epitopes are introduced in one or more VL FRs and/or VH FRs without significantly reducing the binding affinity of an antibody.

In certain embodiments, an antibody described herein or an antigen-binding fragment thereof comprises amino acid sequences with certain percent identity relative to any one of Ab235-Ab255.

The determination of percent identity between two sequences (e.g., amino acid sequences or nucleic acid sequences) can be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and)

(BLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 57, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 57, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab235 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 57, wherein the antibody immunospecifically binds to MET, e.g., human MET ECD (SEQ ID NO:190). In a particular embodiment, the antibody comprises VL CDRs that are identical to the VL CDRs of antibody Ab235 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 66, wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 66, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab235 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 66, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab235 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 57, and (ii) a VH domain having at least 80%, at least 85%, at least 90%, at least 95%, or at least 98% sequence identity to the amino acid sequence of SEQ ID NO: 66, respectively, wherein the antibody immunospecifically binds to MET, e.g., human MET ECD (SEQ ID NO: 1). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab235 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 58, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 58, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab236 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 58, wherein the antibody immunospecifically binds to MET, e.g., human MET ECD (SEQ ID NO:190). In a particular embodiment, the antibody comprises VL CDRs that are identical to the VL CDRs of antibody Ab236 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 67, wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 67, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab236 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 67, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab236 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 58, and (ii) a VH domain having at least 80%, at least 85%, at least 90%, at least 95%, or at least 98% sequence identity to the amino acid sequence of SEQ ID NO: 67, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab236 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 59, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 59, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab237 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 59, wherein the antibody immunospecifically binds to MET, e.g., human MET ECD (SEQ ID NO:190). In a particular embodiment, the antibody comprises VL CDRs that are identical to the VL CDRs of antibody Ab237 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 68 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 68, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab237 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 68, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab237 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 59, and (ii) a VH domain having at least 80%, at least 85%, at least 90%, at least 95%, or at least 98% sequence identity to the amino acid sequence of SEQ ID NO: 68, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab237 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 60, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 60, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab238 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 60, wherein the antibody immunospecifically binds to MET, e.g., human MET ECD (SEQ ID NO:190). In a particular embodiment, the antibody comprises VL CDRs that are identical to the VL CDRs of antibody Ab238 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 69 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 69, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab238 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 69, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab238 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 60, and (ii) a VH domain having at least 80%, at least 85%, at least 90%, at least 95%, or at least 98% sequence identity to the amino acid sequence of SEQ ID NO: 69, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab238 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 61, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 61, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab239 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 61, wherein the antibody immunospecifically binds to MET, e.g., human MET ECD (SEQ ID NO:190). In a particular embodiment, the antibody comprises VL CDRs that are identical to the VL CDRs of antibody Ab239 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 70 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 70, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab239 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 70, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab239 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 61, and (ii) a VH domain having at least 80%, at least 85%, at least 90%, at least 95%, or at least 98% sequence identity to the amino acid sequence of SEQ ID NO: 70, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab239 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 62, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 62, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab240 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 62, wherein the antibody immunospecifically binds to MET, e.g., human MET ECD (SEQ ID NO:190). In a particular embodiment, the antibody comprises VL CDRs that are identical to the VL CDRs of antibody Ab240 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 71 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 71, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab240 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 71, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab240 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 62, and (ii) a VH domain having at least 80%, at least 85%, at least 90%, at least 95%, or at least 98% sequence identity to the amino acid sequence of SEQ ID NO: 71, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab240 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 52, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 52, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab241 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 52, wherein the antibody immunospecifically binds to MET, e.g., human MET ECD (SEQ ID NO:190). In a particular embodiment, the antibody comprises VL CDRs that are identical to the VL CDRs of antibody Ab241 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab241 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 63, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab241 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 52, and (ii) a VH domain having at least 80%, at least 85%, at least 90%, at least 95%, or at least 98% sequence identity to the amino acid sequence of SEQ ID NO: 63, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab241 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 53, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 53, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab242 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 53, wherein the antibody immunospecifically binds to MET, e.g., human MET ECD (SEQ ID NO:190). In a particular embodiment, the antibody comprises VL CDRs that are identical to the VL CDRs of antibody Ab242 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab242 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 63, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab242 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 53, and (ii) a VH domain having at least 80%, at least 85%, at least 90%, at least 95%, or at least 98% sequence identity to the amino acid sequence of SEQ ID NO: 63, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab242 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 54, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 54, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab243 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 54, wherein the antibody immunospecifically binds to MET, e.g., human MET ECD (SEQ ID NO:190). In a particular embodiment, the antibody comprises VL CDRs that are identical to the VL CDRs of antibody Ab243 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab243 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 63, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab243 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 54, and (ii) a VH domain having at least 80%, at least 85%, at least 90%, at least 95%, or at least 98% sequence identity to the amino acid sequence of SEQ ID NO: 63, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab243 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 55, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 55, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab244 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 55, wherein the antibody immunospecifically binds to MET, e.g., human MET ECD (SEQ ID NO:190). In a particular embodiment, the antibody comprises VL CDRs that are identical to the VL CDRs of antibody Ab244 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab244 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 63, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab244 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 55, and (ii) a VH domain having at least 80%, at least 85%, at least 90%, at least 95%, or at least 98% sequence identity to the amino acid sequence of SEQ ID NO: 63, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab244 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 56, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 56, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab245 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 56, wherein the antibody immunospecifically binds to MET, e.g., human MET ECD (SEQ ID NO:190). In a particular embodiment, the antibody comprises VL CDRs that are identical to the VL CDRs of antibody Ab245 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 63, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab245 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 63, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab245 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 56, and (ii) a VH domain having at least 80%, at least 85%, at least 90%, at least 95%, or at least 98% sequence identity to the amino acid sequence of SEQ ID NO: 63, respectively, wherein the antibody immunospecifically binds to MET, e.g., human MET ECD (amino acid residues 25 to 934 of SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab245 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 52, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 52, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab246 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 52, wherein the antibody immunospecifically binds to MET, e.g., human MET ECD (SEQ ID NO:190). In a particular embodiment, the antibody comprises VL CDRs that are identical to the VL CDRs of antibody Ab246 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab246 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 64, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab246 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 52, and (ii) a VH domain having at least 80%, at least 85%, at least 90%, at least 95%, or at least 98% sequence identity to the amino acid sequence of SEQ ID NO: 64, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab246 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 53, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 53, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab247 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 53, wherein the antibody immunospecifically binds to MET, e.g., human MET ECD (SEQ ID NO:190). In a particular embodiment, the antibody comprises VL CDRs that are identical to the VL CDRs of antibody Ab247 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab247 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 64, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab247 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 53, and (ii) a VH domain having at least 80%, at least 85%, at least 90%, at least 95%, or at least 98% sequence identity to the amino acid sequence of SEQ ID NO: 64, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab247 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 54, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 54, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab248 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 54, wherein the antibody immunospecifically binds to MET, e.g., human MET ECD (SEQ ID NO:190). In a particular embodiment, the antibody comprises VL CDRs that are identical to the VL CDRs of antibody Ab248 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab248 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 64, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab248 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 54, and (ii) a VH domain having at least 80%, at least 85%, at least 90%, at least 95%, or at least 98% sequence identity to the amino acid sequence of SEQ ID NO: 64, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab248 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 55, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 55, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab249 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 55, wherein the antibody immunospecifically binds to MET, e.g., human MET ECD (SEQ ID NO:190). In a particular embodiment, the antibody comprises VL CDRs that are identical to the VL CDRs of antibody Ab249 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab249 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 64, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab249 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 55, and (ii) a VH domain having at least 80%, at least 85%, at least 90%, at least 95%, or at least 98% sequence identity to the amino acid sequence of SEQ ID NO: 64, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab249 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 56, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 56, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab250 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 56, wherein the antibody immunospecifically binds to MET, e.g., human MET ECD (SEQ ID NO:190). In a particular embodiment, the antibody comprises VL CDRs that are identical to the VL CDRs of antibody Ab250 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 64, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab250 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 64, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab250 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 56, and (ii) a VH domain having at least 80%, at least 85%, at least 90%, at least 95%, or at least 98% sequence identity to the amino acid sequence of SEQ ID NO: 64, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab250 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 52, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 52, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab251 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 52, wherein the antibody immunospecifically binds to MET, e.g., human MET ECD (SEQ ID NO:190). In a particular embodiment, the antibody comprises VL CDRs that are identical to the VL CDRs of antibody Ab251 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab251 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 65, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab251 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 52, and (ii) a VH domain having at least 80%, at least 85%, at least 90%, at least 95%, or at least 98% sequence identity to the amino acid sequence of SEQ ID NO: 65, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab251 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 53, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 53, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab252 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 53, wherein the antibody immunospecifically binds to MET, e.g., human MET ECD (SEQ ID NO:190). In a particular embodiment, the antibody comprises VL CDRs that are identical to the VL CDRs of antibody Ab252 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab252 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 65, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab252 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 53, and (ii) a VH domain having at least 80%, at least 85%, at least 90%, at least 95%, or at least 98% sequence identity to the amino acid sequence of SEQ ID NO: 65, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab252 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 54, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 54, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab253 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 54, wherein the antibody immunospecifically binds to MET, e.g., human MET ECD (SEQ ID NO:190). In a particular embodiment, the antibody comprises VL CDRs that are identical to the VL CDRs of antibody Ab253 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab253 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 65, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab253 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 54, and (ii) a VH domain having at least 80%, at least 85%, at least 90%, at least 95%, or at least 98% sequence identity to the amino acid sequence of SEQ ID NO: 65, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab253 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 55, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 55, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab254 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 55, wherein the antibody immunospecifically binds to MET, e.g., human MET ECD (SEQ ID NO:190). In a particular embodiment, the antibody comprises VL CDRs that are identical to the VL CDRs of antibody Ab254 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab254 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 65, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab254 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 55, and (ii) a VH domain having at least 80%, at least 85%, at least 90%, at least 95%, or at least 98% sequence identity to the amino acid sequence of SEQ ID NO: 65, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab254 (e.g., as set forth in Tables 1 and 2, Tables 5 and 6, or Tables 7 and 8).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 56, wherein the antibody immunospecifically binds to MET, e.g., human MET ECD (SEQ ID NO:190). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 56, wherein the antibody immunospecifically binds to MET, e.g., human MET ECD (SEQ ID NO:190), and wherein the antibody comprises CDRs (e.g., VL CDRs 1-3) that are identical to the CDRs (e.g., VL CDRs 1-3) of antibody Ab255 (e.g., as set forth in Table 1, Table 5, or Table 7).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 56, wherein the antibody immunospecifically binds to MET, e.g., human MET ECD (SEQ ID NO:190). In a particular embodiment, the antibody comprises VL CDRs that are identical to the VL CDRs of antibody Ab255 (e.g., as set forth in Table 1, Table 5, or Table 7).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65 wherein the antibody immunospecifically binds to MET, e.g., human MET ECD (SEQ ID NO:190). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 65, wherein the antibody immunospecifically binds to MET, e.g., human MET ECD (SEQ ID NO:190), and wherein the antibody comprises CDRs (e.g., VH CDRs 1-3) that are identical to the CDRs (e.g., VH CDRs 1-3) of antibody Ab255 (e.g., as set forth in Table 2, Table 6, or Table 8).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 65, wherein the antibody immunospecifically binds to MET, e.g., human MET ECD (SEQ ID NO:190). In specific embodiments, such an antibody comprises CDRs (e.g., VH CDRs 1-3) identical to the CDRs (e.g., VH CDRs 1-3) of antibody Ab255 (e.g., as set forth in Table 2, Table 6, or Table 8).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 56, and (ii) a VH domain having at least 80%, at least 85%, at least 90%, at least 95%, or at least 98% sequence identity to the amino acid sequence of SEQ ID NO: 65, respectively, wherein the antibody immunospecifically binds to MET, e.g., human MET ECD (SEQ ID NO:190). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab255 (e.g., as set forth in Tables 1 and 2, Tables 5 and 6, or Tables 7 and 8).

Also provided herein are antibodies that bind the same or an overlapping epitope of MET (e.g., an epitope located in an ECD of human MET, such as in a Sema domain or Sema/PSI domain) as an antibody described herein (e.g., antibody Ab235, Ab236, Ab237, Ab238, Ab239, Ab240, Ab241, Ab242, Ab243, Ab244, Ab245, Ab246, Ab247, Ab248, Ab249, Ab250, Ab251, Ab252, Ab253, Ab254, or Ab255), for example, antibodies that compete (e.g., in a dose dependent manner) for binding to MET (e.g., an ECD of human MET) with an antibody described herein (e.g., antibody Ab235, Ab236, Ab237, Ab238, Ab239, Ab240, Ab241, Ab242, Ab243, Ab244, Ab245, Ab246, Ab247, Ab248, Ab249, Ab250, Ab251, Ab252, Ab253, Ab254, or Ab255), or that competitively inhibit (e.g., in a dose dependent manner) an antibody described herein (e.g., antibody Ab235, Ab236, Ab237, Ab238, Ab239, Ab240, Ab241, Ab242, Ab243, Ab244, Ab245, Ab246, Ab247, Ab248, Ab249, Ab250, Ab251, Ab252, Ab253, Ab254, or Ab255) from binding to MET (e.g., an epitope located on the ECD of human MET). In certain embodiments, provided herein are antibodies that bind to one or more of amino acid residues Q328, R331, S336, L337, and N338 of human MET.

In a specific aspect, also provided herein are antibodies that bind the same or an overlapping epitope of MET (e.g., an epitope located in an ECD of human MET, such as in a Sema domain or Sema/PSI domain) as any one of antibody Ab235, Ab236, Ab237, Ab239, Ab241, Ab242, Ab243, Ab244, Ab245, Ab246, Ab247, Ab248, Ab249, Ab250, Ab251, Ab252, Ab253, Ab254, or Ab255, and is capable of inhibiting (e.g., partially inhibiting) phosphorylation of MET and of inhibiting (e.g., partially inhibiting) tumor cell proliferation or tumor growth better as an $IgG_2$ isotype as compared to as an $IgG_1$ isotype. In certain embodiments, provided herein are antibodies that bind to one or more of amino acid residues Q328, R331, S336, L337, and N338 of human MET.

Antibodies that bind to the same or overlapping epitopes of MET (e.g., an epitope located in an ECD of human MET such as in a Sema domain or Sema/PSI domain) can be identified using routine techniques such as those utilized in the examples presented herein. An immunoassay, for example, used to demonstrate the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as MET. Numerous types of competitive binding assays are known, for example: solid phase direct or indirect radioimmunoassay (RIA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using 1-125 label (see Morel et al., (1988) Mol. Immunol. 25(1):7); solid phase direct biotin-avidin EIA (Cheung et al., (1990) Virology 176:546); and direct labeled RIA. (Moldenhauer et al., (1990) Scand J. Immunol. 32:77). Typically, such an assay involves the use of purified antigen (e.g., MET, such as an ECD of human MET) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538; Kuroki et al., Hybridoma, 1992, 11:391-407, and *Using Antibodies: A Laboratory Manual*, Ed Harlow and David Lane editors (Cold Springs Harbor Laboratory Press, Cold Springs Harbor, N.Y., 1999), pp. 386-389.

In certain aspects, competition binding assays can be used to determine whether binding of an antibody is competitively inhibited, e.g., in a dose dependent manner, by another antibody, thereby signaling that the antibodies bind essentially the same epitope, or overlapping epitopes, e.g., sterically overlapping epitopes. Such competition binding assays can include, for example, competition ELISA assays, which can be configured in all number of different formats, using either labeled antigen or labeled antibody. In a particular embodiment, an antibody can be tested in competition binding assays with an antibody described herein, e.g., antibody Ab235, Ab236, Ab237, Ab238, Ab239, Ab240, Ab241, Ab242, Ab243, Ab244, Ab245, Ab246, Ab247, Ab248, Ab249, Ab250, Ab251, Ab252, Ab253, Ab254, or Ab255, or a chimeric or Fab antibody thereof, or an antibody comprising VH CDRs and VL CDRs of any of antibodies Ab235-Ab255.

In specific aspects, provided herein is an antibody which competitively blocks (e.g., in a dose dependent manner) binding of antibodies comprising the amino acid sequences described herein for specific binding to a MET polypeptide (e.g., an ECD of MET, for example human MET), as determined using assays known to one of skill in the art or described herein (e.g., ELISA competitive assays). In particular embodiments, such a competitively blocking antibody inhibits one or more MET activities. In specific aspects, provided herein is an antibody which competes (e.g., in a dose dependent manner) for specific binding to a MET polypeptide (e.g., an ECD of MET, for example human MET), with an antibody comprising the amino acid sequences described herein (e.g., VL and/or VH amino acid sequences of antibody Ab235, Ab236, Ab237, Ab238, Ab239, Ab240, Ab241, Ab242, Ab243, Ab244, Ab245, Ab246, Ab247, Ab248, Ab249, Ab250, Ab251, Ab252, Ab253, Ab254, or Ab255 (see, e.g., SEQ ID NOS: 52-71), as determined using assays known to one of skill in the art or described herein (e.g., ELISA competitive assays).

In specific aspects, provided herein is an antibody which competes (e.g., in a dose dependent manner) for specific binding to a MET polypeptide (e.g., an ECD of MET, for example human MET), with any one of antibodies Ab235-Ab255.

In specific aspects, provided herein is an antibody which competes (e.g., in a dose dependent manner) for specific binding to a MET polypeptide (e.g., an ECD of MET, for example human MET), with an antibody comprising a VL chain region having the amino acid sequence of SEQ ID NO: 52, 53, 54, 55, 56, 57, 58, 59, 60, 61, or 62, and a VH chain region having the amino acid sequence of SEQ ID NO: 62, 63, 64, 65, 66, 67, 68, 69, 70, or 71.

In a specific aspect, also provided herein are antibodies (i) that compete (e.g., in a dose dependent manner) for specific binding to an epitope of a MET polypeptide (e.g., an epitope of an ECD of human MET, such as of a Sema domain or Sema/PSI domain), with any one of antibody Ab235, Ab236, Ab237, Ab239, Ab241, Ab242, Ab243, Ab244, Ab245, Ab246, Ab247, Ab248, Ab249, Ab250, Ab251, Ab252, Ab253, Ab254, or Ab255, and (ii) that are capable of inhibiting (e.g., partially inhibiting) phosphorylation of MET and of inhibiting (e.g., partially inhibiting) tumor cell proliferation or tumor growth, better as an $IgG_2$ isotype as compared to as an $IgG_1$ isotype. In a specific aspect, also provided herein are antibodies (i) that compete (e.g., in a dose dependent manner) for specific binding to an epitope of a MET polypeptide (e.g., an epitope of an ECD of human MET, such as of a Sema domain or Sema/PSI domain), with any one of antibody Ab235, Ab236, Ab237, Ab239, Ab241, Ab242, Ab243, Ab244, Ab245, Ab246, Ab247, Ab248, Ab249, Ab250, Ab251, Ab252, Ab253, Ab254, or Ab255, and (ii) that are capable of inhibiting (e.g., partially inhibiting) phosphorylation of MET and of inhibiting (e.g., partially inhibiting) tumor cell proliferation or tumor growth, such as, for example, a xenograft tumor model (e.g., A549 cells, U87MG cells, Hop92 cells, H596 cells, EBC-1 cells, and SNU-5 cells), better as an $IgG_2$ isotype as compared to as an $IgG_1$ isotype.

In a specific embodiment, an antibody described herein is one that is competitively blocked (e.g., in a dose dependent manner) by an antibody that specifically binds MET and comprises a VL chain region having the amino acid sequence of SEQ ID NO: 52, 53, 54, 55, 56, 57, 58, 59, 60, 61, or 62, and a VH chain region having the amino acid sequence of SEQ ID NO: 62, 63, 64, 65, 66, 67, 68, 69, 70, or 71, for specific binding to a MET polypeptide (e.g., an ECD of MET, for example human MET).

In a specific aspect, also provided herein are antibodies (i) that competitively block (e.g., in a dose dependent manner) any one of antibody Ab235, Ab236, Ab237, Ab239, Ab241, Ab242, Ab243, Ab244, Ab245, Ab246, Ab247, Ab248, Ab249, Ab250, Ab251, Ab252, Ab253, Ab254, or Ab255, for specific binding to an epitope of a MET polypeptide (e.g., an epitope of an ECD of human MET, such as of a Sema domain or Sema/PSI domain), and (ii) that are capable of inhibiting (e.g., partially inhibiting) phosphorylation of MET and of inhibiting (e.g., partially inhibiting) tumor cell proliferation or tumor growth, better as an $IgG_2$ isotype as compared to as an $IgG_1$ isotype.

In specific aspects, provided herein is an antibody, or an antigen-binding fragment thereof, which immunospecifically binds the same epitope as that of an antibody (e.g., any one of antibodies Ab235-Ab255) comprising the amino acid sequences described herein (see, e.g., Tables 1-8) for specific binding to a MET polypeptide (e.g., an ECD of MET, for example human MET, such as of a Sema domain or Sema/PSI domain). Assays known to one of skill in the art or described herein (e.g., ELISA assays) can be used to determine if two antibodies bind to the same epitope.

In a specific embodiment, an antibody described herein, or an antigen-binding fragment thereof, immunospecifically binds to the same epitope as that of an antibody that specifically binds MET (e.g., any one of antibodies Ab235-Ab255) and comprises a VL chain region having the amino acid sequence of SEQ ID NO: 52, 53, 54, 55, 56, 57, 58, 59, 60, 61, or 62, and a VH chain region having the amino acid sequence of SEQ ID NO: 62, 63, 64, 65, 66, 67, 68, 69, 70, or 71.

In a specific aspect, also provided herein are antibodies (i) that immunospecifically binds the same epitope of a MET polypeptide (e.g., an epitope of an ECD of human MET, such as of a Sema domain or Sema/PSI domain) as that of antibody Ab235, Ab236, Ab237, Ab239, Ab241, Ab242, Ab243, Ab244, Ab245, Ab246, Ab247, Ab248, Ab249, Ab250, Ab251, Ab252, Ab253, Ab254, or Ab255; and (ii) that are capable of inhibiting (e.g., partially inhibiting) phosphorylation of MET and of inhibiting (e.g., partially inhibiting) tumor cell proliferation or tumor growth, better as an $IgG_2$ isotype as compared to as an $IgG_1$ isotype.

In one aspect, provided herein are antibodies that immunospecifically bind to MET (e.g., an ECD of human MET or a Sema domain in an ECD of human MET) and that can modulate MET activity and/or expression (e.g., inhibit MET activity and/or expression. In certain aspects, said antibodies modulate ligand-dependent MET activity. In certain aspects, said antibodies modulate MET-amplified (e.g., ligand-independent) MET activity. In certain embodiments, a MET antagonist is provided herein that is an antibody described herein that immunospecifically binds to an ECD of human MET, e.g., a Sema domain of an ECD of human MET, and that inhibits (e.g., partially inhibits) at least one MET activity (e.g., MET phosphorylation or MET signaling). In certain embodiments, a MET antagonist provided herein is an antibody described herein that immunospecifically binds to an ECD of human MET, e.g., a Sema or PSI domain of an ECD of human MET, and that inhibits or decreases/reduces MET expression. In certain embodiments, provided herein are antibodies that immunospecifically bind to MET (e.g., an ECD of human MET or a Sema/PSI domain in an ECD of human MET) and that (a) inhibit MET activity in a cell as determined by inhibition of phosphorylation of MET; (b) induce MET degradation in a cell; and (c) inhibit tumor cell proliferation or tumor growth. In certain embodiments, provided herein are antibodies that immunospecifically bind to MET (e.g., an ECD of human MET or a Sema/PSI domain in an ECD of human MET) and that (a) inhibit phosphorylation of MET; (b) induce MET degradation in a cell; (c) inhibit tumor cell proliferation or tumor growth; and/or (d) inhibit ligand binding to MET. In certain embodiments, provided herein are antibodies that immunospecifically bind to MET (e.g., an ECD of human MET or a Sema/PSI domain in an ECD of human MET) and that (a) induce MET degradation in a cell (e.g., cell with MET amplification or MET mutation); and (b) inhibit ligand binding to MET (e.g., in cells expressing wild-type MET). In certain embodiments, provided herein are antibodies that immunospecifically bind to MET (e.g., an ECD of human MET or a Sema/PSI domain in an ECD of human MET) and that (a) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as IgG$_1$ isotypes; and (b) inhibit ligand binding. In certain embodiments, provided herein are antibodies that immunospecifically bind to MET (e.g., an ECD of human MET or a Sema/PSI domain in an ECD of human MET) and that (a) have increased MET antagonistic activities as IgG$_2$ isotypes (e.g., human IgG$_2$, human IgG$_{2a}$, human IgG$_{2b}$, or a mixture thereof) as compared to the antibodies (e.g., Ab235, Ab236, Ab237, Ab239, and Ab241-Ab255) as IgG$_1$ isotypes; and (b) induces receptor degradation.

In certain embodiments, provided herein are antibodies that immunospecifically bind to MET (e.g., an ECD of human MET or a Sema/PSI domain in an ECD of human MET) and that (a) inhibit phosphorylation of MET; (b) induce MET degradation in a cell; (c) inhibit tumor cell proliferation or tumor growth; and/or (d) inhibit ligand binding to MET, better as an IgG$_2$ (e.g., human IgG$_2$) isotype as compared to as an IgG$_1$ (e.g., human IgG$_1$) isotype. In specific embodiments, an anti-MET antibody provided herein exhibits better MET antagonistic activity (e.g., blocking MET phosphorylation, inducing MET degradation, or inhibiting tumor cell proliferation or tumor growth) as a human IgG$_2$ isotype than a human IgG$_1$ isotype in cells (e.g., EBC-1 cells and SNU-5 cells) having ligand-independent MET activity, for example, cells having MET amplification or a constitutively active MET mutant.

MET activity can relate to any activity of MET such as those known or described in the art. Non-limiting examples of MET activity include: MET receptor dimerization, MET receptor heterodimerization with other receptors (e.g., EGFR, HER2, HER3, or RET), MET receptor phosphorylation (e.g., tyrosine phosphorylation (such as MET ligand-dependent phosphorylation) or autophosphorylation in the cytoplasmic domain), signaling downstream of the MET receptor (e.g., SHC, Grb2, Stat3, Src, Gab 1, PLC-g, p85, PI3K, Crk/CRKL, AKT, Ras, or MAPK/ERK signaling), cell proliferation such as MET ligand (e.g., HGF) induced enhancement of cell proliferation (e.g., cancer cell proliferation), or cell survival (e.g., cancer cells), MET ligand (e.g., HGF) induced anti-apoptosis. MET activity or MET function are used interchangeably herein. In certain aspects, MET activity is induced by MET ligand (e.g., HGF) binding to MET receptor. In certain embodiments, an increase in MET activity or signaling can occur, in the absence of MET ligand (e.g., HGF) binding MET receptor, due to high (or overexpression) expression of MET receptors. High or overexpression of MET in a cell refers to an expression level which is at least about 10%, 20%, 30%, 40%, 50%, 60%, 70%, 80%, 90%, 100%, 150%, 200%, 250%, 300%, 400%, or 500% more than the expression level of a reference cell known to have normal MET expression or MET activity or more than the average expression level of MET in a population of cells or samples known to have normal MET expression or MET activity. Expression levels of MET can be assessed by methods described herein or known to one of skill in the art (e.g., Western blotting, ELISA, or immunohistochemistry). In certain embodiments, provided herein are antibodies that immunospecifically bind to MET (e.g., an ECD of human MET or a Sema/PSI domain in an ECD of human MET) and decrease MET expression. In certain embodiments, provided herein are antibodies that immunospecifically bind to MET (e.g., an ECD of human MET or a Sema/PSI domain in an ECD of human MET) and induce ubiquitination of MET. In certain embodiments, provided herein are antibodies that immunospecifically bind to MET (e.g., an ECD of human MET or a Sema/PSI domain in an ECD of human MET) and induce MET degradation or turnover. In certain embodiments, provided herein are antibodies that immunospecifically bind to MET (e.g., an ECD of human MET or a Sema/PSI domain in an ECD of human MET) and block (e.g., partially block) MET ligand-dependent and MET-amplified (e.g., ligand-independent) MET signaling. Without being bound by any theory, ligand-independent MET activation is may involve association of MET with membrane-spanning proteins, such as, for example integrin activation, plexins, CD44, G protein coupled receptors and other receptor tyrosine kinases, such as, for example, EGFR and RET (see, e.g., Varkaris et al., 2013, Int. J. Cancer, 133(7):1536-1546).

In certain embodiments, anti-MET antibodies provided herein (e.g., Ab235, Ab236, Ab237, Ab239, and Ab241-Ab255) have increased MET antagonistic activities as IgG$_2$ isotypes (e.g., human IgG$_2$, human IgG$_{2a}$, human IgG$_{2b}$, or a mixture thereof) as compared to the antibodies (e.g., Ab235, Ab236, Ab237, Ab239, and Ab241-Ab255) as IgG$_1$ isotypes. Without being bound by any theory, the IgG$_2$ isotype (e.g., human IgG$_2$, human IgG$_{2a}$, and human IgG$_{2b}$ or a mixture thereof) may provide an enhanced alteration in distance or positioning of MET kinase dimer, allowing for enhanced antagonistic properties against MET activity (e.g., ligand-dependent and/or MET-amplified (e.g., ligand-independent) MET activity).

In particular embodiments, anti-MET antibodies provided herein (e.g., Ab235-Ab255) do not have agonist activities. In certain embodiments, anti-MET antibodies provided herein (e.g., Ab235-Ab255) have low agonist activities. Identification of agonist activities is performed by assays known to one of ordinary skill in the art, such as, e.g., cell proliferation and cell scatter assays, ELISA or immunoblot assays to assess phosphorylation of MET or the activity of downstream MET signaling components, such as, for example, MAPK and/or AKT.

In specific embodiments, antibodies described herein specifically bind to an ECD of MET and block or inhibit (e.g., partially inhibit) binding of MET ligand (e.g., HGF) to MET by at least about 5%, 10%, 15%, 20%, 25%, 30%, 35%, 40%, 45%, 50%, 55%, 60%, 65%, 70%, 75%, 80%, 85%, 90%, 95%, 98%, or 100% as assessed by methods described herein or known to one of skill in the art, e.g., ELISA assay, flow cytometry, or competition assay.

In certain aspects, inhibition by anti-MET antibodies described herein (e.g., monoclonal antibody) of MET ligand (e.g., HGF) binding to MET can be characterized by IC$_{50}$ values, which reflects the concentration of anti-MET antibodies achieving 50% inhibition of binding of MET ligand to MET. Thus, in specific embodiments, an anti-MET antibody described herein (e.g., any one of antibodies Ab235-Ab255 or an antigen-binding fragment thereof, or an antibody comprising CDRs of any one of antibodies Ab235-Ab255) inhibits binding of MET ligand to MET with an IC$_{50}$ of at most about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 2 nM, 1 nM, 0.75 nM, 0.5 nM, 0.4 nM, 0.3 nM, 0.2 nM, 0.1 nM, 0.05 nM, 0.01 nM, 0.005 nM, or 0.001 nM, as assessed by methods described herein and/or known to one of skill in the art, (e.g., ELISA assay or flow cytometry). In specific embodiments, an anti-MET antibody described herein inhibits binding of MET ligand to MET with an IC$_{50}$ of at least about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 2 nM, 1 nM, 0.75 nM, 0.5 nM, 0.4 nM, 0.3 nM, 0.2 nM, 0.1 nM, 0.05 nM, 0.01 nM, 0.005 nM, or 0.001 nM, as assessed by methods described herein and/or known to one of skill in the art, (e.g., ELISA assay or flow cytometry). In particular embodiments, an anti-MET antibody described herein inhibits binding of MET ligand to MET with an $IC_{50}$ in the range of about 0.01 nM to 10 nM, 0.1 nM to 20 nM, 0.1 nM to 10 nM, 0.1 nM to 5 nM, or 0.01 nM to 20 nM, as assessed by methods described herein and/or known to one of skill in the art, (e.g., ELISA assay or flow cytometry).

In certain embodiments, provided herein are antibodies that immunospecifically bind to MET (e.g., an ECD of human MET or a Sema/PSI domain in an ECD of human MET) and that (a) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes; and (b) inhibit ligand binding. In certain embodiments, anti-MET antibodies provided herein (e.g., Ab235, Ab236, Ab237, Ab239, and Ab241-Ab255) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes. Without being bound by any theory, the $IgG_2$ isotype (e.g., human $IgG_2$, human $IgG_{2a}$, human $IgG_{2b}$, or a mixture thereof) may provide an enhanced alteration in distance or positioning of MET kinase dimer, allowing for enhanced anti-MET activity. In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) inhibits binding of MET ligand (e.g., HGF) to MET with a lower $IC_{50}$ as an $IgG_2$ isotype (e.g., human $IgG_2$, human $IgG_{2a}$, and human $IgG_{2b}$, or a mixture thereof) than as an $IgG_1$ isotype, as assessed by methods described herein and/or known to one of skill in the art, (e.g., ELISA assay or flow cytometry). In certain embodiments, the $IC_{50}$ of the $IgG_2$ isotype (e.g., human $IgG_2$, human $IgG_{2a}$, and human $IgG_{2b}$, or a mixture thereof) is between at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than the $IC_{50}$ of the $IgG_1$ isotype, as assessed by methods described herein and/or known to one of skill in the art, (e.g., ELISA assay or flow cytometry).

In certain embodiments, an anti-MET antibody described herein (e.g., any one of antibodies Ab235-Ab255 or an antigen-binding fragment thereof, or an antibody comprising CDRs of any one of antibodies Ab235-255) does not block or inhibit MET receptor dimerization. In certain embodiments, an anti-MET antibody described herein only negligibly (e.g., less than about 2% or 3% or within a standard of error or deviation) inhibits or reduces MET receptor dimerization. In certain embodiments, an anti-MET antibody described herein does not induce or enhance MET receptor dimer dissociation. In certain embodiments, an anti-MET antibody described herein only negligibly (e.g., less than about 2% or 3% or within a standard of error or deviation) induces or enhances MET receptor dimer dissociation. In a particular embodiment, an anti-MET antibody described herein can specifically bind to a MET receptor dimer and not block or inhibit MET receptor dimerization. In a particular embodiment, an anti-MET antibody described herein can specifically bind to a MET receptor monomer and not block or inhibit MET receptor dimerization. In certain embodiments, any such antibodies or antigen-binding fragments thereof inhibit ligand binding to MET.

In certain aspects, as an inhibitor of MET activity (e.g., MET antagonist), an antibody described herein (e.g., any one of antibodies Ab235-Ab255, or an antigen-binding fragment thereof, or an antibody comprising CDRs of any one of antibodies Ab235-Ab255) can block or inhibit (e.g., partially inhibit) dimerization of MET. Generally, MET receptor dimerization is induced when MET ligand binds to MET. Thus, in specific embodiments, antibodies described herein specifically bind to MET and block or inhibit (e.g., partially inhibit) dimerization of MET receptors by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoprecipitation assay, relative to dimerization of MET receptors in the presence of MET ligand stimulation without any antibody or with an unrelated antibody (e.g., an antibody that does not immunospecifically bind to MET). In a specific embodiment, antibodies described herein (e.g., any one of antibodies Ab235-Ab255 or an antigen-binding fragment thereof, or an antibody comprising CDRs of any one of antibodies Ab235-255) specifically bind to MET and partially inhibit dimerization of MET receptors by about 25% to 75%. Blocking or inhibition (e.g., partial inhibition) of dimerization of MET receptors by antibodies described herein can be assessed in the presences of MET ligand stimulation. For example, cells expressing MET can be contacted with MET ligand (e.g., HGF) in the presence or absence of anti-MET antibodies described herein, and the level of MET receptor dimerization is determined. In certain embodiments, MET ligand-induced MET receptor dimerization in the absence of anti-MET antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than MET receptor dimerization in the presence of anti-MET antibody provided herein as assessed by methods described herein or known to one of skill in the art (e.g., immunoprecipitation assays). Tyrosine phosphorylation of one or more residues in the cytoplasmic domain of MET can be an indicator of MET receptor dimerization.

In certain embodiments, anti-MET antibodies provided herein (e.g., Ab235, Ab236, Ab237, Ab239, and Ab241-Ab255) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes. Without being bound by any theory, the $IgG_2$ isotype (e.g., human $IgG_2$, human $IgG_{2a}$, and human $IgG_{2b}$, or a mixture thereof) may provide an enhanced alteration in distance or positioning of MET kinase dimer, allowing for enhanced anti-MET activity. In specific embodiments, MET ligand (e.g., HGF)-induced MET receptor dimerization in the presence of an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than MET receptor dimerization in the presence of anti-MET antibody provided herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as an $IgG_2$ isotype (e.g., human $IgG_2$, human $IgG_{2a}$, and human $IgG_{2b}$, or a mixture thereof) as assessed by methods described herein or known to one of skill in the art (e.g., immunoprecipitation assays).

In certain embodiments, an anti-MET antibody described herein can inhibit (e.g., partially inhibit) MET activity by at least about 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein and/or known to one of skill in the art, relative to MET activity in the presence of MET ligand stimulation without any antibody or with an unrelated antibody (e.g., an antibody that does not immunospecifically bind to MET). In certain embodiments, an anti-MET antibody described herein can inhibit (e.g., partially inhibit) MET activity by at least about 25% to about 65% as assessed by methods described herein and/or known to one of skill in the art, relative to MET activity in the presence of MET ligand stimulation without any antibody or with an unrelated antibody (e.g., an antibody that does not immunospecifically bind to MET). Non-limiting examples of MET activity can include, MET receptor dimerization, MET receptor heterodimerization with other receptors (e.g., EGFR, HER2, HER3, or RET), MET receptor phosphorylation (e.g., tyrosine phosphorylation or autophosphorylation in the cytoplasmic domain), signaling downstream of the MET receptor (e.g., SHC, Grb2, Stat3, Src, Gab 1, PLC-g, p85, PI3K, Crk/CRKL, AKT, Ras, or MAPK/ERK signaling), MET ligand (e.g., HGF) induced enhancement of cell proliferation, or cell survival, and MET ligand (e.g., HGF) induced anti-apoptosis. In certain embodiments, anti-MET antibodies provided herein (e.g., Ab235, Ab236, Ab237, Ab239, and Ab241-Ab255) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes. Without being bound by any theory, the $IgG_2$ isotype (e.g., human $IgG_2$, human $IgG_{2a}$, and human $IgG_{2b}$, or a mixture thereof) may provide an enhanced alteration in distance or positioning of MET kinase dimer, allowing for enhanced inhibition of MET activity. In certain embodiments, an anti-MET antibody described herein inhibits ligand-dependent MET activity. In certain embodiments, an anti-MET antibody described herein inhibits MET-amplified (e.g., ligand-independent) MET activity. In certain embodiments, an anti-MET antibody described herein inhibits ligand-dependent and MET-amplified (e.g., ligand-independent) MET activity.

As an inhibitor of MET activity (e.g., MET antagonist), an antibody described herein (e.g., any one of antibodies Ab235-Ab255, or an antigen-binding fragment thereof, or an antibody comprising CDRs of any one of antibodies Ab235-Ab255) can block (e.g., partially block) or inhibit (e.g., partially inhibit) phosphorylation of MET, specifically tyrosine phosphorylation of one or more residues in the cytoplasmic domain of MET. Generally, MET receptor dimerization and phosphorylation is induced when MET ligand (e.g. HGF) binds to MET. However, in certain aspects, MET receptor dimerization and/or phosphorylation can occur independently of MET ligand binding to MET receptor. For example MET receptor dimerization and/or phosphorylation can occur due to gain-of-function mutations or overexpression of MET.

Non-limiting examples of tyrosine residues in the cytoplasmic domain of human MET (e.g., GenBank Accession No. NP_001120972.1 and NP_000236.2) that can be phosphorylated, e.g., upon ligand stimulation, include residues 1003, 1234, 1235, 1349, and 1356 (see, e.g., Organ and Tsao, 2011, Ther. Adv. Med. Oncol., 391 Suppl): S7-S19, e.g., at FIG. 1). In a specific embodiment, an anti-MET antibody described herein can inhibit receptor phosphorylation at tyrosine residue 1234 and/or 1235 of human MET.

Thus, in specific embodiments, antibodies described herein (e.g., any one of antibodies Ab235-Ab255, or an antigen-binding fragment thereof, or an antibody comprising CDRs of any one of antibodies Ab235-Ab255) specifically bind to MET and block, inhibit, or reduce tyrosine phosphorylation in the cytoplasmic domain of MET by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, e.g., ELISA assay as described in Section 6 or immunoblotting assay, relative to phosphorylation in the presence of MET ligand stimulation without any antibody or with an unrelated antibody (e.g., an antibody that does not immunospecifically bind to MET). In particular embodiments, antibodies described herein specifically bind to MET and block or inhibit tyrosine phosphorylation in the cytoplasmic domain of MET by at least about 25%, optionally to about 65% or 75%, as assessed by methods described herein or known to one of skill in the art, e.g., ELISA assay as described in Section 6 or immunoblotting assay. In certain embodiments, antibodies described herein specifically bind to MET and block or inhibit tyrosine phosphorylation of the cytoplasmic domain of MET by at least about 25% to about 80% as assessed by methods described herein or known to one of skill in the art, e.g., ELISA assay as described in Section 6 or immunoblotting assay. In certain embodiments, antibodies described herein (e.g., any one of antibodies Ab235-Ab255, or an antigen-binding fragment thereof, or an antibody comprising CDRs of any one of antibodies Ab235-Ab255) specifically bind to MET and block or inhibit tyrosine phosphorylation of the cytoplasmic domain of MET by at least about 50% to about 80%, 90%, 95% or 100% as assessed by methods described herein or known to one of skill in the art, e.g., ELISA assay as described in Section 6 or immunoblotting assay. In specific embodiments, antibodies described herein specifically bind to MET and block or inhibit tyrosine phosphorylation of the cytoplasmic domain of MET with an $IC_{50}$ of less than about 400 pM or less than about 300 pM as assessed by methods described herein (e.g., phosphorylation inhibition assay with SNU-5 cells, A549 cells, and Hop92 cells expressing wild-type MET as described in Section 6 below) or known to one of skill in the art.

In specific embodiments, antibodies described herein specifically bind to MET and block or inhibit tyrosine phosphorylation of the cytoplasmic domain of MET with an $IC_{50}$ of less than about 200 pM. In specific embodiments, antibodies described herein specifically bind to MET and block or inhibit tyrosine phosphorylation of the cytoplasmic domain of MET with an $IC_{50}$ of less than about 150 pM. In specific embodiments, antibodies described herein specifically bind to MET and block or inhibit tyrosine phosphorylation of the cytoplasmic domain of MET with an $IC_{50}$ of less than about 50 pM. In specific embodiments, antibodies described herein specifically bind to MET and block or inhibit tyrosine phosphorylation of the cytoplasmic domain of MET with an $IC_{50}$ in the range of about 30 pM to about 300 pM, 100 pM to about 500 pM, about 25 pM to about 200 pM, about 40 pM to about 160 pM, about 50 pM to about 125 pM, or about 5 pM to about 100 pM. For example, an $IC_{50}$ for inhibition of tyrosine phosphorylation can be determined by assaying lysates from cells, e.g., SNU-5 cells, A549 cells, and Hop92 cells, recombinantly expressing MET, in ELISA which detects tyrosine phosphorylation, for example, as described in Section 6 below. In certain embodiments, cells, e.g., SNU-5 cells, A549 cells, and Hop92 cells, recombinantly expressing MET, are sorted, e.g., sorted to select for cells highly expressing MET, prior to use in the phosphorylation inhibition assays. In some embodiments, the cells are not sorted prior to use in the phosphorylation inhibition assays.

In specific embodiments, antibodies described herein (e.g., any one of antibodies Ab235-Ab255, or an antigen-binding fragment thereof or an antibody comprising CDRs of any one of antibodies Ab235-Ab255) specifically bind to MET and block or inhibit phosphorylation of one or more tyrosine residues in the cytoplasmic domain of MET by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, e.g., immunoblotting assay, relative to phosphorylation in the presence of MET ligand stimulation without any antibody or with an unrelated antibody (e.g., an antibody that does not immunospecifically bind to MET). In specific embodiments, blocking or inhibition (e.g., partial inhibition) of phosphorylation of one or more tyrosine residues of the cytoplasmic domain of MET by antibodies described herein can be assessed upon MET ligand stimulation. For example, cells expressing MET are contacted with MET ligand in the presence or absence of anti-MET antibodies described herein, and the level of phosphorylation of one or more tyrosine residues in the cytoplasmic domain of MET can be determined.

In certain embodiments, MET ligand induced phosphorylation of one or more tyrosine residues of the cytoplasmic domain of MET in the absence of anti-MET antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than MET ligand induced phosphorylation of one or more tyrosine residues of the cytoplasmic domain of MET in the presence of anti-MET antibody, as assessed by methods described herein or known to one of skill in the art (e.g., immunoblotting assays), relative to phosphorylation in the presence of MET ligand stimulation without any antibody or with an unrelated antibody (e.g., an antibody that does not immunospecifically bind to MET).

In certain embodiments, anti-MET antibodies provided herein (e.g., Ab235, Ab236, Ab237, Ab239, and Ab241-Ab255) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes. Without being bound by any theory, the $IgG_2$ isotype (e.g., human $IgG_2$, human $IgG_{2a}$, human $IgG_{2b}$, or a mixture thereof) may provide an enhanced alteration in distance or positioning of MET kinase dimer, allowing for enhanced anti-MET activity. In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) inhibits tyrosine phosphorylation of the cytoplasmic domain of MET with a lower $IC_{50}$ as an $IgG_2$ isotype (e.g., human $IgG_2$, human $IgG_{2a}$, and human $IgG_{2b}$, or a mixture thereof) than as an $IgG_1$ isotype, as assessed by methods described herein and/or known to one of skill in the art, (e.g., ELISA assay or immunoblot). In certain embodiments, the $IC_{50}$ of the $IgG_2$ isotype (e.g., human $IgG_2$, human $IgG_{2a}$, and human $IgG_{2b}$, or a mixture thereof) is between at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than the $IC_{50}$ of the $IgG_1$ isotype, as assessed by methods described herein and/or known to one of skill in the art, (e.g., ELISA assay or immunoblot). In certain embodiments, the $IC_{50}$ of the $IgG_2$ isotype (e.g., human $IgG_2$, human $IgG_{2a}$, and human $IgG_{2b}$, or a mixture thereof) is between at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than the $IC_{50}$ of the $IgG_1$ isotype, as assessed by methods described herein and/or known to one of skill in the art, (e.g., ELISA assay or immunoblot).

In certain embodiments, an anti-MET antibody described herein (e.g., any one of antibodies Ab235-Ab239 and Ab241-Ab255 or antigen-binding fragment thereof, or an antibody comprising CDRs of any one of antibodies Ab235-Ab255) inhibits tyrosine phosphorylation of the cytoplasmic domain of MET with a lower $IC_{50}$ as compared to the $IC_{50}$ for the inhibition of tyrosine phosphorylation of the cytoplasmic domain of MET mediated by a humanized anti-MET antibody that does not bind the SEMA domain ("anti-MET-1") or a bivalent, $IgG_4$ anti-MET antibody that binds to the SEMA domain ("anti-MET-2"). In certain embodiments, the $IC_{50}$ of the anti-MET antibody described herein is about between at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than the $IC_{50}$ of the anti-MET-1 or anti-MET-2 antibody. In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) inhibits tyrosine phosphorylation of the cytoplasmic domain of MET (e.g., in a cell, such as, for example, a SNU-5 cell, an EBC-1 cell, an A549 cell, a U87MG cell, a H596 cell, a Hop92 cell, or in a tumor cell) as an $IgG_2$ with a maximal percent inhibition of at least about 40%, 45%, 50%, 55%, 60%, 65%, 70%, 75%, 80%, 85%, 90%, 95%, or 100%.

In specific embodiments, antibodies described herein specifically bind to MET and induce or enhance MET receptor degradation (e.g., in a cell, such as, for example, SNU-5 cell, an A549 cell, a U87MG cell, a H596 cell, a Hop92 cell, or in a tumor cell) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to degradation in the absence of antibody or in the presence of an unrelated antibody (e.g., an antibody that does not immunospecifically bind to MET). In specific embodiments, antibodies described herein specifically bind to MET and induce or enhance MET receptor degradation by at least about 25% or 35%, optionally to about 75%, as assessed by methods described herein or known to one of skill in the art (e.g., pulse-chase assays), relative to degradation in the absence of antibody or in the presence of an unrelated antibody (e.g., an antibody that does not immunospecifically bind to MET). In specific embodiments, antibodies described herein specifically bind to MET and induce or enhance MET receptor degradation (e.g., in a cell, such as, for example, SNU-5 cell, an A549 cell, a U87MG cell, a H596 cell, a Hop92 cell, or in a tumor cell) by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to degradation in the absence of antibody or in the presence of an unrelated antibody (e.g., an antibody that does not immunospecifically bind to MET).

In certain embodiments, provided herein are antibodies that immunospecifically bind to MET (e.g., an ECD of human MET or a Sema/PSI domain in an ECD of human MET) and that (a) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes; and (b) induces receptor degradation. In certain embodiments, anti-MET antibodies provided herein (e.g., Ab235, Ab236, Ab237, Ab239, and Ab241-Ab255) have increased MET antagonistic activities as $IgG_2$ isotypes (e.g., human $IgG_2$, human $IgG_{2a}$, human $IgG_{2b}$, or a mixture thereof) as compared to the antibodies (e.g., Ab235, Ab236, Ab237, Ab239, and Ab241-Ab255) as $IgG_1$ isotypes. Without being bound by any theory, the $IgG_2$ isotype (e.g., human $IgG_2$, human $IgG_{2a}$, and human $IgG_{2b}$, or a mixture thereof) may provide an enhanced alteration in distance or positioning of MET kinase dimer, allowing for enhanced anti-MET activity. In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) induces or enhances MET receptor degradation (e.g., in a cell, such as, for example, SNU-5 cell, an A549 cell, a U87MG cell, a H596 cell, a Hop92 cell, or in a tumor cell) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than MET receptor degradation, in the presence of the anti-MET antibody or antigen-binding fragment thereof, as an $IgG_2$ isotype (e.g., human $IgG_2$, human $IgG_{2a}$, and human $IgG_{2b}$, or a mixture thereof) as assessed by methods described herein or known to one of skill in the art (e.g., pulse-chase assays or immunoblot assays). In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) induces or enhances MET receptor degradation (e.g., in a cell, such as, for example, a SNU-5 cell, an EBC-1 cell, an A549 cell, a U87MG cell, a H596 cell, a Hop92 cell, or in a tumor cell) as an $IgG_2$ with a maximal percent induction/enhancement of at least about 40%, 45%, 50%, 55%, 60%, 65%, 70%, 75%, 80%, 85%, 90%, 95%, or 100%.

In specific embodiments, antibodies described herein specifically bind to MET and induce or enhance MET receptor ubiquitination (e.g., in a cell, such as, for example, SNU-5 cell, an A549 cell, a U87MG cell, a H596 cell, a Hop92 cell, or in a tumor cell) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., immunoprecipitation and immunoblot assays), relative to ubiquitination in the absence of antibody or in the presence of an unrelated antibody (e.g., an antibody that does not immunospecifically bind to MET). In specific embodiments, antibodies described herein specifically bind to MET and induce or enhance MET receptor ubiquitination by at least about 25% or 35%, optionally to about 75%, as assessed by methods described herein or known to one of skill in the art (e.g., immunoprecipitation and immunoblot assays), relative to ubiquitination in the absence of antibody or in the presence of an unrelated antibody (e.g., an antibody that does not immunospecifically bind to MET). In specific embodiments, antibodies described herein specifically bind to MET and induce or enhance MET receptor ubiquitination (e.g., in a cell, such as, for example, SNU-5 cell, an A549 cell, a U87MG cell, a H596 cell, a Hop92 cell, or in a tumor cell) by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to ubiquitination in the absence of antibody or in the presence of an unrelated antibody (e.g., an antibody that does not immunospecifically bind to MET).

In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) induces or enhances MET receptor ubiquitination (e.g., in a cell, such as, for example, SNU-5 cell, an A549 cell, a U87MG cell, a H596 cell, a Hop92 cell, or in a tumor cell) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than MET receptor ubiquitination in the absence of antibody or in the presence of the anti-MET antibody or antigen-binding fragment thereof, as an $IgG_2$ isotype (e.g., human $IgG_2$, human $IgG_{2a}$, and human $IgG_{2b}$, or a mixture thereof) as assessed by methods described herein or known to one of skill in the art (e.g., pulse-chase assays or immunoblot assays).

Techniques for quantitating or monitoring ubiquitination and/or degradation (e.g., kinetics or rate of degradation) of cell surface receptors are well known in the art and can involve a variety of fluorescent and radioactive techniques (see, e.g., International Patent Application Publication No. WO 2008/153926 A2). For example, pulse chase experiments or experiments using radiolabeled ligands such as $^{125}$I-HGF can be carried out to quantitatively measure degradation of MET. Alternatively, MET degradation can be analyzed by western blot or ELISA analysis, see, for example, Section 6.

In specific embodiments, antibodies described herein specifically bind to MET and induce or enhance MET receptor internalization (e.g., in a cell, such as, for example, SNU-5 cell, an A549 cell, a U87MG cell, a H596 cell, a Hop92 cell, or in a tumor cell) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to internalization in the absence of antibody or in the presence of an unrelated antibody (e.g., an antibody that does not immunospecifically bind to MET). In specific embodiments, antibodies described herein specifically bind to MET and induce or enhance MET receptor internalization by at least about 25% or 35%, optionally to about 75%, as assessed by methods described herein or known to one of skill in the art (e.g., pulse-chase assays), relative to internalization in the presence of an unrelated antibody (e.g., an antibody that does not immunospecifically bind to MET). In specific embodiments, antibodies described herein specifically bind to MET and induce or enhance MET receptor internalization (e.g., in a cell, such as, for example, SNU-5 cell, an A549 cell, a U87MG cell, a H596 cell, a Hop92 cell, or in a tumor cell) by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to internalization in the absence of antibody or in the presence of an unrelated antibody (e.g., an antibody that does not immunospecifically bind to MET).

In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) induces or enhances MET receptor internalization (e.g., in a cell, such as, for example, SNU-5 cell, an A549 cell, a U87MG cell, a H596 cell, a Hop92 cell, or in a tumor cell) as human IgG$_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than MET receptor internalization in the presence of anti-MET antibody provided herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as a human IgG$_2$ isotype (e.g., human IgG$_2$, human IgG$_{2a}$, and human IgG$_{2b}$, or a mixture thereof) as assessed by methods described herein or known to one of skill in the art (e.g., flow cytometry, pulse-chase assays or immunoblot assays).

Techniques for quantitating or monitoring receptor internalization (e.g., kinetics or rate of internalization) of cell surface receptors are well known in the art and may involve, for example, a variety of fluorescent and radioactive techniques (see, e.g., International Patent Application Publication No. WO 2008/153926 A2). For example, pulse chase experiments or experiments using radiolabeled ligands such as $^{125}$I-HGF can be carried out to quantitatively measure internalization of MET.

Moreover, signaling events downstream of MET receptor phosphorylation can serve as indicators of MET activity. For example, MET ligand (e.g., HGF) binding to its receptor MET stimulates several distinct signaling pathways, including for example members of phosphatidylinositol (PI) 3-kinases, and mitogen-activated protein kinase (MAPK) (see Trusolino et al., Nat. Rev. Mol. Cell Biol., 2010, 11:834-848). Phosphorylated tyrosines in the cytoplasmic domain of MET can provide for binding sites for, for example, PI3K and Grb2.

Thus, in certain aspects, anti-MET antibodies described herein which act as inhibitors of MET activity (e.g., any one of antibodies Ab235-Ab255, or an antigen-binding fragment thereof or an antibody comprising CDRs of any one of antibodies Ab235-Ab255) can inhibit signaling of a member of the PI3K-Akt, STAT, NFκB or MAPK pathway kinases. In particular embodiments, anti-MET antibodies described herein which act as inhibitors of MET activity can inhibit binding (or inhibit interaction) to the cytoplasmic domain of MET, and/or to one or more members of the PI3K-Akt, STAT, NFκB or MAPK pathway kinases. In certain embodiments, anti-MET antibodies described herein which act as inhibitors of MET activity can inhibit activation by MET of one or more members of the PI3K-Akt, STAT, NFκB or MAPK pathway kinases. In certain embodiments, anti-MET antibodies described herein which act as inhibitors of MET activity can inhibit phosphorylation (e.g., tyrosine phosphorylation in the cytoplasmic domain) of one or more members of the PI3K-Akt, STAT, NFκB or MAPK pathway kinases.

In particular embodiments, anti-MET antibodies described herein which act as inhibitors of MET activity (e.g., any one of antibodies Ab235-Ab255, or an antigen-binding fragment thereof or an antibody comprising CDRs of any one of antibodies Ab235-Ab255) can inhibit downstream signaling such as, for example, phosphorylation of MAPK, phosphorylation of PI3K, or phosphorylation of AKT. Thus, in certain embodiments, an anti-MET antibody described herein can inhibit or reduce phosphorylation of MAPK (e.g., MET ligand (e.g., HGF) induced phosphorylation of MAPK) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in Section 6 or immunoblotting assay, relative to phosphorylation in the presence of MET ligand stimulation without any antibody or with an unrelated antibody (e.g., an antibody that does not immunospecifically bind to MET). In certain embodiments, an anti-MET antibody described herein can inhibit or reduce phosphorylation of AKT (e.g., MET ligand (e.g., HGF) induced phosphorylation of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in Section 6 or immunoblotting assay, relative to phosphorylation in the presence of MET ligand stimulation without any antibody or with an unrelated antibody (e.g., an antibody that does not immunospecifically bind to MET).

In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) can inhibit downstream signaling, such as, for example, signaling of a member of the PI3K-Akt, STAT, NFκB or MAPK pathway kinases, as an IgG$_2$ isotype (e.g., human IgG$_2$, human IgG$_{2a}$, human IgG$_{2b}$, or a mixture thereof) at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold greater than such downstream signaling in the absence of antibody or in the presence of anti-MET antibody or antigen-binding fragment thereof, as an IgG$_1$ isotype as assessed by methods described herein or known to one of skill in the art (e.g., ELISA and immunoassays).

In certain aspects, an anti-MET antibody described herein which can act as an inhibitor of MET activity (e.g., any one of antibodies Ab235-Ab255, or an antigen-binding fragment thereof or an antibody comprising CDRs of any one of antibodies Ab235-Ab255) or activity can inhibit cellular proliferation of cells (e.g., cancer cells, such as, for example, SNU-5 cells, EBC-1 cells, U87MG cells, A549 cells, and H596 cells), for example, cells that express MET and that respond to MET signaling (e.g., cells that proliferate in response to MET ligand stimulation and MET signaling). In certain aspects, an anti-MET antibody described herein which can act as an inhibitor of MET activity (e.g., any one of antibodies Ab235-Ab255, or an antigen-binding fragment thereof or an antibody comprising CDRs of any one of antibodies Ab235-Ab255) or activity can inhibit cellular proliferation of cancer cells expressing MET, such as, for example, SNU-5 cells, EBC-1 cells, U87MG cells, A549 cells, and H596 cells), for example, cells that express MET and that respond to MET signaling (e.g., cells that proliferate in response to MET ligand stimulation and MET signaling). Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In specific embodiments, antibodies described herein (e.g., any one of antibodies Ab235-Ab255, or an antigen-binding fragment thereof or an antibody comprising CDRs of any one of antibodies Ab235-Ab255) specifically bind to MET and inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay).

In specific embodiments, antibodies described herein specifically bind to MET and block or inhibit cellular proliferation of cells (e.g., cancer cells, such as, for example, SNU-5 cells, EBC-1 cells, U87MG cells, A549 cells, and H596 cells) with an IC$_{50}$ of less than about 400 pM or less than about 300 pM as assessed by methods described herein (e.g., as described in Section 6 below) or known to one of skill in the art. In specific embodiments, antibodies described herein specifically bind to MET and block or inhibit cellular proliferation of cells (e.g., cancer cells, such as, for example, SNU-5 cells, EBC-1 cells, U87MG cells, A549 cells, and H596 cells) with an IC$_{50}$ of less than about 300 nM. In specific embodiments, antibodies described herein specifically bind to MET and block or inhibit cellular proliferation with an IC$_{50}$ of less than about 150 nM. In specific embodiments, antibodies described herein specifically bind to MET and block or inhibit cellular proliferation with an IC$_{50}$ of less than about 50 nM. In specific embodiments, antibodies described herein specifically bind to MET and block or inhibit cellular proliferation with an IC$_{50}$ in the range of about 100 nM to about 500 nM, about 25 nM to about 200 nM, or about 40 nM to about 160 nM, about 50 nM to about 125 nM, or about 5 nM to about 100 nM. In certain embodiments, antibodies described herein specifically bind to MET and block or inhibit cellular proliferation of U87MG cells with an IC$_{50}$ in the range of about 1 nM to about 50 nM, about 5 nM to about 30 nM, or about 9 nM to about 25 nM. In certain embodiments, antibodies described herein specifically bind to MET and block or inhibit cellular proliferation of U87MG cells with an IC$_{50}$ of less than about 50 nM, less than about 40 nM, less than about 30 nM, less than about 20 nM, less than about 10 nM, or less than about 5 nM. In certain embodiments, antibodies described herein specifically bind to MET and block or inhibit cellular proliferation of A549 cells with an IC$_{50}$ in the range of about 1 nM to about 30 nM, about 2.5 nM to about 20 nM, or about 4 nM to about 15 nM. In certain embodiments, antibodies described herein specifically bind to MET and block or inhibit cellular proliferation of A549 cells with an IC$_{50}$ of less than about 20 nM, less than about 10 nM, less than about 7.5 nM, less than about 6 nM, less than about 5 nM, or less than about 4.5 nM. In certain embodiments, antibodies described herein specifically bind to MET and block or inhibit cellular proliferation of H596 cells with an IC$_{50}$ in the range of about 0.01 nM to about 2 nM, about 0.1 nM to about 1.5 nM, or about 0.2 nM to about 1 nM. In certain embodiments, antibodies described herein specifically bind to MET and block or inhibit cellular proliferation of H596 cells with an IC$_{50}$ of less than about 1.5 nM, less than about 1 nM, less than about 0.5 nM, less than about 0.01 nM, less than about 0.05 nM, or less than about 0.01 nM.

In certain embodiments, anti-MET antibodies provided herein (e.g., Ab235, Ab236, Ab237, Ab239, and Ab241-Ab255) have increased MET antagonistic activities as IgG$_2$ isotypes (e.g., human IgG$_2$, human IgG$_{2a}$, human IgG$_{2b}$, or a mixture thereof) as compared to the antibodies (e.g., Ab235, Ab236, Ab237, Ab239, and Ab241-Ab255) as IgG$_1$ isotypes. Without being bound by any theory, the IgG$_2$ isotype (e.g., human IgG$_2$, human IgG$_{2a}$, and human IgG$_{2b}$, or a mixture thereof) may provide an enhanced alteration in distance or positioning of MET kinase dimer, allowing for enhanced anti-MET activity. In specific embodiments, inhibition of cellular proliferation of cells (e.g., cancer cells, such as, for example, SNU-5 cells, EBC-1 cells, U87MG cells, A549 cells, and H596 cells), for example, cells that express MET and that respond to MET signaling (e.g., cells that proliferate in response to MET ligand stimulation and MET signaling) in the presence of an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as an IgG$_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than inhibition of cellular proliferation in the presence of the anti-MET antibody or antigen-binding fragment thereof, as an IgG$_2$ isotype (e.g., human IgG$_2$, human IgG$_{2a}$, and human IgG$_{2b}$, or a mixture thereof) as assessed by methods described herein or known to one of skill in the art (e.g., BrdU incorporation assays).

In certain aspects, an anti-MET antibody described herein which can act as an inhibitor of MET activity (e.g., any one of antibodies Ab235-Ab255, or an antigen-binding fragment thereof or an antibody comprising CDRs of any one of antibodies Ab235-Ab255) can reduce or inhibit survival of cells (e.g., cancer cells, such as, for example, SNU-5 cells, EBC-1 cells, U87MG cells, A549 cells, and H596 cells), for example, cells that express MET and that respond to MET signaling (e.g., cells that proliferate in response to MET ligand stimulation and MET signaling). Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In specific embodiments, antibodies described herein (e.g., any one of antibodies Ab235-Ab255, or an antigen-binding fragment thereof or an antibody comprising CDRs of any one of antibodies Ab235-Ab255) specifically bind to MET and inhibit (e.g., partially inhibit) cell survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay).

In specific embodiments, inhibition of cell survival in the presence of an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than inhibition of cell survival in the absence of antibody or in the presence of the anti-MET antibody or an antigen-binding fragment thereof, as an $IgG_2$ isotype (e.g., human $IgG_2$, human $IgG_{2a}$, and human $IgG_{2b}$, or a mixture thereof) as assessed by methods described herein or known to one of skill in the art (e.g., trypan blue exclusion assays).

Cells and cell lines which are appropriate for use in the assays described herein relating to MET activity are readily available (e.g., ATCC) or can be readily identified using methods known in the art. For example, cells and/or cell lines that express MET endogenously or that possess MET signaling or activity are known to one of skill in the art. In certain embodiments, cells or cell lines that are appropriate for use in the assays described herein can express MET, either endogenously or recombinantly. In particular embodiments, cells or cell lines for use in cell proliferation assays can express MET, endogenously or recombinantly, and proliferate or increase proliferation in response to MET ligand (e.g., HGF) stimulation. Cells or cell lines for use in cell viability assays can express MET, endogenously or recombinantly, and exert changes in cell viability in response to MET ligand (e.g., HGF) stimulation. Cells or cell lines for use in apoptosis assays can express MET, endogenously or recombinantly, and exert changes in apoptosis in response to MET ligand (e.g., HGF) stimulation. Cells or cell lines for use in cell proliferation, cell viability, or other assays can express MET, endogenously or recombinantly, and exert changes in proliferation or activation of other cell types response to MET ligand (e.g., HGF) stimulation.

Non-limiting examples of cells that can be used in the methods and assays described herein include SNU-5 cells, EBC-1 cells, U87MG cells, A549 cells, Hop92 cells, and H596 cells. Non-limiting examples of cells that can be used in the methods and assays described herein to assess ligand (e.g., HGF) independent MET signaling and activity include EBC-1 cells and SNU-5 cells. In specific embodiments, cells that can be used in the methods and assays described herein to assess ligand-independent MET activity include MET amplified cells such as MET amplified tumor cells or cells expressing mutant MET, for example a constitutively active mutant MET. Non-limiting examples of cells that can be used in the methods and assays described herein to assess ligand (e.g., HGF) dependent MET signaling and activity include A549 cells, U87MG cells, Hop92 cells, and H596 cells. In specific embodiments, cells that can be used in the methods and assays described herein to assess ligand-dependent MET activity include cells expressing wild-type MET, for example tumor cells expressing wild-type MET, or cells (e.g., tumor cells) expressing normal levels of MET, e.g., cells that do not contain MET amplification. Other non-limiting examples of cells that can be used in the methods and assays described herein include primary cells, transformed cells, stem cells, mast cells, primordial germ cells, oocytes, spermatocytes, embryonic stem cells, hematopoietic cells, erythroleukemia cells (e.g., F36P and TF-1 cell lines), colorectal cancer cell lines, such as SNU-C1, SW48, RKO, COLO 205, SW1417, LS411N, NCI-H508, HT-29, SK-CO-1, SW1116, SW948, T84, LS123, LoVo, and SW837, gastric cancer cell lines, such as HGC27, GCIY, MKN7, TMK1, ECC12, AGS, CLS-145, 23132/87, MKN-45, SK-GT-2, HGC-27, and KATO-III, lung cancer cell lines, such as H526, DMS153, DMS79, NCI-H2126, NCI-H1299, NCI-H1437, NCI-H1563, NCI-H1573, NCI-H1975, HCl-H661, and HCC827, melanoma cell lines, such as HMCB, SK-MEL-1, SK-MEL-3, SK-MEL-24, SH-4, RPMI-7951, SKA375, G-361, and WM-115, human myeloid leukemia cell lines, such as MOTE cells; gastrointestinal stromal tumor cell lines such as ST-882, GIST430, and GIST882; neuroblastoma cell lines such as SK-N-SH, SK-SY5Y, H-EP1, SK-N-BE(2), SK-N-BE(ZkM17), SK-N-BE(2)C, LA-N-1, or LA-N-1-5s; small cell lung carcinoma cell lines such as H526, ECC12, TMK1, MKN7, GCIY, and HGC27. In particular embodiments, cells that can be used in the methods and assays described herein include immune cells, such as macrophages, dendritic cells, and natural killer (NK) cells. In particular embodiments, cells that can be used in the methods and assay described herein include H1299 cells.

Alternatively, cells and cell lines that express MET, e.g., human MET, can routinely be generated recombinantly. Non-limiting examples of cells that can be engineered to express MET recombinantly include COS cells, HEK 293 cells, CHO cells, H1299 cells, fibroblasts (e.g., human fibroblasts) such as NIH3T3 cells, and MEFS. In a specific embodiment, cells for use in the methods described herein are H1299 cells expressing human MET ECD (e.g., SEQ ID NO:190).

In certain aspects, an anti-MET antibody described herein, which can act as an inhibitor of MET activity (e.g., any one of antibodies Ab235-Ab255, or an antigen-binding fragment thereof or an antibody comprising CDRs of any one of antibodies Ab235-Ab255), is capable of inhibiting or reducing metastasis, inhibiting tumor growth or inducing tumor regression in mouse model studies. For example, tumor cell lines can be introduced into nude mice, and the mice can be administered anti-MET antibodies described herein one or more times, and tumor progression of the injected tumor cells can be monitored over a period of weeks and/or months. In some cases, administration of anti-MET antibodies to the nude mice can occur prior to introduction of the tumor cell lines. Any appropriate tumor cell line (e.g., tumor cell line expressing MET) can be used in the mouse xenograft models described herein. Non-limiting examples of tumor cell lines for use in these xenograft mouse models include non-small cell lung carncinoma cell line H1299, megakaryoblastic leukemia cell lines such as MO7e; gastrointestinal stromal tumor cell lines such as ST-882, GIST430, GIST48, GIST48B and GIST882; human erythroleukemic cell lines such as HEL and TF-1; human promyelocytic leukemia cell line, HL60; neuroblastoma cell lines such as SK-N-SH, SK-SY5Y, H-EP1, SK-N—BE(2), SK-N-BE(ZkM17), SK-N-BE(2)C, LA-N-1, or LA-N-1-5s; and small cell lung carcinoma cell lines such as H526, DMS153, DMS79, ECC12, TMK1, MKN7, GCIY, and HGC27. Additional cell lines include A549 cells, SNU-5 cells, EBC-1 cells, Hop92 cells, and H596 cells. In a specific embodiment, a tumor cell line for use in a xenograft mouse model is the GIST882, GIST430, GIST48, GIST48B, HEL, HL60, H526, DMS153, or DMS79 cell line. In certain embodiments, suitable cell lines for use in xenograft tumor models can be generated by recombinantly expressing MET.

In specific embodiments, antibodies described herein (e.g., any one of antibodies Ab235-Ab255, or an antigen-binding fragment thereof or an antibody comprising CDRs of any one of antibodies Ab235-Ab255) specifically bind to MET and inhibit tumor growth or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art. In specific embodiments, antibodies described herein (e.g., any one of antibodies Ab235-Ab255 or an antigen-binding fragment thereof, or an antibody comprising CDRs of any one of antibodies Ab235-Ab255) specifically bind to MET and inhibit tumor growth or induce tumor regression in a mouse model by at least about 25% or 35%, optionally to about 75%, as assessed by methods described herein or known to one of skill in the art. In specific embodiments, antibodies described herein specifically bind to MET and inhibit tumor growth or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art.

In specific embodiments, tumor growth or induce tumor regression in a mouse model in the presence of an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than inhibition of tumor growth or induction of tumor regression in a mouse model in the presence of the anti-MET antibody or antigen-binding fragment thereof, as an $IgG_2$ isotype (e.g., human $IgG_2$, human $IgG_{2a}$, and human $IgG_{2b}$, or a mixture thereof) as assessed by methods described herein or known to one of skill in the art.

Determining tumor growth inhibition or tumor regression can be assessed, for example, by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain aspects, anti-MET antibodies described herein bind specifically to MET antigen and can increase survival of animals in tumor xenograft models. In specific embodiments, antibodies described herein (e.g., any one of antibodies Ab235-Ab255 or an antigen-binding fragment thereof, or an antibody comprising CDRs of any one of antibodies Ab235-Ab255) specifically bind to MET and increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, antibodies described herein (e.g., any one of antibodies Ab235-Ab255 or an antigen-binding fragment thereof, or an antibody comprising CDRs of any one of antibodies Ab235-Ab255) specifically bind to MET and increase survival of mice in tumor xenograft models by at least about 25% or 35%, optionally to about 75%, as assessed by methods described herein or known to one of skill in the art. In specific embodiments, antibodies described herein specifically bind to MET and increase survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. In specific embodiments, survival of mice in tumor xenograft models in the presence of an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than survival of mice in tumor xenograft models in the presence of the anti-MET antibody, or antigen-binding fragment thereof, as an $IgG_2$ isotype (e.g., human $IgG_2$, human $IgG_{2a}$, and human $IgG_{2b}$, or a mixture thereof) as assessed by methods described herein or known to one of skill in the art. Survival can, for example, be determined by plotting a survival curve of number of surviving mice against time (e.g., days or weeks) after tumor cell line injection.

In specific embodiments, antibodies described herein specifically bind to MET and inhibit endothelial-to-mesenchymal transition (EMT) (e.g., in a cell, such as, for example, DU145 cells) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., immunoprecipitation and immunoblot assays), relative to EMT inhibition in the presence of an unrelated antibody (e.g., an antibody that does not immunospecifically bind to MET). In specific embodiments, antibodies described herein specifically bind to MET and inhibit EMT by at least about 25% or 35%, optionally to about 75%, as assessed by methods described herein or known to one of skill in the art (e.g., immunoprecipitation and immunoblot assays), relative to EMT inhibition in the absence of antibody or in the presence of an unrelated antibody (e.g., an antibody that does not immunospecifically bind to MET). In specific embodiments, antibodies described herein specifically bind to MET and inhibit EMT (e.g., in a cell, such as, for example, DU145 cells) by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., DU145 cell scatter assay), relative to EMT inhibition in the absence of antibody or in the presence of an unrelated antibody (e.g., an antibody that does not immunospecifically bind to MET). In certain embodiments, an anti-MET antibody described herein (e.g., any one of antibodies Ab235-Ab255 or an antigen-binding fragment thereof, or an antibody comprising CDRs of any one of antibodies Ab235-Ab255) inhibits EMT with an $IC_{50}$ of at most about 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM, as assessed by methods described herein and/or known to one of skill in the art, (e.g., DU145 cell scatter assays). In specific embodiments, an anti-MET antibody described herein inhibits EMT with an $IC_{50}$ of at least about 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM, as assessed by methods described herein and/or known to one of skill in the art, (e.g., DU145 cell scatter assays). In particular embodiments, an anti-MET antibody described herein inhibits binding of MET ligand to MET with an $IC_{50}$ in the range of about 0.1 nM to 500 nM, 0.1 nM to 100 nM, or 0.1 nM to 50 nM, as assessed by methods described herein and/or known to one of skill in the art, (e.g., DU145 cell scatter assays).

In specific embodiments, an anti-MET antibody described herein (e.g., any one of antibodies Ab235, Ab236, Ab237, Ab239, and Ab241-Ab255 or antigen-binding fragment thereof, or an antibody comprising CDRs of any one of antibodies Ab235, Ab236, Ab237, Ab239, and Ab241-Ab255) inhibits EMT (e.g., in a cell, such as, for example, DU145 cells) as an $IgG_1$ isotype is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold less than EMT inhibition in the presence of the anti-MET antibody, or antigen-binding fragment thereof, as an $IgG_2$ isotype (e.g., human $IgG_2$, human $IgG_{2a}$, and human $IgG_{2b}$, or a mixture thereof) as assessed by methods described herein or known to one of skill in the art (e.g., DU145 cell scatter assays). Techniques for quantitating or monitoring EMT of cell surface receptors are well known in the art and involve DU145 cell scatter assays, see, for example, Section 6.

5.2 Antibody Conjugates

In some embodiments, provided herein are antibodies (e.g., monoclonal antibodies such as chimeric or humanized antibodies), or antigen-binding fragments thereof, linked, for example conjugated or fused, to an agent, e.g., a diagnostic, detectable or therapeutic agent, for example, a polypeptide or small molecule. The linked, e.g., conjugated or fused, antibodies can be useful, e.g., for monitoring or prognosing the onset, development, progression and/or severity of a condition or disease, for example, as part of a clinical testing procedure, such as determining the efficacy of a particular therapy, by, for example, imaging procedures. The linked, e.g., conjugated or fused, antibodies can be useful, e.g., for treating or managing a condition or disorder described herein, or for treating or managing effects of a condition or disorder described herein. Antibodies described herein can also be conjugated to a molecule (e.g., polyethylene glycol) which can affect one or more biological and/or molecular properties of the antibodies, for example, stability (e.g., in serum), half-life, solubility, and antigenicity.

In a particular aspect, provided herein is a conjugate comprising an agent (e.g., therapeutic agent) linked to an antibody described herein (or an antigen-binding fragment thereof), which antibody immunospecifically binds to an ECD of human MET, for example, an antibody comprising CDRs of any one of antibodies Ab235-Ab255, for example as set forth in Tables 1, 2, and 5-8.

In particular embodiments, antibodies and antigen-binding fragments thereof can be linked to detectable molecules or substances including, but not limited to, various enzymes, prosthetic groups (such as, but not limited to, streptavidin/biotin and avidin/biotin), fluorescent molecules, bioluminescent molecules, radioactive molecules, such as radioisotopes, quantum dots, or other nanoparticles, and positron emitting metals using various positron emission tomographies, and non-radioactive paramagnetic metal ions. In other particular embodiments, antibodies, or antigen-binding fragments thereof, can be linked to a therapeutic agent, such as a cytotoxin, e.g., a cytostatic or cytocidal agent, or a radioactive metal ion, e.g., alpha-emitters. For example, a cytotoxin or cytotoxic agent includes any agent that is detrimental to cells.

In one embodiment, the antibody or antigen-binding fragment is conjugated or fused directly to an agent, e.g., a diagnostic or therapeutic agent. In another specific embodiment, the antibody or antigen-binding fragment, and agent are conjugated or fused via one or more linkers. In particular embodiments, a linker is an enzyme-cleavable linker and/or a disulfide linker.

In yet other embodiments, antibodies or antigen-binding fragments described herein can be fused to agents, such as peptides, to facilitate purification. For example, such a peptide can be a hexa-histidine peptide, such as the tag provided in a pQE vector (QIAGEN, Inc.), among others, many of which are commercially available. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating agents, including polypeptides, to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Antibodies and antigen-binding fragments described herein can also be attached to solid supports. Such solid supports can include, but are not limited to, glass, cellulose, polyacrylamide, nylon, polystyrene, polyvinyl chloride or polypropylene. Such attachment can be useful, for example, for immunoassays or purification of the target antigen.

In a certain aspect, an antibody described herein or an antigen-binding fragment thereof is an extracellular drug conjugate (ECD) comprising an antibody linked to a drug which acts outside of the cell, optionally by a linker (see, e.g., PCT International Patent Application Publication No. WO 2011/031870). For example, after an ECD binds a target cell, the drug sends a signal into the cell and internalization of the conjugate is not required.

5.3 Antibody Production

Antibodies or an antigen-binding fragments described herein that immunospecifically bind to MET (e.g., ECD of human MET) can be produced by any method known in the art, for example, by chemical synthesis or by recombinant expression techniques. Such methods can employ conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, NY; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Monoclonal antibodies can, for example, be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced recombinantly from host cells engineered to express an antibody described herein (e.g., anti-MET antibody comprising the CDRs of any one of antibodies Ab235-Ab255) or a fragment thereof, for example, a light chain and/or heavy chain of such an antibody.

Further, the antibodies described herein or antigen-binding fragments thereof can also be generated using various phage display methods known in the art. In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

Antibodies described herein can, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

Antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized.

Antibodies described herein include antibody fragments which recognize specific MET antigens (e.g., ECD of MET) and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region. Alternatively, antibody fragments described herein can routinely be produced via well known recombinant expression techniques. See, e.g., PCT publication No. WO 92/22324; Mullinax et al., 1992, BioTechniques 12(6):864-869; Sawai et al., 1995, AJRI 34:26-34; and Better et al., 1988, Science 240:1041-1043.

Antibodies described herein can, for example, include humanized antibodies, e.g., deimmunized or composite human antibodies. A humanized antibody can comprise human constant region sequences. In certain embodiments, a humanized antibody can be selected from any class of immunoglobulins, including IgM, IgG, IgD, IgA and IgE, and any isotype, including IgG$_1$, IgG$_2$, IgG$_3$ and IgG$_4$. In certain embodiments, a humanized antibody can comprise kappa or lambda light chain constant sequences.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody. Such antibodies can comprise human constant region sequences, e.g., human light chain and/or heavy chain constant regions.

A deimmunized antibody is an antibody in which T-cell epitopes have been removed. Methods for making deimmunized antibodies have been described. See, e.g., Jones et al., Methods Mol Biol. 2009; 525:405-23, xiv, and De Groot et al., Cell. Immunol. 244:148-153(2006)). Deimmunized antibodies comprise T-cell epitope-depleted variable regions and human constant regions. Briefly, VH and VL of an antibody are cloned and T-cell epitopes are subsequently identified by testing overlapping peptides derived from the VH and VL of the antibody in a T cell proliferation assay. T cell epitopes are identified via in silico methods to identify peptide binding to human MHC class II. Mutations are introduced in the VH and VL to abrogate binding to human MHC lass II. Mutated VH and VL are then utilized to generate the deimmunized antibody.

Antibodies described herein can, for example, be multispecific, e.g., bispecific, antibodies. Methods for making multispecific (e.g, bispecific antibodies) have been described, see, for example, U.S. Pat. Nos. 7,951,917, 7,183,076, 8,227,577, 5,837,242, 5,989,830, 5,869,620, 6,132,992, and 8,586,713.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Human antibodies can be produced using any method known in the art. For example, well known transgenic mice which are incapable of expressing functional endogenous murine immunoglobulins, but which can express human immunoglobulin genes, can be used. Alternatively, for example, phage display techniques, described above, can be utilized. Moreover, in some embodiments, human antibodies can, for example, be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., ECD of human MET). Such methods are known and are described in the art, see, e.g., Shinmoto et al., Cytotechnology, 2004, 46:19-23; Naganawa et al., Human Antibodies, 2005, 14:27-31.

5.3.1 Polynucleotides, Cells and Vectors

In certain aspects, provided herein are polynucleotides comprising a nucleotide sequence encoding an antibody described herein or a fragment thereof (e.g., a variable light chain region and/or variable heavy chain region) that immunospecifically binds to a MET antigen, and vectors, e.g., vectors comprising such polynucleotides for recombinant expression in host cells (e.g., E. coli and mammalian cells). In certain aspects, provided herein are cells (e.g., host cells). Also provided herein are methods of making the antibodies and antigen-binding fragments described herein.

In certain aspects, provided herein are polynucleotides comprising a nucleotide sequence encoding the light chain or heavy chain of an antibody described herein. In certain embodiments, provided herein are polynucleotides comprising a nucleotide sequence encoding the light chain and heavy chain of an antibody described herein. The polynucleotides can comprise nucleotide sequences encoding a light chain comprising the VL FRs and CDRs of antibodies described herein (see, e.g., Tables 1, 5, and 7, and Table 3, respectively). The polynucleotides can comprise nucleotide sequences encoding a heavy chain comprising the VH FRs and CDRs of antibodies described herein (see, e.g., Tables 2, 6, and 8, and Table 4, respectively). In specific embodiments, a polynucleotide described herein encodes a VL chain region comprising the amino acid sequence of SEQ ID NO: 52, 53, 54, 55, 56, 57, 58, 59, 60, 61, or 62. In specific embodiments, a polynucleotide described herein encodes a VH chain region comprising the amino acid sequence of any one of SEQ ID NOs: 63, 64, 65, 66, 67, 68, 69, 70, or 71.

In particular embodiments, provided herein are polynucleotides comprising a nucleotide sequence encoding an anti-MET antibody comprising three VL chain CDRs, e.g., containing VL CDR1, VL CDR2, and VL CDR3 of any one of antibodies Ab235-Ab255 (e.g., see Tables 1, 5, and 7). In specific embodiments, provided herein are polynucleotides comprising three VH chain CDRs, e.g., containing VH CDR1, VH CDR2, and VH CDR3 of any one of antibodies Ab235-Ab255 (e.g., see Tables 2, 6, and 8). In specific embodiments, provided herein are polynucleotides comprising a nucleotide sequence encoding an anti-MET antibody comprising three VH chain CDRs, e.g., containing VL CDR1, VL CDR2, and VL CDR3 of any one of antibodies Ab235-Ab255 (e.g., see Tables 1, 5, and 7) and three VH chain CDRs, e.g., containing VH CDR1, VH CDR2, and VH CDR3 of any one of antibodies Ab235-Ab255 (e.g., see Tables 2, 6, and 8).

In particular embodiments, provided herein are polynucleotides comprising a nucleotide sequence encoding an anti-MET antibody comprising a VL chain region, e.g., containing FR1-CDR1-FR2-CDR2-FR3-CDR3-FR4, comprising an amino acid sequences described herein (e.g., see Tables 1, 5, and 7, or Table 3). In specific embodiments, provided herein are polynucleotides comprising a nucleotide sequence encoding an anti-MET antibody comprising a VH chain region, e.g., containing FR1-CDR1-FR2-CDR2-FR3-CDR3-FR4, comprising an amino acid sequence described herein (e.g., see Tables 2, 6, and 8, or Table 4).

In certain embodiments, a polynucleotide described herein comprises a nucleotide sequence encoding an antibody provided herein comprising a variable light (VL) chain region comprising an amino acid described herein (e.g., see Table 9), wherein the antibody immunospecifically binds to a MET polypeptide, e.g., a human MET polypeptide, for example, an ECD of MET (e.g., human MET), for example SEQ ID NO:190.

In certain embodiments, a polynucleotide described herein comprises a nucleotide sequence encoding an antibody provided herein comprising a variable heavy (VH) chain region comprising an amino acid sequence described herein (e.g., see Table 10), wherein the antibody immunospecifically binds to a MET polypeptide, e.g., a human MET polypeptide, for example, an ECD of MET (e.g., human MET), for example SEQ ID NO:190.

In certain aspects, a polynucleotide comprises a nucleotide sequence encoding an antibody described herein comprising a VL chain region comprising one or more VL FRs having the amino acid sequence described herein (e.g., see Table 3), wherein the antibody immunospecifically binds to a MET polypeptide, e.g., a human MET polypeptide, for example, an ECD of MET (e.g., human MET), for example SEQ ID NO:190. In certain aspects, a polynucleotide comprises a nucleotide sequence encoding an antibody described herein comprising a VH chain region comprising one or more VH FRs having the amino acid sequence described herein (e.g., see Table 4), wherein the antibody immunospecifically binds to a MET polypeptide, e.g., a human MET polypeptide, for example, an ECD of MET (e.g., human MET), for example SEQ ID NO:190.

In specific embodiments, a polynucleotide provided herein comprises a nucleotide sequence encoding an antibody described herein comprising: framework regions (e.g., framework regions of the VL domain and VH domain) that are human framework regions, wherein the antibody immunospecifically binds a MET polypeptide, e.g., a human MET polypeptide, for example, an ECD of MET (e.g., human MET), for example SEQ ID NO:190.

In a certain embodiment, a polynucleotide provided herein comprises a nucleotide sequence as described in Table 11 or 16, encoding a VH or a VL, respectively, of an antibody described herein (e.g., Ab235-Ab255), which immunospecifically binds to a MET polypeptide, e.g., a human MET polypeptide, for example, an ECD of MET (e.g., human MET), for example SEQ ID NO:190.

TABLE 11

VL Nucleic Acid Sequences

| Antibody | Nucleotide sequences |
|---|---|
| Ab235 VL | CAAATTGTTCTCACCCAGTCTCCAGCAATCATGTCTACGTCTCCAGGGGAGAAGGTCACC<br>ATGACCTGCAGTGCCAGCTCAAGTGTAAATTATATGTTCTGGTACCAGCAGAAGGCAGG<br>ATCCTCCCCCAGACTCCTGATTTATGACACATTCAATCTGGCTTCTGGAGTCCCTGTTCGC<br>TTCAGTGGCAGTGGGTCTGGGACCTCTTACTCTCTCACAATCAGCCGAATGGAGGCTGAA<br>GATGCTGCCACTTATTACTGCCAGCAGTGGAGTATTTACCCGTACACGTTCGGAGGGGG<br>GACCAAGCTGGAAATAAAGCGG (SEQ ID NO: 196) |
| Ab236 VL | CAAATTGTTCTCACCCAGTCTCCAGCAATCATGTCTGCATCTCCAGGGGAGAAGGTCACC<br>ATGACCTGCAGTGCCAGCTCAAGTGTAAGTTACATGTTCTGGTACCAGCAGAAGCCAGG<br>ATCCTCCCCCAGACTCCTGATTTATGACACATCCGACCTGGCTTCTGGAGTCCCTGTTCG<br>CTTCAGTGGCAGTGGGTCTGGGACCTCTTACTCTCTCACAATCAGCCGAATGGAGGCTGA<br>AGATGCTGCCACTTATTACTGCCAGCAGTGGAGTAATTACCCGTACACGTTCGGAGGGG<br>GGACCAAGCTGGAAATAAAACGG (SEQ ID NO: 197) |
| Ab237 VL | GACATTCAGATGACACAGTCTCCAGGTTCCCTGTCTGCATCTCTGGGAGAAACTGTCACC<br>ATCGAATGTCTAGCAAGTGCGGATATTCACAGTAATTTAGCTTGGTATCAGCAGAAGCC<br>AGGGAATTCTCCTCAGCTCCTGATCTATTATGGAAATAACTTGAATGATGGCGTCCCATC<br>ACGGTTCAGTGGCAGTGGATCTGGCACACAGTATTCTCTGAAGATCAACAGCCTGCAAT<br>CTGAAGATGTCTCGATTTATTTCTGTCAACAGAGTTATGATAGTCCTCCAACGTTTGGAG<br>CTGGGACCAAGCTGGAACTGAAACGG (SEQ ID NO: 198) |

TABLE 11-continued

VL Nucleic Acid Sequences

| Antibody | Nucleotide sequences |
|---|---|
| Ab238 VL | GATATCCGGATGACACAGTCTCCAGCTTCCCTGTCTGCATCTCTGGGAGAAACTGTCAAC<br>ATCAGTTGTCTAGCAAGTGAGGACATTTACAGTGATTTAGCATGGTATCAGCAGAAGCC<br>AGGGAAATCTCCTCAACTCCTGATCTATAATGCAAATACCTTGCAAATGGGGTCCCTTC<br>AGTGTTTAGTGGCAGTGGATCTGGCACACAGTATTCTCTAAAAATAAACAACCTGCACTC<br>TGAAGATGTCGCGACTTACTTCTGTCAACAATATAACAATTATCCTCCGACGTTCGGTGG<br>AGGCACCAAGGTGGAATTGAAACGG (SEQ ID NO: 199) |
| Ab239 VL | CAGTTCACGCTGACTCAACCAAAGTCCGTGTCAGGATCTTTAAGAAGCACTATCACCATT<br>CCCTGTGTGCGCAGCAGTGGTGACATTGGCGATAGGTATGTGAGCTGGTACCAGCAACG<br>CTTGGGAAGACCCCCCCTCAATGTGATCTATGCTGCTGATCAAAGACCTTCTGAAGTGTC<br>TGATCGGTTCTCGGGCTCCATCGACAGCTCCTCTAACTCAGCCTCACTGACCATCACTGA<br>TCTGCAGATGGATGATGAGGCCGACTACTTCTGTCAGTCTTACGATAGTAATATTGATAT<br>TGTTTTCGGTGGTGGAACCAAGCTCACTGTCCTCGGT (SEQ ID NO: 200) |
| Ab240 VL | GACATCCAGATGACCCAGACTCCATTCTACATGCCTGCATCTCTGGGAGAGCGAGTCAC<br>CATCAGTTGCAGAGCAAGTCAGGGTATTAGTAAATATCTAAATTGGTATCAGCAGAAAC<br>CAGATGGAACGATTAAAACCCTGATCTACTACACATCCAATTTACAGTCTGGTGTCCCAT<br>CAAGGTTCAGTGGCAGTGGGTCTGGGACAGATTATTCTCTCACCATCAGCGGCCTGGAG<br>CCTGAAGATTTTGCAGTGTATTACTGCCAACAGTACGATAGTTCTCCATTCACGTTCGGC<br>TCAGGGACGAAGTTGGAAATAAAACGG (SEQ ID NO: 201) |
| Ab241 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTCAGCTCCTGATCTATTATGGAAATAACTTGAATGATGGCGTCCCATC<br>ACGGTTCAGTGGCAGTGGATCTGGCACAGACTATACCCTGAAGATCAACAGCCTGCAAT<br>CTGAAGATGTCGCCATTTATTTCTGTCAACAGAGTTATGATAGTCCTCCAACGTTTGGAC<br>AGGGGACCAAGCTGGAAATCAAA (SEQ ID NO: 202) |
| Ab242 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTATACCCTGACCATCAGCAGCCTGCAA<br>TCTGAAGATGTCGCCATTTATTTCTGTCAACAGAGTTATGATAGTCCTCCAACGTTTGGA<br>CAGGGGACCAAGCTGGAAATCAAA (SEQ ID NO: 203) |
| Ab243 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTATACCCTGACCATCAGCAGCCTGCAA<br>CCCGAAGATGTCGCCATTTATTTCTGTCAACAGAGTTATGATAGTCCTCCAACGTTTGGA<br>CAGGGGACCAAGCTGGAAATCAAA (SEQ ID NO: 204) |
| Ab244 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTTCACCCTGACCATCAGCAGCCTGCAA<br>CCCGAAGATGTCGCCATTTATTTCTGTCAACAGAGTTATGATAGTCCTCCAACGTTTGGA<br>CAGGGGACCAAGCTGGAAATCAAA (SEQ ID NO: 205) |
| Ab245 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTTCACCCTGACCATCAGCAGCCTGCAA<br>CCCGAAGATGTCGCCACCTATTTCTGTCAACAGAGTTATGATAGTCCTCCAACGTTTGGA<br>CAGGGGACCAAGCTGGAAATCAAA (SEQ ID NO: 206) |
| Ab246 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTCAGCTCCTGATCTATTATGGAAATAACTTGAATGATGGCGTCCCATC<br>ACGGTTCAGTGGCAGTGGATCTGGCACAGACTATACCCTGAAGATCAACAGCCTGCAAT<br>CTGAAGATGTCGCCATTTATTTCTGTCAACAGAGTTATGATAGTCCTCCAACGTTTGGAC<br>AGGGGACCAAGCTGGAAATCAAA (SEQ ID NO: 207) |
| Ab247 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTATACCCTGACCATCAGCAGCCTGCAA<br>TCTGAAGATGTCGCCATTTATTTCTGTCAACAGAGTTATGATAGTCCTCCAACGTTTGGA<br>CAGGGGACCAAGCTGGAAATCAAA (SEQ ID NO: 208) |

TABLE 11-continued

VL Nucleic Acid Sequences

| Antibody | Nucleotide sequences |
|---|---|
| Ab248 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTATACCCTGACCATCAGCAGCCTGCAA<br>CCCGAAGATGTCGCCATTTATTTCTGTCAACAGAGTTATGATAGTCCTCCAACGTTTGGA<br>CAGGGGACCAAGCTGGAAATCAAA (SEQ ID NO: 209) |
| Ab249 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTTCACCCTGACCATCAGCAGCCTGCAA<br>CCCGAAGATGTCGCCATTTATTTCTGTCAACAGAGTTATGATAGTCCTCCAACGTTTGGA<br>CAGGGGACCAAGCTGGAAATCAAA (SEQ ID NO: 210) |
| Ab250 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTTCACCCTGACCATCAGCAGCCTGCAA<br>CCCGAAGATGTCGCCACCTATTTCTGTCAACAGAGTTATGATAGTCCTCCAACGTTTGGA<br>CAGGGGACCAAGCTGGAAATCAAA (SEQ ID NO: 211) |
| Ab251 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTCAGCTCCTGATCTATTATGGAAATAACTTGAATGATGGCGTCCCATC<br>ACGGTTCAGTGGCAGTGGATCTGGCACAGACTATACCCTGAAGATCAACAGCCTGCAAT<br>CTGAAGATGTCGCCATTTATTTCTGTCAACAGAGTTATGATAGTCCTCCAACGTTTGGAC<br>AGGGGACCAAGCTGGAAATCAAA (SEQ ID NO: 212) |
| Ab252 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTATACCCTGACCATCAGCAGCCTGCAA<br>TCTGAAGATGTCGCCATTTATTTCTGTCAACAGAGTTATGATAGTCCTCCAACGTTTGGA<br>CAGGGGACCAAGCTGGAAATCAAA (SEQ ID NO: 213) |
| Ab253 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTATACCCTGACCATCAGCAGCCTGCAA<br>CCCGAAGATGTCGCCATTTATTTCTGTCAACAGAGTTATGATAGTCCTCCAACGTTTGGA<br>CAGGGGACCAAGCTGGAAATCAAA (SEQ ID NO: 214) |
| Ab254 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTTCACCCTGACCATCAGCAGCCTGCAA<br>CCCGAAGATGTCGCCATTTATTTCTGTCAACAGAGTTATGATAGTCCTCCAACGTTTGGA<br>CAGGGGACCAAGCTGGAAATCAAA (SEQ ID NO: 215) |
| Ab255 VL | GACATTCAGATGACACAGTCTCCAAGCTCCCTGTCTGCATCTGTGGGAGACAGAGTCAC<br>CATCACCTGTCTAGCAAGTGCGGATATTCACAGTAATTTAGCTTGGTATCAGCAGAAGCC<br>AGGGAAGGCCCCTAAGCTCCTGATCTATTATGGAAATAACTTGAATGATGGCGTCCCAT<br>CACGGTTCAGTGGCAGTGGATCTGGCACAGACTTCACCCTGACCATCAGCAGCCTGCAA<br>CCCGAAGATGTCGCCACCTATTTCTGTCAACAGAGTTATGATAGTCCTCCAACGTTTGGA<br>CAGGGGACCAAGCTGGAAATCAAA (SEQ ID NO: 216) |

TABLE 12

VH Nucleic Acid Sequences

| Antibody | Nucleotide sequences |
|---|---|
| Ab235 VH | CAGGTTCAGCTGCAGCAGTCTGGAGCTGAGTTGATGAAGCCTGGGGCCTCAGTGAAGAT<br>ATCCTGCAAGGCTACTGGCTACACATTCAGTAACTACTGGATAGAGTGGGTAAAGCAGA<br>GGCCTGGACATGGCCTTGAATGGATTGGAGAGATTTTACCTGGAAGTGATTATACTAAG<br>TATAATGAGAAATTCAAGGGCAAGGCCACATTCACTGCAGATACATCCTCCAACACAGC<br>CTACATGCAGCTCAGCAGCCTGACATCTGAGGACTCTGCCGTCTATTACTGTGCAAGACC<br>CTCTACAATTCCCCCTGACTGCTGGGGCCAAGGCACCACTCTCACAGTCTCCTCA (SEQ<br>ID NO: 217) |

TABLE 12-continued

VH Nucleic Acid Sequences

| Antibody | Nucleotide sequences |
|---|---|
| Ab236 VH | CAGGCTCAGCTGCAACAGTCTGGAGCTGAGCTGATGAAGCCTGGGGCCTCAGTGAAGAT<br>ATCCTGCAAGGCTACTGGCTACATATTCAGTAGTTATTGGATAGAGTGGGTAAAGCAGA<br>GGCCTGGACATGGCCTTGAGTGGATTGGAGAGATTTTACCTGGAAGTGATTTTATTAAGT<br>ACAGTGAGAAGTTCAAGGGCAAGGCCACATTCACTGCAGATACGTCCTCCAATACAGCC<br>TACATGCAACTCAGCAACCTGACATCTGAGGACTCTGCCGTCTATTACTGTGCAAGACCC<br>TCTACGGTTCCCCCTGACTGCTGGGGCCAAGGCACCACTCTCACAGTCTCCTCA<br>(SEQ ID<br>NO: 218) |
| Ab237 VH | GAGGTGCAGCTGGTGGAGTCTGGAGGAGGCTTGGTGCAGCCTGGAAGGTCCCTGAAACT<br>CTCCTGTGCAGCCTCAGGATTCACTTTCAGTGACTCGTACATGGCCTGGGTCCGCCAGGC<br>TCCGACGAAGGGTCTGGAATGGGTCGCATCCATTAGTTCTGATGGTGGTGGCACTTACTA<br>TCGAGACTCCGTGAAGGGCCGATTCTCTATCTCCAGAGATAATGCGAAAAGCAGCCTCT<br>ACCTGCAAATGGACAGTCTGCGGTCTGAGGACACGGCCACTTATTACTGTACAACAGAG<br>GGGATTTATACTACGGATTATTACCCTTATTGCTTTAATTATTGGGGCCACGGAGTCATG<br>GTCACAGTCTCCTCA (SEQ ID NO: 219) |
| Ab238 VH | CAGGTTACTCTGAAAGAGTCTGGCCCTGGGATATTGCAGCCCTCCCAGACCCTCAGTCTG<br>ACTTGCACTTTCTCTGGGTTTTCACTGAGCACTTATGGTATGGGTGTGGCCTGGATTCGTC<br>AGCCGTCAGGGAAGGATCTGGAGTGGCTGGCAAACATTTGGTGGGATGATGTTAACTAC<br>TCCAATCCATCTCTGAAGAACCGACTCACAATCTCCAAGGACACCTCCAACAACCAAGT<br>TTTCCTCCAGATCACCAATGTGGACACTGCAGAAACTGCCACATATTACTGTGCTCGGAT<br>CGGTACATCCCATATTGTGGATGCCTGGGGTCAAGGAGCTTCAGTCACTGTCTCCTCA<br>(SEQ ID NO: 220) |
| Ab239 VH | GAGGTGCAGCTGGTGGAATCTGGGGGAGGCTTAGTGCAGCCTGGAAGGTCCCTGAAACT<br>CTCCTGTGCAGCCTCAGGATTCAGTTTCACTGACTGTTACATGGCCTGGGTCCGCCAGGC<br>TCCAACGAAGGGTCTGGAGTGGGTCGCATCCATTAGTTCTGATGGTGGTGGCACTTACTA<br>TCGAGACTCCGTGAAGGGCCGATTTACTATCTCCAGAGATAATGCAAGAAGCAGCCTAT<br>ACCTAGAAATGGACAGTCTGAGGTCTGAGGACACGGCCACTTATTATTGTACCACAGAA<br>AGATACTATGATGGTACTTACTACGGCTACTGGTACTTTGACTTCTGGGGCCCAGGAACC<br>ATGGTCACCGTGTCCTCA (SEQ ID NO: 221) |
| Ab240 VH | CAGGTGCAGCTGAAGGAGTCAGGACCTGGTCTGGTGCAGCCCTCACAGACCCTGTCCCT<br>CACCTGCTCTGTCTCTGGACTCTCACTAACCACCAATAGTGTACACTGGATTCGCCAGCC<br>TCCGGGAAGGGGTCTGGAGTGGATGGGAGTAATATGGGGTGATGGAAGCACAGACTAT<br>AATTCAGCTCTCAAATCCCGACTGACCATCAGCCGGGACACCTCCAGGAGCCAAGTCTT<br>CTTAAAAATGAACAGTCTGCAAACTGATGACACAGCCATTTACTTCTGTGCCAGAGACC<br>CGTATCAGAACTACTTTGATTACTGGGGCCAAGGAGTCAAGGTCACAGTCTCCTCA (SEQ<br>ID NO: 222) |
| Ab241 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGGACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 223) |
| Ab242 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGGACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 224) |
| Ab243 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGGACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 225) |
| Ab244 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGGACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 226) |

TABLE 12-continued

VH Nucleic Acid Sequences

| Antibody | Nucleotide sequences |
|---|---|
| Ab245 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGGACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 227) |
| Ab246 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 228) |
| Ab247 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 229) |
| Ab248 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 230) |
| Ab249 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 231) |
| Ab250 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAGCAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAGTCATG<br>GTCACAGTCTCCTCA (SEQ ID NO: 232) |
| Ab251 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAACAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAACCATG<br>GTCACAGTCTCCTCA (SEQ ID NO: 233) |
| Ab252 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAACAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAACCATG<br>GTCACAGTCTCCTCA (SEQ ID NO: 234) |
| Ab253 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAACAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAACCATG<br>GTCACAGTCTCCTCA (SEQ ID NO: 235) |

TABLE 12-continued

VH Nucleic Acid Sequences

| Antibody | Nucleotide sequences |
|---|---|
| Ab254 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAACAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAACCATG<br>GTCACAGTCTCCTCA (SEQ ID NO: 236) |
| Ab255 VH | GAGGTGCAGCTGGTGGAGTCTGGAGGAGGCTTGGTGCAGCCTGGAGGCTCCCTGAAACT<br>CTCCTGTGCAGCCTCAGGATTCACTTTCAGTGACTCGTACATGGCCTGGGTCCGCCAGGC<br>TCCGGGCAAGGGTCTGGAATGGGTCGCATCCATTAGTTCTGATGGTGGTGGCACTTACTA<br>TCGAGACTCCGTGAAGGGCCGATTCACCATCTCCAGAGATAATGCGAAAAACAGCCTCT<br>ACCTGCAAATGAACAGTCTGCGGACCGAGGACACGGCCACTTATTACTGTACAACAGAG<br>GGGATTTATACTACGGATTATTACCCTTATTGCTTTAATTATTGGGGCCAGGGAACCATG<br>GTCACAGTCTCCTCA (SEQ ID NO: 237) |

In certain embodiments, a polynucleotide provided herein is operably linked to a promoter for expression of such polynucleotide sequence in a host cell. In certain embodiments, the promoter is derived from the genome of mammalian cells (e.g., metallothionein promoter) or from mammalian viruses (e.g., the adenovirus late promoter, the vaccinia virus 7.5K promoter). In a specific embodiment, the expression of nucleotide sequences encoding antibodies described herein is regulated by a constitutive promoter, inducible promoter or tissue specific promoter.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody described herein, which immunospecifically binds to a MET polypeptide, e.g., a human MET polypeptide, for example, an ECD of MET (e.g., human MET), for example SEQ ID NO:190, wherein the antibody comprises a light chain, and wherein the amino acid sequence of the VL chain region can comprise any amino acid sequence described herein (e.g., SEQ ID NO: 52, 53, 54, 55, 56, 57, 58, 59, 60, 61, or 62), and wherein the constant region of the light chain comprises the amino acid sequence of a human kappa light chain constant region. In another particular embodiment, a polynucleotide provided herein comprises a nucleotide sequence encoding an antibody described herein, which immunospecifically binds to a MET polypeptide, e.g., a human MET polypeptide, for example, an ECD of MET (e.g., human MET), for example SEQ ID NO:190, and comprises a light chain, wherein the amino acid sequence of the VL chain region can comprises any amino acid sequence described herein (e.g., SEQ ID NO: 52, 53, 54, 55, 56, 57, 58, 59, 60, 61, or 62), and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to a MET polypeptide, e.g., a human MET polypeptide, for example, an ECD of MET (e.g., human MET), for example SEQ ID NO:190, wherein the antibody comprises a heavy chain, wherein the amino acid sequence of the VH chain region can comprise any amino acid sequence described herein (e.g., SEQ ID NO: 63, 64, 65, 66, 67, 68, 69, 70, or 71), and wherein the constant region of the heavy chain comprises the amino acid sequence of a human gamma ($\gamma$) heavy chain constant region, for example, human gamma ($\gamma$) 1 heavy chain constant region, human gamma ($\gamma$) 2 heavy chain constant region, human gamma ($\gamma$) 3 heavy chain constant region, or human gamma ($\gamma$) 4 heavy chain constant region. In a particular embodiment, a polynucleotide provided herein comprises a nucleotide sequence encoding an antibody described herein, which immunospecifically binds to a MET polypeptide, e.g., a human MET polypeptide, for example, an ECD of MET (e.g., human MET), for example SEQ ID NO:190, wherein the antibody comprises a heavy chain, wherein the amino acid sequence of the VH chain region can comprise any amino acid sequence described herein (e.g., SEQ ID NO: 63, 64, 65, 66, 67, 68, 69, 70, or 71), and wherein the constant region of the heavy chain comprises the amino acid sequence of a human gamma ($\gamma$) 2 heavy chain constant region, for example, human gamma ($\gamma$) 2a and/or 2b heavy chain constant region.

In yet another specific embodiment, a polynucleotide provided herein comprises a nucleotide sequence encoding an antibody described herein (or an antigen-binding fragment thereof), which immunospecifically binds a MET polypeptide, e.g., a human MET polypeptide, for example, an ECD of MET (e.g., human MET), for example SEQ ID NO:190, wherein the antibody comprises a VL chain region and a VH chain region comprising any amino acid sequences described herein, and wherein the constant regions comprise the amino acid sequences of the constant regions of a human $IgG_1$ (e.g., isotype a, z, or f) or human $IgG_4$.

In yet another specific embodiment, a polynucleotide provided herein comprises a nucleotide sequence encoding an antibody described herein (or an antigen-binding fragment thereof), which immunospecifically binds a MET polypeptide, e.g., a human MET polypeptide, for example, an ECD of MET (e.g., human MET), for example SEQ ID NO:190, wherein the antibody comprises a VL chain region and a VH chain region comprising any amino acid sequences described herein, and wherein the constant regions comprise the amino acid sequences of the constant regions of a human IgG$_2$ (e.g., human IgG$_{2a}$ or human IgG$_{2b}$). In a specific embodiment, the constant regions are of a human IgG$_2$ alpha isotype (e.g., human IgG$_2$a). In a specific embodiment, the constant regions are of a human IgG$_2$ beta isotype (e.g., human IgG$_{2b}$). In a specific embodiment, the constant regions are a mixture of human IgG$_{2a}$ and human IgG$_{2b}$ isotypes.

In a specific embodiment, provided herein are polynucleotides comprising a nucleotide sequence encoding an anti-MET antibody, or an antigen-binding fragment or domain thereof, designated herein, see, e.g., Tables 1-10, for example antibody Ab235-Ab255.

Also provided herein are polynucleotides encoding an anti-MET antibody or a fragment thereof that are optimized, e.g., by codon/RNA optimization, replacement with heterologous signal sequences, and elimination of mRNA instability elements. Methods to generate optimized nucleic acids encoding an anti-MET antibody or a fragment thereof (e.g., light chain, heavy chain, VH domain, or VL domain) for recombinant expression by introducing codon changes and/ or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-MET antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-MET antibody encoded by polynucleotides that have not been optimized.

The polynucleotides described herein can be produced and the nucleotide sequences of the polynucleotides determined, by any method known in the art. Nucleotide sequences encoding antibodies described herein, e.g., antibodies comprising sequences described in Tables 1-10, and, optionally, comprising constant region sequences, for example, human constant region sequences, can be determined using methods well known in the art, e.g., nucleotide codons known to encode particular amino acids can be identified and assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR. Alternatively, a polynucleotide encoding an antibody described herein can be generated from nucleic acid or nucleic acids using methods well known in the art (e.g., PCR and other molecular cloning methods).

5.3.2 Cells and Vectors

In certain aspects, provided herein are cells (e.g., host cells) expressing (e.g., recombinantly) antibodies described herein (or an antigen-binding fragment thereof) which specifically bind to an ECD of human MET and related polynucleotides and expression vectors. Provided herein are vectors (e.g., expression vectors) comprising polynucleotides comprising nucleotide sequences encoding anti-MET antibodies or a fragment for recombinant expression in host cells, preferably in mammalian cells. Also provided herein are host cells comprising such vectors for recombinantly expressing anti-MET antibodies described herein (e.g., human or humanized antibody). In a particular aspect, provided herein are methods for producing an antibody described herein, comprising expressing such an antibody from a host cell.

Recombinant expression of an antibody described herein (e.g., a full-length antibody, heavy and/or light chain of an antibody, or a single chain antibody described herein) that specifically binds to an ECD of human MET involves construction of an expression vector containing a polynucleotide that encodes the antibody. Once a polynucleotide encoding an antibody molecule, heavy and/or light chain of an antibody, or a fragment thereof (e.g., heavy and/or light chain variable domains) described herein has been obtained, the vector for the production of the antibody molecule can be produced by recombinant DNA technology using techniques well-known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., an antibody comprising the CDRs of any one of antibodies Ab235-Ab255) or a fragment thereof. Thus, provided herein are host cells containing a polynucleotide encoding an antibody described herein or fragments thereof, or a heavy or light chain thereof, or fragment thereof, or a single chain antibody described herein (e.g., an antibody comprising the CDRs of any one of antibodies Ab235-Ab255), operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein (e.g., an antibody comprising the CDRs of any one of antibodies Ab235-Ab255), or a fragment thereof. In specific embodiments, a host cell contains two different vectors, a first vector comprising a polynucleotide encoding a heavy chain or a heavy chain variable region of an antibody described herein (e.g., an antibody comprising the CDRs of any one of antibodies Ab235-Ab255), or a fragment thereof, and a second vector comprising a polynucleotide encoding a light chain or a light chain variable region of an antibody described herein (e.g., an antibody comprising the CDRs of any one of antibodies Ab235-Ab255), or a fragment thereof. In other embodiments, a first host cell comprises a first vector comprising a polynucleotide encoding a heavy chain or a heavy chain variable region of an antibody described herein (e.g., an antibody comprising the CDRs of any one of antibodies Ab235-Ab255), or a fragment thereof, and a second host cell comprises a second vector comprising a polynucleotide encoding a light chain or a light chain variable region of an antibody described herein (e.g., an antibody comprising the CDRs of any one of antibodies Ab235-Ab255). In specific embodiments, a heavy chain/heavy chain variable region expressed by a first cell associated with a light chain/light chain variable region of a second cell to form an anti-MET antibody described herein (e.g., antibody comprising the CDRs of any one of antibodies Ab235-Ab255) or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-MET antibody described herein (e.g., antibody comprising the CDRs of any one of antibodies Ab235-Ab255), and a second vector comprising a polynucleotide encoding a heavy chain/heavy chain variable region of an anti-MET antibody described herein (e.g., antibody comprising the CDRs of any one of antibodies Ab235-Ab255).

A variety of host-expression vector systems can be utilized to express antibody molecules described herein (e.g., an antibody comprising the CDRs of any one of antibodies Ab235-Ab255) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein (e.g., an antibody comprising the CDRs of any one of antibodies Ab235-Ab255) or an antigen-binding fragment thereof are CHO cells, for example CHO cells from the CHO GS System™ (Lonza). In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein which immunospecifically bind to an ECD of MET is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 81:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT20 and T47D, NS0 (a murine myeloma cell line that does not endogenously produce any immunoglobulin chains), CRL7O3O and HsS78Bst cells. In certain embodiments, anti-MET antibodies described herein (e.g., an antibody comprising the CDRs of any one of antibodies Ab235-Ab255) are produced in mammalian cells, such as CHO cells.

For long-term, high-yield production of recombinant proteins, stable expression cells can be generated. For example, cell lines which stably express an anti-MET antibody described herein (e.g., an antibody comprising the CDRs of any one of antibodies Ab235-Ab255) or an antigen-binding fragment thereof can be engineered. In specific embodiments, a cell provided herein stably expresses a light chain/light chain variable domain and a heavy chain/heavy chain variable domain which associate to form an antibody described herein (e.g., an antibody comprising the CDRs of any one of antibodies Ab235-Ab255) or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-MET antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-215); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or antigen-binding fragment described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.4 Pharmaceutical Compositions and Kits

Provided herein are compositions, pharmaceutical compositions, and kits comprising one or more antibodies (e.g., anti-MET antibodies comprising CDRs of any one of antibodies Ab235-Ab255) described herein, or antigen-binding fragments thereof, or conjugates thereof. In particular aspects, compositions (e.g., pharmaceutical compositions) described herein can be for in vitro, in vivo, or ex vivo uses. Non-limiting examples of uses include uses to modulate (e.g., inhibit or induce/enhance) MET activity and uses to manage or treat a disorder, for example, cancer, an immunological disorder (e.g., autoimmune disorder or inflammatory) or vascular disorder. In specific embodiments, provided herein is a pharmaceutical composition comprising an antibody (e.g., a humanized antibody) described herein (or an antigen-binding fragment thereof) and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Formulations containing one or more antibodies provided herein (e.g., antibodies comprising CDRs of any one of antibodies Ab235-Ab255) or an antigen-binding fragment thereof can be prepared for storage by mixing the antibody having the desired degree of purity with optional physiologically acceptable carriers, excipients or stabilizers (*Remington's Pharmaceutical Sciences* (1990) Mack Publishing Co., Easton, PA; *Remington: The Science and Practice of Pharmacy,* 21st ed. (2006) Lippincott Williams & Wilkins, Baltimore, MD). Such formulations can, for example, be in the form of, e.g., lyophilized formulations or aqueous solutions. Pharmaceutical carriers suitable for administration of the antibodies provided herein include any such carriers known to those skilled in the art to be suitable for the particular mode of administration. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations to be used for in vivo administration can be sterile. This can be readily accomplished, for example, by filtration through, e.g., sterile filtration membranes.

In specific aspects, the pharmaceutical compositions provided herein contain therapeutically effective amounts of one or more of the antibodies or antigen-binding fragments provided herein in a pharmaceutically acceptable carrier. Such pharmaceutical compositions are useful in the prevention, treatment, management or amelioration of a condition or disorder described herein or one or more symptoms thereof.

Compositions provided herein can contain one or more antibodies provided herein (e.g., antibodies comprising CDRs of any one of antibodies Ab235-Ab255) or an antigen-binding fragment thereof. In one embodiment, compositions are provided wherein antibodies or antigen-binding fragments described herein are formulated into suitable pharmaceutical preparations, such as solutions, suspensions, powders, sustained release formulations or elixirs in sterile solutions or suspensions for parenteral administration, or as transdermal patch preparation and dry powder inhalers.

In one embodiment, compositions provided herein are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody provided herein (e.g., antibody comprising CDRs of any one of antibodies Ab235-Ab255) is included in the pharmaceutically acceptable carrier in an effective amount sufficient to exert a therapeutically useful effect in the absence of, or with minimal or negligible, undesirable side effects on the patient treated.

Concentrations of anti-MET antibody in a pharmaceutical composition provided herein will depend on, e.g., the physicochemical characteristics of the antibody, the dosage schedule, and amount administered as well as other factors known to those of skill in the art.

Pharmaceutical compositions described herein are provided for administration to humans or animals (e.g., mammals) in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals in unit dosage form, such as tablets, capsules, pills, powders, granules, and oral or nasal solutions or suspensions, and oil-water emulsions containing suitable quantities of an anti-MET antibody or pharmaceutically acceptable derivatives thereof. The antibody is, in one embodiment, formulated and administered in unit-dosage forms or multiple-dosage forms. Unit-dose forms as used herein refers to physically discrete units suitable for human or animal (e.g., mammal) subjects and packaged individually as is known in the art. Each unit-dose contains a predetermined quantity of an anti-MET antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles. Hence, in specific aspects, multiple dose form is a multiple of unit-doses which are not segregated in packaging.

In certain embodiments, one or more anti-MET antibodies described herein (e.g., antibodies comprising CDRs of any one of antibodies Ab235-Ab256) or an antigen-binding fragment thereof are in a liquid pharmaceutical formulation. Liquid pharmaceutically administrable compositions can, for example, be prepared by dissolving, dispersing, or otherwise mixing an antibody and optional pharmaceutical adjuvants in a carrier, such as, for example, water, saline, aqueous dextrose, glycerol, glycols, and the like, to thereby form a solution or suspension. In certain embodiments, a pharmaceutical composition provided herein to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, PA; *Remington: The Science and Practice of Pharmacy*, 21st ed. (2006) Lippincott Williams & Wilkins, Baltimore, MD.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

In certain embodiments, intravenous or intraarterial infusion of a sterile aqueous solution containing an anti-MET antibody or fragment described herein is an effective mode of administration. Another embodiment is a sterile aqueous or oily solution or suspension containing an anti-MET antibody described herein injected as necessary to produce the desired pharmacological effect.

In specific embodiments, an anti-MET antibody described herein can be suspended in micronized or other suitable form. The form of the resulting mixture depends upon a number of factors, including the intended mode of administration and the solubility of the compound in the selected carrier or vehicle.

In other embodiments, the pharmaceutical formulations are lyophilized powders, which can be reconstituted for administration as solutions, emulsions and other mixtures. They can also be reconstituted and formulated as solids or gels.

Lyophilized powder can, for example, be prepared by dissolving an anti-MET antibody provided herein, in a suitable solvent. In some embodiments, the lyophilized powder is sterile. Suitable solvents can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. A suitable solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides an example of a formulation. In one embodiment, the resulting solution will be apportioned into vials for lyophilization. Lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier.

In certain aspects, anti-MET antibodies provided herein can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

Anti-MET antibodies and other compositions provided herein can also be formulated to be targeted to a particular tissue, organ, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, anti-MET antibodies described herein are targeted (or otherwise administered) to the visual organs, bone marrow, gastrointestinal tract, lungs, brain, or joints. In specific embodiments, an anti-MET antibody described herein is capable of crossing the blood-brain barrier.

Provided herein is a pharmaceutical pack or kit comprising one or more containers filled with one or more of the ingredients of the pharmaceutical compositions described herein, such as one or more anti-MET antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits comprising one or more of the antibodies or antibody fragments described herein. In one embodiment, a kit comprises an antibody or antibody fragment described herein, in one or more containers. In a specific embodiment, kits described herein contain a substantially isolated MET antigen (e.g., ECD of human MET) as a control. In another specific embodiment, the kits described herein further comprise a control antibody which does not react with a MET antigen. In another specific embodiment, kits described herein contain one or more elements for detecting the binding of a modified antibody to a MET antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized MET antigen. The MET antigen provided in the kit can also be attached to a solid support. In a more specific embodiment, the detecting means of the above described kit includes a solid support to which a MET antigen is attached. Such a kit can also include a non-attached reporter-labeled anti-human antibody or anti-mouse/rat antibody. In this embodiment, binding of the antibody to the MET antigen can be detected by binding of the said reporter-labeled antibody.

5.5 Uses and Methods

In particular aspects, provided herein are methods of modulating MET activity with an anti-MET antibody (e.g., any one of antibodies Ab235-Ab255 or an antibody comprising CDRs of any one of antibodies Ab235-Ab255) or an antigen-binding fragment thereof described herein. In certain embodiments, the anti-MET antibody is a MET antagonist.

In specific embodiments, provided herein are methods of inhibiting (e.g., partially inhibiting) MET activity with an anti-MET antibody described herein which is a MET antagonist. In certain embodiments, provided herein are methods of managing or treating a condition or disorder using an anti-MET antibody described herein (e.g., any one of antibodies Ab235-Ab255 or an antibody comprising CDRs of any one of antibodies Ab235-Ab255) which is a MET antagonist. In certain embodiments, provided herein are methods of protecting against a condition or disorder using an anti-MET antibody described herein which is a MET antagonist or inhibitor.

In particular embodiments, provided herein are methods for managing, treating, preventing or protecting against cancer (e.g., colorectal cancer, gastric cancer, lung cancer, or melanoma), metastasis, or angiogenesis in a subject (e.g., a human subject), comprising administering to a subject in need thereof a therapeutically effective amount of an antibody (e.g., an antibody comprising CDRs of any one of antibodies Ab235-Ab255) or an antigen-binding fragment described herein that binds specifically to an ECD of human MET. In certain embodiments, provided herein is a method of alleviating, inhibiting or reducing the progression or severity of one or more symptoms associated with cancer, metastasis, or angiogenesis.

In certain embodiments, the anti-MET antibody or antigen-binding fragment thereof for use in the methods provided herein is an antibody (e.g., a monoclonal antibody, such as a humanized monoclonal antibody) comprising CDRs of any one of antibodies Ab235-Ab255, for example, as set forth in Tables 1, 2, or 5-8. In particular embodiments, the anti-MET antibody inhibits a MET activity (e.g., phosphorylation of MET, MET signaling, inhibition of cell proliferation, inhibition of ligand binding to MET, or inhibition of tumor growth). In particular embodiments, the MET activity is MET-amplified (e.g., ligand-independent) MET activity. In particular embodiments, the MET activity is ligand-dependent MET activity. In particular embodiments, the MET activity is ligand-dependent and MET-amplified (e.g., ligand-independent) MET activity.

As used herein, "administer" or "administration" refers to the act of injecting or otherwise physically delivering a substance (e.g., a humanized anti-MET antibody provided herein or an antigen-binding fragment thereof) to a subject or a patient (e.g., human), such as by mucosal, topical, intradermal, parenteral, intravenous, subcutaneous, intramuscular delivery and/or any other method of physical delivery described herein or known in the art.

As used herein, the terms "effective amount" or "therapeutically effective amount" refer to an amount of a therapy (e.g., an antibody or pharmaceutical composition provided herein) which is sufficient to reduce and/or ameliorate the severity and/or duration of a given condition, disorder or disease (e.g., cancer, metastasis, or angiogenesis) and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy (e.g., a therapy other than an anti-MET antibody provided herein). In some embodiments, "effective amount" as used herein also refers to the amount of an antibody described herein to achieve a specified result.

As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

As used herein, the terms "manage," "managing," and "management" refer to the beneficial effects that a subject derives from a therapy (e.g., a prophylactic or therapeutic agent), which does not result in a cure of a condition associated with MET. In certain embodiments, a subject is administered one or more therapies (e.g., prophylactic or therapeutic agents, such as an antibody described herein) to "manage" a condition or disorder described herein, one or more symptoms thereof, so as to prevent the progression or worsening of the condition or disorder.

As used herein, the terms "impede" or "impeding" in the context of a condition or disorder provided herein (e.g., autoimmune disorder, immunological disorder, cancer, or inflammation) refer to the total or partial inhibition (e.g., less than 100%, 95%, 90%, 80%, 70%, 60%, 50%, 40%, 30%, 20%, 10%, or 5%) or blockage of the development, recurrence, onset or spread of a condition or disorder provided herein (e.g., cancer, metastasis, or angiogenesis) and/or symptom related thereto, resulting from the administration of a therapy or combination of therapies provided herein (e.g., a combination of prophylactic or therapeutic agents, such as an antibody described herein).

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) can be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (63$^{rd}$ ed., 2009).

As used herein, the terms "subject" and "patient" are used interchangeably. As used herein, a subject is a mammal such as a non-primate (e.g., cows, pigs, horses, cats, dogs, goats, rabbits, rats, mice, etc.) or a primate (e.g., monkey and human), for example a human. In one embodiment, the subject is a mammal, e.g., a human, diagnosed with a condition or disorder provided herein (e.g., cancer, metastasis, or angiogenesis). In another embodiment, the subject is a mammal, e.g., a human, at risk of developing a condition or disorder provided herein (e.g., cancer, metastasis, or angiogenesis). In certain embodiments, the subject, such as a cancer subject, has overexpression of HGF. In particular embodiments, the cancer is characterized by overexpression of HGF. In another particular embodiment, the subject, such as a cancer subject, has tumor stroma which is characterized by overexpression of HGF. In another embodiment, the subject is human.

In certain embodiments, MET is amplified in the subject, e.g., the human subject. Identification of MET amplification in a sample from a subject can be performed by assays known to one of ordinary skill in the art, such as, e.g., quantitative reverse transcription PCR, immunoblot assays, DNA fingerprinting, karyotyping (for example, by multi-color fluorescence in situ hybridization (mFISH)), comparative genome hybridization, and gene expression profiling. As a non-limiting example, protein expression of tumor samples can be characterized using immunohistochemical assays to measure the amount of MET protein present in a sample. In certain embodiments, MET amplification in a subject results in ligand-independent MET signaling in cells of the subject. Identification of ligand-independent MET signaling in the subject can be performed by assays known to one of ordinary skill in the art, such as, e.g., quantitative reverse transcription PCR or immunoblot assays. For example, primary cells from the subject can be extracted and cultured in the presence and absence of MET ligand (e.g., HGF), and MET downstream signaling events, such as, e.g., phosphorylation of MAPK and/or AKT, can be assessed by, e.g., ELISA or immunoblot. In certain embodiments, a subject comprises cells (e.g., tumor cells) that express a MET mutant, for example a constitutively active MET mutant. In certain embodiments, a subject expresses a MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site. In certain embodiments, a subject expresses a MET protein comprising an isoleucine amino acid substitution at MET amino acid residue Thr1010. In certain embodiments, a subject has cancer, wherein cancer cells in the subject express mutant MET, e.g., constitutively active mutant MET. In certain embodiments, a subject has cancer, wherein cancer cells in the subject express a MET comprising one or more deletions in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site. In certain embodiments, a subject has cancer, wherein cancer cells in the subject express a MET protein comprising an isoleucine amino acid substitution at MET amino acid residue Thr1010. Identification of mutations or deletions in a sample from a subject can be performed by assays known to one of ordinary skill in the art, such as, e.g., DNA extraction, generation of complementary DNA, and cDNA sequencing. The cDNA sequence, for example, can be utilized to obtain the translation product by methods known to one of ordinary skill in the art. Genetic deletions and amino acid substitutions can be identified by, for example, comparing the sequence from the sample from the subject to a wild type and/or consensus sequence.

In certain embodiments, MET is amplified in the subject treated in accordance with the methods provided herein. Identification of MET amplification in a sample from a subject is performed by assays known to one of ordinary skill in the art, such as, e.g., quantitative reverse transcription PCR or immunoblot assays. In certain embodiments, the subject expresses an EGFR with one or more amino acid substitutions and/or deletions such that the EGFR is constitutively active. Identification of mutations or deletions in a sample from a subject are performed by assays known to one of ordinary skill in the art, such as, e.g., DNA extraction, generation of complementary DNA, and cDNA sequencing. The cDNA sequence, for example, is utilized to obtain the translation product by methods known to one of ordinary skill in the art. Genetic deletions and amino acid substitutions are identified by, for example, comparing the sequence from the sample from the subject to a wild type and/or consensus sequence.

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., a condition or disorder provided herein (e.g., cancer, metastasis, or angiogenesis) or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., cancer, metastasis, or angiogenesis, or one or more symptoms or condition associated therewith). In certain embodiments, the term "therapy" refers to a therapy other than an anti-MET antibody described herein or pharmaceutical composition thereof. In specific embodiments, an "additional therapy" and "additional therapies" refer to a therapy other than a treatment using an anti-MET antibody described herein or pharmaceutical composition thereof. In a specific embodiment, a therapy includes the use of an anti-MET antibody described herein as an adjuvant therapy. For example, using an anti-MET antibody described herein in conjunction with a drug therapy, biological therapy, surgery, and/or supportive therapy.

Provided herein are methods of managing or treating a condition (e.g., cancer, metastasis, or angiogenesis) by inhibiting an activity of MET with an anti-MET antibody (e.g., any one of antibodies Ab235, Ab236, Ab237, Ab238, Ab239, Ab240, Ab241, Ab242, Ab243, Ab244, Ab245, Ab246, Ab247, Ab248, Ab249, Ab250, Ab251, Ab252, Ab253, Ab254, and Ab255, or an antibody comprising CDRs of any one of antibodies Ab235-Ab255) described herein that acts as a MET antagonist. A non-limiting example of a condition which can be treated or managed with a MET antagonist includes cancer (e.g., colorectal cancer, gastric cancer, lung cancer, or melanoma such as uveal melanoma), described in more detail below.

Provided herein is a method of managing, preventing, protecting against, or treating cancer (e.g., colorectal cancer, gastric cancer, lung cancer, or melanoma such as uveal melanoma) in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In particular embodiments, such a method involves inhibition of tumor growth, cancer cell proliferation, and cancer cell migration. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

Provided herein is a method of managing, preventing, protecting against, or treating colorectal cancer in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In particular embodiments, such a method involves inhibition of tumor growth, cancer cell proliferation, and cancer cell migration. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

Provided herein is a method of managing, preventing, protecting against, or treating gastric cancer in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In particular embodiments, such a method involves inhibition of tumor growth, cancer cell proliferation, and cancer cell migration. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

Provided herein is a method of managing, preventing, protecting against, or treating lung cancer in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In particular embodiments, such a method involves inhibition of tumor growth, cancer cell proliferation, and cancer cell migration. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

Provided herein is a method of managing, preventing, protecting against, or treating cancer characterized by MET-amplified (e.g., ligand-independent) MET signaling, such as, for example, a cancer characterized by MET amplification, in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In particular embodiments, such a method involves inhibition of tumor growth, cancer cell proliferation, and cancer cell migration. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

Provided herein is a method of managing, preventing, protecting against, or treating melanoma (e.g., BRAF-mutant melanoma), such as uveal melanoma, in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In particular embodiments, such a method involves inhibition of tumor growth, cancer cell proliferation, and cancer cell migration. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

Non-limiting examples of cancers which can be managed, prevented, protected against, or treated in the methods provided herein include colorectal, gastric, lung (e.g., non-small cell lung), melanoma (e.g., uveal melanoma), stomach, esophagus, brain, liver, kidney, head and neck, thyroid, ovary, prostate, pancreas, breast, colon, oral, muscular, bone, glioma, or lymphoid cancer. In certain embodiments, the cancer expresses or overexpresses MET. In certain embodiments, the cancer expresses MET comprising a mutation. In certain embodiments, the cancer expresses a MET gene comprising one or more deletions in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site. In certain embodiments, the cancer expresses MET comprising an isoleucine amino acid substitution at MET amino acid residue Thr1010.

In certain embodiments, the cancer a BRAF mutation, e.g., BRAF V600E or V600K. In certain embodiments, the cancer is melanoma with a BRAF mutation, e.g., BRAF V600E or V600K. In certain embodiments, the cancer expresses or overexpresses EGFR. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In one aspect, provided herein is a method of managing, preventing, protecting against, or treating metastasis (e.g., metastasis associated with colorectal cancer, gastric cancer, lung cancer, or melanoma) in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

In a particular embodiment, provided herein is a method of inhibiting or reducing tumor growth or cancer (e.g., colorectal cancer, gastric cancer, lung cancer, or melanoma) cell proliferation in a subject, comprising administering to a subject in need thereof a therapeutically effective amount of an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits a MET activity or inhibits or reduces MET expression. In certain embodiments, the constant regions of the antibody comprise the amino acid sequences of the constant regions of a human $IgG_2$. In certain embodiments, the constant regions of the antibody comprise the amino acid sequences of the constant regions of a human $IgG_{2a}$. In certain embodiments, the constant regions of the antibody comprise the amino acid sequences of the constant regions of a human $IgG_{2b}$. In certain embodiments, the constant regions of the antibody comprises the amino acid sequences of the constant regions of a mixture of a human $IgG_{2a}$ and a human $IgG_{2b}$.

In a specific embodiment, provided herein is a method of treating cancer (e.g., colorectal cancer, gastric cancer, lung cancer, or melanoma such as uveal melanoma) in a subject comprising administering (e.g., administering concurrently or sequentially) to a subject in need thereof (i) an antibody described herein (e.g., any one of antibodies Ab235-Ab255, or an antibody comprising CDRs of any one of antibodies Ab235-Ab255; see, e.g., Table 1, 2, 5, 6, 7, or 8) or antigen-binding fragment thereof which specifically binds to an ECD of human MET and inhibits MET, and (ii) another anti-cancer agent. In certain embodiments, the anti-cancer agent is a chemotherapeutic agent (e.g., microtubule disassembly blocker, antimetabolite, topoisomerase inhibitor, and DNA crosslinker or damaging agent). In certain embodiments, the anti-cancer agent is a tyrosine kinase inhibitor (e.g., GLEEVEC® (imatinib mesylate) or SUTENT (SU11248 or Sunitinib)). Other non-limiting examples of tyrosine kinase inhibitors include AMG706 (motesanib), RADOOI, PKC412, gefitinib (IRESSA™), erlotinib (TARCEVA®), sorafenib (NEXAVAR®), pazopanib (VOTRIENT™), axitinib, bosutinib, cediranib (RECENTIN®), SPRYCEL® (dasatinib), lapatinib (TYKERB®), lestaurtinib, neratinib, nilotinib (TASIGNA®), semaxanib, toceranib (PALLADIA™), vandetanib (ZACTIMA™), and vatalanib. In certain embodiments, the anti-cancer agent is an EGFR inhibitor. In certain embodiments, the EGFR inhibitor is cetuximab, erlotinib, gefitinib, or AZD9291. In certain embodiments, the anti-cancer agent is a BRAF inhibitor. In certain embodiments, the BRAF inhibitor is vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis). In certain embodiments, the anti-cancer agent is a MEK inhibitor. In certain embodiments, the MEK inhibitor is selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals). In certain embodiments, the anti-cancer agent is a histone deacetylase inhibitor (e.g., vorinostat or suberoylanilide hydroxamic acid (SAHA)). In certain embodiments, the anti-cancer agent is an anti-growth factor receptor antibody (e.g., anti-EGFR antibody, anti-VEGFR antibody, or anti-KIT antibody), or anti-growth factor antibody (e.g., anti-EGF antibody, anti-VEGF antibody). In certain embodiments, the constant regions of the antibody comprise the amino acid sequences of the constant regions of a human IgG$_2$. In certain embodiments, the constant regions of the antibody comprise the amino acid sequences of the constant regions of a human IgG$_{2a}$. In certain embodiments, the constant regions of the antibody comprise the amino acid sequences of the constant regions of a human IgG$_{2b}$. In certain embodiments, the constant regions of the antibody comprises the amino acid sequences of the constant regions of a mixture of a human IgG$_{2a}$ and a human IgG$_{2b}$.

In a specific embodiment, provided herein is a method of inhibiting angiogenesis in a subject in need thereof comprising administering (e.g., administering concurrently or sequentially) to a subject in need thereof (i) an antibody described herein (e.g., any one of antibodies Ab221, Ab224, Ab225, and Ab227-Ab234, for example, Ab227-Ab230, Ab233 and Ab234, or an antibody comprising CDRs of any one of antibodies Ab221, Ab224, Ab225, and Ab227-Ab234, for example, Ab227-Ab230, Ab233 and Ab234) or antigen-binding fragment thereof which specifically binds to an ECD of human MET and inhibits MET, and (ii) an anti-angiogenic agent, such as, for example, and anti-VEGF antibody.

In certain embodiments, the constant regions of the antibody comprise the amino acid sequences of the constant regions of a human IgG$_2$. In certain embodiments, the constant regions of the antibody comprise the amino acid sequences of the constant regions of a human IgG$_{2a}$. In certain embodiments, the constant regions of the antibody comprise the amino acid sequences of the constant regions of a human IgG$_{2b}$. In certain embodiments, the constant regions of the antibody comprises the amino acid sequences of the constant regions of a mixture of a human IgG$_{2a}$ and a human IgG$_{2b}$.

In one aspect, provided herein is a method of resensitizing a subject diagnosed with cancer to an EGFR targeted therapy (e.g., cetuximab, gefitinib, erlotinib or AZD9291), comprising administering to the subject a therapeutically effective amount of an anti-MET antibody or antigen binding fragment thereof described herein (e.g., Ab235-Ab255). In a particular aspect, the method of resensitizing a subject diagnosed with cancer to an EGFR targeted therapy (e.g., cetuximab, gefitinib, erlotinib or AZD9291) comprises administering to the subject a therapeutically effective amount of an anti-MET antibody or antigen binding fragment thereof described herein (e.g., Ab235-Ab255) and an EGFR targeted therapy (e.g., cetuximab, gefitinib, erlotinib or AZD9291). In specific aspect, the EGFR targeted therapy (e.g., cetuximab, gefitinib, erlotinib or AZD9291) being administered in combination with an anti-MET antibody (e.g., Ab235-Ab255) is the same EGFR targeted therapy (e.g., cetuximab, gefitinib, erlotinib or AZD9291) to which the subject had been resistant. In a specific aspect, the subject had been diagnosed with an EGFR-associated cancer, for example, a cancer expressing EGFR or a cancer comprising an EGFR mutation. In a specific aspect, the subject had been diagnosed with cancer with EGFR expression or overexpression. In a specific aspect, the subject had been diagnosed with cancer with mutated EGFR. In a certain aspect, the subject had been diagnosed with cancer characterized by EGFR expression. In a certain aspect, the subject had been diagnosed with cancer characterized by (i) EGFR expression and (ii) EGFR gene expression or amplification or EGFR overexpression. In a certain other aspect, methods provided herein comprise measuring the expression level of EGFR, for example EGFR amplification or protein expression or overexpression. In a particular aspect, methods provided herein comprise measuring the expression level of EGFR. In a certain aspect, methods provided herein comprise measuring the expression level of EGFR and identifying a subject having cancer or suspected of having cancer that expresses EGFR. In a particular aspect, the subject had been treated previously with an EGFR-targeted therapy (e.g., cetuximab, gefitinib, erlotinib or AZD9291). In a certain aspect, the subject had acquired resistance to treatment with the EGFR targeted therapy (e.g., cetuximab, gefitinib, erlotinib or AZD9291). In a particular embodiment, the EGFR targeted therapy is cetuximab. In another particular embodiment, the EGFR targeted therapy is gefitinib. In another particular embodiment, the EGFR targeted therapy is erlotinib. In another particular embodiment, the EGFR targeted therapy is AZD9291. In certain embodiments, such methods are methods of managing. In certain embodiments, such methods are methods of treating. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site. In certain aspects, methods described herein for resensitizing a subject diagnosed with cancer to an EGFR targeted therapy (e.g., cetuximab, gefitinib, erlotinib or AZD9291) achieve reduction in tumor growth or tumor cell proliferation by at least about 5%, 10%, 15%, 20%, 25%, 30%, 35%, 40%, 45%, 50%, 60%, 70%, 80%, 90%, or 95% relative to tumor growth or tumor cell proliferation prior to administration of an anti-MET antibody described herein (e.g., Ab235-Ab255). Nonlimiting examples of methods for characterizing response to therapy, such as resensitization, include measuring serum concentration of EGFR by ELISA or similar assays, cytological examination of aspirated pleural fluid for the presence of carcinoma cells, and immunohistochemical assays. For example, methods described herein for resensitizing a subject diagnosed with cancer to an EGFR-targeted therapy (e.g., cetuximab, gefitinib, erlotinib or AZD9291) achieve one or more of the following: (i) reduction in carcinoma cells in pleural fluid, for example by at least about 5%, 10%, 15%, 20%, 25%, 30%, 35%, 40%, 45%, 50%, 60%, 70%, 80%, 90%, or 95%; (ii) reduction in the amount of accumulated pleural fluid; or (iii) reduction in serum concentration of EGFR as determined by ELISA or similar assays by at least about 5%, 10%, 15%, 20%, 25%, 30%, 35%, 40%, 45%, 50%, 60%, 70%, 80%, 90%, or 95%. In a particular aspect, methods described herein for resensitizing a subject diagnosed with cancer to an EGFR-targeted therapy (e.g., cetuximab, gefitinib, erlotinib or AZD9291) achieve one or more of the following for a period of at least about 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 60 weeks, 70 weeks, 80 weeks, 90 weeks, or 100 weeks: (i) reduction in carcinoma cells in pleural fluid, for example by at least about 5%, 10%, 15%, 20%, 25%, 30%, 35%, 40%, 45%, 50%, 60%, 70%, 80%, 90%, or 95%; (ii) reduction in the amount of accumulated pleural fluid; or (iii) reduction in serum concentration of EGFR as determined by ELISA or similar assays by at least about 5%, 10%, 15%, 20%, 25%, 30%, 35%, 40%, 45%, 50%, 60%, 70%, 80%, 90%, or 95%. In a particular embodiment, the EGFR targeted therapy is cetuximab. In another particular embodiment, the EGFR targeted therapy is gefitinib. In another particular embodiment, the EGFR targeted therapy is erlotinib. In another particular embodiment, the EGFR targeted therapy is AZD9291. In certain embodiments, such methods are methods of managing. In certain embodiments, such methods are methods of treating. In certain embodiments, the cancer is non-small cell lung carcinoma.

In one aspect, provided herein is a method of resensitizing an EGFR expressing tumor or tumor cell in a subject to an EGFR targeted therapy (e.g., cetuximab, gefitinib, erlotinib or AZD9291), comprising administering to the subject a therapeutically effective amount of an anti-MET antibody or antigen binding fragment thereof described herein (e.g., Ab235-Ab255). In a particular embodiment, the EGFR targeted therapy is cetuximab. In another particular embodiment, the EGFR targeted therapy is gefitinib. In another particular embodiment, the EGFR targeted therapy is erlotinib. In another particular embodiment, the EGFR targeted therapy is AZD9291. In certain embodiments, such methods are methods of managing. In certain embodiments, such methods are methods of treating. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In certain aspects, methods provided herein, such as methods of managing or treating cancer, further comprise administering to the subject a therapeutically effective amount of an EGFR targeted therapy (e.g., cetuximab, gefitinib, erlotinib or AZD9291) in combination with the anti-MET antibody or antigen binding fragment thereof described herein (e.g., Ab235-Ab255). In a particular aspect, the EGFR targeted therapy (e.g., cetuximab, gefitinib, erlotinib or AZD9291) being administered in combination with an anti-MET antibody (e.g., Ab235-Ab255) is the same EGFR targeted therapy to which the subject had been resistant. In one aspect, the cancer is characterized as expressing EGFR. In a certain other aspect, methods provided herein comprise measuring the expression level of EGFR, for example EGFR amplification or EGFR protein expression. In a particular aspect, methods provided herein comprise measuring the expression level of EGFR. In a particular aspect, methods provided herein comprise measuring the expression level of EGFR and identifying a subject having cancer or suspected of having cancer that expresses EGFR. In a particular aspect, the EGFR targeted therapy is cetuximab, gefitinib, erlotinib or AZD9291. In a certain aspect, the cancer is non-small cell lung carcinoma. In another aspect, the cancer is metastatic. In a certain aspect, the cancer to be treated or managed by the methods described herein has been characterized as being resistant to treatment with an anti-EGFR antibody such as cetuximab, gefitinib, erlotinib or AZD9291, for example, prior to treatment with an anti-MET antibody described herein (e.g., Ab235-Ab255). In a particular aspect, the EGFR targeted therapy (e.g., cetuximab, gefitinib, erlotinib or AZD9291) is administered concurrently with the antibody or antigen binding fragment thereof. In a specific aspect, the EGFR targeted therapy (e.g., cetuximab, gefitinib, erlotinib or AZD9291) and the anti-MET antibody or antigen binding fragment thereof are administered sequentially. In one aspect, the anti-MET antibody or antigen binding fragment thereof (e.g., Ab235-Ab255) is administered after surgical removal of a tumor of the cancer. In a certain aspect, the EGFR targeted therapy (e.g., cetuximab, gefitinib, erlotinib or AZD9291) and the anti-MET antibody or antigen binding fragment thereof (e.g., Ab235-Ab255) are administered after surgical removal of a tumor of the cancer. In a certain aspect, the method of managing or treating cancer further comprises administering to the subject cetuximab, gefitinib, erlotinib or AZD9291. In a particular embodiment, the EGFR targeted therapy is cetuximab. In another particular embodiment, the EGFR targeted therapy is gefitinib. In another particular embodiment, the EGFR targeted therapy is erlotinib. In another particular embodiment, the EGFR targeted therapy is AZD9291. In certain embodiments, such methods are methods of managing. In certain embodiments, such methods are methods of treating. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In one aspect, provided herein is a method of resensitizing a subject diagnosed with cancer to a BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)), comprising administering to the subject a therapeutically effective amount of an anti-MET antibody or antigen binding fragment thereof described herein (e.g., Ab235-Ab255). In a particular aspect, the method of resensitizing a subject diagnosed with cancer to a BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) comprises administering to the subject a therapeutically effective amount of an anti-MET antibody or antigen binding fragment thereof described herein (e.g., Ab235-Ab255) and a BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)). In specific aspect, the BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) being administered in combination with an anti-MET antibody (e.g., Ab235-Ab255) is the same BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) to which the subject had been resistant. In a specific aspect, the subject had been diagnosed with a BRAF-associated cancer, for example, a cancer expressing BRAF or a cancer comprising a BRAF mutation. In a specific aspect, the subject had been diagnosed with cancer with BRAF expression or overexpression. In a specific aspect, the subject had been diagnosed with cancer with mutated BRAF. In a certain aspect, the subject had been diagnosed with cancer characterized by BRAF expression. In a certain aspect, the subject had been diagnosed with cancer characterized by (i) BRAF expression and (ii) BRAF gene expression or amplification or BRAF overexpression. In a certain other aspect, methods provided herein comprise measuring the expression level of BRAF, for example BRAF amplification or protein expression or overexpression. In a particular aspect, methods provided herein comprise measuring the expression level of BRAF. In a certain aspect, methods provided herein comprise measuring the expression level of BRAF and identifying a subject having cancer or suspected of having cancer that expresses BRAF. In a particular aspect, the subject had been treated previously with a BRAF-targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)). In a certain aspect, the subject had acquired resistance to treatment with the BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)). In a particular embodiment, the BRAF targeted therapy is vemurafenib (ZELBORAF®). In another particular embodiment, the BRAF targeted therapy is dabrafenib (TAFINLAR®). In another particular embodiment, the BRAF targeted therapy is encorafenib (LGX818, Novartis). In another particular embodiment, the BRAF targeted therapy is PLX-4720. In another particular embodiment, the BRAF targeted therapy is PLX-3603 (RO5212054, Roche/Genentech). In another particular embodiment, the BRAF targeted therapy is PLX-8394 (Daiichi Sankyo). In another particular embodiment, the BRAF targeted therapy is CEP-32496 (Ambit Biosciences). In another particular embodiment, the BRAF targeted therapy is XL281 (BMS-908662, Exelixis). In another particular embodiment, the BRAF targeted therapy is RAF265 (CHIR-265, Novartis). In certain embodiments, such methods are methods of managing. In certain embodiments, such methods are methods of treating. In certain embodiments, the cancer is melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In certain aspects, methods described herein for resensitizing a subject diagnosed with cancer to a BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) achieve reduction in tumor growth or tumor cell proliferation by at least about 5%, 10%, 15%, 20%, 25%, 30%, 35%, 40%, 45%, 50%, 60%, 70%, 80%, 90%, or 95% relative to tumor growth or tumor cell proliferation prior to administration of an anti-MET antibody described herein (e.g., Ab235-Ab255). Nonlimiting examples of methods for characterizing response to therapy, such as resensitization, include measuring serum concentration of BRAF by ELISA or similar assays, cytological examination of skin biopsy for the presence of carcinoma cells, and immunohistochemical assays. For example, methods described herein for resensitizing a subject diagnosed with cancer to a BRAF-targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) achieve one or more of the following: (i) reduction in carcinoma cells in skin biopsy, for example by at least about 5%, 10%, 15%, 20%, 25%, 30%, 35%, 40%, 45%, 50%, 60%, 70%, 80%, 90%, or 95%; (ii) reduction in the amount of accumulated skin biopsy; or (iii) reduction in serum concentration of BRAF as determined by ELISA or similar assays by at least about 5%, 10%, 15%, 20%, 25%, 30%, 35%, 40%, 45%, 50%, 60%, 70%, 80%, 90%, or 95%. In a particular aspect, methods described herein for resensitizing a subject diagnosed with cancer to a BRAF-targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) achieve one or more of the following for a period of at least about 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 60 weeks, 70 weeks, 80 weeks, 90 weeks, or 100 weeks: (i) reduction in carcinoma cells in skin biopsy, for example by at least about 5%, 10%, 15%, 20%, 25%, 30%, 35%, 40%, 45%, 50%, 60%, 70%, 80%, 90%, or 95%; (ii) reduction in the amount of accumulated skin biopsy; or (iii) reduction in serum concentration of BRAF as determined by ELISA or similar assays by at least about 5%, 10%, 15%, 20%, 25%, 30%, 35%, 40%, 45%, 50%, 60%, 70%, 80%, 90%, or 95%. In a particular embodiment, the BRAF targeted therapy is vemurafenib (ZELBORAF®). In another particular embodiment, the BRAF targeted therapy is dabrafenib (TAFINLAR®). In another particular embodiment, the BRAF targeted therapy is encorafenib (LGX818, Novartis). In another particular embodiment, the BRAF targeted therapy is PLX-4720. In another particular embodiment, the BRAF targeted therapy is PLX-3603 (RO5212054, Roche/Genentech). In another particular embodiment, the BRAF targeted therapy is PLX-8394 (Daiichi Sankyo). In another particular embodiment, the BRAF targeted therapy is CEP-32496 (Ambit Biosciences). In another particular embodiment, the BRAF targeted therapy is XL281 (BMS-908662, Exelixis). In another particular embodiment, the BRAF targeted therapy is RAF265 (CHIR-265, Novartis). In certain embodiments, such methods are methods of managing. In certain embodiments, such methods are methods of treating. In certain embodiments, the cancer is melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In one aspect, provided herein is a method of resensitizing a BRAF expressing tumor or tumor cell in a subject to a BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)), comprising administering to the subject a therapeutically effective amount of an anti-MET antibody or antigen binding fragment thereof described herein (e.g., Ab235-Ab255). In a particular embodiment, the BRAF targeted therapy is vemurafenib (ZELBORAF®). In another particular embodiment, the BRAF targeted therapy is dabrafenib (TAFINLAR®). In another particular embodiment, the BRAF targeted therapy is encorafenib (LGX818, Novartis). In another particular embodiment, the BRAF targeted therapy is PLX-4720. In another particular embodiment, the BRAF targeted therapy is PLX-3603 (RO5212054, Roche/Genentech). In another particular embodiment, the BRAF targeted therapy is PLX-8394 (Daiichi Sankyo). In another particular embodiment, the BRAF targeted therapy is CEP-32496 (Ambit Biosciences). In another particular embodiment, the BRAF targeted therapy is XL281 (BMS-908662, Exelixis). In another particular embodiment, the BRAF targeted therapy is RAF265 (CHIR-265, Novartis). In certain embodiments, such methods are methods of managing. In certain embodiments, such methods are methods of treating. In certain embodiments, the cancer is melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In certain aspects, methods provided herein, such as methods of managing or treating cancer, further comprise administering to the subject a therapeutically effective amount of a BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) in combination with the anti-MET antibody or antigen binding fragment thereof described herein (e.g., Ab235-Ab255). In a particular aspect, the BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) being administered in combination with an anti-MET antibody (e.g., Ab235-Ab255) is the same BRAF targeted therapy to which the subject had been resistant. In one aspect, the cancer is characterized as expressing BRAF. In a certain other aspect, methods provided herein comprise measuring the expression level of BRAF, for example BRAF amplification or BRAF protein expression. In a particular aspect, methods provided herein comprise measuring the expression level of BRAF. In a particular aspect, methods provided herein comprise measuring the expression level of BRAF and identifying a subject having cancer or suspected of having cancer that expresses BRAF. In a particular aspect, the BRAF targeted therapy is vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis). In a certain aspect, the cancer is melanoma. In another aspect, the cancer is metastatic. In a certain aspect, the cancer to be treated or managed by the methods described herein has been characterized as being resistant to treatment with an anti-BRAF antibody such as vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis), for example, prior to treatment with an anti-MET antibody described herein (e.g., Ab235-Ab255). In a particular aspect, the BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) is administered concurrently with the antibody or antigen binding fragment thereof. In a specific aspect, the BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) and the anti-MET antibody or antigen binding fragment thereof are administered sequentially. In one aspect, the anti-MET antibody or antigen binding fragment thereof (e.g., Ab235-Ab255) is administered after surgical removal of a tumor of the cancer. In a certain aspect, the BRAF targeted therapy (e.g., vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis)) and the anti-MET antibody or antigen binding fragment thereof (e.g., Ab235-Ab255) are administered after surgical removal of a tumor of the cancer. In a certain aspect, the method of managing or treating cancer further comprises administering to the subject vemurafenib (ZELBORAF®), dabrafenib (TAFINLAR®), encorafenib (LGX818, Novartis), PLX-4720, PLX-3603 (RO5212054, Roche/Genentech), PLX-8394 (Daiichi Sankyo), CEP-32496 (Ambit Biosciences), XL281 (BMS-908662, Exelixis), or RAF265 (CHIR-265, Novartis). In a particular embodiment, the BRAF targeted therapy is vemurafenib (ZELBORAF®). In another particular embodiment, the BRAF targeted therapy is dabrafenib (TAFINLAR®). In another particular embodiment, the BRAF targeted therapy is encorafenib (LGX818, Novartis). In another particular embodiment, the BRAF targeted therapy is PLX-4720. In another particular embodiment, the BRAF targeted therapy is PLX-3603 (RO5212054, Roche/Genentech). In another particular embodiment, the BRAF targeted therapy is PLX-8394 (Daiichi Sankyo). In another particular embodiment, the BRAF targeted therapy is CEP-32496 (Ambit Biosciences). In another particular embodiment, the BRAF targeted therapy is XL281 (BMS-908662, Exelixis). In another particular embodiment, the BRAF targeted therapy is RAF265 (CHIR-265, Novartis). In certain embodiments, such methods are methods of managing. In certain embodiments, such methods are methods of treating. In certain embodiments, the cancer is melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In one aspect, provided herein is a method of resensitizing a subject diagnosed with cancer to a MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)), comprising administering to the subject a therapeutically effective amount of an anti-MET antibody or antigen binding fragment thereof described herein (e.g., Ab235-Ab255). In a particular aspect, the method of resensitizing a subject diagnosed with cancer to a MEK targeted therapy (e.g., selumetinib (AZD6244, ARRY-142866, AstraZeneca), WX-554 (Wilex), trametinib (MEKINIST®; GlaxoSmithKline), refametinib (*Ardea* Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) comprises administering to the subject a therapeutically effective amount of an anti-MET antibody or antigen binding fragment thereof described herein (e.g., Ab235-Ab255) and a MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)). In specific aspect, the MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) being administered in combination with an anti-MET antibody (e.g., Ab235-Ab255) is the same MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) to which the subject had been resistant. In a specific aspect, the subject had been diagnosed with a MEK-associated cancer, for example, a cancer expressing MEK or a cancer comprising a MEK mutation. In a specific aspect, the subject had been diagnosed with cancer with MEK expression or overexpression. In a specific aspect, the subject had been diagnosed with cancer with mutated MEK. In a certain aspect, the subject had been diagnosed with cancer characterized by MEK expression. In a certain aspect, the subject had been diagnosed with cancer characterized by (i) MEK expression and (ii) MEK gene expression or amplification or MEK overexpression. In a certain other aspect, methods provided herein comprise measuring the expression level of MEK, for example MEK amplification or protein expression or overexpression. In a particular aspect, methods provided herein comprise measuring the expression level of MEK. In a certain aspect, methods provided herein comprise measuring the expression level of MEK and identifying a subject having cancer or suspected of having cancer that expresses MEK. In a particular aspect, the subject had been treated previously with a MEK-targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)). In a certain aspect, the subject had acquired resistance to treatment with the MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)). In a particular embodiment, the MEK targeted therapy is selumetinib (AZD6244, ARRY-142866, AstraZeneca). In a particular embodiment, the MEK targeted therapy is WX-554 (Wilex). In a particular embodiment, the MEK targeted therapy is trametinib (MEKINIST®; GlaxoSmithKline). In a particular embodiment, the MEK targeted therapy is refametinib (Ardea Biosciences). In a particular embodiment, the MEK targeted therapy is E-6201 (Eisai). In a particular embodiment, the MEK targeted therapy is MEK-162 (Novartis). In a particular embodiment, the MEK targeted therapy is cobimetinib (GDC-0973; XL-518; Exelixis, Roche). In a particular embodiment, the MEK targeted therapy is TAK-733 (Takeda Phamaceuticals). In a particular embodiment, the MEK targeted therapy is binimetinib (Array BioPharma). In a particular embodiment, the MEK targeted therapy is PD-0325901 (Pfizer). In a particular embodiment, the MEK targeted therapy is pimasertib (MSC1936369; EMD Serono). In a particular embodiment, the MEK targeted therapy is MSC2015103 (EMD Serono). In a particular embodiment, the MEK targeted therapy is WX-554 (WILEX). In a particular embodiment, the MEK targeted therapy is RO48987655 (CH4987655; CIF/RG7167; Chugai Pharmaceuticals). In certain embodiments, such methods are methods of managing. In certain embodiments, such methods are methods of treating. In certain embodiments, the cancer is melanoma. In certain embodiments, the melanoma is uveal melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In certain aspects, methods described herein for resensitizing a subject diagnosed with cancer to a MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) achieve reduction in tumor growth or tumor cell proliferation by at least about 5%, 10%, 15%, 20%, 25%, 30%, 35%, 40%, 45%, 50%, 60%, 70%, 80%, 90%, or 95% relative to tumor growth or tumor cell proliferation prior to administration of an anti-MET antibody described herein (e.g., Ab235-Ab255). Nonlimiting examples of methods for characterizing response to therapy, such as resensitization, include measuring serum concentration of MEK by ELISA or similar assays, cytological examination of skin biopsy for the presence of carcinoma cells, and immunohistochemical assays. For example, methods described herein for resensitizing a subject diagnosed with cancer to a MEK-targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) achieve one or more of the following: (i) reduction in carcinoma cells in skin biopsy, for example by at least about 5%, 10%, 15%, 20%, 25%, 30%, 35%, 40%, 45%, 50%, 60%, 70%, 80%, 90%, or 95%; (ii) reduction in the amount of accumulated skin biopsy; or (iii) reduction in serum concentration of MEK as determined by ELISA or similar assays by at least about 5%, 10%, 15%, 20%, 25%, 30%, 35%, 40%, 45%, 50%, 60%, 70%, 80%, 90%, or 95%. In a particular aspect, methods described herein for resensitizing a subject diagnosed with cancer to a MEK-targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) achieve one or more of the following for a period of at least about 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 60 weeks, 70 weeks, 80 weeks, 90 weeks, or 100 weeks: (i) reduction in carcinoma cells in skin biopsy, for example by at least about 5%, 10%, 15%, 20%, 25%, 30%, 35%, 40%, 45%, 50%, 60%, 70%, 80%, 90%, or 95%; (ii) reduction in the amount of accumulated skin biopsy; or (iii) reduction in serum concentration of MEK as determined by ELISA or similar assays by at least about 5%, 10%, 15%, 20%, 25%, 30%, 35%, 40%, 45%, 50%, 60%, 70%, 80%, 90%, or 95%. In a particular embodiment, the MEK targeted therapy is selumetinib (AZD6244, ARRY-142866, AstraZeneca). In a particular embodiment, the MEK targeted therapy is WX-554 (Wilex). In a particular embodiment, the MEK targeted therapy is trametinib (MEKINIST®; GlaxoSmithKline). In a particular embodiment, the MEK targeted therapy is refametinib (Ardea Biosciences). In a particular embodiment, the MEK targeted therapy is E-6201 (Eisai). In a particular embodiment, the MEK targeted therapy is MEK-162 (Novartis). In a particular embodiment, the MEK targeted therapy is cobimetinib (GDC-0973; XL-518; Exelixis, Roche). In a particular embodiment, the MEK targeted therapy is TAK-733 (Takeda Phamaceuticals). In a particular embodiment, the MEK targeted therapy is binimetinib (Array BioPharma). In a particular embodiment, the MEK targeted therapy is PD-0325901 (Pfizer). In a particular embodiment, the MEK targeted therapy is pimasertib (MSC1936369; EMD Serono). In a particular embodiment, the MEK targeted therapy is MSC2015103 (EMD Serono). In a particular embodiment, the MEK targeted therapy is WX-554 (WILEX). In a particular embodiment, the MEK targeted therapy is RO48987655 (CH4987655; CIF/RG7167; Chugai Pharmaceuticals). In certain embodiments, such methods are methods of managing. In certain embodiments, such methods are methods of treating. In certain embodiments, the cancer is melanoma. In certain embodiments, the melanoma is uveal melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In one aspect, provided herein is a method of resensitizing a MEK expressing tumor or tumor cell in a subject to a MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)), comprising administering to the subject a therapeutically effective amount of an anti-MET antibody or antigen binding fragment thereof described herein (e.g., Ab235-Ab255). In a particular embodiment, the MEK targeted therapy is selumetinib (AZD6244, ARRY-142866, AstraZeneca). In a particular embodiment, the MEK targeted therapy is WX-554 (Wilex). In a particular embodiment, the MEK targeted therapy is trametinib (MEKINIST®; GlaxoSmithKline). In a particular embodiment, the MEK targeted therapy is refametinib (Ardea Biosciences). In a particular embodiment, the MEK targeted therapy is E-6201 (Eisai). In a particular embodiment, the MEK targeted therapy is MEK-162 (Novartis). In a particular embodiment, the MEK targeted therapy is cobimetinib (GDC-0973; XL-518; Exelixis, Roche). In a particular embodiment, the MEK targeted therapy is TAK-733 (Takeda Phamaceuticals). In a particular embodiment, the MEK targeted therapy is binimetinib (Array BioPharma). In a particular embodiment, the MEK targeted therapy is PD-0325901 (Pfizer). In a particular embodiment, the MEK targeted therapy is pimasertib (MSC1936369; EMD Serono). In a particular embodiment, the MEK targeted therapy is MSC2015103 (EMD Serono). In a particular embodiment, the MEK targeted therapy is WX-554 (WILEX). In a particular embodiment, the MEK targeted therapy is RO48987655 (CH4987655; CIF/RG7167; Chugai Pharmaceuticals). In certain embodiments, such methods are methods of managing. In certain embodiments, such methods are methods of treating. In certain embodiments, the cancer is melanoma. In certain embodiments, the melanoma is uveal melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

In certain aspects, methods provided herein, such as methods of managing or treating cancer, further comprise administering to the subject a therapeutically effective amount of a MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) in combination with the anti-MET antibody or antigen binding fragment thereof described herein (e.g., Ab235-Ab255). In a particular aspect, the MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) being administered in combination with an anti-MET antibody (e.g., Ab235-Ab255) is the same MEK targeted therapy to which the subject had been resistant. In one aspect, the cancer is characterized as expressing MEK. In a certain other aspect, methods provided herein comprise measuring the expression level of MEK, for example MEK amplification or MEK protein expression. In a particular aspect, methods provided herein comprise measuring the expression level of MEK. In a particular aspect, methods provided herein comprise measuring the expression level of MEK and identifying a subject having cancer or suspected of having cancer that expresses MEK. In a particular aspect, the MEK targeted therapy is selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals). In a certain aspect, the cancer is melanoma. In another aspect, the cancer is metastatic. In a certain aspect, the cancer to be treated or managed by the methods described herein has been characterized as being resistant to treatment with an anti-MEK antibody such as selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals), for example, prior to treatment with an anti-MET antibody described herein (e.g., Ab235-Ab255). In a particular aspect, the MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) is administered concurrently with the antibody or antigen binding fragment thereof. In a specific aspect, the MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) and the anti-MET antibody or antigen binding fragment thereof are administered sequentially. In one aspect, the anti-MET antibody or antigen binding fragment thereof (e.g., Ab235-Ab255) is administered after surgical removal of a tumor of the cancer. In a certain aspect, the MEK targeted therapy (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals)) and the anti-MET antibody or antigen binding fragment thereof (e.g., Ab235-Ab255) are administered after surgical removal of a tumor of the cancer. In a certain aspect, the method of managing or treating cancer further comprises administering to the subject selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Phamaceuticals), binimetinib (Array BioPharma), PD-0325901 (Pfizer), pimasertib (MSC1936369; EMD Serono), MSC2015103 (EMD Serono), WX-554 (WILEX), or RO48987655 (CH4987655; CIF/RG7167; Chugai Pharmaceuticals). In a particular embodiment, the MEK targeted therapy is selumetinib (AZD6244, ARRY-142866, AstraZeneca). In a particular embodiment, the MEK targeted therapy is WX-554 (Wilex). In a particular embodiment, the MEK targeted therapy is trametinib (MEKINIST®; GlaxoSmithKline). In a particular embodiment, the MEK targeted therapy is refametinib (Ardea Biosciences). In a particular embodiment, the MEK targeted therapy is E-6201 (Eisai). In a particular embodiment, the MEK targeted therapy is MEK-162 (Novartis). In a particular embodiment, the MEK targeted therapy is cobimetinib (GDC-0973; XL-518; Exelixis, Roche). In a particular embodiment, the MEK targeted therapy is TAK-733 (Takeda Phamaceuticals). In a particular embodiment, the MEK targeted therapy is binimetinib (Array BioPharma). In a particular embodiment, the MEK targeted therapy is PD-0325901 (Pfizer). In a particular embodiment, the MEK targeted therapy is pimasertib (MSC1936369; EMD Serono). In a particular embodiment, the MEK targeted therapy is MSC2015103 (EMD Serono). In a particular embodiment, the MEK targeted therapy is WX-554 (WILEX). In a particular embodiment, the MEK targeted therapy is RO48987655 (CH4987655; CIF/RG7167; Chugai Pharmaceuticals). In certain embodiments, such methods are methods of managing. In certain embodiments, such methods are methods of treating. In certain embodiments, the cancer is melanoma. In certain embodiments, the melanoma is uveal melanoma. In certain embodiments, the cancer is non-small cell lung carcinoma (e.g., lung adenocarcinoma). In certain embodiments, the cancer is a brain glioma. In certain embodiments, the cancer is a gastric cancer. In certain embodiments, the cancer comprises cancer cells expressing MET comprising one or more mutations, e.g., deletions, in exon 14 (encoding, e.g., Leu964-Asp1010) of the human MET gene. In specific embodiments, the one or more mutations in exon 14 (encoding, e.g., Leu964-Asp1010) of the human MET gene confers reduced HGF-induced receptor degradation. In specific embodiments, the one or more mutations in exon 14 (encoding, e.g., Leu964-Asp1010) of the human MET gene mutates or removes the Tyr1003 site.

An anti-MET antibody described herein or an antigen-binding fragment thereof, which is a MET antagonist for use in the methods provided herein is capable of inhibiting (e.g., partially inhibiting) or decreasing/reducing MET expression and/or a MET activity. Activities of MET are known in the art. In specific embodiments, an anti-MET antibody described herein which is a MET antagonist inhibits (e.g., partially inhibits) one or more of the following MET activities: phosphorylation (e.g., autophosphorylation) of MET receptor (e.g., cytoplasmic domain of MET, such as cytoplasmic kinase domain of MET), receptor internalization, receptor degradation, MET ligand (e.g., HGF) binding to MET receptor, cell migration, cell survival, MET receptor homodimerization, and downstream signaling pathways (e.g., MAPK cascade, PI3K-Akt axis, STAT pathway, and NF-κB pathway). Methods for measuring these activities are known in the art.

In specific embodiments, an anti-MET antibody described herein which is a MET antagonist inhibits (e.g., partially inhibits), by at least about 10%, 20%, 30%, 40%, 50%, 60%, 70%, 80%, 90%, 97%, 98%, 99%, or 100%, one or more such MET activities.

5.5.1 Diagnostic Uses

In one aspect, anti-MET antibodies described herein and antigen-binding fragments thereof, which specifically bind to an ECD of human MET can be used for diagnostic purposes to detect, diagnose, or monitor a condition described herein (e.g., a condition involving MET and/or abnormal MET signaling and/or abnormal MET expression), such as cancer (e.g., colorectal cancer, gastric cancer, lung cancer, or melanoma). In specific embodiments, anti-MET antibodies described herein or an antigen-binding fragment thereof for use in diagnostic purposes are labeled. Methods provided herein for diagnostic purposes to detect, diagnose, or monitor a condition described herein can be in vitro methods, in situ methods, or ex vivo methods. Methods provided herein for diagnostic purposes to detect, diagnose, or monitor a condition described herein can be in vivo methods.

In certain embodiments, provided herein are methods for the detection of a condition described herein, such as cancer, comprising: (a) assaying the expression of MET in a sample of a subject using one or more antibodies described herein (e.g., any one of antibodies Ab235-Ab255, or an antibody comprising CDRs of any one of antibodies Ab235-Ab255) or an antigen-binding fragment thereof; and (b) comparing the level of MET expression with a control level, e.g., levels in normal tissue samples (e.g., from a patient not having a condition described herein, or from the same patient before onset of the condition), whereby an increase or decrease in the assayed level of MET expression compared to the control level of MET expression is indicative of a condition described herein.

In certain embodiments, provided herein are methods for the detection of cancer expressing MET (e.g., overexpressing MET), comprising: (a) assaying the expression of MET in a sample of a subject using one or more antibodies described herein (e.g., any one of antibodies Ab235-Ab255, or an antibody comprising CDRs of any one of antibodies Ab235-Ab255) or an antigen-binding fragment thereof; and (b) comparing the level of MET expression with a control level, e.g., levels in normal samples (e.g., from a patient not having cancer, a patient having cancer that does not overexpress MET, or from the same patient before onset of cancer). In specific aspects, an increase or decrease in the assayed level of MET expression compared to a control level of MET expression is indicative of cancer expressing MET.

In a specific embodiment, provided herein is a method of diagnosing a MET-expressing cancer in a patient, wherein the method comprises the steps of:
(a) contacting a biological sample from the patient with one or more antibodies described herein (e.g., any one of antibodies Ab235-Ab255, or an antibody comprising CDRs of any one of antibodies Ab235-Ab255) or an antigen-binding fragment thereof;
(b) detecting binding of the antibody or antigen-binding fragment to MET to determine a MET protein level in the biological sample from the patient; and
(c) comparing the MET protein level with a standard MET protein level.

In a specific embodiment, provided herein is a method of monitoring MET protein level during treatment of a MET-expressing cancer in a patient, wherein the method comprises the steps of:
(a) contacting a biological sample from the patient with one or more antibodies described herein (e.g., any one of antibodies Ab235-Ab255, or an antibody comprising CDRs of any one of antibodies Ab235-Ab255) or an antigen-binding fragment thereof;
(c) detecting binding of the antibody or antigen-binding fragment to MET to determine a MET protein level in the biological sample from the patient; and
(d) comparing the MET protein level with a standard MET protein level.

Any sample (e.g., bodily fluid or tissue sample) from a subject can be used in diagnostic methods provided herein. Non-limiting examples of samples which can be used in diagnostic methods provided herein include, serum sample, plasma sample, tissue sample, urine sample, tumor sample, and stool sample.

In one embodiment, described herein are methods for treating a cancer (e.g. a non-small cell lung cancer) in a patient, comprising administering to the patient a therapeutically effective amount of a one or more antibodies described herein (e.g., any one of antibodies Ab235-Ab255, or an antibody comprising CDRs of any one of antibodies Ab235-Ab255) or an antigen-binding fragment thereof, wherein the patient has a tumor that has been characterized in that cells from the tumor: i) express a MET receptor comprising one or more mutations or deletions in exon 14 (encoding, e.g., Leu964-Asp1010) of the human MET gene. In certain embodiments, cells from the tumor overexpress the MET receptor.

In certain embodiments, described herein are methods for determining whether a patient diagnosed with cancer (e.g., a non-small cell lung cancer) is indicated as likely to be responsive to treatment with a therapeutically effective amount of a one or more antibodies described herein (e.g., any one of antibodies Ab235-Ab255, or an antibody comprising CDRs of any one of antibodies Ab235-Ab255) or an antigen-binding fragment thereof, comprising measuring the expression (e.g., protein level) of a MET receptor in a sample of tumor cells from the patient, and further comprising determining whether the tumor cells express a MET receptor comprising one or more mutations or deletions in exon 14 (encoding, e.g., Leu964-Asp1010) of the human MET gene; wherein the expression of a MET receptor comprising one or more mutations or deletions in exon 14 (encoding, e.g., Leu964-Asp1010) of the human MET gene indicates that the patient diagnosed with said cancer is likely to be responsive to treatment. In certain embodiments, said methods for determining comprise a first step of obtaining the sample from a tumor from the patient. In certain embodiments, said methods comprise an additional step of administering to a patient indicated as likely to be responsive to treatment a therapeutically effective amount of one or more antibodies described herein (e.g., any one of antibodies Ab235-Ab255, or an antibody comprising CDRs of any one of antibodies Ab235-Ab255) or an antigen-binding fragment thereof.

Antibodies described herein can be used to assay MET levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:

3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin.

In one embodiment, monitoring of a condition described herein (e.g., a condition involving MET and/or abnormal MET signaling and/or abnormal MET expression), such as cancer, is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

6. EXAMPLES

The examples in this section (i.e., Section 6) are offered by way of illustration, and not by way of limitation.

6.1 Example 1: Generation of Anti-MET Antibodies 6.1.1 Materials and Methods
6.1.1.1 Generation of Anti-MET Antibodies Murine monoclonal antibodies, such as mouse and rat monoclonal antibodies, that specifically bind to the extracellular domain (ECD) of human MET were obtained from mice and rats immunized with a recombinant human MET-ECD and using hybridoma technology to generate hybridoma clones. A recombinant human MET-ECD with an Fc tag (MET-ECD-Fc; Sinobiological (Catalogue #10692-H03H)) or human MET-ECD with a His tag (MET-ECD-His) were used for immunization. Below is a representation of the amino acid sequence of an ECD of human MET (hu-MET-ECD) with a C-terminal His tag and a signal peptide (amino acid residues 1-24) which is processed and not present in the mature form of the ECD used for immunization:

```
                                              (SEQ ID NO: 195)
  1 MKAPAVLAPG ILVLLFTLVQ RSNGECKEAL AKSEMNVNMK
    YQLPNFTAET PIQNVILHEH

61 HIFLGATNYI YVLNEEDLQK VAEYKTGPVL EHPDCFPCQD
    CSSKANLSGG VWKDNINMAL

121 VVDTYYDDQL ISCGSVNRGT CQRHVFPHNH TADIQSEVHC
    IFSPQIEEPS QCPDCVVSAL

181 GAKVLSSVKD RFINFFVGNT INSSYFPDHP LHSISVRRLK
    ETKDGFMFLT DQSYIDVLPE

241 FRDSYPIKYV HAFESNNFIY FLTVQRETLD AQTFHTRIIR
    FCSINSGLHS YMEMPLECIL

301 TEKRKKRSTK KEVFNILQAA YVSKPGAQLA RQIGASLNDD
    ILFGVFAQSK PDSAEPMDRS

361 AMCAFPIKYV NDFFNKIVNK NNVRCLQHFY GPNHEHCFNR
    TLLRNSSGCE ARRDEYRTEF
```

```
                     -continued
421 TTALQRVDLF MGQFSEVLLT SISTFIKGDL TIANLGTSEG
    RFMQVVVSRS GPSTPHVNFL

481 LDSHPVSPEV IVEHTLNQNG YTLVITGKKI TKIPLNGLGC
    RHFQSCSQCL SAPPFVQCGW

541 CHDKCVRSEE CLSGTWTQQI CLPAIYKVFP NSAPLEGGTR
    LTICGWDFGF RRNNKFDLKK

601 TRVLLGNESC TLTLSESTMN TLKCTVGPAM NKHFNMSIII
    SNGHGTTQYS TFSYVDPVIT

661 SISPKYGPMA GGTLLTLTGN YLNSGNSRHI SIGGKTCTLK
    SVSNSILECY TPAQTISTEF

721 AVKLKIDLAN RETSIFSYRE DPIVYEIHPT KSFISGGSTI
    TGVGKNLNSV SVPRMVINVH

781 EAGRNFTVAC QHRSNSEIIC CTTPSLQQLN LQLPLKTKAF
    FMLDGILSKY FDLIYVHNPV

841 FKPFEKPVMI SMGNENVLEI KGNDIDPEAV KGEVLKVGNK
    SCENIHLHSE AVLCTVPNDL

901 LKLNSELNIE WKQAISSTVL GKVIVQPDQN FTLEHHHHHH HH
```

Briefly, Balb/c mice and Wistar rats were immunized with a MET immunogen corresponding to hu-MET-ECD (mature form without the signal peptide). Prior to immunization, the hu-MET-ECD immunogen was emulsified in Freund's Complete Adjuvant. Booster immunizations also were emulsified in Freund's Incomplete Adjuvant.

Antibody serum titers were determined after immunization by ELISA, and cell fusion was performed to generate hybridoma cells. For cell fusion, spleen cells were obtained from the spleens of immunized mice and rats. Hybridoma cells were generated by fusing the lymphocytes with NS0 myeloma fusion partner cells. The hybridoma cells were then screened for binding activity and antagonist activity, such as inhibition of MET phosphorylation induced by HGF (a MET ligand).

A primary screen was performed with IgG-specific secondary antibody to identify hybridoma clones secreting IgG antibodies. Selected samples were expanded for further screening.

Pre-subclones were screened a second time for binding to the MET immunogen (i.e., the ECD of human MET) by ELISA and for blocking MET phosphorylation by cell based assays, which are described in more detail in the sections below. Pre-subclones were also screened for blocking MET phosphorylation activity and agonistic activity, wherein clones with high blocking MET phosphorylation activity and low or no agonistic activity were selected. For each screening method, clones were ranked and the best clones were selected for subcloning.

Subclones were tested for binding to the hu-MET-ECD immunogen by ELISA, for blocking MET phosphorylation by cell based assays, for no or low agonistic activity by cell based assays, for cell proliferation inhibition by cell based assays, and for cell scatter inhibition by cell based assays. From these screening procedures, mouse IgG$_1$ kappa isotype antibodies, and rat IgG$_{2a}$ antibodies with a kappa chain or lambda chain were identified.

The sequences of the light chain and heavy chain variable regions of these mouse and rat antibodies were obtained by PCR methods. The sequences of the variable light chain region and the variable heavy chain region, as well as the sequences of the CDRs and framework regions (FRs) were determined based on the Kabat numbering system.

Humanized antibodies, such as deimmunized antibodies, e.g., composite human antibodies were generated. Accordingly, additional anti-MET antibodies, such as composite human antibodies, were designed using Composite Human Antibody™ technology (Antitope Ltd., Cambridge, United Kingdom) based on the VH and VL amino acid sequences of rat/mouse anti-MET antibodies obtained from the screening process described above to produce anti-MET antibodies with composite human amino acid sequences. Three heavy chain variable region sequences (H1, H2, and H3) and five light chain variable region sequences (L1, L2, L3, L4, and L5) were selected to be used for gene synthesis, expression in mammalian cells and testing for direct binding to human MET-ECD as well as activity in blocking hepatocyte growth factor (HGF)-induced phosphorylation of MET.

Nucleic acid molecules encoding the H (heavy chain) and L (light chain) variable region amino acid sequences were cloned directly into expression vectors for human $IgG_1$ VH chains and human Vκ chains. All constructs were confirmed by sequencing. Vectors encoding $IgG_1$ VH (H1-H3) and Vκ (L1-L5) chains were transfected into NS0 cells in different combinations to produce antibodies. Cells transiently transfected with non-linearized DNA were incubated for four days prior to harvesting supernatants which were used directly in assays or for purification. Stable transfections to establish cell lines expressing the antibodies were carried out using linearized DNA and were subsequently drug-selected. Supernatants from drug-resistant colonies for each construct were tested for IgG titre using an $IgG_1$ ELISA, and the best expressing lines were selected based on an above-background (usually >0.1 μg/ml) IgG titre in the supernatant, and expanded in the presence of drug selection through 24-well and 6-well plates, T75 and T175 tissue culture flasks, with screening for IgG expression at every stage. Antibody expression was confirmed by Coomassie Blue stained SDS-PAGE.

Based on these methods, anti-MET antibodies Ab235-Ab255 were generated. See Tables 9 and 10 (VL/VH amino acid sequences, respectively) and Tables 11 and 12 (VL-encoding/VH-encoding nucleic acid sequences, respectively).

6.1.1.2 Binding Affinity by Fluorescent Activated Cell Sorting ("FACS")

Antibodies were labeled with Alexa 647 (Invitrogen) according to the manufacturer's instructions. A549 cells (a human lung adenocarcinoma epithelial cell line) were removed from T175 cells with 10 mL of 2 mM EDTA in PBS and the flask was rinsed with 5 mL of PBS. The cells were spun down at 1,200 RPM for 3 minutes. The cells were resuspended in pre-chilled FACS buffer and the cells were counted. The cells were then diluted to $1\times10^6$ cells/mL and incubated in FACS buffer on ice for 1 hour. 100 μL of cells were transferred to wells of U-Bottom 96 well plate and cells were pelleted at 1,200 rpm for 3 minutes and the buffer was discarded. The antibodies (100 nM initial concentration) were diluted in FACS buffer. 50 μL of diluted antibody was added to the cells and the cells were incubated on ice for 4 hours to allow antibody binding to reach equilibrium. The cells were pelleted at 1,200 rpm for 3 minutes and the buffer was discarded. Next, the cells were washed with 200 μL of FACS buffer four times (spin at 1,200 rpm for 3 minutes at 4° C.). The cells were resuspended in 100 μL of FACS buffer and run on an Accuri-C6 FACS machine. The mean fluorescence intensity of each point was plotted using specific binding program with GraphPad Prism software, and binding affinity was calculated.

6.1.1.3 Species Specificity Determination

Antibodies were labeled with Alexa 647 (Invitrogen) according to the manufacturer's instructions. Human (A549), monkey (4MBr5), dog (MDCK), and mouse (MS1) cells were removed from T175 cells with 10 mL of 2 mM EDTA in PBS and the flask was rinsed with 5 mL of PBS. The cells were spun down at 1,200 RPM for 3 minutes. The cells were resuspended in pre-chilled FACS buffer and the cells were counted. The cells were then diluted to 1×106 cells/mL and incubated in FACS buffer on ice for 1 hour. 100 μL of cells were transferred to wells of U-Bottom 96 well plate and cells were pelleted at 1,200 rpm for 3 minutes and the buffer was discarded. The Alexa-647-labeled antibodies were diluted to a final concentration of 6 nM. 50 μL of the diluted 6 nM Alexa-647-labeled antibody was incubated on ice for 4 hours to allow antibody binding to reach equilibrium. The cells were pelleted at 1,200 rpm for 3 minutes and the buffer was discarded. Next, the cells were washed with 200 μL of FACS buffer four times (spin at 1,200 rpm for 3 minutes at 4° C.). The cells were resuspended in 100 μL of FACS buffer and run on an Accuri-C6 FACS machine. The mean fluorescence intensity of each point was plotted using specific binding program with GraphPad Prism software, and binding affinity was calculated.

6.1.1.4 MET Antibody Binding Domain Mapping

Five μg of human cMET ECD, mouse cMET ECD or human/mouse chimera cMET ECD was diluted into 10 mL of borate buffer, 100 μL was added to each well of a 96 well plate, and the plate was incubated at 4° C. overnight. The borate buffer was removed and 200 μL of the blocking buffer was added and allowed to incubate at room temperature for one hour. The blocking buffer was removed by flicking the plate into a sink and antibody dilutions or positive or negative controls were added to the plate in a volume of 100 μL and incubated at room temperature for one hour and then washed three times with TBST. The plate was then incubated with 100 μL per well of HRP-conjugated antibody diluted 1:5000 in 1% BSA TBST (0.05% Tween) at room temperature for 1 hour. The plate was then washed three times with TBST and residual TBST was removed by tapping the plate on a paper towel. The luminescence was then measured as previously described 6.1.1.5 ELISA Assay to Assess Competition with Fluorescently Labeled Antibody Antibodies were labeled with Alexa 647 (Invitrogen) according to the manufacturer's instructions. A549 cells were removed from T175 cells with 10 mL of 2 mM EDTA in PBS and the flask was rinsed with 5 mL of PBS. The cells were spun down at 1,200 RPM for 3 minutes. The cells were resuspended in pre-chilled FACS buffer and the cells were counted. The cells were then diluted to 1×106 cells/mL and incubated in FACS buffer on ice for 1 hour. 100 μL of cells were transferred to wells of U-Bottom 96 well plate and cells were pelleted at 1,200 rpm for 3 minutes and the buffer was discarded. The antibodies (600 nM initial concentration) were diluted in FACS buffer and Alexa-647-labeled antibodies were diluted to a final concentration of 6 nM. 25 μL of the diluted 6 nM Alexa-647-labeled antibody, and 25 μL of the unlabeled diluted antibody at varying concentrations was added to each well and the cells were incubated on ice for 4 hours to allow antibody binding to reach equilibrium. The cells were pelleted at 1,200 rpm for 3 minutes and the buffer was discarded. Next, the cells were washed with 200 μL of FACS buffer four times (spin at 1,200 rpm for 3 minutes at 4° C.). The cells were resuspended in 100 μL of FACS buffer and run on an Accuri-C6 FACS machine. The mean fluorescence intensity of each point was plotted using specific binding program with GraphPad Prism software, and binding affinity was calculated.

6.1.1.6 ELISA Analyses to Assess Competition with Antibody

The binding of anti-MET antibodies to recombinant MET extracellular domain ("MET-ECD") was analyzed by competition ELISA. A four-fold dilution series of test antibody (10 μg/ml to 0.0024 μg/ml) was premixed with a constant concentration of a reference antibody (e.g., Ab237C) (0.016 μg/ml, final concentration) before incubating for 1 hour at room temperature on plates pre-coated with MET-ECD-His. The binding of the reference antibody was detected with goat anti-rat IgG Fc conjugated with HRP (Bethyl cat. no. A110-236P) and TMB substrate (Thermo Scientific cat. no. 34029). The reaction was stopped with 3M HCl, absorbance read at 450 nm on a Dynex Technologies MRX TC II plate reader and the binding curves plotted. Binding curves were used to calculate $IC_{50}$ values for each test antibody normalized to the $IC_{50}$ of the reference antibody.

6.1.1.7 FACS Analyses to Assess Competition with Antibody

The binding of anti-MET antibodies to cell surface MET was analyzed by competition FACS analysis using A549 NSCLC cells (ATCC cat. no. CCL-185). A four-fold dilution series of test antibody (10 μg/ml to 0.0097 μg/ml) was premixed with a constant concentration of a reference anti-MET antibody (e.g., Ab237C antibody) (0.02 μg/ml, final concentration) in FACS buffer. A total of $3 \times 10^5$ A549 NSCLC cells were added per dilution of antibody and incubated on ice for 1 hour. Cells were washed and a 1:100 dilution of PE-labeled goat anti-rat IgG antibody (BioLegend cat. no. 405406) in FACS buffer was added before incubation on ice for 1 hour. Cells were washed, resuspended in 300 μl of FACS buffer and the binding of the reference anti-MET antibody (e.g., Ab237C antibody) to A549 cells expressing surface MET was analyzed using a Beckton Dickinson FACScalibur. The geometric mean fluorescence intensity was plotted against antibody concentration. The $IC_{50}$ of each of the test antibodies was calculated relative to the $IC_{50}$ of the reference antibody.

6.1.1.8 ELISA Phosphorylation Analyses

A549 cells, a lung carcinoma cell line, or U87MG cells, a glioma cell line, were seeded at a concentration of 25,000 cells per well of a 96 well plate and incubated overnight at under standard conditions (herein, "standard conditions" refers to the incubation of cells at 5% $CO_2$, 37° C.). 24 hours prior to the assay, the cells are rinsed with 100 μL per well with phosphate buffered saline ("PBS"). Next the cells were starved in 100 μL per well of F12K starvation medium (Gibco) comprising penicillin/streptomycin and L-glutamine overnight under standard conditions. To determine the $IC_{50}$, the medium is removed from the plates and the cells are incubated with antibodies diluted in starvation medium for 2 hours under standard conditions. Next, 50 μg/mL of HGF is diluted 1:60 in serum free medium DMEM and 5 μL is added to each well for a final ligand concentration of 80 ng/mL and incubated for 10 minutes under standard conditions. The cells are washed with chilled 2×PBS. Next, the cells are incubated on ice for 1 hour with 100 μL per well of lysis buffer (50 mM Tris pH 7.4, 150 mM NaCl, 1 mM EDTA, 1% Triton X-100, protease inhibitors, 1 mM Na vanadate).

To prepare the ELISA capture plate, plates were coated with 100 μL per well of anti-MET antibody (Cell Signaling cat. No. 3148) diluted 1:2000 in 1× borate buffer (Thermo Scientific) overnight at 4° C. Next, the coating antibodies were removed and the plates were blocked with 200 μL per well of 5% bovine serum albumin ("BSA") in tris-buffered saline tween ("TBST") at room temperature for 1 hour. The blocking buffer was removed and the whole lysates were added to the ELISA plate and incubated at room temperature for 2 hours. The plates were then washed three times with TBST and subsequently incubated with 100 per well of anti-1234/1235 MET XP antibody (Cell Signaling cat. No. 3077) diluted 1:5000 in 1% BSA TBST (0.05% Tween) at room temperature for 2 hours. The plates are then washed three times with TBST and subsequently incubated with 100 μL per well of anti-rabbit-HRP antibody (Invitrogen cat. No. 656120) diluted 1:5000 in 1% BSA TBST (0.05% Tween) at room temperature for 1 hour. The plates were then washed three times with TBST and tapped on paper towel to remove all remnants of wash buffer. Finally, SuperSignal® West Pico reagents (Thermoscientific) are mixed 1:1 and 100 μL is added to each well. The luminescence was read on a plate reader with Luminescence Glow protocol.

6.1.1.9 Akt and Mapk Phosphorylation Analyses

A549 cells were incubated with only HGF or only the indicated antibodies for 24 hours. Western blots were generated from total protein separated on a 10% SDS-PAGE gel. Resolved protein was transferred to nitrocellulose (Bio-Rad), blocked for 1 h with 5% skim milk at 25° C., and then incubated with the indicated antibody overnight at 4° C. The anti-pAkt antibody, anti-pMAPK antibody (Cell Signaling cat. No. 9271 and Cell Signaling cat. No. 4370, respectively), and anti-1234/1235 MET XP antibody (Cell Signaling cat. No. 3077) were used at a concentration of 1 μg/mL in 5% skim milk. Secondary mouse and rabbit antibodies (GE Healthcare) were used at a 1:5000 dilution for 1 h at 25° C. SuperSignal® West Picto Chemiluminescent HRP Substrate (Thermo Scientific cat. No. 34078) was used as directed.

6.1.1.10 Receptor Interaction Assays

His-tagged MET extracellular domain was diluted to 2 μg/mL in PBS and 100 was added to each well of a 96-well white high binding plate overnight at room temperature. The plates were then washed three times with TBST and 300 μL of the blocking buffer (1% BSA/TBS) and incubated at room temperature for one hour. The blocking buffer was removed after the incubation. To prepare a 2× antibody solution in blocking buffer, 200 nM antibody was diluted 1:3 for a total of steps by combining 100 μL of the antibody with 200 μL of starvation medium. Similarly, a 2× Biotinylated-HGF dilution was prepared in blocking buffer for a final concentration of 0.3 nM. 50 μL of the 2× antibody solution and 50 μL of the 2× Biotinylated-HGF solution was mixed, and the 100 μL mixture was added to each well. The cells were incubated at room temperature for two hours. The plates were then washed three times with TBST. Next, 100 μL of a 1:2000 dilution of streptavidin-HRP in blocking solution was added to each well and incubated for one hour at room temperature. The plate was then washed three times with TBST. Finally, SuperSignal® West Pico reagents were mixed 1:1 and 100 μL was added to each well. The luminescence was measured on a plate reader according to the Luminescence Glow protocol.

6.1.1.11 Antibody-Induced Receptor Degradation Assays

For Western blot analysis, U87-MG, a glioblastoma cell line, or A549 cells were seeded at 10,000 or 20,000 cells per well in 24-well plates in complete medium (Dulbecco's modified eagle medium with 5% fetal bovine serum, 5% penicillin streptomycin) and cultured for 24 hrs under standard conditions. A549 cells were rinsed with PBS and starved with F12K starvation medium overnight under standard conditions. U87MG cells were rinsed with PBS and starved with MEM overnight under standard conditions. Cells were then treated with the indicated antibody at a final concentration of 1 nM or with 1 nM of HGF for 24 hours. Next, cells were washed two times with cold PBS and harvested in 250 μl per well lysis buffer. Next, equal amount of cell lysates were analyzed by SDS-PAGE and transferred to nitrocellulose membrane. The blots were blocked in TBS+0.1% Tween+3% BSA for 2 hours at room temperature with shaking. The blots were then washed 3× with TBS+ 0.1% Tween and incubated with 1:500 dilution of cMET antibody (Cell Signaling) and a 1:2000 dilution of rabbit anti-tubulin (Cell Signaling) overnight with shaking at 4° C. Next, the blots were washed three times with TBS+0.1% Tween and then incubated with 1:2500 anti-mouse HRP secondary and 1:5000 anti-rabbit HRP secondary antibodies (Invitrogen) in for 2 hours with shaking at room temperature. Finally, the blots were washed three times with TBS+ 0.1% Tween and one time with TBS, developed using Thermo's SuperSignal® West Pico substrate (1:1 mix) and photographed on a Bio-Rad imager.

For ELISA analysis, A549 cells were seeded at 25,000 cells per well in 96 well plates and cultured overnight under standard conditions. Cells were serum starved overnight under standard conditions. Cells were then treated with 1 nM HGF or 1 nM testing antibody for 24 hrs. After incubation, cells were washed with cold PBS and lysed in 100 μL lysis buffer. To prepare the ELISA capture plate, the plates were coated with 100 μL per well of anti c-MET antibody diluted 1:2000 in 1× borate buffer 4° C. overnight. The lysates were loaded to the plate and allowed to bind at room temperature for 2 hours. The plates were washed three times with TBST and subsequently incubated with 100 μL per well of biotinylated anti-cMET antibody (R&D Systems cat. No. BAF358; 0.2 mg/mL) diluted 1:2000 in TBST 1% BSA for 2 hours at room temperature. The plates were then washed three times with TBST and tapped on paper towel to remove all remnants of wash buffer. Finally, SuperSignal® West Pico reagents were mixed 1:1 and 100 μL was added to each well. The luminescence was measured on a plate reader according to the Luminescence Glow protocol.

For Western blot analysis, A549 cells (e.g., 7×10$^6$) were seeded into 15 cm dishes in complete medium and cultured for 24 hrs. Cells were rinsed with PBS and starved overnight, then treated with the indicated antibodies at a final concentration of 1 nM or 1 nM of HGF for 15 minutes. The cells were washed twice with cold PBS, collected by scraping, and spun (e.g., 1200RPM in a 4° C. micro-centrifuge); and the pellets were resuspended in 300 μl lysis buffer. Subsequently, equal amounts of cell lysates were immunoprecipitated with 5 μls of Anti-cMET antibody (e.g., Cell Signaling, Cat #8198) and electrophoresed by SDS-PAGE and transferred to nitrocellulose membrane. The blots were blocked in TBS+0.1% Tween+3% BSA for 2 hours at room temperature with shaking, washed once with TBS+0.1% Tween, and then incubated with 1:1000 dilution of Anti-Ubiquitin antibody (Cell Signaling, Cat #3936) in TBS+ 0.1% Tween+3% BSA overnight. The blots were washed three times with TBS+0.1% Tween, and then incubated with 1:2500 anti-mouse HRP secondary antibody for 1 hour with shaking at room temperature. Then the blots were washed three times with TBS+0.1% Tween and one time with TBS, developed using Thermo's SuperSignal West Pico substrate (1:1 mix) and photographed on the Bio-Rad imager.

6.1.1.12 In Vivo Analysis of MET Degradation

U87MG subcutaneous xenograft tumor mouse models were treated with PBS (n=3), control chimeric IgG$_1$ anti-KLH antibody (3 mg/kg; n=3), or with Ab237C (3 mg/kg; n=3) on day 0 and day 3. Mice were sacrificed on day 4 and fresh frozen paraffin embedded (FFPE) tumors were prepared. Five μm sections were prepared, deparaffinized, and rehydrated as followed: (1) wash in Histoclear (Electron Microscopy Services, Cat #64110-04) three times for three minutes each; (2) wash in 100% ethanol two times for three minutes each; wash in 95% ethanol two times for three minutes each; wash in 70% ethanol one time for three minutes, and rinse with distilled water. For antigen retrieval, the slides were treated for thirty-five minutes in citrate buffer in a vegetable steamer, cooled to room temperature, and rinsed with deionized water. Endogenous peroxides were quenched with 3% hydrogen peroxide for 15 minutes and rinsed with distilled water. For immunohistochemistry, the slides were blocked with 2.5% horse serum (Vector Labs Kits, ImmPRESS anti-rabbit MP-7401) for 30 minutes at room temperature. Excess horse serum was shaken off. The slides were subsequently incubated overnight at 4° C. in a humidified chamber with primary antibody in 3% BSA/PBS. Primary antibodies included: Cell Signalling (D1C2) #8198 1:300, 50 pg/mL, rabbit. Ig control antibody was purchased from Vector Labs (rabbit IgG+I-1000, 5 mg/mL). IgG control was diluted to match the primary antibody concentration of 0.167 μg/mL. The slides were rinsed with PBS with 0.1% tween 20 (PBST), transferred to a slide rack, and immersed in PBS/0.1% tween 20 for 1 hour with two changes of PBST. The slides were then incubated with secondary antibody: ImmPRESS reagent secondary (rabbit-HRP, Vector Labs MP-7401) was added to the slides and the slides were returned to the humidified chamber for one hour. The slides were subsequently rinsed and then transferred to a rack and placed in PBST for 1.5 minutes with three changes of PBST. The excess PBST was then shaken off. For development, IMMPACT DAB substrate (Vector Labs SK-4105), 0.2 mL/slide, with 1 drop of chromagen/1 mL of buffer was added to the slides for 10 minutes, followed by rinsing with distilled water. Nuclei were stained with hematoxylin (a few drops per slide) and then rinsed in acidified water (2% glacial acetic acid). The slides were then rinsed with water and three drops of aqueous mounting media (DAKO) were added to the slides and the slides were covered with coverslips. Slides were imaged at 20× and 40× with a Nikon Eclipse microscope.

6.1.2 Results 6.1.2.1 Generation of Anti-MET Antibodies

Table 13 lists the heavy and light chain isotypes of anti-MET antibodies generated from mice and rats, from generation of chimeric antibodies, and from composite human technology.

| Antibody Name | Heavy Chain | Light chain |
|---|---|---|
| Ab235 | Mouse IgG$_1$ | κ |
| Ab236 | Mouse IgG$_1$ | κ |
| Ab237 | Rat IgG$_{2a}$* | κ |
| Ab238 | Rat IgG$_{2a}$ | κ |
| Ab239 | Rat IgG$_{2a}$ | λ |
| Ab235C | Human IgG$_1$ | κ |
| Ab236C | Human IgG$_1$ | κ |
| Ab237C | Human IgG$_1$ | κ |
| Ab238C | Human IgG$_1$ | κ |
| Ab239C | Human IgG$_1$ | λ (variable region) and κ (constant region) |
| Ab241 | Human IgG$_1$ | κ |
| Ab242 | Human IgG$_1$ | κ |
| Ab243 | Human IgG$_1$ | κ |
| Ab244 | Human IgG$_1$ | κ |

-continued

| Antibody Name | Heavy Chain | Light chain |
|---|---|---|
| Ab245 | Human IgG$_1$ | κ |
| Ab246 | Human IgG$_1$ | κ |
| Ab247 | Human IgG$_1$ | κ |
| Ab248 | Human IgG$_1$ | κ |
| Ab249 | Human IgG$_1$ | κ |
| Ab250 | Human IgG$_1$ | κ |
| Ab251 | Human IgG$_1$ | κ |
| Ab252 | Human IgG$_1$ | κ |
| Ab253 | Human IgG$_1$ | κ |
| Ab254 | Human IgG$_1$ | κ |
| Ab255 | Human IgG$_1$ | κ |

*Rat IgG$_2$ has high sequence homology to mouse IgG$_1$ and human IgG$_1$.

6.1.2.2 Anti-MET Antibodies Bind to the Extracellular Domain of MET

The ability of the putative anti-MET antibodies to bind MET was determined. FACS analyses performed as described in Section 6.1.1.7 revealed that the anti-MET antibodies effectively bind to cell-surface expressed MET (Table 14). Further, ELISA assay with recombinant MET-ECD demonstrated that the generated anti-MET antibodies effectively bind to MET-ECD (Table 14), specifically. Further, the anti-MET antibodies were unable to bind to chimeric fusion proteins comprising murine SEMA/PSI domains and human Ig domains. Given that the anti-MET antibodies bind human MET, but not murine MET, these data indicate that the anti-MET antibodies bind to the SEMA/PSI domain of MET. These data indicate that anti-MET antibodies described herein, such as Ab235, Ab236, Ab237, Ab238, and Ab239, as well as antibodies comprising the same CDRs as these antibodies and having similar features (e.g., binding epitope and affinity), are effective at binding to human MET and are capable of specifically binding the ECD.

Table 14 recites the EC$_{50}$ for binding of Ab235, Ab236, Ab237, Ab238, and Ab239 to cell-surface MET or recombinant MET-ECD

| Antibody | Binding Domain | Cell Surface MET binding affinity (FACS) EC$_{50}$ (nM) | MET-ECD Binding (ELISA) EC$_{50}$ (nM) |
|---|---|---|---|
| Ab235 | SEMA/PSI | 1.4 | 1.2 |
| Ab236 | SEMA/PSI | 0.5 | 0.45 |
| Ab237 | SEMA/PSI | 0.4 | 0.14 |
| Ab238 | SEMA/PSI | 0.3 | 0.7 |
| Ab239 | SEMA/PSI | 0.2 | 0.5 |

6.1.2.3 Species Specificity of Anti-MET Antibodies

The species specificity of anti-MET antibodies Ab235, Ab236, Ab237, Ab238, and Ab239 were evaluated as described in Section 6.1.1.3. Briefly, human (A549 cells), monkey (4MBr5 cells), dog (MDCK cells), or mouse (MS1 cells) cells were incubated with anti-MET antibody and binding of the antibody to the cell-surface expressed MET was assessed by FACS. Each of the five antibodies tested (i.e., Ab235, Ab236, Ab237, Ab238, and Ab239) were able to specifically bind to both human and monkey cells, while they did not exhibit the capacity to specifically bind dog or mouse cells.

6.1.2.4 Epitope Binding of Anti-MET Antibodies

Competition studies were performed as described in Section 6.1.1.7 to determine whether certain anti-MET antibodies share the same or a similar epitope. Briefly, FACS was utilized to determine the ability of the Alexa-647-labeled Ab235 to bind cell surface expressed MET in the presence of titrated, unlabeled antibody Ab235, Ab236, Ab237, Ab238, or Ab239. Incubation with a control anti-MET antibody that binds the IgG domains of MET (Ab240) did not inhibit the binding of labeled Ab235. In contrast, incubation with unlabeled antibody Ab235, Ab236, Ab237, Ab238, and Ab239 successfully inhibited, in a concentration-dependent manner, the binding of labeled Ab235 to cell surface expressed MET. Further, the IC$_{50}$ (the concentration of the antibody that achieves 50% inhibition of binding) of Ab235, Ab236, Ab237, Ab238, and Ab239 was calculated to be approximately 3 nM, 1 nM, 0.5 nM, 1 nM, and 0.8 nM, respectively. These results demonstrate that antibodies Ab235, Ab236, Ab237, Ab238, and Ab239 target a similar epitope in human MET-ECD.

FACs competition studies were also performed as described in Section 6.1.1.7, to study the binding properties of anti-MET antibodies Ab241-Ab255 compared to an Ab237 chimeric antibody comprising human IgG$_1$ (Ab237C). The FACS competition studies determined the ability of labeled Ab237C (human IgG$_1$ isotype) to bind to cell surface expressed MET in the presence of titrated Ab241, Ab242, Ab243, Ab244, Ab245, Ab246, Ab247, Ab248, Ab249, Ab250, Ab251, Ab252, Ab253, Ab254, or Ab255 anti-MET antibody. Incubation with any of Ab241, Ab242, Ab243, Ab244, Ab245, Ab246, Ab247, Ab248, Ab249, Ab250, Ab251, Ab252, Ab253, Ab254, and Ab255 successfully inhibited the binding of labeled Ab237C to cell surface expressed MET. The relative IC$_{50}$ value of Ab241, Ab242, Ab243, Ab244, Ab245, Ab246, Ab247, Ab248, Ab249, Ab250, Ab251, Ab252, Ab253, Ab254, and Ab255 was calculated to be approximately 1.22, 1.03, 1.07, 0.93, 0.86, 1.15, 1.01, 1.17, 0.70, 0.86, 0.99, 1.06, 0.91, 0.78, and 0.72, respectively, based on the IC$_{50}$ value of Ab237C; the relative IC$_{50}$ value was calculated by dividing the value from the IC$_{50}$ of Ab237C, for example, the relative IC$_{50}$ value of Ab237C is 1 nM. The anti-MET antibodies tested all demonstrated binding to MET within 1.2-fold of Ab237C binding to MET, and some showed a relative IC$_{50}$ less than 1 indicating stronger binding affinity than Ab237C. These data demonstrate the ability of the anti-MET antibodies tested to bind to cell-surface expressed, native MET, and in particular, to the same or similar epitope of human MET-ECD.

ELISA assays were performed as described in Section 6.1.1.6 to determine the binding of the antibodies to MET-ECD to further corroborate the data from the FACS binding competition studies. The binding of labeled Ab237C in the presence of titrated Ab241, Ab242, Ab243, Ab244, Ab245, Ab246, Ab247, Ab248, Ab249, Ab250, Ab251, Ab252, Ab253, Ab254, or Ab255 anti-MET antibody to MET-ECD immobilized on ELISA plates were tested. Incubation with any of Ab241, Ab242, Ab243, Ab244, Ab245, Ab246, Ab247, Ab248, Ab249, Ab250, Ab251, Ab252, Ab253, Ab254, and Ab255 successfully inhibited, in a concentration-dependent manner, the binding of labeled Ab237C to MET-ECD. Further, the IC$_{50}$ of Ab241, Ab242, Ab243, Ab244, Ab245, Ab246, Ab247, Ab248, Ab249, Ab250, Ab251, Ab252, Ab253, Ab254, and Ab255 was calculated to be approximately 0.97, 0.82, 0.92, 1.07, 1.09, 0.81, 0.82, 1.04, 1.00, 1.13, 0.98, 0.99, 0.94, 0.80, and 0.90, respectively, relative to the IC$_{50}$ of Ab237C, which is standardized to 1 nM. The anti-MET antibodies tested all demonstrate a relative IC$_{50}$ within 1.15-fold of Ab237C, and some showed a relative IC$_{50}$ less than 1 indicating stronger binding affinity than Ab237C. These data, consistent with the FACS binding competition data, demonstrated that all the anti-MET antibodies tested bind specifically to the extracellular domain of purified MET, and to the same or similar epitope of MET-ECD.

6.1.2.5 Anti-MET Antibodies Block MET Activation

HGF induces kinase activity upon binding to MET, consequently triggering the trans-phosphorylation of MET Tyrosine 1234 and Tyrosine 1235. To assess the ability of anti-MET antibodies to block MET activity, ligand-induced MET-phosphorylation studies were performed as described in Section 6.1.1.8. Briefly, A549 or U87MG cells were incubated with the anti-MET antibodies and the level of MET Tyr1234 and Tyr1235 phosphorylation was determined by ELISA. Anti-MET antibodies Ab235, Ab236, Ab237, Ab238, Ab239, Ab237C, Ab244, Ab245, Ab249, Ab250, Ab254, and Ab255 were able to block HGF-induced phosphorylation of MET at Tyr1234 and Tyr1235. The $IC_{50}$ of antibodies Ab235, Ab236, Ab237, Ab238, and Ab239 were calculated to be approximately 217 pM, 76 pM, 40 pM, 93 pM, and 90 pM, respectively, in A549 cells. At the higher concentrations tested (e.g., >10 nM), all five of antibodies Ab235-Ab239 achieved complete inhibition of MET phosphorylation to background level. The relative $IC_{50}$ of antibodies Ab244, Ab245, Ab249, Ab250, Ab254, and Ab255 were calculated to be approximately 0.44, 0.23, 0.47, 0.21, 0.23, and 0.25, respectively, based on the $IC_{50}$ of Ab237C; the relative $IC_{50}$ value was calculated by dividing the value from the $IC_{50}$ of Ab237C (the relative $IC_{50}$ value of Ab237C is 1 nM). The $IC_{50}$ of antibodies Ab235C, Ab236, Ab237, Ab238, and Ab239 were calculated to be approximately 71 pM, 47 pM, 43 pM, 29 pM, and 44 pM, respectively, in U87MG cells.

In addition, Ab237 and Ab239 were able to potently inhibit MET phosphorylation in Hop92 cells, which are lung carcinoma cells containing a MET comprising a T1010I mutation, which results in overactive MET signaling. Ab237- and Ab239-mediated MET phosphorylation inhibition in Hop92 cells is 3- to 4-fold more potent than inhibition with a humanized anti-MET antibody comprising the amino acid sequences of SEQ ID NO:296 (VH) and SEQ ID NO:297 (VL), as in h224G11 (ABT-700; AbbVie) ("anti-MET-1") or a bivalent, $IgG_4$ anti-MET antibody comprising the amino acid sequences of SEQ ID NO:294 (VH) and SEQ ID NO:295 (VL), as in emibituzumab (Lilly) ("anti-MET-2"). These data indicate that anti-MET antibodies described herein, such as Ab235, Ab236, Ab237, Ab238, Ab239, Ab237C, Ab244, Ab245, Ab249, Ab250, Ab254, and Ab255, as well as antibodies comprising the same CDRs as these antibodies and having similar features (e.g., binding epitope and affinity), are effective against inhibiting ligand (HGF)-induced phosphorylation of MET at Tyr1234 and Tyr1235. Furthermore, these data indicate that the anti-MET antibodies tested inhibit MET activation and signaling, for example in cancer cells with overactive MET signaling via a MET mutation, such as the T1010I mutation, as compared to other anti-MET antibodies, such as anti-MET-1 and/or anti-MET-2.

6.1.2.6 Anti-MET Antibodies Block AKT and MAPK Phosphorylation

HGF-induced MET activation promotes intracellular MET tyrosine phosphorylation and the recruitment of signaling protein complexes resulting in the activation of downstream signaling pathways. Anti-MET antibodies described herein were assayed for the ability to inhibit or block MET signaling, such as, for example, AKT and/or MAPK phosphorylation. The assays were carried out as described in Section 6.1.1.9, using A549 NSCLC cells. Briefly, upon treatment with HGF in the presence and absence of anti-MET antibodies, the phosphorylation of AKT and MAPK were analyzed by western blot. In contrast to treatment with a negative control (e.g., chimeric $IgG_1$ anti-KLH antibody), HGF treatment results in MET activation (as determined by an induction in phosphorylated MET) and activation of the downstream components AKT and MAPK (as determined by an induction in phosphorylated AKT and MAPK, respectively); see FIG. 2, lanes 2, 1, and 5, respectively). In contrast, treatment with either Ab237C or crizotinib (a small molecule inhibitor of MET, see, for example, Rodig and Shapiro, Curr. Opin. Investig. Drugs. 11(12):1477-1490 (2010)), inhibited activation of MET and reduces the activation of downstream signaling components Akt and MAPK (FIG. 2, lanes 3 and 4, respectively). Treatment with Ab237C induced a significant reduction in MET protein levels, which was not observed in cells treated with crizotinib or control IgG antibody. These data indicate that anti-MET antibodies described herein, such as Ab235, Ab236, Ab237, Ab238, and Ab239, as well as antibodies comprising the same CDRs as these antibodies and having similar features (e.g., binding epitope and affinity), are effective against inhibiting activation of MET and the downstream signaling components AKT and MAPK.

6.1.2.7 Anti-MET Antibodies Block Ligand-Receptor Interaction

Given that the anti-MET antibodies tested bind to the extracellular domain of MET and block HGF-induced signaling (see, Sections 6.1.2.2 and 6.1.2.6, respectively), the ability of the antibodies to inhibit the interaction between MET and its ligand HGF was assessed as described in Section 6.1.1.10. Pre-treatment with a control chimeric $IgG_1$ anti-KLH antibody did not diminish the binding interaction between MET and HGF. In contrast, incubation with Ab235, Ab236, Ab237, Ab238, or Ab239 effectively inhibited the binding interaction between MET and HGF. The $IC_{50}$ of antibodies Ab235, Ab236, Ab237, Ab238, and Ab239 were calculated to be approximately 2 nM, 0.5 nM, 0.5 nM, 0.4 nM, and 0.3 nM, respectively. These data indicate that anti-MET antibodies described herein, such as Ab235, Ab236, Ab237, Ab238, and Ab239, as well as antibodies comprising the same CDRs as these antibodies and having similar features (e.g., binding epitope and affinity), are effective against inhibiting ligand (HGF) interaction with the MET receptor.

6.1.2.8 Anti-MET Antibodies Induce MET Degradation

The mechanism of antibody-induced MET inhibition was investigated, specifically, the impact of anti-MET antibodies on MET stability. The stability of MET upon incubation with the anti-MET antibodies was assessed as described in Section 6.1.1.11. Briefly, cells were incubated with HGF, or with certain anti-MET antibodies and MET protein levels were assessed by western blot and ELISA assay. Incubation with anti-MET antibodies for twenty four hours resulted in decreased accumulation of MET protein in the -glioblastoma cell line U87MG and the non-small cell lung cancer cell line A549 (FIGS. 3A and 3B and FIGS. 3C and 3D, respectively). Furthermore, incubation with anti-MET antibodies decreased the accumulation of MET protein in the tumor cell line H596, which are adenosquamous carcinoma cells which encode a MET gene comprising a deletion in exon 14, and Hop92, which are lung carcinoma cells which express a MET comprising a T1010I amino acid substitution (FIGS. 3E and 3F, respectively).

To confirm that the degradation of MET in the presence of certain anti-MET antibodies is observed in vivo, MET degradation was analyzed in a U87MG subcutaneous xenograft tumor model in the presence of Ab237C as described in Section 6.1.1.12. Consistent with in vitro results, treatment with Ab237C markedly decreases MET protein levels as determined by immunohistochemistry of tumor samples in contrast with control treatments (FIGS. 4C, 4A, and 4B, respectively).

These data indicate that anti-MET antibodies described herein, such as Ab235, Ab236, Ab237, Ab238, and Ab239, as well as antibodies comprising the same CDRs as these antibodies and having similar features (e.g., binding epitope and affinity), are effective against degrading MET in vitro and in vivo. That is, MET protein levels decreased in tumor cells after antibody treatment independently of whether tumor cells were grown in tissue culture or as subcutaneous tumor xenografts. Thus, the antibodies function both by blocking HGF binding and promoting MET turnover.

6.1.2.9 Anti-MET Antibodies Induce MET Ubiquitination

HGF binding to MET induces rapid ubiquitination and degradation of MET (see, e.g., Taher et al. J Immunol. 169(7):3793-3800 (2002)). To ascertain whether the antibody-induced MET degradation (e.g., Ab235, Ab236, Ab237, Ab238, Ab239, and Ab237C; see, Section 6.1.2.8) is correlated with MET ubiquitination, A549 cells were treated with anti-MET antibodies Ab237C and Ab237C-IgG$_2$ (Ab237C comprising a human IgG$_2$ constant region instead of an IgG$_1$ constant region), MET was immunoprecipitated, and the immunoprecipitated samples were analyzed for ubiquitin by immunoblot as described in Section 6.1.1.11. As expected, incubation with HGF induces ubiquitination of MET. In addition, incubation with Ab237C or Ab237C-IgG$_2$ also resulted in ubiquitination of MET, while incubation with control Ig or in the absence of HGF did not result in ubiquitination (FIG. 5). These data indicate that anti-MET antibodies described herein, such as Ab237, as well as antibodies comprising the same CDRs as these antibodies and having similar features (e.g., binding epitope and affinity), are effective against inducing MET ubiquitination.

6.1.3 Conclusions

In conclusion, anti-MET antibodies with the ability to bind both cell-surface expressed MET and recombinant MET-ECD were generated. Moreover, competition analyses demonstrated that the antibodies share the same or similar epitope. The anti-MET antibodies described herein, such as Ab235, Ab236, Ab237, Ab238, and Ab239, were able to bind to both human and monkey cells expressing MET, but not dog or mouse cells expressing MET, demonstrating species specificity of these antibodies. Further, the anti-MET antibodies described herein, e.g., Ab235-Ab255, are capable of inhibiting MET activity, such as MET phosphorylation at amino acid residues Tyr1234 and Tyr1235 (key residues in MET activation), as well as downstream signaling events such as Akt phosphorylation and MAPK phosphorylation, and of blocking ligand (HGF)-receptor (MET) interaction. Moreover, MET is ubiquitinated and degraded upon treatment with the anti-MET antibodies described herein, such as Ab235, Ab236, Ab237, Ab238, and Ab239. Consequently, these data show that a series of anti-MET antibodies have been identified that can potently inhibit MET signaling, and indicate that anti-MET antibodies comprising the CDRs of Ab235, Ab236, Ab237, Ab238, and Ab239 can inhibit MET activity.

6.2 Example 2: Anti-Tumor Properties of Anti-MET Antibodies 6.2.1 Materials and Methods 6.2.1.1 Tumor Cell Proliferation Analyses For U87MG, A549, and EBC1 cells, approximately 1,000-2,000 cells per well are seeded in 50 µL in Costar Ultra-low binding U-bottom plate and incubated for 4-8 days for spheroid formation. Fifty µL of 3×HGF (prepared in serum-free medium) was added to each well for a final HGF concentration of 50 ng/mL. Fifty mL of a 3× antibody solution (prepared in serum-free medium, final concentration of 300 nM) was added to each well. The cells were incubated for 5 days under standard conditions. After the incubation, 100 µl of Cell Titer Glow reagent (Promega) was added to each well and the plates were kept on an orbital shaker for 20 minutes. The mixture was then transferred to a black-wall clear bottom plate and the luminescence signal was determined using a plate reader as previously described.

For H596 cells (an adenosquamous carcinoma cell line), 5,000 cells per well were seeded in 100 µL in black wall clear bottom 96 well plates and cultured overnight under standard conditions. The cells were then serum-starved overnight. Next, 50 µL of a 2×HGF serum-free solution containing 0.5% FBS was added to each well for a final concentration of 50 ng/mL. In addition, 50 µL of a 2× antibody serum-free solution containing 0.5% FBS was added to each well (final concentration of 300 nM). The cells were incubated for 4 days under standard conditions. The cells were then incubated with Cell Titer Glow reagent and the luminescence signal as determined as previously described. The cells were then incubated for an additional 5 days under standard conditions. Finally, the cells were again incubated with Cell Titer Glow reagent and the luminescence signal was determined as previously described.

6.2.1.2 DU145 Cell Scatter Assay

For DU145 cells, a metastatic prostate carcinoma cell line, approximately 3,000 cells per well were seeded in 96 well black wall clear bottom plates and culture overnight under standard conditions. The cells were treated with 25 ng/mL of HGF in the presence or absence of a testing antibody for 24 hours in F12K starvation medium. After 24 hours, the cells were fixed with 4% paraformaldehyde in PBS for 10 minutes at room temperature followed by three washes with PBS. The cells were then permeabilized with 0.1% triton in PBS at room temperature for 10 minutes and subsequently stained with Hoechst H33258 (10 µg/mL) for 1 hour at room temperature. The cells were then washed three times with PBS. Images were acquired using OPERA imager and analyzed using the built-in cell cluster algorism. Cell scattering effect was quantitated by measuring percentage of cell present in cluster. Cell cluster was defined as group containing more than 3 cells.

6.2.1.3 U87MG Orthotopic Tumor Model

U87MG glioma cells (ATCC®, Manassas, VA, cat #HTB-14) were implanted intracranially into nude mice (e.g., 1×10$^6$ cells per mouse using a 27 g fixed needle syringe. Mice, in groups of 10, were administered one or more of the following depending on the experiment: PBS, a chimeric IgG$_1$ anti-KLH antibody, crizotinib, Ab235C, Ab236C, Ab237C, Ab237-IgG$_2$, Ab237-IgG$_4$, or Ab237-monovalent.

6.2.1.4 Bioluminescence of Tumors

U87MG human glioma cell line cells engineered to stably express luciferase (a protein encoded by the firefly luciferase gene), U87MG-luc, were implanted intracranially into nude mice (e.g., 1×10$^6$ cells per mouse) using a 27 g fixed needle syringe. Mice, in groups of 10, were administered one or more of the following depending on the experiment: PBS, a chimeric IgG$_1$ anti-KLH antibody (30 mg/kg), crizotinib (25 mg/kg), Ab235C (30 mg/kg), Ab236C (30 mg/kg), and Ab237C.

Bioluminescence imaging (BLI) images for 10-15 mice at approximately 28 days post-implant were obtained to observe tumor growth. If tumors were not yet distinguishable, BLI images for the animals were obtained again 4-5 days later. Animals with tumors that reached the desired size (e.g., mean bioluminescence signal of $5 \times 10^6$ photons/sec) were selected, randomized amongst treatment/control groups with pair matching to achieve 10% mean tumor burden matching between groups. Then animals in the treatment/control groups were imaged on days 3, 7, 14, and 21 post-treatment. Tumor measurements were made in units of photons/second.

6.2.1.5 U87MG Subcutaneous Tumor Model

Cell Culture: The U87MG glioblastoma tumor cells (ATCC®, Manassas, VA, cat #HTB-14) were maintained in vitro as a monolayer culture in DMEM medium supplemented with 10% heat inactivated fetal bovine serum, at 37° C. in an atmosphere of 5% $CO_2$ in air. The cells growing in an exponential growth phase were harvested and counted for tumor inoculation.

Animals and Tumor Inoculation: BALB/c nude, female, 6-8 weeks, weighing approximately 18-20 g were inoculated with U87MG cells. Each mouse were inoculated subcutaneously at the right flank with U87MG tumor cells ($5 \times 10^6$) in 100 µl of medium for tumor development. The treatments started when the average tumor size reached approximately 150-200 mm$^3$. Animals in each group (n=10) were treated with anti-MET antibodies and certain controls at indicated doses. For example, in certain experiments, 30 mg/kg (10 µl/g dosing volume) of one PBS, chimeric IgG$_1$ anti-KLH antibody, monovalent Ab237C, Ab237C-IgG$_2$, Ab237C-IgG$_4$ and Ab237C were administered intraperitoneally biweekly for three weeks.

Tumor sizes were measured twice weekly in two dimensions using a caliper, and the volumes were expressed in mm$^3$ using the formula: V=0.5 a×b$^2$ where a and b are the long and short diameters of the tumor, respectively. Tumor growth inhibition (TGI) was calculated for each group according to the following formula: TGI (%)=[1−(Ti−T0)/(Vi−V0)]×100; Ti was the tumor volume of treatment group on a specific day, T0 was the tumor volume of the treatment group on the first day, Vi was the tumor volume of vehicle control group on a specific day and V0 was the tumor volume of the vehicle group on the first day of treatment. Tumor weight was measured at study termination. The T/C value (in percent) is calculated where T and C are the mean tumor weights of the treated and control groups, respectively.

6.2.2 Results 6.2.2.1 Anti-MET Antibodies Inhibit Tumor Cell Proliferation

Several cancers are attributed to overactive MET signaling (see, e.g., Trusolino et al. Nat. Rev. Mol. Cell. Biol. 11:834-848 (2010)). Given the ability of the anti-MET antibodies to degrade MET and inhibit MET signaling (see, Sections 6.1.2.8 and 6.1.2.6, respectively), the ability of anti-MET antibodies described herein to abrogate tumor proliferation was assessed. Briefly, U87MG or A549 tumor cells were incubated with HGF and in the presence or absence of an anti-MET antibody described herein, such as Ab235, Ab236, Ab237, Ab238, or Ab239, and cellular proliferation was assessed, for example, by luminescence as described above. Treatment with Ab235, Ab236, Ab237, Ab238, or Ab239 inhibited tumor cell proliferation. The IC$_{50}$ of antibodies Ab235, Ab236, Ab237, Ab238, and Ab239 were calculated to be approximately 25 nM, 9 nM, 5.5 nM, 25 nM, and 19 nM, respectively, in U87MG cells, and approximately 6.6 nM, 6.3 nM, 1.7 nM, 4.8 nM, and 4.4 nM, respectively, in A549 cells. Moreover, the tested antibodies potently inhibit proliferation of H596 cells, which express a mutated form of MET, without the 47 amino acids encoded by exon 14, indicating that subjects expressing such a mutated form of MET can be amenable to treatment with the antibodies described herein. Moreover, treatment of U87MG cells with Ab235, Ab236, Ab237, Ab238, or Ab239 in the absence of HGF did not result in growth-promoting agonistic activity induced by the tested antibodies (FIG. 6A). The IC$_{50}$ of antibodies Ab235, Ab236, Ab237, Ab238, and Ab239 were calculated to be approximately 0.8 nM, 0.6 nM, 0.08 nM, 0.2 nM, and 0.2 nM, respectively, in H596 cells. In each cell type tested, Ab237 has a markedly lower IC$_{50}$ as compared to other anti-MET antibodies. These data indicate that anti-MET antibodies described herein, such as Ab235, Ab236, Ab237, Ab238, and Ab239, as well as antibodies comprising the same CDRs as these antibodies and having similar features (e.g., binding epitope and affinity), are effective against inhibiting tumor cell proliferation.

6.2.2.2 Anti-MET Antibodies Inhibit DU145 Cell Scatter

HGF is a known inducer of endothelial to mesenchymal transition ("EMT"), also referred to as cell scatter (see, e.g., Thiery and Sleeman, Nat. Rev. Mol. Cell Biol. 2:131-142 (2006)), the process by which epithelial cells lose their cell-to-cell adhesions and acquire the capacity to migrate independently. Cell scattering is involved in the initiation of metastasis (see, e.g., Tsai and Yang, Genes & Dev. 27:2192-2206 (2013)). Since anti-MET antibodies described herein are able to inhibit tumor cell proliferation (Section 6.2.2.1), the impact of anti-MET antibodies on cell scattering was assessed as described in Section 6.2.1.2. Briefly, DU145 metastatic prostate carcinoma cells were treated with HGF in the presence or absence of the anti-MET antibody and the cell scattering was determined by quantification of cell clusters. Treatment with anti-MET antibodies described herein, such as Ab235, Ab236, Ab237, Ab238, or Ab239, efficiently inhibited DU145 cell scatter. The IC$_{50}$ of antibodies Ab235, Ab236, Ab237, Ab238, and Ab239 were calculated to be approximately 0.48 nM, 0.08 nM, 0.08 nM, 1.4 nM, and 0.24 nM, respectively. Antibodies Ab235, Ab236, Ab237, Ab238, and Ab239 were able to inhibit DU145 cell scatter by approximately 72-80%, 64-66%, 77-81%, 77-96%, and 58-77%, respectively. These data indicate that anti-MET antibodies described herein, such as Ab235, Ab236, Ab237, Ab238, and Ab239, as well as antibodies comprising the same CDRs as these antibodies and having similar features (e.g., binding epitope and affinity), are effective against inhibiting EMT.

6.2.2.3 Anti-MET Antibodies Inhibit Tumor Growth In Vivo

The ability of the anti-MET antibodies to inhibit tumor growth in vivo is assessed as described in Sections 6.2.1.3, 6.2.1.4, and 6.2.1.5. Briefly, the U87MG orthotopic mouse model was treated with a control chimeric IgG$_1$ anti-KLH antibody, a small molecule inhibitor of MET (crizotinib; 25 mg/kg perorally), or with chimeric Ab235 or Ab236 (Ab235C or Ab236C, respectively; 30 mg/kg intravenously) and bioluminescence of the implanted tumor cells were measured at 28, 31, 35, 42, and 49 days post implant (FIGS. 6B and 6C). Treatment was performed biweekly, every three to four days, for seven weeks. Treatment with a control chimeric IgG$_1$ anti-KLH antibody or with crizotinib resulted in similar tumor growth as determined by bioluminescence signal in an orthotopic model. Surprisingly, treatment of mice with Ab235C or Ab236C resulted in a statistically significant inhibition in tumor growth by 49 days post tumor implant (FIGS. 6B and 6C).

Furthermore, treatment with chimeric Ab235, Ab236, Ab237, and Ab239 antibodies (Ab235C, Ab236C, Ab237C, and Ab239C, respectively; 30 mg/kg, intravenously, twice per week) delayed tumor growth in a U87MG subcutaneous xenograft model better than vehicle or a negative control chimeric $IgG_1$ anti-KLH antibody, and Ab237C displayed the most potent effects amongst the test antibodies (FIG. 7A). These data indicate that anti-MET antibodies described herein, such as Ab235, Ab236, Ab237, and Ab239, as well as antibodies comprising the same CDRs as these antibodies and having similar features (e.g., binding epitope and affinity), are effective against inhibiting tumor progression in vivo.

Moreover, dose escalation with Ab237C in a U87MG subcutaneous xenograft model demonstrated that a dose of as little as 1 mg/kg of Ab237C was able to delay tumor growth (FIG. 7B). Notably, 30 mg/kg Ab237C treatment induced tumor growth inhibition comparable to 50 mg/kg crizotinib treatment. Moreover, Ab237C was well tolerated and did not lead to weight loss or observational toxicity. These data indicate that the anti-MET antibody Ab237C as well as antibodies comprising the CDRs of Ab237C are effective against inhibiting tumor progression in vivo in a dose dependent manner.

6.2.3 Conclusions

The anti-MET antibodies described herein, such as Ab235, Ab236, Ab237, Ab238, and Ab239, as well as antibodies comprising the same CDRs as these antibodies and having similar functional features (e.g., binding epitope and affinity), display anti-tumor attributes. The antibodies are able to inhibit tumor cell proliferation in vitro, inhibit cell scattering (a precursor to metastasis), and impair tumor growth in vivo. Taken together, these data indicate that the anti-MET antibodies described herein, such as Ab235, Ab236, Ab237, Ab238, and Ab239, as well as antibodies comprising the same CDRs as these antibodies and having similar features (e.g., binding epitope and affinity), exhibit anti-tumor activities which can be useful in the treatment of cancer, such as glioma.

6.3 Example 3: The Effect of Ig Isotype Exchange on Anti-MET Antibodies

6.3.1 Materials and Methods
6.3.1.1 Isotype Switching

To perform isotype switching, the VL and VH chain regions of antibodies described herein were cloned in frame with the constant regions of a human $IgG_2$ or $IgG_4$. The resulting constructs were subsequently transiently expressed in 293 cells and the resulting antibodies were purified.

6.3.1.2 U87MG Glioblastoma Xenograft Model

Studies with U87MG glioblastoma xenograft mouse models were performed essentially as described above in Section 6.2.1.5. Briefly, U87MG tumor cells (ATCC®, Manassas, VA, cat #HTB-14), growing in an exponential growth phase, were inoculated into BALB/c nude mice (female, 6-8 weeks, weighing approximately 18-20 g). Each mouse were inoculated subcutaneously at the right flank with U87MG tumor cells (e.g., $5 \times 10^6$ cells) in 100 µl of medium for tumor development. The treatments started when the average tumor size reached approximately 150-200 mm³. Animals in each group (n=10) were treated with anti-MET antibodies and certain controls at indicated doses. Tumor sizes were measured twice weekly in two dimensions using a caliper, and the volume were expressed in mm³ using the formula: $V=0.5 \; a \times b^2$ where a and b are the long and short diameters of the tumor, respectively. Tumor growth inhibition (TGI) was calculated for each group according to the following formula: TGI (%)=[1−(Ti−T0)/(Vi−V0)]×100; Ti was the tumor volume of treatment group on a specific day, T0 was the tumor volume of the treatment group on the first day, Vi was the tumor volume of vehicle control group on a specific day and V0 was the tumor volume of the vehicle group on the first day of treatment.

6.3.1.3 SNU-5 Xenograft Model

Cell Culture: The SNU-5 human gastric cancer tumor cells (ATCC®, Manassas, VA, cat #CRL-5973), a MET-amplified cell line, were maintained in vitro as a monolayer culture in IMDM medium supplemented with 20% heat inactivated fetal bovine serum, at 37° C. in an atmosphere of 5% $CO_2$ in air. Cells growing in an exponential growth phase were harvested and counted for tumor inoculation.

Animals: BALB/c nude, female, 6-8 weeks mice weighing approximately 18-20 g were used for SNU-5 tumor cell innoculation.

Tumor Inoculation: Each mouse was inoculated subcutaneously at the right flank with tumor cells (e.g., $5 \times 10^6$) in 100 µl of medium for tumor development. The treatments were started when the average tumor size reaches approximately 150-200 mm³. Animals in each group (n=10) were treated with anti-MET antibodies and certain controls at indicated doses. For example, in certain experiments, 30 mg/kg (10 µl/g dosing volume) of one of PBS, chimeric $IgG_1$ anti-KLH antibody, monovalent Ab237C, Ab237C-$IgG_2$, Ab237C-$IgG_4$, or Ab237C were administered intraperitonealy biweekly for three weeks.

Tumor sizes were measured twice weekly in two dimensions using a caliper, and the volume were expressed in mm³ using the formula: $V=0.5 \; a \times b^2$ where a and b are the long and short diameters of the tumor, respectively. Tumor growth inhibition (TGI) was calculated for each group according to the following formula: TGI (%)=[1−(Ti−T0)/(Vi−V0)]×100; Ti was the tumor volume of treatment group on a specific day, T0 was the tumor volume of the treatment group on the first day, Vi was the tumor volume of vehicle control group on a specific day and V0 was the tumor volume of the vehicle group on the first day of treatment. Tumor weight was measured at study termination. The T/C value (in percent) is calculated where T and C are the mean tumor weights of the treated and control groups, respectively.

6.3.2 Results
6.3.2.1 Ab237 Isotype Exchange Enhances Potency

Immunoglobulin isotype exchanges for anti-MET antibodies were performed as described in Section 6.3.1.1 to explore the impact on antibody function. Anti-MET antibodies comprising human $IgG_2$ constant regions were generated. After generation of $IgG_2$ antibodies, it is expected that both alpha and beta ($IgG_{2a}$ and $IgG_{2b}$, respectively) isoforms are present. Switching the Ab237C human $IgG_1$ isotype with a human $IgG_4$ isotype ("Ab237C-$IgG_4$") had minimal impact of SNU-5 cell proliferation inhibition as compared to Ab237C (FIG. 8A). Surprisingly, switching the Ab237C $IgG_1$ human isotype with a human $IgG_2$ isotype dramatically enhanced inhibition of MET phosphorylation in SNU-5 cells, relative to both Ab237C and Ab237C $IgG_4$ (FIG. 8A). Ab237C-$IgG_2$ also exhibited enhanced MET degradation in SNU-5 cells as compared to Ab237C and Ab237C-$IgG_4$ (FIG. 8B). Moreover, Ab237C-$IgG_2$ is significantly more potent in the SNU-5 and EBC-1 (lung squamous cell carcinoma cell line) cellular proliferation inhibition as compared to Ab237C and Ab237C-IgG$_4$, as well as a monovalent form of Ab237 (FIGS. 8C and 8D). These unexpected results indicate that exchanging the human IgG$_1$ constant region of anti-MET antibody Ab237C with a human IgG$_2$ constant region dramatically enhances Ab237C functionality, such as blocking MET activity and anti-cancer activity. SNU-5 and EBC-1 cells are both MET-amplified cell lines. In U87MG cells in vitro, Ab237-IgG$_2$ antibody inhibited MET phosphorylation to the same extent as Ab237C and Ab237-IgG$_4$ antibodies. However, due to signal saturation, there was not much room for isotype switching to generate additional improvement in the two dimensional cell culture of U87MG cells, in contrast to the three dimensional xenograft models presented below.

6.3.2.2 A Humanized Form of Ab237 Potently Inhibits MET Activity

To determine if a humanized form of antibody Ab237 comprising a human IgG$_2$ constant region also exerts the ability to inhibit MET activity, MET phosphorylation was evaluated in A549 cells (FIG. 8E) and SNU5 cells (FIG. 8F) upon treatment with Ab237C-IgG$_2$ or a humanized form of Ab237 comprising a human IgG$_2$ constant region ("hum-Ab237-IgG$_2$"). As with Ab237 treatment of cells, treatment with hum-Ab237C-IgG$_2$ potently inhibited phosphorylation of MET, indicating that humanized forms of Ab237 comprising human IgG$_2$ constant regions are able to inhibit MET activation in vitro (FIGS. 8E and 8F). Moreover, treatment of SNU5 cells with hum-Ab237C-IgG$_2$ potently inhibited cellular proliferation, with a nearly identical profile as the inhibition of cellular proliferation with Ab237C-IgG$_2$ (FIG. 8G).

6.3.2.3 the Impact of Ig Isotype Exchange on Antibody Potency is Antibody-Dependent To determine the effects of Ig framework exchange in other anti-MET antibodies described herein, human IgG$_2$ constant region variants were generated for Ab235C, Ab236C, Ab238C and Ab239C (herein referred to as "Ab235C-IgG$_2$", "Ab236C-IgG$_2$", "Ab238C-IgG$_2$" and "Ab239C-IgG$_2$", respectively). As noted above, after generation of IgG$_2$ antibodies, it is expected that both alpha and beta (IgG$_{2a}$ and IgG$_{2b}$, respectively) isoforms are present. As discussed above, Ab235C-Ab239C robustly inhibit MET phosphorylation and induce MET degradation in SNU-5 cells. Interestingly, exchanging the human IgG$_1$ framework to a human IgG$_2$ framework for Ab235C, Ab236C, and Ab239C, but not for Ab238C, resulted in enhanced potency in inhibiting MET phosphorylation and inducing MET degradation in SNU-5 cells (FIGS. 9A, 9B, 9C, and 9D).

In particular, antibodies Ab238C, Ab238C-IgG$_2$, Ab239C, Ab239C-IgG$_2$, and Ab237C-IgG$_2$ were able to inhibit MET phosphorylation in SNU-5 cells by 19%, 24%, 33%, 75%, and 72%, respectively, as compared to 12% inhibition for a control chimeric human IgG$_1$ anti-KLH antibody (FIG. 9A). Antibodies Ab238C, Ab238C-IgG$_2$, Ab239C, Ab239C-IgG$_2$, and Ab237C-IgG$_2$ were able to induce MET degradation in SNU-5 cells with a maximal percent induction of MET degradation of 39%, 35%, 36%, 75%, and 81%, respectively, as compared to 17% maximal percent induction for a control chimeric human IgG$_1$ anti-KLH antibody (FIG. 9B). Antibodies Ab235C, Ab235C-IgG$_2$, Ab236C, and Ab236C-IgG$_2$ were able to inhibit MET phosphorylation in SNU-5 cells by 10%, 64%, 17%, and 75%, respectively (FIG. 9C). Antibodies Ab235C, Ab235C-IgG$_2$, Ab236C, and Ab236C-IgG$_2$ were able to induce MET degradation in SNU-5 cells with a maximal percent induction of MET degradation of 6%, 64%, 19%, and 69%, respectively (FIG. 9D). These data indicate that certain anti-MET antibodies described herein, such as Ab235, Ab236, Ab237 and Ab239, are more effective at inhibiting MET activities and inducing MET degradation as human IgG$_2$ isotypes as compared to human IgG$_1$ isotypes.

6.3.2.4 Ab237C-IgG$_2$ and a Humanized Form of Ab237 Potently Inhibit Tumor Growth as Compared to Competitor Anti-MET Antibodies The anti-tumor properties of Ab237C-IgG$_2$ were assessed as described in Sections 6.3.1.2 and 6.3.1.3. In a U87 xenograft model, Ab237C-IgG$_2$ was more effective at delaying tumor growth as compared to the human IgG$_1$ and human IgG$_4$ Ab237C isotypes (FIG. 10A). In a SNU5 gastric cancer xenograft model, Ab237C (IgG$_1$) and Ab237C-IgG$_4$ delayed tumor growth as compared to control treatment (FIG. 10B), but surprisingly, in this SNU5 gastric cancer xenograft model, Ab237C-IgG$_2$ completely eliminated the tumor (FIG. 10B). These data demonstrate the unexpected ability of the Ab237C antibody to exhibit significantly improved anti-tumor properties when converted into a human IgG$_2$ isotype. Furthermore, it is of significant note that Ab237-IgG$_2$ antibody treatment led to profound SNU-5 tumor growth inhibition but also sustained tumor regression for up to >90 days following antibody treatment. Moreover, 90% of the SNU-5 mice treated with Ab237-IgG$_2$ showed no detectable tumor mass during the term of the study.

These data also indicate that anti-MET antibodies described herein, such as Ab235, Ab236, Ab237, and Ab239, are more effective against inhibiting tumor progression in vivo as a human IgG$_2$ isotype as compared to a human IgG$_1$ isotype.

Next, the anti-tumor properties of Ab237C-IgG$_2$ and a humanized form of Ab237 which is an IgG$_2$ isotype (hum-Ab237C-IgG$_2$) were assessed as described in Sections 6.3.1.2 and 6.3.1.3 as compared to anti-MET antibodies that have been tested in the clinic. Ab316 is a monovalent IgG$_1$ anti-MET antibody comprising the amino acid sequences of SEQ ID NO:298 (light chain), SEQ ID NO:299 (heavy chain knob), and SEQ ID NO:300 (heavy chain hole), as in onartuzumab (MetMAb; Genentech/Roche). Ab317 is an IgG$_4$ anti-MET antibody comprising the amino acid sequences of SEQ ID NO:294 (VH) and SEQ ID NO:295 (VL), as in emibituzumab (Lilly). Ab318 is an IgG$_1$ anti-MET antibody comprising the amino acid sequences of SEQ ID NO:296 (VH) and SEQ ID NO:297 (VL), as in h224G11 (ABT-700; AbbVie).

In a SNU-5 xenograft model, Ab237C-IgG$_2$ was more effective at delaying tumor growth as compared to Ab316, Ab317, and Ab318, and completely eliminated the tumor (FIG. 11A). Likewise, an IgG$_2$ isotype of a humanized form of the Ab237 antibody (hum-Ab237C-IgG$_2$) also demonstrated the ability to completely eliminate the tumor (FIG. 11B). Moreover, Ab237C-IgG$_2$ was also more effective at delaying tumor growth as compared to Ab316, Ab317, and Ab318, in a U87 xenograft model (FIG. 11C). Finally, hum-Ab237C-IgG$_2$ was more effective at delaying tumor growth as compared to Ab316, Ab317, and Ab318 in a U87 xenograft model (FIG. 11D).

6.3.3 Conclusions

The data presented in these examples demonstrate that the antibodies described herein inhibit MET activities, such as MET phosphorylation, MET degradation, and tumor cell proliferation. For example, Ab235, Ab236, Ab237, and Ab239 do so without exhibiting growth-promoting agonist activity. Further, these data also demonstrate that exchanging the IgG$_1$ constant region of anti-MET antibodies Ab235, Ab236, Ab237 and Ab239 to a human IgG$_2$ isotype dramatically increases antibody functionality, such as the abilities of the antibodies to inhibit MET activities, such as MET phosphorylation, MET degradation, and tumor cell proliferation. Moreover, Ab237 and a humanized Ab237, in particular, IgG$_2$ isotypes of these Ab237 antibodies, very effectively inhibit both MET-ligand-dependent and MET-amplified (e.g., ligand-independent) tumor growth in vivo. This is in contrast to onartuzumab, for example, which solely targets receptor-ligand intereaction and blocks only ligand-dependent MET activation (Martens et al., 2006, Clin. Cancer. Res. 12(20 Pt 1):6144-6152).

6.4 Example 4: Further Epitope and Degradation Pathway Characterization 6.4.1 Materials and Methods
6.4.1.1 FACS Cross-Species Binding Analysis To measure antibody binding affinities against cell surface receptor, antibodies were labeled with the Alexa647 antibody labeling kit and purified per manufacturer's instruction (Invitrogen). A549 (human), 4MBr5 (monkey), MDCK (canine), and MS1 (murine) cells were resuspended in pre-chilled FACS buffer, incubated on ice for 1 hr and distributed to 96-well plates at 10$^5$ cell/well. Serial dilutions of labeled antibodies were added to each well and incubated on ice for 4 hrs to allow antibody binding to reach equilibrium. Mean fluorescence intensity was analyzed using a FACS reader (ACCURI™-C6; BD Biosciences), and apparent binding affinities were determined using GRAPHPAD PRISM® software.

6.4.1.2 Antibody Binding by ELISA

To measure antibody binding by ELISA, 10 μg of human, murine or chimeric MET-ECD was coated onto 96-well plates (Costar). Serial dilutions of antibodies were added to the plates and incubated at room temperature for 1 hr prior to the addition of HRP-conjugated secondary antibody. Luminescence was measured with BioTek SYNERGY™ HT plate reader, and binding EC$_{50}$ values were determined using GRAPHPAD PRISM® software.

6.4.1.3 Recombinant Protein Expression and Purification.

Chimeric MET-ECD was generated by ligation of DNA encoding amino acids 1-561 of murine MET with DNA encoding amino acids 562-932 of human MET and insertion into Xba I/Xho I sites of pcDNA3.3-His8 vector. Both human and chimeric MET-ECD-His (amino acids 1-932) was expressed in 293F cells by transient transfection and protein was purified using Ni-NTA affinity column followed by size exclusion chromatography.

6.4.2 Results
6.4.2.1 Antibody Binding Epitope Characterization

In order to determine the antibody epitope, a cross-species binding analysis was performed on Ab237. The analysis revealed that Ab237 bound with high affinity to MET expressed on human (A549) and monkey (4MBr5) cell lines, but not to canine (MDCK) or murine (MS1) cell lines reported to express high levels of MET (Table 15).

TABLE 15

FACS binding of anti-MET antibodies to human, monkey, canine and murine cell line expression MET.

| Clone | Human (A549) | Monkey (4MBr5) | Canine (MDCK) | Murine (MS1) |
|---|---|---|---|---|
| Ab235 | + | + | − | − |
| Ab236 | + | + | − | − |
| Ab237 | + | + | − | − |
| Ab238 | + | + | − | − |
| Ab239 | + | + | − | − |

This finding was extended using ELISA assays. Ab237 bound human MET-ECD with high affinity (EC50=0.02 nM) but no detectable binding was observed with a murine MET-ECD (Table 16). In addition, a chimeric protein containing the murine MET SEMA domain fused with human MET PSI-Ig domain completely abolished the binding of Ab237, suggesting that antibody epitope was located within the SEMA domain (Table 16).

TABLE 16

ELISA binding of anti-MET antibodies to human, murine and chimeric MET-ECD.

| Clone | Human MET-ECD (nM) | Human-SEMA Murine-PSI chimera | Murine MET-ECD |
|---|---|---|---|
| Ab235 | 0.13 | — | — |
| Ab236 | 0.05 | — | — |
| Ab237 | 0.02 | — | — |
| Ab238 | 0.09 | — | — |
| Ab239 | 0.04 | — | — |

Protein sequence comparison of human, monkey, canine and murine MET receptors and published crystallographic structure of the MET SEMA-PSI domain (Stamos et al., 2004, EMBO J. 23(12):2325-2335) revealed that several surface-exposed amino acids may contribute to the difference in binding of Ab237 to MET from various species. Of the 15 amino acids that differ in human and murine SEMA domains, five of the surface-exposed amino acids are located in close vicinity (Q328/R331/5336/L337/N338). This surface-exposed cluster in the human MET (hMET) protein was replaced with corresponding amino acids from canine or murine MET. hMET mutants were then transfected into CHO cells and antibody binding affinity was measured by flow cytometry. Compared to wild-type hMET receptor, which bound Ab237 with sub-nanomolar affinity, the hMET receptor with murine or canine mutations completely abolished Ab237 binding but had no influence on control antibody that binds the Ig domains of MET (Table 17).

TABLE 17

Epitope mapping of Ab237 and Ab238 by mutagenesis analysis.

| hMET Mutation | Ab237 Binding (nM) | Ab238 Binding (nM) | Control Met Antibody Binding (nM) | Mutation Description |
|---|---|---|---|---|
| WT | 0.11 | 0.36 | 0.82 | WT |
| R331K/S336N | ND | ND | 0.84 | human to canine |
| Q328H/R331K/S336N | ND | ND | 0.56 | human to canine |
| R331K/L337P | ND | ND | 1.5 | human to murine |

TABLE 17-continued

Epitope mapping of Ab237 and Ab238 by mutagenesis analysis.

| hMET Mutation | Ab237 Binding (nM) | Ab238 Binding (nM) | Control Met Antibody Binding (nM) | Mutation Description |
|---|---|---|---|---|
| Q328N/R331K/ L337P/N338S | ND | ND | 1.6 | human to murine |

(ND = not detectable).

Similarly, Ab238 binding to hMET receptor also involved Q328/R331/5336/L337/N338, as mutations of this amino acid cluster completely eliminated Ab238 binding to similar extent as Ab237 (Table 17), indicating that Ab237 and Ab238 share overlapping epitopes located in the SEMA domain. Competitive binding assays (see Section 6.1.2.4) demonstrated that antibodies Ab235-Ab239 and Ab241-Ab255 all shared similar epitopes, indicating that these antibodies share overlapping epitopes located in the SEMA domain.

6.4.2.2 Antibody-Promoted MET Degradation Through Exon 14-Independent Pathways Involve Ubiquitination but not Shedding An ELISA assay was used to determine whether Ab237 could induce receptor degradation through membrane protease-mediated receptor shedding. A549 cells were incubated with 1 nM of antibody (Ab237, Ab238, or control) for 24 hrs and release of soluble MET extracellular domain (sMET-ECD) protein into cell culture medium was quantitated using an ELISA assay. Consistent with prior reports, treatment of cells with PMA (phorbol 12-myristate 13-acetate) induced substantial MET shedding and released sMET-ECD into the culture medium, while no shedding was detected in HGF-treated samples (FIG. 12A). Treatment of cells with the anti-MET antibodies did not lead to MET shedding, indicating that the observed antibody-induced receptor degradation proceeded through a different pathway.

Whether the anti-MET antibodies promote MET ubiquitination and degradation was investigated next. A549 cells were stimulated with 1 nM of HGF or anti-MET antibodies for 15 min. Cell lysates were precipitated with anti-ubiquitin antibody conjugated agarose (Santa Cruz) followed by immunoblotting with anti-MET antibody (Cell Signaling Technology). Both HGF and antibody treatment for 15 min induced potent receptor ubiquitination (FIG. 12B). Thus, these antibodies promote receptor degradation utilizing the ubiquitination mechanism instead of protease-mediated shedding. This is in contrast with membrane protease-mediated receptor shedding observed previously with antibodies such as DN30 (Schleter, 2010, J. Biol. Chem. 285 (34):26335-26340).

MET exon 14 mutations have been reported in many cancers (The Cancer Genome Atlas Research Network, 2014, Nature, 511(7511):543-550; Frampton et al., 2015, Cancer Discov. 5(8):850-859). MET exon 14 mutations confer reduced HGF-induced receptor degradation. Deletion of exon 14 (Leu964-Asp1010) removes the Tyr1003 site necessary for Cbl binding leading to a substantial decrease HGF-induced receptor degradation as previously reported (Kong-Beltram et al., 2006, Cancer Res. 66(1):283-289). It has been suggested that the presence of exon 14 mutation in human gastric tumors may explain MET overexpression in the absence of MET gene amplification observed in this tumor type (Lee et al., 2015, Oncotarget 6(29):28211-28222). In a non-small-cell lung cancer cell line H596, a functional MET protein is expressed without the 47 amino acids encoded by exon 14 (Kong-Beltram et al., 2006, Cancer Res. 66(1):283-289). In this cell line, it has been demonstrated that HGF-induced MET degradation is compromised by the absence of Tyr1003 (Kong-Beltram et al., 2006, Cancer Res. 66(1):283-289). Incubation of H596 cells with 1 nM HGF for 24 hrs led to only 30% receptor degradation compared to approximately 80% degradation in cell lines expressing wild-type MET such as A549 and U87MG cells. In contrast, incubation with 1 nM HGF and 1 nM of Ab237 or Ab238 antibody for 24 hrs was still capable of inducing >70% of MET degradation (FIG. 13A). In a cell proliferation assay, addition of anti-MET antibodies led to significant growth inhibition of H596 cells in the presence of 1 nM HGF in culture medium (FIG. 13B).

Thus, addition of Ab237 or Ab238 anti-MET antibodies to the exon 14 mutant cells resulted in substantial MET degradation, indicating that these anti-MET antibodies employ degradation pathways different from HGF-induced MET degradation and less dependent on the exon 14-encoded juxtamembrane region that contains the Cbl binding site.

In order to determine if the antibody-induced MET degradation observed herein requires MET kinase activity, the effect of MET kinase inhibitor crizotinib on HGF and anti-MET antibody-induced degradation was studied. Cells pre-treated with 1 µM of crizotinib completely blocked HGF-induced MET phosphorylation (FIG. 2, see Section 6.1.2.6), and completely inhibited HGF-induced MET degradation (FIG. 14). Unlike its effect on HGF, crizotinib only partially reduced Ab237- and Ab238-induced MET degradation (FIG. 14). Altogether, however, these results indicate that the degradation pathway of these antibodies is not the one utilized by HGF and differs from protease-induced shedding. Importantly, the degradation pathway of these antibodies remains functional in exon 14 mutant cancer cells.

6.4.3 Conclusions

The data in this example showed that Ab237 and Ab238 share overlapping epitopes located in the SEMA domain. Furthermore, the antibodies (e.g., Ab237) utilize alternative degradation pathways that are not utilized by HGF and that differ from protease-induced shedding, such that the antibodies remain functional in exon 14 mutant cancer cells, a frequently mutated region in MET-amplified cancers.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. A monoclonal antibody or antigen-binding fragment thereof that binds to human MET, wherein the antibody or antigen-binding fragment thereof comprises:
   a. a light chain variable region ("VL") comprising:
      i. a VL CDR1 comprising the amino acid sequence of SEQ ID NO: 13;
      ii. a VL CDR2 comprising the amino acid sequence of SEQ ID NO: 14; and
      iii. a VL CDR3 comprising the amino acid sequence of SEQ ID NO: 15; and
   b. a heavy chain variable region ("VH") comprising:
      i. a VH CDR1 comprising the amino acid sequence of SEQ ID NO: 16;
      ii. a VH CDR2 comprising the amino acid sequence of SEQ ID NO: 17; and
      iii. a VH CDR3 comprising the amino acid sequence of SEQ ID NO: 18.

2. The antibody or antigen-binding fragment of claim 1, wherein the antibody or antigen-binding fragment thereof comprises:
   a. a VL comprising an amino acid sequence that is at least 80%, at least 85%, at least 90%, at least 95%, at least 98%, or 100% identical to SEQ ID NO: 56; and
   b. a VH comprising an amino acid sequence that is at least 80%, at least 85%, at least 90%, at least 95%, at least 98%, or 100% identical to SEQ ID NO: 63.

3. The antibody or antigen-binding fragment thereof of claim 1, wherein the antibody comprises a human IgG constant region.

4. The antibody or antigen-binding fragment thereof of claim 3, wherein the antibody comprises a human IgG2 constant region.

5. The antibody or antigen-binding fragment thereof of claim 1, wherein the antibody comprises a human kappa light chain constant region or a human lambda light chain constant region.

6. The antibody or antigen-binding fragment thereof of claim 1, wherein the antibody is a chimeric antibody or a humanized antibody.

7. The antibody or antigen-binding fragment thereof of claim 1, wherein the antibody is a bispecific antibody or antigen-binding fragment thereof.

8. The antibody or antigen-binding fragment thereof of claim 1, wherein the antibody or antigen-binding fragment thereof is fused to a heterologous polypeptide.

9. The antibody or antigen-binding fragment thereof of claim 1, wherein the antibody or the antigen-binding fragment thereof is conjugated to an agent.

10. A composition comprising a therapeutically effective amount of the antibody or antigen-binding fragment of claim 1.

11. An isolated cell producing the antibody or antigen-binding fragment of claim 1.

12. A kit comprising the antibody or antigen-binding fragment of claim 1.

13. The antibody or antigen-binding fragment of claim 1, wherein:
   a. the VL comprises an amino acid sequence that is identical to SEQ ID NO: 56; and b. the VH comprises an amino acid sequence that is identical to SEQ ID NO: 63.

14. A monoclonal antibody or antigen-binding fragment thereof that binds to human MET, wherein the antibody or antigen-binding fragment thereof comprises:
   a. a VL comprising the same VL CDR1, VL CDR2 and VL CDR3 present in the VL as shown in SEQ ID NO: 56; and
   b. a VH comprising the same VH CDR1, VH CDR2 and VH CDR3 present in the VH as shown in SEQ ID NO: 63.

15. The antibody or antigen-binding fragment of claim 14, wherein:
   a. the VL comprises:
      i. a VL CDR1 comprising the amino acid sequence of SEQ ID NO: 145;
      ii. a VL CDR2 comprising the amino acid sequence of SEQ ID NO: 146; and
      iii. a VL CDR3 comprising the amino acid sequence of SEQ ID NO: 264; and
   b. the VH comprises:
      i. a VH CDR1 comprising the amino acid sequence of SEQ ID NO: 142;
      ii. a VH CDR2 comprising the amino acid sequence of SEQ ID NO: 143; and
      iii. a VH CDR3 comprising the amino acid sequence of SEQ ID NO: 144.

16. The antibody or antigen-binding fragment of claim 14, wherein:
   a. the VL comprises:
      i. a VL CDR1 comprising the amino acid sequence of SEQ ID NO: 175;
      ii. a VL CDR2 comprising the amino acid sequence of SEQ ID NO: 176; and
      iii. a VL CDR3 comprising the amino acid sequence of SEQ ID NO: 177; and
   b. the VH comprises:
      i. a VH CDR1 comprising the amino acid sequence of SEQ ID NO: 172;
      ii. a VH CDR2 comprising the amino acid sequence of SEQ ID NO: 173; and
      iii. a VH CDR3 comprising the amino acid sequence of SEQ ID NO: 174.

* * * * *